(12) United States Patent
Palle et al.

(10) Patent No.: US 8,252,797 B2
(45) Date of Patent: Aug. 28, 2012

(54) HETEROCYCLIC COMPOUNDS AS ADENOSINE RECEPTOR ANTAGONIST

(75) Inventors: Venkata Palle, Pune (IN); Sujay Basu, Pune (IN); Yogesh Waman, Pune (IN); Vidya Ramdas, Pune (IN); Dinesh Barawkar, Pune (IN); Meena Patel, Pune (IN); Anil Panmand, Pune (IN)

(73) Assignee: Advinus Therapeutics Pvt. Ltd., Bangalore (IN)

( * ) Notice: Subject to any disclaimer, the term of this patent is extended or adjusted under 35 U.S.C. 154(b) by 318 days.

(21) Appl. No.: 12/411,956

(22) Filed: Mar. 26, 2009

(65) Prior Publication Data

US 2009/0298744 A1   Dec. 3, 2009

(51) Int. Cl.
| | |
|---|---|
| *C07D 473/06* | (2006.01) |
| *C07D 473/04* | (2006.01) |
| *A61K 31/522* | (2006.01) |
| C07D 231/14 | (2006.01) |
| C07D 261/04 | (2006.01) |
| A61P 11/06 | (2006.01) |
| A61P 37/08 | (2006.01) |

(52) U.S. Cl. ........... 514/252.16; 514/263.22; 514/263.4; 514/263.2; 544/267; 544/269; 544/270; 544/229; 544/310; 544/268; 548/240; 548/531; 548/374.1

(58) Field of Classification Search .................. 544/267, 544/269, 270; 514/263.2, 263.22, 263.4, 514/252.16

See application file for complete search history.

(56) References Cited

U.S. PATENT DOCUMENTS

| | | | | |
|---|---|---|---|---|
| 5,696,124 A * | 12/1997 | Kufner-Muhl et al. | .. | 514/263.34 |
| 6,117,878 A * | 9/2000 | Linden | ...................... | 514/263.34 |
| 6,894,021 B2 * | 5/2005 | Belardinelli et al. | ............. | 514/1 |
| 7,335,655 B2 * | 2/2008 | Baraldi et al. | ............. | 514/234.2 |
| 7,579,348 B2 * | 8/2009 | Wang et al. | ................. | 514/234.2 |
| 7,795,268 B2 * | 9/2010 | Zeng et al. | ................. | 514/263.2 |
| 2003/0229106 A1 * | 12/2003 | Kalla et al. | ................. | 514/263.2 |
| 2004/0180948 A1 * | 9/2004 | Linden et al. | ................. | 514/447 |
| 2005/0059683 A1 * | 3/2005 | Zablocki et al. | ............ | 514/263.2 |
| 2005/0101778 A1 * | 5/2005 | Kalla et al. | ..................... | 544/269 |
| 2005/0261316 A1 * | 11/2005 | Kalla et al. | ................. | 514/263.2 |
| 2006/0058322 A1 * | 3/2006 | Zeng et al. | ................. | 514/263.2 |
| 2007/0249598 A1 | 10/2007 | Wang et al. | | |
| 2007/0274910 A1 * | 11/2007 | Wilson et al. | ................. | 424/1.65 |
| 2008/0176845 A1 | 7/2008 | Sitaraman et al. | | |
| 2008/0194593 A1 * | 8/2008 | Kalla et al. | ................. | 514/263.2 |
| 2008/0318983 A1 * | 12/2008 | Kalla et al. | ................. | 514/263.2 |
| 2009/0156544 A1 * | 6/2009 | Elzein et al. | ..................... | 514/46 |
| 2010/0105706 A1 * | 4/2010 | Zeng et al. | ............... | 514/263.22 |
| 2011/0118276 A1 * | 5/2011 | Leung | ...................... | 514/252.16 |

FOREIGN PATENT DOCUMENTS

| | | |
|---|---|---|
| WO | 2005021548 | 3/2005 |
| WO | 2006091898 | 8/2006 |
| WO | 2006091936 | 8/2006 |
| WO | 2008027585 | 3/2008 |

* cited by examiner

*Primary Examiner* — Mark Berch
(74) *Attorney, Agent, or Firm* — K&L Gates LLP

(57) ABSTRACT

Compounds of the present disclosure are fused pyrimidine compounds of formula (I), its tautomers, polymorphs, stereoisomers, prodrugs, solvate or a pharmaceutically acceptable salts thereof, as Adenosine receptor antagonists.

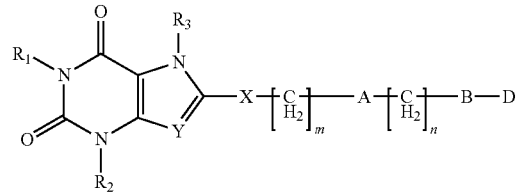

I

Processes of their preparation are also described in the disclosure.

12 Claims, No Drawings

HETEROCYCLIC COMPOUNDS AS ADENOSINE RECEPTOR ANTAGONIST

FIELD OF THE INVENTION

The present invention relates to a series of novel substituted fused pyrimidine compounds, their tautomers, polymorphs, stereoisomers, prodrugs, solvates, pharmaceutically acceptable salts, pharmaceutical compositions containing them and methods of treating conditions and diseases that are mediated by adenosine receptor (AR) activity. These compounds are useful in the treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

BACKGROUND OF THE INVENTION

Inflammatory and immunological reactions protect the host from invasion by microorganisms and eliminate debris at sites of tissue injury but they can also be responsible for significant tissue damage. Thus, regulatory mechanisms that limit damage from an overly exuberant immune response have evolved. It is increasingly apparent that adenosine, a purine nucleoside that is elaborated at injured and inflamed sites, has a central role in the regulation of inflammatory responses and in limiting inflammatory tissue destruction.

Adenosine is a ubiquitous purine nucleoside, playing a pivotal role in many biological processes such as energy generation, cell proliferation and proteins metabolism (European Journal of Pharmacology 533 (2006) 77-88). It acts on immune cells like mast cells, monocytes, macrophages, neutrophils, eosinophils, lymphocytes, airway smooth muscle cells, endothelial cells and airway epithelia. It is normally present in human tissues at low concentrations, but in response to metabolic stress, such as that encountered in the course of inflammatory events or during tissue hypoxia, a rapid increase in adenosine tissue levels takes place. Once generated, adenosine elicits its biological activities by interacting with its receptors (Jacobson and Gao, 2006). There are four known subtypes of adenosine receptors (ARs)—referred to as $A_1$, $A_{2A}$, $A_{2B}$ and $A_3$. It has been known for long time that intracellular signals activated by adenosine receptors include either stimulation or inhibition of adenyl cyclase. In general, $A_1$ and $A_3$ receptors are coupled to pertussis toxin inhibited Gi coupled signal transduction proteins whereas $A_2$ receptors ($A_{2A}$ and $A_{2B}$) are $G\alpha,s$ linked receptors and stimulate adenylyl cyclase and cAMP.

Adenosine accumulation during ischemia and inflammation protects tissues from injury (Linden et al, 2001). Adenosine is related both structurally and metabolically to the bioactive nucleotides adenosine triphosphate (ATP), adenosine diphosphate (ADP), adenosine monophosphate (AMP) and cyclic adenosine mono-phosphate (cAMP); to the biochemical methylating agent S-adenosyl-L-methione, and structurally to the coenzymes NAD, FAD and coenzyme A; and to RNA. Together adenosine and these related compounds are important in the regulation of many aspects of cellular metabolism (Poulsen and Quinn, 1998).

Adenosine signaling is known to serve apoptotic, angiogenic and pro-inflammatory functions and might be relevant to the pathogenesis of asthma and chronic obstructive pulmonary disease (Trends in Pharmacological Sciences, Vol. 24, No. 8, August 2003). Extracellular adenosine acts as a local modulator with a generally cytoprotective function in the body. Its effects on tissue protection and repair fall into four categories: increasing the ratio of oxygen supply to demand; protecting against ischaemic damage by cell conditioning; triggering anti-inflammatory responses; and the promotion of angiogenesis.

The $A_{2B}$ adenosine receptor subtype (see Feoktistov, I., Biaggioni, I. Pharmacol. Rev. 1997, 49, 381-402) has been identified in a variety of human and murine tissues and is involved in the regulation of vascular tone, smooth muscle growth, angiogenesis, hepatic glucose production, bowel movement, intestinal secretion, and mast cell degranulation.

$A_{2B}$ receptors have been implicated in mast cell activation and asthma, control of vascular tone, cardiac myocyte contractility, cell growth and gene expression, vasodilation, regulation of cell growth, intestinal function, and modulation of neurosecretion (Pharmacological Reviews Vol. 49, No. 4).

$A_{2B}$ receptors modulate mast cell function. Adenosine activates adenylate cyclase and protein kinase C, and potentiates stimulated mediator release in mouse bone marrow derived mast cells. (TiPS—April 1998 (Vol. 19)). Activation of $A_{2B}$ receptors in HMC-1 augments IL-8 release and potentiates PMA-induced secretion of IL-8. Thus, adenosine would contribute to the asthmatic response by acting on the mast cell to enhance the release of proinflammatory mediators. (Pulmonary Pharmacology & Therapeutics 1999, 12, 111-114). In COPD, transformation of pulmonary fibroblasts into myofibroblasts is considered a major mechanism. Activation of the $A_{2B}$ AR is involved in this process. Selective $A_{2B}$ antagonists are expected to have beneficial effect on pulmonary fibrosis (Curr. Drug Targets, 2006, 7, 699-706; Am. J. Resper. Cell. Mol. Biol., 2005, 32, 228). $A_{2B}$ antagonists can be used as wound healing agents. Activation of the $A_{2B}$ AR promotes angiogenesis by increasing the release of angiogenic factors and $A_{2B}$ antagonists are useful to block angiogenesis (Circ. Res., 2002, 90, 531-538). $A_{2B}$ AR may be involved in the inhibition cardiac fibroblast (CF) proliferation (Am. J. Physiol. Heart Circ. Physiol., 2004, 287, H2478-H2486). Adenosine stimulates Cl-secretion in the intestinal epithelia pointing towards a possible treatment for cystic fibrosis patients with CFTR mutation (Am. J. Respir. Cell Mol. Biol., 2008, 39, 190-197). High affinity $A_{2B}$ antagonists are effective in hot plate model suggestive of the role of $A_{2B}$ in nociception and can be used as potential analgesic agents (The J. of Pharmacol. and Exp. Ther., 2004, 308, 358-366).

A2B receptor is involved in release of IL-6. Increasing evidence suggests that IL-6 plays a role in Alzheimer's disease in the context of inflammatory process associated with disease. Hence A2B receptor antagonist might be useful for Alzheimer's disease.

The A2B ARs are involved in the stimulation of nitric oxide production during Na+-linked glucose or glutamine absorption. They are involved in glucose production in hepatocytes upon agonist stimulation. A2B-receptor antagonists showed an anti-diabetic potential mainly by increasing plasma insulin levels under conditions when the adenosine tonus was elevated in-vivo and increased insulin release in-vitro (J Pharm. Pharmacol. 2006 December; 58(12):1639-45). Thus A2B antagonists may serve as a novel target for the treatment of this metabolic disease.

A2B receptor is a negative modulator of TNF-α hence A2B agonists might have application in the management of sepsis.

The A2B ARs are also important for adenosine-mediated inhibition of cardiac fibroblast functions. Adenosine receptor agonists inhibit rat cardiac fibroblasts with pharmacology suggestive of A2B receptor indicating role of A2B in cardiac remodelling and abnormal growth in cardiovascular diseases. Drugs that stimulate adenosine $A_{2B}$ receptors or increase adenosine levels are new candidates for preventing cardiac remodeling after MI (Circulation. 2006 Oct. 31; 114(18): 1923-32. Epub 2006 Oct. 16.).

Direct injections of adenosine into the corpus cavernosum of impotence patients produce a brief erection and if this effect is also mediated by A2B receptors in humans, it will be possible to develop stable and selective agonists that can be given locally.

An adenosine receptor-mediated signal-transduction pathway in the dermal papilla cells (DPCs) of hair contributes to minoxidil-induced hair growth through A2B receptor (J. Invest. Dermatol. 2007 June; 127(6):1318-25. Epub 2007 Feb. 15). Thus A2B agonists might stimulate hair growth through FGF-7 upregulation in DPCs.

In view of the physiological effects mediated by adenosine receptor, several A2B receptor antagonists have been recently disclosed for the treatment or prevention of asthma, bronchoconstriction, allergic diseases, hypertension, atherosclerosis, reperfusion injury, myocardial ischemia, retinopathy, inflammation, gastrointestinal tract disorders, cell proliferation diseases and/or diabetes mellitus. See for example WO2008002902, WO2007149277, WO2007017096, WO2007109547, WO2006091896, WO2006015357, WO2005042534, WO2005021548, WO2004106337, WO2003000694, WO2003082873, WO2003006465, WO2003053361, WO2003002566, WO2003063800, WO2003042214, WO2003035639, EP1283056, WO200073307, WO2000125210, WO2000073307, US20050119287, US20060281927.

It has now been found that compounds of the present invention are potent antagonists of the A2B adenosine receptor and can therefore be used in the treatment of the diseases mentioned herein above.

Under normal physiological conditions, A1 ARs are quiescent; however, A1 ARs are upregulated in conditions of stress, such as ischaemia, and in conditions of inflammation, typified by the inflammatory airway involvement in human asthmatics. A1 ARs are upregulated in airway epithelium and bronchial smooth muscle in human asthmatics. A1 ARs have been described on a number of different human cell types that are important in the pathophysiology of asthma, including APCs, human airway epithelial and bronchial smooth muscle cells, lymphocytes, mast cells, neutrophils, monocytes, macrophages, fibroblasts and endothelial cells. Activation of $A_1$ ARs on these different cell types induces the release of mediators and cytokines that lead to airway hyperreactivity, inflammation and airway remodelling. Activation of $A_1$ ARs on human asthmatic bronchial tissue produces bronchoconstriction. On human airway epithelial cells, activation of $A_1$ ARs causes an increase in expression of the MUC 2 gene responsible for mucus hypersecretion. Moreover, activation of $A_1$ ARs on a number of different human cells produces pro-inflammatory effects. Taken together, these effects of $A_1$ ARs in humans suggest that the $A_1$ AR antagonists could play potential therapeutic role in inflammatory diseases (C N Wilson, British J. of Pharm., 2008, 155, 475-86 and references cited therein). $A_1$ AR antagonists have been shown to have efficacy in rodent models of asthma and inflammation ((J. Pharmacol. Exp. Ther. 315, 329-336, 2005; Eur. J. Pharmacol., 551, 116-124, 2006). $A_1$ antagonists have also been shown to have therapeutic potential in diseases such as hypertention, congestive heart failure where underlying mechanism is diuresis. There are several compounds in development for these indications (J. Am. Soc. Nephrol. 10, 714-720, 1999; Circulation, 105, 1348-1353, 2002; J. Pharmacol. Exp. Ther. 308, 846-856, 2004). $A_1$ AR antagonists are reported to reduce infarct size. It has been suggested that the ability of $A_1$ AR antagonists to reduce the infarct size is also mediated by antagonism at $A_{2B}$ AR (Circulation, 1996, 9, 94; J. Pharmacol. Exp. Ther., 2000, 292, 3, 929-938)

Activation of A3 ARs induces the release of preformed mediators from basophils and produces bronchoconstriction, eosinophil migration into airways and mucus hypersecretion in animals, A3 AR antagonists have been recommended for development as anti-asthma drugs (Fishman and Bar-Yehuda, 2003; Nadeem and Mustafa, 2006). A3 AR antagonists have also been shown to play therapeutic role in various diseases including cardio-protection (Vasc. Pharmacol., 2005, 42, 271; J. Pharm. Exp. Ther., 2006, 319, 1200) and cancer (WO200010391).

Since several ARs have been implicated in asthma/COPD diseases pathophysiology, a pan AR antagonist may have therapeutic advantage.

It has now been found that some of the compounds of the present invention are non-selective antagonists of ARs and can therefore be used in the treatment of above mentioned diseases.

SUMMARY OF THE INVENTION

In various embodiments, the present invention provides compounds of formula (I), their tautomers, polymorphs, stereoisomers, prodrugs, solvates, pharmaceutically acceptable salts, pharmaceutical compositions containing them and methods of treating conditions and diseases that are mediated by adenosine $A_{2B}$ receptor activity

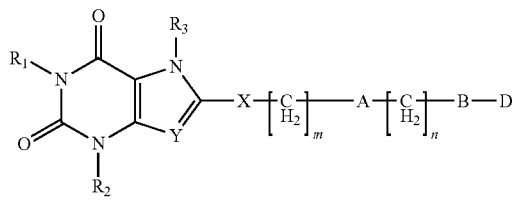

or its tautomers, polymorphs, stereoisomers, prodrugs, solvate or a pharmaceutically acceptable salts thereof, wherein, Y is selected from N or CH;

$R^1$ and $R^2$ are independently selected from a group consisting of hydrogen, alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl;
wherein alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$;
wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $-S(O)_pR^c$;

wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2;

$R^3$ is selected from a group consisting of hydrogen and alkyl;

wherein alkyl is unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, $-SO_3H$, aryl, aryloxy, cycloalkyloxy, heteroaryl, aminocarbonylamino, heteroaryloxy, heterocyclyl, heterocyclyloxy, hydroxyamino, alkoxyamino, $CF_3$, nitro, $S(O)_2NR^aR^a$, $NR^aS(O)_2R^a$ and $-S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $-S(O)_pR^c$;

wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2;

X is either an unsubstituted or substituted arylene or an unsubstituted or substituted heteroarylene;

A is selected from a group consisting of $-O-$, $-C(O)NR^4-$, $-NR^4C(O)-$ and $-(CR^5R^6)_q-$;

wherein q is 1 or 2, and $R^4$ is selected from a group consisting of hydrogen and alkyl, wherein alkyl is either unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, $-SO_3H$, aryl, aryloxy, cycloalkyloxy, heteroaryl, aminocarbonylamino, heteroaryloxy, heterocyclyl, heterocyclyloxy, hydroxyamino, alkoxyamino, $CF_3$, nitro, $-S(O)_2NR^aR^a$, $NR^aS(O)_2R^a$ and $-S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $-S(O)_pR^c$;

wherein each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; $R^c$ is alkyl, aryl, or heteroaryl and p is 0, 1 or 2;

$R^5$ and $R^6$ are independently selected from a group consisting of hydrogen, halogen, alkyl, hydroxyl, alkoxy and $-C(O)R^7$;

wherein alkyl and alkoxy are unsubstituted, or substituted with halogen, hydroxy, hydroxyalkyl, $CF_3$;
or $R^5$ and $R^6$ together represent O, S or cycloalkyl;

$R^7$ is selected from hydroxyl, and unsubstituted or substituted amino;

m and n are independently selected from 0, 1, 2, 3, 4, 5, and 6;

B is selected from a group consisting of unsubstituted or substituted alkynyl, unsubstituted or substituted alkenyl, unsubstituted or substituted cycloalkyl and unsubstituted or substituted heterocyclyl; and D is selected from the group consisting of substituted aryl, substituted heteroaryl, substituted arylalkyl, substituted heteroarylalkyl, substituted cycloalkylalkyl and substituted heterocyclylalkyl, wherein aryl, heteroaryl, arylalkyl, heteroarylalkyl, cycloalkylalkyl and heterocyclylalkyl are substituted with 1, 2, or 3 substituents independently selected from alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, alkoxycarbonylamino, azido, cyano, halogen, hydroxy, hydroxyalkyl, $CF_3$, $OCF_3$, keto, thiocarbonyl, carboxy, alkylcarboxy, carboxyalkyl, $-SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $-C(O)R$, $-S(O)_2NR^aR^a$, $-NR^aS(O)_2R^a$ and $-S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, $-OCF_3$, amino, substituted amino, cyano and $-S(O)_pR^c$;

wherein R is selected from a group consisting of hydrogen, hydroxyl, alkyl, alkoxy, amino, monoalkylamino, dialkylamino and heterocyclyl; each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2.

The present invention also provides compounds of formula I or its tautomers, polymorphs, stereoisomers, prodrugs, solvate or a pharmaceutically acceptable salt thereof that may have other AR antagonism such as $A_1$ $A_{2A}$ and $A_3$ apart from $A_{2B}$ AR antagonism.

The present invention also relates to a process of preparation of compounds of formula-I. These and other features, aspects, and advantages of the present subject matter will become better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

DEFINITIONS

In the structural formulae given herein and throughout the present disclosure, the following terms have the indicated meaning, unless specifically stated otherwise.

The term "optionally substituted" as used herein means that the group in question is either unsubstituted or substituted with one or more of the substituents specified. When the group in question is substituted with more than one substituent, the substituent may be same or different.

The term "alkyl" refers to a monoradical branched or unbranched saturated hydrocarbon chain having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methyl, ethyl, n-propyl, isopropyl, n-butyl, iso-butyl, t-butyl, n-hexyl, n-decyl, tetradecyl, and the like.

The term "alkylene" refers to a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, preferably 1, 2, 3, 4, 5, 6, 7, 8, 9 or 10 carbon atoms, more preferably 1, 2, 3, 4, 5 or 6 carbon atoms. This term is exemplified by groups such as methylene (—CH2-), ethylene (—CH2CH2-), the propylene isomers (e.g., —CH2CH2CH2- and —CH(CH3)CH2-) and the like.

The term "substituted alkyl" or "substituted alkylene" refers to: 1) an alkyl group or alkylene group as defined above, having 1, 2, 3, 4 or 5 substituents, preferably 1, 2 or 3 substituents, selected from the group consisting of alkenyl, alkynyl, alkoxy, cycloalkyl, cycloalkenyl, acyl, acylamino, acyloxy, amino, monoalkylamino, dialkylamino, arylamino, heteroarylamino, aminocarbonyl, alkoxycarbonylamino, azido, cyano, halogen, hydroxy, hydroxyalkyl, keto, thiocarbonyl, carboxy, carboxyalkyl, —SO3H, aryl, aryloxy, heteroaryl, aminocarbonylamino, heteroaryloxy, heterocyclyl, heterocyclyloxy, hydroxyamino, alkoxyamino, nitro, —S(O)2NRaRa, —NRaS(O)2Ra and —S(O)pRb, where each Ra is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where Rb is hydrogen, alkyl, aryl, heteroaryl or heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2;

or 2) an alkyl group or alkylene group as defined above that is interrupted by 1, 2, 3, 4, 5, 6, 7, 8, 9 or 10 atoms independently chosen from oxygen, sulfur and NRd-, where Rd is chosen from hydrogen, alkyl, cycloalkyl, cycloalkenyl, aryl, heteroaryl and heterocyclyl or groups selected from carbonylalkyl, carboxyester, carboxyamide and sulfonyl. All substituents may be optionally further substituted by alkyl, alkoxy, halogen, CF3, amino, substituted amino, cyano, or —S(O)pRc, in which Rc is alkyl, aryl, or heteroaryl and p is 0, 1, or 2;

or 3) an alkyl group or alkylene as defined above that has 1, 2, 3, 4 or 5 substituents as defined above, as well as interrupted by 1, 2, 3, 4, 5, 6, 7, 8, 9 or 10 atoms as defined above.

The term "alkenyl" refers to a monoradical of a branched or unbranched unsaturated acyclic hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 double bond (vinyl), preferably 1 double bond. Preferred alkenyl groups include ethenyl or vinyl (—CH=CH2), 1-propylene or allyl (—CH2CH=CH2), isopropylene (—C(CH3)=CH2), bicyclo [2.2.1]heptene, and the like.

The term "alkenylene" refers to a diradical of a branched or unbranched unsaturated acyclic hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 double bond (vinyl), preferably 1 double bond.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, thiocarbonyl, carboxy, carboxyalkyl, SO3H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$ where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_p$R$^c$, where R$^c$ is alkyl, aryl, or heteroaryl and p is 0, 1 or 2.

The term "alkynyl" refers to a monoradical of a branched or unbranched unsaturated acyclic hydrocarbon, preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 2, 3, 4, 5 or 6 sites of acetylene (triple bond) unsaturation, preferably 1 triple bond. Preferred alkynyl groups include ethynyl, (—C≡CH), propargyl (or prop-1-yn-3-yl, —CH$_2$C≡CH), homopropargyl (or but-1-yn-4-yl, —CH$_2$CH$_2$C≡CH) and the like.

The term "alkynylene" refers to a diradical of a branched or unbranched unsaturated acyclic hydrocarbon group preferably having from 2, 3, 4, 5, 6, 7, 8, 9, 10, 11, 12, 13, 14, 15, 16, 17, 18, 19 or 20 carbon atoms, more preferably 2, 3, 4, 5, 6, 7, 8, 9 or 10 carbon atoms and even more preferably 2, 3, 4, 5 or 6 carbon atoms and having 1, 3, 4, 5 or 6 sites of acetylene (triple bond) unsaturation, preferably 1 triple bond.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_p$R$^c$ where R$^c$ is alkyl, aryl, or heteroaryl and p is 0, 1 or 2. The term "cycloalkyl" refers to carbocyclic groups of from 3 to 20 carbon atoms having a single cyclic ring or multiple condensed rings which may be partially unsaturated. Such cycloalkyl groups include, by way of example, single ring structures such as cyclopropyl, cyclobutyl, cyclopentyl, cyclopentenyl, cyclohexyl, cyclohexenyl, cyclooctyl, and the like, or multiple ring structures such as adamantanyl, bicyclo

[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like. In the above mentioned cycloalkyl ring, one or two methylene groups may be replaced by C(O).

The term "substituted cycloalkyl" refers to cycloalkyl groups having 1, 2, 3, 4 or 5 substituents, and preferably 1, 2, or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, oxo, thiocarbonyl, aryl, aryloxy, heteroaryl, aminosulfonyl, aminocarbonylamino, heteroaryloxy, heterocyclyl, heterocyclyloxy, hydroxyamino, alkoxyamino, nitro, —C(O)R and —S(O)$_p$R$^b$, where R is hydrogen, hydroxyl, alkoxy, alkyl and cyclocalkyl, heterocyclyloxy where R$^b$ is alkyl, aryl, heteroaryl or heterocyclyl and p is 0, 1 or 2. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

"Halo" or "Halogen", alone or in combination with any other term means halogens such as chloro (Cl), fluoro (F), bromo (Br) and iodo (I).

"Haloalkyl" refers to a straight chain or branched chain haloalkyl group with 1 to 6 carbon atoms. The alkyl group may be partly or totally halogenated. Representative examples of haloalkyl groups include but are not limited to fluoromethyl, chloromethyl, bromomethyl, difluoromethyl, dichloromethyl, dibromomethyl, trifluoromethyl, trichloromethyl, 2-fluoroethyl, 2-chloroethyl, 2-bromoethyl, 2,2,2-trifluoroethyl, 3-fluoropropyl, 3-chloropropyl, 3-bromopropyl and the like.

The term "alkoxy" refers to the group R'"—O—, where R'" is optionally substituted alkyl or optionally substituted cycloalkyl, or optionally substituted alkenyl or optionally substituted alkynyl; or optionally substituted cycloalkenyl, where alkyl, alkenyl, alkynyl, cycloalkyl and cycloalkenyl are as defined herein. Representative examples of alkoxy groups include but are not limited to methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "aminocarbonyl" refers to the group —C(O)NR'R' where each R' is independently hydrogen, alkyl, aryl, heteroaryl, heterocyclyl or both R' groups are joined to form a heterocyclic group (e.g. morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "acylamino" refers to the group —NR"C(O)R" where each R" is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "acyloxy" refers to the groups —OC(O)-alkyl, —OC(O)-cycloalkyl, OC(O)-aryl, —OC(O)-heteroaryl, and —OC(O)-heterocyclyl. Unless otherwise constrained by the definition, all substituents may be optionally further substituted by alkyl, carboxy, carboxyalkyl, aminocarbonyl, hydroxy, alkoxy, halogen, CF3, amino, substituted amino, cyano, or —S(O)pRc, where Rc is alkyl, aryl, or heteroaryl and p is 0, 1 or 2.

"Alkoxyalkyl" refers to alkyl groups as defined above wherein at least one of the hydrogen atoms of the alkyl group is replaced by an alkoxy group as defined above. Representative examples of alkoxyalkyl groups include but are not limited to methoxymethyl, methoxyethyl, ethoxymethyl and the like.

"Aryloxyalkyl" refers to the group -alkyl-O-aryl. Representative examples of aryloxyalkyl include but are not limited to phenoxymethyl, naphthyloxymethyl, phenoxyethyl, naphthyloxyethyl and the like.

"Di alkylamino" refers to an amino group, to which two same or different straight chain or branched chain alkyl groups with 1 to 6 carbon atoms are bound. Representative examples of di alkylamino include but are not limited to dimethylamino, diethylamino, methylethylamino, dipropylamino, dibutylamino and the like.

"Cycloalkylalkyl" refers to an alkyl radical as defined above which is substituted by a cycloalkyl radical as defined above. Representative examples of cycloalkylalkyl include but are not limited to cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl and the like.

"Aminoalkyl" refers to an amino group that is attached to (C$_{1-6}$)alkylene as defined herein. Representative examples of aminoalkyl include but are not limited to aminomethyl, aminoethyl, 1-aminopropyl, 2-aminopropyl, and the like. The amino moiety of aminoalkyl may be substituted once or twice with alkyl to provide alkylaminoalkyl and dialkylaminoalkyl respectively. Representative examples of alkylaminoalkyl include but are not limited to methylaminomethyl, methylaminoethyl, methylaminopropyl, ethylaminoethyl and the like. Representative examples of dialkylaminoalkyl include but are not limited to dimethylaminomethyl, dimethylaminoethyl, dimethylaminopropyl, N-methyl-N-ethylaminoethyl and the like.

The term "aryl" refers to an aromatic carbocyclic group of 6 to 20 carbon atoms having a single ring (e.g. phenyl) or multiple rings (e.g. biphenyl), or multiple condensed (fused) rings (e.g. naphthyl or anthranyl). Preferred aryls include phenyl, naphthyl and the like.

The term "arylene" refers to a diradical of an aryl group as defined above. This term is exemplified by groups such as 1,4-phenylene, 1,3-phenylene, 1,2-phenylene, 1,4'-biphenylene, and the like.

Unless otherwise constrained the aryl or arylene groups may optionally be substituted with 1, 2, 3 4 or 5 substituents, preferably 1, 2 or 3 substituents, selected from the group consisting of alkyl, alkoxy, cycloalkyl, cycloalkenyl, acyl, acylamino, acyloxy, amino, aminocarbonyl, alkoxycarbonylamino, azido, cyano, halogen, hydroxy, carboxy, carboxyalkyl, —SO3H, aryl, aryloxy, heteroaryl, aminosulfonyl, aminocarbonylamino, heteroaryloxy, heterocyclyl, heterocyclyloxy, hydroxyamino, alkoxyamino, nitro, —S(O)$_2$NRaRa, —NRaS(O)2Ra and —S(O)pRb where each Ra is independently selected from the group consisting of hydrogen, alkyl, cycloalkyl, cycloalkylalkyl, aryl, arylalkyl, heteroaryl heteroarylalkyl, heterocyclyl and heterocyclylalkyl; where Rb is hydrogen, alkyl, aryl, heterocyclyl or heteroaryl and p is 0, 1 or 2. Unless otherwise constrained by the definition, all substituents may optionally be further substituted by 1, 2 or 3 substituents chosen from alkyl, carboxy, carboxyalkyl, aminocarbonyl, hydroxy, alkoxy, halogen, CF3, amino, substituted amino, cyano, and —S(O)pRc where Rc is hydrogen, alkyl, aryl, or heteroaryl and p is 0, 1 or 2.

The term "arylalkyl" refers to an aryl group covalently linked to an alkylene group, where aryl and alkylene are defined herein.

"Optionally substituted arylalkyl" refers to an optionally substituted aryl group covalently linked to an optionally substituted alkylene group. Such arylalkyl groups are exemplified by benzyl, phenethyl, naphthylmethyl, and the like.

The term "aryloxy" refers to the group aryl-O— wherein the aryl group is as defined above, and includes optionally substituted aryl groups as also defined above.

The term "arylthio" refers to the group —S-aryl, where aryl is as defined herein including optionally substituted aryl groups as also defined above.

The term "substituted amino" refers to the group —NR'R' where each R' is independently selected from the group consisting of hydrogen, alkyl, cycloalkyl, carboxyalkyl, alkoxycarbonyl, aryl, heteroaryl and heterocyclyl. Unless otherwise constrained by the definition, all substituents may optionally be further substituted by 1, 2 or 3 substituents chosen from alkyl, carboxy, carboxyalkyl, aminocarbonyl, hydroxy, alkoxy, halogen, CF3, amino, substituted amino, cyano, and —S(O)pRc, where Rc is alkyl, aryl, or heteroaryl and p is 0, 1 or 2.

The term "carboxyalkyl" refers to the groups -alkylene-C(O)OH.

The term "alkylcarboxyalkyl" refers to the groups -alkylene-C(O)ORd where Rd is alkyl, cycloalkyl, where alkyl, cycloalkyl are as defined herein, and may be optionally further substituted by alkyl, halogen, CF3, amino, substituted amino, cyano, or —S(O)pRc, in which Rc is alkyl, aryl, or heteroaryl and p is 0, 1 or 2.

The term "alkylcarboxy" refers to the group —C(O)O-alkyl, where the alkyl is as defined herein and may be optionally substituted by alkyl, halogen, CF3, amino, substituted amino, cyano, or —S(O)pRc, in which Rc is alkyl, aryl, or heteroaryl and p is 0, 1 or 2.

The term "alkylcarboxyalkyloxy" refers to the group -alkylene-C(O)O-alkylene-O—, where alkylene is as defined herein.

The term "heteroaryl" refers to an aromatic cyclic group having 1, 2, 3, 4, 5, 6, 7, 8, 9, 10, 11, 12, 13, 14, or 15 carbon atoms and 1, 2, 3 or 4 heteroatoms selected from oxygen, nitrogen and sulfur within at least one ring. Such heteroaryl groups can have a single ring (e.g. pyridyl or furyl) or multiple condensed rings (e.g. indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine pyrazine, pyrimidine, pyridazine, indolizine, isoindole, indole, indazole, purine, quinolizine, isoquinoline, quinoline, phthalazine, quinoxaline, quinazoline, cinnoline, pteridine, carbazole, carboline, phenanthridine, acridine, phenanthroline, isothiazole, phenazine, isoxazole, phenoxazine, phenothiazine, furan, thiophene, oxazole, thiazole, triazole, triazine and the like. The term "heteroarylene" refers to a diradical of a heteroaryl group as defined above.

Unless otherwise constrained the heteroaryl or heterarylene groups can be optionally substituted with 1, 2, 3, 4 or 5 substituents, preferably 1, 2 or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, thiocarbonyl, carboxy, carboxyalkyl, —SO$_3$H, aryl, aryloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and S(O)$_p$R$^b$, where each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; where R$^b$ is hydrogen, alkyl, aryl, heterocyclyl or heteroaryl, and p is 0, 1 or 2. Unless otherwise constrained by the definition, all substituents may optionally be further substituted by 1-3 substituents chosen from alkyl, carboxy, carboxyalkyl, aminocarbonyl, hydroxy, alkoxy, halogen, CF3, amino, substituted amino, cyano, and —S(O)nRc, where Rc is alkyl, aryl, or heteroaryl and n is 0, 1 or 2.

The term "heteroarylalkyl" refers to a heteroaryl group covalently linked to an alkylene group, where heteroaryl and alkylene are defined herein.

"Optionally substituted heteroarylalkyl" refers to an optionally substituted heteroaryl group covalently linked to an optionally substituted alkylene group. Such heteroarylalkyl groups are exemplified by 3-pyridylmethyl, quinolin-8-ylethyl, 4-methoxythiazol-2-ylpropyl, and the like.

The term "heterocyclyl" refers to a saturated or partially unsaturated group having a single ring or multiple condensed rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholinyl, piperidinyl, piperazinyl, dihydropyridinyl, tetrahydroquinolinyl and the like. In the above mentioned heterocyclyl ring, one or two methylene groups may independently be replaced by one of C(O), S(O) or SO2. Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, oxo, —C(O)R where R is hydrogen, hydroxyl, alkoxy, alkyl and cyclocalkyl, thiocarbonyl, carboxy, carboxyalkyl, aryl, aryloxy, heteroaryl, aminosulfonyl, aminocarbonylamino, heteroaryloxy, heterocyclyl, heterocyclyloxy, hydroxyamino, alkoxyamino, nitro, and —S(O)pRb, where Rb is hydrogen, alkyl, aryl, heterocyclyl or heteroaryl and p is 0, 1 or 2. Unless otherwise constrained by the definition, all substituents may optionally be further substituted by 1-3 substituents chosen from alkyl, carboxy, carboxyalkyl, aminocarbonyl, hydroxy, alkoxy, halogen, CF3, amino, substituted amino, cyano, and —S(O)Rc, where Rc is alkyl, aryl, or heteroaryl and n is 0, 1 or 2.

The term "heterocyclylalkyl" refers to a heterocyclyl group covalently linked to an alkylene group, where heterocyclyl and alkylene are defined herein.

"Optionally substituted heterocyclylalkyl" refers to an optionally substituted heterocyclyl group covalently linked to an optionally substituted alkylene group.

The term "heteroaryloxy" refers to the group heteroaryl-O—.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O).

"Substituted sulfoxide" refers to a group —S(O)R, in which R is substituted alkyl, substituted aryl, or substituted heteroaryl, as defined herein.

The term "sulfone" refers to a group —S(O)$_2$.

The term "substituted sulfone" refers to a group —S(O)2R, in which R is alkyl, aryl, or heteroaryl.

The compounds of the present invention may have the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The compounds described herein may contain one or more chiral centers and/or double bonds and therefore, may exist as stereoisomers, such as double-bond isomers (i.e., geometric isomers), regioisomers, enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the person skilled in the art. The compounds may also exist in several tautomeric forms including the enol form, the keto form and mixtures thereof. Accordingly, the chemical structures depicted herein encompass all possible tautomeric forms of the illustrated or identified compounds.

Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

"Prodrug" refers to a derivative of a drug molecule as, for example, esters, carbonates, carbamates, ureas, amides or phosphates that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be supplied exogenously.

"Pharmaceutically acceptable salt" embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

DETAILED DESCRIPTION OF THE INVENTION

The present invention provides compounds of formula I, or its tautomers, polymorphs, stereoisomers, prodrugs, solvate or a pharmaceutically acceptable salts thereof, pharmaceutical compositions containing them and methods of treating conditions and diseases that are mediated by adenosine $A_{2B}$ receptor activity,

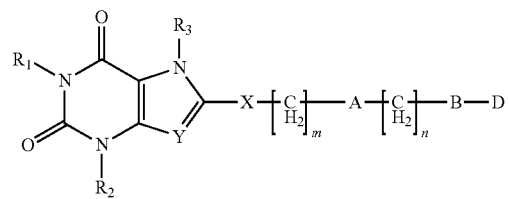

or its tautomers, polymorphs, stereoisomers, prodrugs, solvate or a pharmaceutically acceptable salts thereof, wherein, Y is selected from N or CH;

$R^1$ and $R^2$ are independently selected from a group consisting of hydrogen, alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl;

wherein alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, —SO$_3$H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)$_2$NR$^a$R$^a$, —NR$^a$S(O)$_2$R$^a$ and —S(O)$_p$R$^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $—S(O)_pR^c$;

wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2;

$R^3$ is selected from a group consisting of hydrogen and alkyl;

wherein alkyl is unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy, $—SO_3H$, aryl, aryloxy, cycloalkyloxy, heteroaryl, aminocarbonylamino, heteroaryloxy, heterocyclyl, heterocyclyloxy, hydroxyamino, alkoxyamino, $CF_3$, nitro, $S(O)_2NR^aR^a$, $NR^aS(O)_2R^a$ and $—S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $—S(O)_pR^c$;

wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2;

X is either an unsubstituted or substituted arylene or an unsubstituted or substituted heteroarylene;

A is selected from a group consisting of $—O—$, $—C(O)NR^4—$, $—NR^4C(O)—$ and $—(CR^5R^6)_q—$;

wherein q is 1 or 2, and $R^4$ is selected from a group consisting of hydrogen and alkyl, wherein alkyl is either unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, $—SO_3H$, aryl, aryloxy, cycloalkyloxy, heteroaryl, aminocarbonylamino, heteroaryloxy, heterocyclyl, heterocyclyloxy, hydroxyamino, alkoxyamino, $CF_3$, nitro, $—S(O)_2NR^aR^a$, $NR^aS(O)_2R^a$ and $—S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, amino, substituted amino, cyano and $—S(O)_pR^c$;

wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; $R^c$ is alkyl, aryl, or heteroaryl and p is 0, 1 or 2;

$R^5$ and $R^6$ are independently selected from a group consisting of hydrogen, halogen, alkyl, hydroxyl, alkoxy and $—C(O)R^7$;

wherein alkyl and alkoxy are unsubstituted, or substituted with halogen, hydroxy, hydroxyalkyl, $CF_3$;

or $R^5$ and $R^6$ together represent O, S or cycloalkyl;

$R^7$ is selected from hydroxyl, and unsubstituted or substituted amino;

m and n are independently selected from 0, 1, 2, 3, 4, 5, and 6;

B is selected from a group consisting of unsubstituted or substituted alkynyl, unsubstituted or substituted alkenyl, unsubstituted or substituted cycloalkyl and unsubstituted or substituted heterocyclyl; and D is selected from the group consisting of substituted aryl, substituted heteroaryl, substituted arylalkyl, substituted heteroarylalkyl, substituted cycloalkylalkyl and substituted heterocyclylalkyl, wherein aryl, heteroaryl, arylalkyl, heteroarylalkyl, cycloalkylalkyl and heterocyclylalkyl are substituted with 1, 2, or 3 substituents independently selected from alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, alkoxycarbonylamino, azido, cyano, halogen, hydroxy, hydroxyalkyl, $CF_3$, $OCF_3$, keto, thiocarbonyl, carboxy, alkylcarboxy, carboxyalkyl, $—SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $—C(O)R$, $—S(O)_2NR^aR^a$, $—NR^aS(O)_2R^a$ and $—S(O)_pR^b$;

wherein each substituent is unsubstituted or substituted with 1, 2, or 3 substituents independently selected from alkyl, carboxy, carboxyalkyl, aminocarbonyl, hydroxy, alkoxy, halogen, $CF_3$, $—OCF_3$, amino, substituted amino, cyano and $—S(O)_pR^c$;

wherein R is selected from a group consisting of hydrogen, hydroxyl, alkyl, alkoxy, amino, monoalkylamino, dialkylamino and heterocyclyl; each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2.

In one embodiment, compounds of the invention comprise compounds of formula I excluding compounds:

wherein X is a heteroarylene, A is $—(CR^5R^6)_q—$, B is alkynylene or alkenylene, D is phenyl, pyridyl, pyrimidinyl, and $R^5$ and $R^6$ together is O.

As described herein above, the present invention provides novel fused pyrimidine compounds of formula (I), their tautomers, polymorphs, stereoisomers, prodrugs, solvates, pharmaceutically acceptable salts, pharmaceutical compositions containing them, methods for preparing said compounds and methods for the treatment, prevention or suppression of diseases and disorders that may be susceptible to improvement by antagonism of the adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases. According to an embodiment of the present invention, Y is N; $R^1$ and $R^2$ are independently selected from a group consisting of hydrogen, alkyl, alkenyl and alkynyl;
  wherein alkyl, alkenyl and alkynyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, —$S(O)_2NR^aR^a$, —$NR^aS(O)_2R^a$ and —$S(O)_pR^b$;
    wherein each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; and p is 0, 1 or 2;
$R^3$ is selected from a group consisting of hydrogen and alkyl;
  wherein alkyl is unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, keto, thiocarbonyl, carboxy, alkylcarboxy, carboxyalkyl, carboxyalkyloxy, alkylcarboxyalkyloxy —$SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $S(O)_2NR^aR^a$, —$NR^aS(O)_2R^a$ and —$S(O)_pR^b$;
    wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; and p is 0, 1 or 2;
X is either an unsubstituted or substituted arylene or an unsubstituted or substituted heteroarylene;
A is selected from a group consisting of —O—, —C(O)$NR^4$—, —$NR^4C(O)$— and —$(CR^5R^6)_q$—;
  wherein q is 1 or 2, and $R^4$ is selected from a group consisting of hydrogen and alkyl,
    wherein alkyl is either unsubstituted or substituted with halogen, $CF_3$ and aryl;
$R^5$ and $R^6$ are independently selected from a group consisting of hydrogen, halogen, alkyl and hydroxyl;
  or
$R^5$ and $R^6$ together represent O or cycloalkyl;
m and n are independently selected from 0, 1 and 2;
B is selected from a group consisting of unsubstituted or substituted alkynyl, unsubstituted or substituted cycloalkyl and unsubstituted or substituted heterocyclyl; and
D is selected from the group consisting of substituted aryl, substituted heteroaryl, substituted arylalkyl, substituted heteroarylalkyl, substituted cycloalkylalkyl and substituted heterocyclylalkyl,
  wherein aryl, heteroaryl, arylalkyl, heteroarylalkyl, cycloalkylalkyl and heterocyclylalkyl are substituted with 1, 2, or 3 substituents independently selected from alkyl, alkoxy, acyl, acylamino, acyloxy, amino, monoalkylamino, dialkylamino, arylamino, cycloalkylamino, cyano, halogen, hydroxy, hydroxyalkyl, $CF_3$, $OCF_3$, carboxy, alkylcarboxy, carboxyalkyl, —$SO_3H$, aryl, heteroaryl, heterocyclyl, —C(O)R, —$S(O)_2NR^aR^a$, —$NR^aS(O)_2R^a$ and —$S(O)_pR^b$;
    wherein each substituent is unsubstituted or substituted with 1, 2, or 3 substituents independently selected from alkyl, carboxy, carboxyalkyl, aminocarbonyl, hydroxy, alkoxy, halogen, $CF_3$, —$OCF_3$, amino, substituted amino, cyano and —$S(O)_pR^c$;
      wherein R is selected from a group consisting of amino, monoalkylamino, dialkylamino and heterocyclyl; each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2.

According to an embodiment of the present invention, wherein Y is N; $R^1$ and $R^2$ are independently selected from a group consisting of hydrogen and alkyl;
  wherein alkyl is unsubstituted or substituted with alkenyl, alkoxy, acylamino, amino, monoalkylamino, dialkylamino, halogen, hydroxy, hydroxyalkyl, carboxy, alkylcarboxy, carboxyalkyl, —$SO_3H$ and aryl;
$R^3$ is selected from a group consisting of hydrogen and alkyl;
X is either an unsubstituted or substituted arylene or an unsubstituted or substituted heteroarylene;
A is selected from a group consisting of —O—, —C(O)$NR^4$—, —$NR^4C(O)$— and —$(CR^5R^6)_q$—;
  wherein q is 1 and $R^4$ is selected from a group consisting of hydrogen and alkyl,
    wherein alkyl is either unsubstituted or substituted with halogen, $CF_3$ and aryl;
$R^5$ and $R^6$ are independently selected from a group consisting of hydrogen, halogen, alkyl and hydroxyl;
  or
$R^5$ and $R^6$ together represent O or cycloalkyl;
m and n are independently selected from 0, 1 and 2;
B is selected from a group consisting of unsubstituted or substituted alkynyl, unsubstituted or substituted cycloalkyl and unsubstituted or substituted heterocyclyl; and
D is selected from the group consisting of substituted aryl, substituted heteroaryl, substituted arylalkyl, substituted heteroarylalkyl, substituted cycloalkylalkyl and substituted heterocyclylalkyl,
  wherein aryl, heteroaryl, arylalkyl, heteroarylalkyl, cycloalkylalkyl and heterocyclylalkyl are substituted with 1, 2, or 3 substituents independently selected from alkyl, alkoxy, acyl, acylamino, acyloxy, amino, monoalkylamino, dialkylamino, arylamino, cycloalkylamino, cyano, halogen, hydroxy, hydroxyalkyl, $CF_3$, $OCF_3$, carboxy, alkylcarboxy, carboxyalkyl, —$SO_3H$, aryl, heteroaryl, heterocyclyl, —C(O)R, —$S(O)_2NR^aR^a$, —$NR^aS(O)_2R^a$ and —$S(O)_pR^b$;
    wherein each substituent is unsubstituted or substituted with 1, 2, or 3 substituents independently selected from alkyl, carboxy, carboxyalkyl, aminocarbonyl, hydroxy, alkoxy, halogen, $CF_3$, —$OCF_3$, amino, substituted amino, cyano and —$S(O)_pR^c$;
      wherein R is selected from a group consisting of amino, monoalkylamino, dialkylamino and heterocyclyl; each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl;

$R^b$ is hydrogen, alkyl, aryl, heteroaryl or heterocyclyl; $R^c$ is alkyl, aryl, or heteroaryl; and p is 0, 1 or 2.

According to an embodiment of the present invention, X is pyrazolyl, isoxazolyl, phenyl, pyridyl, oxazolyl or pyrimidyl.

According to another embodiment of the present invention, B is an alkynylene.

In another embodiment of the present invention, B is heterocyclyl or cycloalkyl.

Particular embodiments of the present invention are
1,3-Dipropyl-8-[1-(3-p-tolyl-prop-2ynyl)-1H-pyrazol-4-yl]-3,7-dihydro-purine-2,6-dione,
8-{1-[3-(3-Fluoro-phenyl)-prop-2-ynyl]-1H-pyrazol-4-yl}-1,3-dimethyl-3,7-dihydro-purine-2,6-dione,
8-{1-[3-(4-Fluoro-phenyl)-prop-2-ynyl]-1H-pyrazol-4-yl}-1,3-dimethyl-3,7-dihydro-purine-2,6-dione,
8-{1-[3-(4-Fluoro-phenyl)-prop-2-ynyl]-1H-pyrazol-4-yl}-1,3-dipropyl-3,7-dihydro-purine-2,6-dione,
8-{1-[3-(4-Methoxy-phenyl)-prop-2-ynyl]-1H-pyrazol-4-yl}-1,3-dimethyl-3,7-dihydro-purine-2,6-dione,
8-{1-[3-(4-Methoxy-phenyl)-prop-2-ynyl]-1H-pyrazol-4-yl}-1,3-dipropyl-3,7-dihydro-purine-2,6-dione,
8-{1-[3-(2,4-Difluoro-phenyl)-prop-2-ynyl]-1H-pyrazol-4-yl}-1,3-dipropyl-3,7-dihydro-purine-2,6-dione,
8-{1-[3-(3-trifluoromethoxy-phenyl)-prop-2-ynyl]-1H-pyrazol-4-yl}-1,3-dipropyl-3,7-dihydro-purine-2,6-dione,
8-{1-[3-(3-trifluoromethyl-phenyl)-prop-2-ynyl]-1H-pyrazol-4-yl}-1,3-dipropyl-3,7-dihydro-purine-2,6-dione,
8-{1-[3-(4-trifluoromethyl-phenyl)-prop-2-ynyl]-1H-pyrazol-4-yl}-1,3-dimethyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester,
3-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester,
3-{3-[4-(2,6-Dioxo-1,3-dipropyl-2,3,6,7-tetrahydro-1H-purin-8-yl)-pyrazol-1-yl]-prop-1-ynyl}-benzonitrile,
8-{1-[3-(3-Methoxy-phenyl)-prop-2-ynyl]-1H-pyrazol-4-yl}-1,3-dipropyl-3,7-dihydro-purine-2,6-dione,
2-{3-[4-(2,6-Dioxo-1,3-dipropyl-2,3,6,7-tetrahydro-1H-purin-8-yl)-pyrazol-1-yl]-prop-1-ynyl}-benzoic acid methyl ester,
8-{1-[4-(4-Fluoro-phenyl)-but-3-ynyl]-1H-pyrazol-4-yl}-1,3-dipropyl-3,7-dihydro-purine-2,6-dione,
8-{1-[4-(3-Fluoro-phenyl)-but-3-ynyl]-1H-pyrazol-4-yl}-1,3-dipropyl-3,7-dihydro-purine-2,6-dione,
1,3-Dipropyl-8-[1-(4-p-tolyl-but-3-ynyl)-1H-pyrazol-4-yl]-3,7-dihydro-purine-2,6-dione,
1,3-Dipropyl-8-{1-[4-(3-trifluoromethyl-phenyl)-but-3-ynyl]-1H-pyrazol-4-yl}-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-benzoic acid,
1,3-Dipropyl-8-{1-[3-(2-trifluoromethyl-phenyl)-prop-2-ynyl]-1H-pyrazol-4-yl}-3,7-dihydro-purine-2,6-dione,
1,3-Dipropyl-8-[1-(3-m-tolyl-prop-2-ynyl)-1H-pyrazol-4-yl]-3,7-dihydro-purine-2,6-dione,
3-Ethyl-1-propyl-8-{1-[3-(3-trifluoromethoxy-phenyl)-prop-2-ynyl]-1H-pyrazol-4-yl}-3,7-dihydro-purine-2,6-dione,
3-Ethyl-1-propyl-8-{1-[3-(4-trifluoromethyl-phenyl)-prop-2-ynyl]-1H-pyrazol-4-yl}-3,7-dihydro-purine-2,6-dione,
3-Ethyl-1-propyl-8-[1-(3-p-tolyl-prop-2-ynyl)-1H-pyrazol-4-yl]-3,7-dihydro-purine-2,6-dione,
3-Ethyl-8-{1-[3-(3-fluoro-phenyl)-prop-2-ynyl]-1H-pyrazol-4-yl}-1-propyl-3,7-dihydro-purine-2,6-dione,
1,3-Dipropyl-8-{1-[3-(4-trifluoromethyl-phenyl)-prop-2-ynyl]-1H-pyrazol-4-yl}-3,7-dihydro-purine-2,6-dione,
1,3-Dipropyl-8-{1-[3-(4-trifluoromethoxy-phenyl)-prop-2-ynyl]-1H-pyrazol-4-yl}-3,7-dihydro-purine-2,6-dione,
3-Ethyl-8-{1-[3-(4-fluoro-phenyl)-prop-2-ynyl]-1H-pyrazol-4-yl}-1-propyl-3,7-dihydro-purine-2,6-dione,
3-{3-[4-(3-Ethyl-2,6-dioxo-1-propyl-2,3,6,7-tetrahydro-1H-purin-8-yl)-pyrazol-1-yl]-prop-1-ynyl}-benzoic acid,
3-Ethyl-1-propyl-8-[1-(3-m-tolyl-prop-2-ynyl)-1H-pyrazol-4-yl]-3,7-dihydro-purine-2,6-dione,
3-Ethyl-8-{1-[3-(4-methoxy-phenyl)-prop-2-ynyl]-1H-pyrazol-4-yl}-1-propyl-3,7-dihydro-purine-2,6-dione,
3-Ethyl-1-propyl-8-{1-[3-(4-trifluoromethoxy-phenyl)-prop-2-ynyl]-1H-pyrazol-4-yl}-3,7-dihydro-purine-2,6-dione,
3-Ethyl-8-{1-[3-(3-methoxy-phenyl)-prop-2-ynyl]-1H-pyrazol-4-yl}-1-propyl-3,7-dihydro-purine-2,6-dione,
4-{3-[4-(3-Ethyl-2,6-dioxo-1-propyl-2,3,6,7-tetrahydro-1H-purin-8-yl)-pyrazol-1-yl]-prop-1-ynyl}-benzoic acid,
4-{3-[4-(2,6-Dioxo-1,3-dipropyl-2,3,6,7-tetrahydro-1H-purin-8-yl)-pyrazol-1-yl]-prop-1-ynyl}-benzonitrile,
(3-{3-[4-(2,6-Dioxo-1,3-dipropyl-2,3,6,7-tetrahydro-1H-purin-8-yl)-pyrazol-1-yl]-prop-1-ynyl}-phenoxy)-acetic acid,
8-{1-[3-(3-tert-Butyl-phenyl)-prop-2-ynyl]-1H-pyrazol-4-yl}-1,3-dipropyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzoic acid,
(3-{3-[4-(2,6-Dioxo-1,3-dipropyl-2,3,6,7-tetrahydro-1H-purin-8-yl)-pyrazol-1-yl]-prop-1-ynyl}-phenyl)-acetic acid,
(4-{3-[4-(2,6-Dioxo-1,3-dipropyl-2,3,6,7-tetrahydro-1H-purin-8-yl)-pyrazol-1-yl]-prop-1-ynyl}-phenyl)-acetic acid,
8-{1-[3-(3-Fluoro-phenyl)-prop-2-ynyl]-1H-pyrazol-4-yl}-1,3-dipropyl-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-N-isopropyl-benzamide,
1,3-Dipropyl-8-(1-{3-[3-(pyrrolidine-1-carbonyl)-phenyl]-prop-2-ynyl}-1H-pyrazol-4-yl)-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-4-methyl-benzoic acid,
8-{1-[3-(3-Chloro-phenyl)-prop-2-ynyl]-1H-pyrazol-4-yl}-1,3-dipropyl-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-4-methoxy-benzoic acid,
5-{3-[4-(2,6-Dioxo-1,3-dipropyl-2,3,6,7-tetrahydro-1H-purin-8-yl)-pyrazol-1-yl]-prop-1-ynyl}-pyridine-2-carboxylic acid methyl ester,
1,3-Dipropyl-8-{3-[3-(3-trifluoromethyl-phenyl)-prop-2-ynyloxy]-isoxazol-5-yl}-3,7-dihydro-purine-2,6-dione,
8-{3-[3-(2,4-Difluoro-phenyl)-prop-2-ynyloxy]-isoxazol-5-yl}-1,3-dipropyl-3,7-dihydro-purine-2,6-dione,
8-{3-[3-(4-Fluoro-phenyl)-prop-2-ynyloxy]-isoxazol-5-yl}-1,3-dipropyl-3,7-dihydro-purine-2,6-dione,
8-{3-[3-(3-Fluoro-phenyl)-prop-2-ynyloxy]-isoxazol-5-yl}-1,3-dipropyl-3,7-dihydro-purine-2,6-dione,
1,3-Dipropyl-8-{3-[3-(4-trifluoromethyl-phenyl)-prop-2-ynyloxy]-isoxazol-5-yl}-3,7-dihydro-purine-2,6-dione,
1,3-Dipropyl-8-[3-(3-p-tolyl-prop-2-ynyloxy)-isoxazol-5-yl]-3,7-dihydro-purine-2,6-dione,
8-{3-[3-(3-tert-Butyl-phenyl)-prop-2-ynyloxy]-isoxazol-5-yl}-1,3-dipropyl-3,7-dihydro-purine-2,6-dione, 1,3-Dipropyl-8-{3-[3-(3-trifluoromethoxy-phenyl)-prop-2-ynyloxy]-isoxazol-5-yl}-3,7-dihydro-purine-2,6-dione,
8-{1-Methyl-5-[3-(3-trifluoromethyl-phenyl)-prop-2-ynyloxy]-1H-pyrazol-3-yl}-1,3-dipropyl-3,7-dihydro-purine-2,6-dione,
8-{1-Methyl-5-[3-(4-trifluoromethoxy-phenyl)-prop-2-ynyloxy]-1H-pyrazol-3-yl}-1,3-dipropyl-3,7-dihydro-purine-2,6-dione,
8-{5-[3-(3-Methoxy-phenyl)-prop-2-ynyloxy]-1-methyl-1H-pyrazol-3-yl}-1,3-dipropyl-3,7-dihydro-purine-2,6-dione,
1,3-Dipropyl-8-{4-[3-(4-trifluoromethoxy-phenyl)-prop-2-ynyloxy]-phenyl}-3,7-dihydro-purine-2,6-dione,
1,3-Dipropyl-8-[4-(3-p-tolyl-prop-2-ynyloxy)-phenyl]-3,7-dihydro-purine-2,6-dione,
8-{4-[3-(3-Fluoro-phenyl)-prop-2-ynyloxy]-phenyl}-1,3-dipropyl-3,7-dihydro-purine-2,6-dione,
3-{3-[4-(2,6-Dioxo-1,3-dipropyl-2,3,6,7-tetrahydro-1H-purin-8-yl)-phenoxy]-prop-1-ynyl}-benzoic acid ethyl ester,
3-{3-[4-(2,6-Dioxo-1,3-dipropyl-2,3,6,7-tetrahydro-1H-purin-8-yl)-phenoxy]-prop-1-ynyl}-benzoic acid,
1,3-Dipropyl-8-{4-[3-(4-trifluoromethyl-phenyl)-prop-2-ynyloxy]-phenyl}-3,7-dihydro-purine-2,6-dione,
8-{4-[3-(4-Fluoro-phenyl)-prop-2-ynyloxy]-phenyl}-1,3-dipropyl-3,7-dihydro-purine-2,6-dione,
1,3-Dipropyl-8-{4-[3-(3-trifluoromethoxy-phenyl)-prop-2-ynyloxy]-phenyl}-3,7-dihydro-purine-2,6-dione,
8-{4-[3-(3-Methoxy-phenyl)-prop-2-ynyloxy]-phenyl}-1,3-dipropyl-3,7-dihydro-purine-2,6-dione,
8-{6-[3-(4-Fluoro-phenyl)-prop-2-ynyloxy]-pyridin-3-yl}-1,3-dipropyl-3,7-dihydro-purine-2,6-dione,
1,3-Dipropyl-8-{3-[3-(3-trifluoromethyl-phenyl)-prop-2-ynyloxy]-phenyl}-3,7-dihydro-purine-2,6-dione,
1,3-Dipropyl-8-{3-[3-(3-trifluoromethoxy-phenyl)-prop-2-ynyloxy]-phenyl}-3,7-dihydro-purine-2,6-dione,
8-{3-[3-(3-Fluoro-phenyl)-prop-2-ynyloxy]-phenyl}-1,3-dipropyl-3,7-dihydro-purine-2,6-dione,
1,3-Dipropyl-8-{3-[3-(4-trifluoromethyl-phenyl)-prop-2-ynyloxy]-phenyl}-3,7-dihydro-purine-2,6-dione,
1,3-Dipropyl-8-[3-(3-p-tolyl-prop-2-ynyloxy)-phenyl]-3,7-dihydro-purine-2,6-dione,
8-{1-[4-(4-Methyl-piperazin-1-yl)-but-2-ynyl]-1H-pyrazol-4-yl}-1,3-dipropyl-3,7-dihydro-purine-2,6-dione,
1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid ethyl ester,
1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid,
8-(1-{4-[4-(4-Chloro-phenyl)-4-hydroxy-piperidin-1-yl]-but-2-ynyl}-1H-pyrazol-4-yl)-1,3-dipropyl-3,7-dihydro-purine-2,6-dione,
1,3-Dipropyl-8-(1-{4-[4-(3-trifluoromethyl-phenyl)-piperazin-1-yl]-but-2-ynyl}-1H-pyrazol-4-yl)-3,7-dihydro-purine-2,6-dione,
1,3-Dimethyl-8-{1-[4-(4-methyl-piperazin-1-yl)-but-2-ynyl]-1H-pyrazol-4-yl}-3,7-dihydro-purine-2,6-dione,
1-Propyl-8-[1-(3-p-tolyl-prop-2-ynyl)-1H-pyrazol-4-yl]-3,7-dihydro-purine-2,6-dione,
1-Propyl-8-{1-[3-(3-trifluoromethyl-phenyl)-prop-2-ynyl]-1H-pyrazol-4-yl}-3,7-dihydro-purine-2,6-dione,
1-Propyl-8-{1-[3-(3-trifluoromethoxy-phenyl)-prop-2-ynyl]-1H-pyrazol-4-yl}-3,7-dihydro-purine-2,6-dione,
8-{1-[3-(4-Fluoro-phenyl)-prop-2-ynyl]-1H-pyrazol-4-yl}-1-propyl-3,7-dihydro-purine-2,6-dione,
8-{1-[3-(3-Fluoro-phenyl)-prop-2-ynyl]-1H-pyrazol-4-yl}-1-propyl-3,7-dihydro-purine-2,6-dione,
1-Propyl-8-{1-[3-(4-trifluoromethyl-phenyl)-prop-2-ynyl]-1H-pyrazol-4-yl}-3,7-dihydro-purine-2,6-dione,
1-Propyl-8-{1-[3-(4-trifluoromethoxy-phenyl)-prop-2-ynyl]-1H-pyrazol-4-yl}-3,7-dihydro-purine-2,6-dione,
3-{3-[4-(2,6-Dioxo-1-propyl-2,3,6,7-tetrahydro-1H-purin-8-yl)-pyrazol-1-yl]-prop-1-ynyl}-benzoic acid,
8-{1-[3-(4-Fluoro-phenyl)-prop-2-ynyl]-1H-pyrazol-4-yl}-7-methyl-1,3-dipropyl-3,7-dihydro-purine-2,6-dione,
7-Methyl-1,3-dipropyl-8-{1-[3-(3-trifluoromethoxy-phenyl)-prop-2-ynyl]-1H-pyrazol-4-yl}-3,7-dihydro-purine-2,6-dione,
7-Methyl-1,3-dipropyl-8-[1-(3-p-tolyl-prop-2-ynyl)-1H-pyrazol-4-yl]-3,7-dihydro-purine-2,6-dione,
7-Methyl-8-{1-[4-(4-methyl-piperazin-1-yl)-but-2-ynyl]-1H-pyrazol-4-yl}-1,3-dipropyl-3,7-dihydro-purine-2,6-dione,
8-{1-[3-(3-Fluoro-phenyl)-prop-2-ynyl]-1H-pyrazol-4-yl}-methyl-1,3-dipropyl-3,7-dihydro-purine-2,6-dione,
8-{1-[3-(3-Methoxy-phenyl)-prop-2-ynyl]-1H-pyrazol-4-yl}-7-methyl-1,3-dipropyl-3,7-dihydro-purine-2,6-dione,
8-{1-[3-(3-tert-Butyl-phenyl)-prop-2-ynyl]-1H-pyrazol-4-yl}-7-methyl-1,3-dipropyl-3,7-dihydro-purine-2,6-dione,
(3-{3-[4-(7-Methyl-2,6-dioxo-1,3-dipropyl-2,3,6,7-tetrahydro-1H-purin-8-yl)-pyrazol-1-yl]-prop-1-ynyl}-phenoxy)-acetic acid,
8-{1-[3-(3-Hydroxymethyl-phenyl)-prop-2-ynyl]-1H-pyrazol-4-yl}-1,3-dipropyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzenesulfonamide,
3-{3-[4-(2,6-Dioxo-1,3-dipropyl-2,3,6,7-tetrahydro-1H-purin-8-yl)-pyrazol-1-yl]-prop-1-ynyl}-benzamide,
4-(3-Trifluoromethyl-phenyl)-but-3-ynoic acid [5-(2,6-dioxo-1,3-dipropyl-2,3,6,7-tetrahydro-1H-purin-8-yl)-2-methyl-2H-pyrazol-3-yl]-amide,
4-(3-Fluoro-phenyl)-but-3-ynoic acid [5-(2,6-dioxo-1,3-dipropyl-2,3,6,7-tetrahydro-1H-purin-8-yl)-2-methyl-2H-pyrazol-3-yl]-amide,
4-(2,6-Dioxo-1,3-dipropyl-2,3,6,7-tetrahydro-1H-purin-8-yl)-N-[3-(3-trifluoromethyl-phenyl)-prop-2-ynyl]-benzamide,
8-{1-[4-(3-Fluoro-phenyl)-2-hydroxy-but-3-ynyl]-1H-pyrazol-4-yl}-1,3-dipropyl-3,7-dihydro-purine-2,6-dione,
2-[4-(2,6-Dioxo-1,3-dipropyl-2,3,6,7-tetrahydro-1H-purin-8-yl)-pyrazol-1-yl]-4-(3-fluoro-phenyl)-but-3-ynoic acid,
2-[4-(2,6-Dioxo-1,3-dipropyl-2,3,6,7-tetrahydro-1H-purin-8-yl)-pyrazol-1-yl]-4-(3-fluoro-phenyl)-but-3-ynoic acid amide,
8-{1-[4-(4-Fluoro-phenyl)-4-hydroxy-but-2-ynyl]-1H-pyrazol-4-yl}-1,3-dipropyl-3,7-dihydro-purine-2,6-dione,
8-{1-[4-(4-Fluoro-phenyl)-but-2-ynyl]-1H-pyrazol-4-yl}-1,3-dipropyl-3,7-dihydro-purine-2,6-dione,
8-{1-[3-(4-Fluoro-phenyl)-1,1-dimethyl-prop-2-ynyl]-1H-pyrazol-4-yl}-1,3-dipropyl-3,7-dihydro-purine-2,6-dione,
1,3-Dipropyl-8-{1-[(E)-3-(3-trifluoromethyl-phenyl)-allyl]-1H-pyrazol-4-yl}-3,7-dihydro-purine-2,6-dione,
1,3-Dipropyl-8-{1-[(Z)-3-(3-trifluoromethyl-phenyl)-allyl]-1H-pyrazol-4-yl}-3,7-dihydro-purine-2,6-dione,
1,3-dimethyl-6-[1-[3-(3-fluorophenyl)prop-2-ynyl]pyrazol-4-yl]-5H-pyrrolo[3,2-d]pyrimidine-2,4-dione,
8-[1-[3-(3-fluorophenyl)prop-2-ynyl]pyrazol-4-yl]-1,3-dipropyl-7H-purine-2,6-dione,
8-[1-[4-(3-fluorophenyl)-2-hydroxy-but-3-ynyl]pyrazol-4-yl]-1,3-dipropyl-7H-purine-2,6-dione,
8-[1-[3-(4-fluorophenyl)-1,1-dimethyl-prop-2-ynyl]pyrazol-4-yl]-1,3-dipropyl-7H-purine-2,6-dione, 1,3-Dipropyl-8-{1-[2-(3-trifluoromethyl-phenyl)-cyclopropylmethyl]-1H-pyrazol-4-yl}-3,7-dihydro-purine-2,6-dione,
8-{1-[2-(3-Fluoro-phenyl)-cyclopropylmethyl]-1H-pyrazol-4-yl}-1,3-dipropyl-3,7-dihydro-purine-2,6-dione,
8-{1-[2-(4-Fluoro-phenyl)-cyclopropylmethyl]-1H-pyrazol-4-yl}-1,3-dipropyl-3,7-dihydro-purine-2,6-dione,
1,3-Dipropyl-8-{1-[2-(4-trifluoromethyl-phenyl)-cyclopropylmethyl]-1H-pyrazol-4-yl}-3,7-dihydro-purine-2,6-dione,
8-{1-[1-(4-Isopropyl-phenyl)-5-oxo-pyrrolidin-3-ylmethyl]-1H-pyrazol-4-yl}-1,3-dipropyl-3,7-dihydro-purine-2,6-dione,
8-{1-[1-(4-Fluoro-phenyl)-5-oxo-pyrrolidin-3-ylmethyl]-1H-pyrazol-4-yl}-1,3-dipropyl-3,7-dihydro-purine-2,6-dione,
8-{1-[5-Oxo-1-(4-trifluoromethoxy-phenyl)-pyrrolidin-3-ylmethyl]-1H-pyrazol-4-yl}-1,3-dipropyl-3,7-dihydro-purine-2,6-dione,
8-{1-[5-Oxo-1-(3-trifluoromethyl-phenyl)-pyrrolidin-3-ylmethyl]-1H-pyrazol-4-yl}-1,3-dipropyl-3,7-dihydro-purine-2,6-dione,
8-[1-(5-Oxo-1-p-tolyl-pyrrolidin-3-ylmethyl)-1H-pyrazol-4-yl]-1,3-dipropyl-3,7-dihydro-purine-2,6-dione,
8-[1-(5-Oxo-1-m-tolyl-pyrrolidin-3-ylmethyl)-1H-pyrazol-4-yl]-1,3-dipropyl-3,7-dihydro-purine-2,6-dione,
8-{1-[5-Oxo-1-(3-trifluoromethyl-benzyl)-pyrrolidin-3-ylmethyl]-1H-pyrazol-4-yl}-1,3-dipropyl-3,7-dihydro-purine-2,6-dione,
8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione,
8-{1-[1-(3-Fluoro-phenyl)-5-oxo-pyrrolidin-3-ylmethyl]-1H-pyrazol-4-yl}-1,3-dipropyl-3,7-dihydro-purine-2,6-dione,
8-{1-[1-(3-Methoxy-phenyl)-5-oxo-pyrrolidin-3-ylmethyl]-1H-pyrazol-4-yl}-1,3-dipropyl-3,7-dihydro-purine-2,6-dione,
3-Ethyl-8-{1-[1-(4-methoxy-phenyl)-5-oxo-pyrrolidin-3-ylmethyl]-1H-pyrazol-4-yl}-1-propyl-3,7-dihydro-purine-2,6-dione,
3-Ethyl-8-{1-[5-oxo-1-(3-trifluoromethyl-benzyl)-pyrrolidin-3-ylmethyl]-1H-pyrazol-4-yl}-1-propyl-3,7-dihydro-purine-2,6-dione,
8-{1-[1-(4-Methoxy-phenyl)-5-oxo-pyrrolidin-3-ylmethyl]-1H-pyrazol-4-yl}-1,3-dipropyl-3,7-dihydro-purine-2,6-dione,
4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile,
3-Ethyl-8-{1-[1-(4-fluoro-phenyl)-5-oxo-pyrrolidin-3-ylmethyl]-1H-pyrazol-4-yl}-1-propyl-3,7-dihydro-purine-2,6-dione,
3-Ethyl-8-{1-[1-(3-fluoro-phenyl)-5-oxo-pyrrolidin-3-ylmethyl]-1H-pyrazol-4-yl}-1-propyl-3,7-dihydro-purine-2,6-dione,
3-Ethyl-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione,
8-{1-[5-Oxo-1-(3-trifluoromethoxy-phenyl)-pyrrolidin-3-ylmethyl]-1H-pyrazol-4-yl}-1,3-dipropyl-3,7-dihydro-purine-2,6-dione,
3-Ethyl-8-{1-[5-oxo-1-(3-trifluoromethoxy-phenyl)-pyrrolidin-3-ylmethyl]-1H-pyrazol-4-yl}-1-propyl-3,7-dihydro-purine-2,6-dione,
3-Ethyl-8-{1-[5-oxo-1-(4-trifluoromethyl-benzyl)-pyrrolidin-3-ylmethyl]-1H-pyrazol-4-yl}-1-propyl-3,7-dihydro-purine-2,6-dione,
8-{1-[1-(3-Fluoro-benzyl)-5-oxo-pyrrolidin-3-ylmethyl]-1H-pyrazol-4-yl}-1,3-dipropyl-3,7-dihydro-purine-2,6-dione,
8-{1-[5-Oxo-1-(2-trifluoromethyl-benzyl)-pyrrolidin-3-ylmethyl]-1H-pyrazol-4-yl}-1,3-dipropyl-3,7-dihydro-purine-2,6-dione,
8-{1-[5-Oxo-1-(4-trifluoromethoxy-benzyl)-pyrrolidin-3-ylmethyl]-1H-pyrazol-4-yl}-1,3-dipropyl-3,7-dihydro-purine-2,6-dione,
8-{1-[1-(4-Methyl-benzyl)-5-oxo-pyrrolidin-3-ylmethyl]-1H-pyrazol-4-yl}-1,3-dipropyl-3,7-dihydro-purine-2,6-dione,
4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzoic acid,
8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione,
3-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile,
8-{1-[5-Oxo-1-(4-trifluoromethyl-phenyl)-pyrrolidin-3-ylmethyl]-1H-pyrazol-4-yl}-1,3-dipropyl-3,7-dihydro-purine-2,6-dione,
8-{1-[1-(2,4-Difluoro-phenyl)-5-oxo-pyrrolidin-3-ylmethyl]-1H-pyrazol-4-yl}-1,3-dipropyl-3,7-dihydro-purine-2,6-dione,
8-{1-[1-(4-Fluoro-phenyl)-5-oxo-pyrrolidin-3-ylmethyl]-1H-pyrazol-4-yl}-1-propyl-3,7-dihydro-purine-2,6-dione,
8-{1-[1-(2-Chloro-4-fluoro-phenyl)-5-oxo-pyrrolidin-3-ylmethyl]-1H-pyrazol-4-yl}-1,3-dipropyl-3,7-dihydro-purine-2,6-dione,
8-{1-[1-(2-Chloro-4-trifluoromethyl-phenyl)-5-oxo-pyrrolidin-3-ylmethyl]-1H-pyrazol-4-yl}-1,3-dipropyl-3,7-dihydro-purine-2,6-dione,
3-Ethyl-8-{1-[5-oxo-1-(4-trifluoromethyl-phenyl)-pyrrolidin-3-ylmethyl]-1H-pyrazol-4-yl}-1-propyl-3,7-dihydro-purine-2,6-dione,
8-{1-[2-Oxo-1-(3-trifluoromethyl-phenyl)-pyrrolidin-3-ylmethyl]-1H-pyrazol-4-yl}-1,3-dipropyl-3,7-dihydro-purine-2,6-dione,
8-{1-[1-(3-Fluoro-phenyl)-2-oxo-pyrrolidin-3-ylmethyl]-1H-pyrazol-4-yl}-1,3-dipropyl-3,7-dihydro-purine-2,6-dione,
8-{1-[2-Oxo-1-(4-trifluoromethoxy-phenyl)-pyrrolidin-3-ylmethyl]-1H-pyrazol-4-yl}-1,3-dipropyl-3,7-dihydro-purine-2,6-dione,
1,3-Dipropyl-8-{1-[1-(3-trifluoromethyl-phenyl)-pyrrolidin-3-ylmethyl]-1H-pyrazol-4-yl}-3,7-dihydro-purine-2,6-dione,
1,3-Dipropyl-8-{1-[1-(4-trifluoromethoxy-phenyl)-pyrrolidin-3-ylmethyl]-1H-pyrazol-4-yl}-3,7-dihydro-purine-2,6-dione,
1,3-Dipropyl-8-[1-(1-p-tolyl-pyrrolidin-3-ylmethyl)-1H-pyrazol-4-yl]-3,7-dihydro-purine-2,6-dione,
8-{1-[1-(4-Methoxy-phenyl)-pyrrolidin-3-ylmethyl]-1H-pyrazol-4-yl}-1,3-dipropyl-3,7-dihydro-purine-2,6-dione,
8-{1-[1-(3-Methoxy-phenyl)-pyrrolidin-3-ylmethyl]-1H-pyrazol-4-yl}-1,3-dipropyl-3,7-dihydro-purine-2,6-dione, 1,3-Dipropyl-8-{1-[1-(3-trifluoromethyl-benzyl)-pyrrolidin-3-ylmethyl]-1H-pyrazol-4-yl}-3,7-dihydro-purine-2,6-dione,
8-{4-[1-(4-Fluorophenyl)-5-oxo-pyrrolidin-3-ylmethoxy]phenyl}-1,3-dipropyl-3,7-dihydropurine-2,6-dione,
1,3-Dipropyl-8-{4-[1-(3-trifluoromethyl-phenyl)-pyrrolidin-3-yloxy]-phenyl}-3,7-dihydro-purine-2,6-dione,
8-{3-[1-(4-Fluoro-phenyl)-5-oxo-pyrrolidin-3-ylmethoxy]-isoxazol-5-yl}-1,3-dipropyl-3,7-dihydro-purine-2,6-dione,
8-{4-[5-Oxo-1-(3-trifluoromethyl-phenyl)-pyrrolidin-3-ylmethoxy]-phenyl}-1,3-dipropyl-3,7-dihydro-purine-2,6-dione,
8-{4-[1-(4-Fluoro-phenyl)-pyrrolidin-3-yloxy]-phenyl}-1,3-dipropyl-3,7-dihydro-purine-2,6-dione,
8-{6-[5-Oxo-1-(3-trifluoromethyl-phenyl)-pyrrolidin-3-ylmethoxy]-pyridin-3-yl}-1,3-dipropyl-3,7-dihydro-purine-2,6-dione,
8-{3-[1-(3-Fluoro-phenyl)-5-oxo-pyrrolidin-3-ylmethoxy]-isoxazol-5-yl}-1,3-dipropyl-3,7-dihydro-purine-2,6-dione,
8-{3-[5-Oxo-1-(3-trifluoromethyl-phenyl)-pyrrolidin-3-ylmethoxy]-isoxazol-5-yl}-1,3-dipropyl-3,7-dihydro-purine-2,6-dione,
8-{6-[1-(3-Fluoro-phenyl)-5-oxo-pyrrolidin-3-ylmethoxy]-pyridin-3-yl}-1,3-dipropyl-3,7-dihydro-purine-2,6-dione,
8-{6-[1-(4-Fluoro-phenyl)-5-oxo-pyrrolidin-3-ylmethoxy]-pyridin-3-yl}-1,3-dipropyl-3,7-dihydro-purine-2,6-dione,
8-{4-[1-(3-Fluoro-phenyl)-5-oxo-pyrrolidin-3-ylmethoxy]-phenyl}-1,3-dipropyl-3,7-dihydro-purine-2,6-dione,
8-{4-[1-(3-Fluoro-phenyl)-piperidin-4-yloxy]-phenyl}-1,3-dipropyl-3,7-dihydro-purine-2,6-dione,
8-{6-[1-(3-Fluoro-phenyl)-piperidin-4-yloxy]-pyridin-3-yl}-1,3-dipropyl-3,7-dihydro-purine-2,6-dione,
8-{3-[1-(3-Fluoro-phenyl)-piperidin-4-yloxy]-isoxazol-5-yl}-1,3-dipropyl-3,7-dihydro-purine-2,6-dione,
8-{4-[1-(4-Fluoro-phenyl)-piperidin-4-yloxy]-phenyl}-1,3-dipropyl-3,7-dihydro-purine-2,6-dione,
8-{3-[1-(4-Fluoro-phenyl)-piperidin-4-yloxy]-isoxazol-5-yl}-1,3-dipropyl-3,7-dihydro-purine-2,6-dione,
1,3-Dipropyl-8-{4-[1-(4-trifluoromethyl-phenyl)-piperidin-4-yloxy]-phenyl}-3,7-dihydro-purine-2,6-dione,
1,3-Dipropyl-8-{3-[1-(4-trifluoromethyl-phenyl)-piperidin-4-yloxy]-isoxazol-5-yl}-3,7-dihydro-purine-2,6-dione,
8-{6-[1-(3-Fluoro-phenyl)-pyrrolidin-3-yloxy]-pyridin-3-yl}-1,3-dipropyl-3,7-dihydro-purine-2,6-dione,
1,3-Dipropyl-8-{6-[1-(4-trifluoromethyl-phenyl)-piperidin-4-yloxy]-pyridin-3-yl}-3,7-dihydro-purine-2,6-dione,
8-{6-[1-(4-Fluoro-phenyl)-piperidin-4-yloxy]-pyridin-3-yl}-1,3-dipropyl-3,7-dihydro-purine-2,6-dione,
1,3-Dipropyl-8-{6-[1-(3-trifluoromethyl-phenyl)-piperidin-4-yloxy]-pyridin-3-yl}-3,7-dihydro-purine-2,6-dione,
1,3-Dipropyl-8-{6-[1-(3-trifluoromethyl-phenyl)-pyrrolidin-3-yloxy]-pyridin-3-yl}-3,7-dihydro-purine-2,6-dione,
1,3-Dipropyl-8-{4-[1-(3-trifluoromethyl-phenyl)-piperidin-4-yloxy]-phenyl}-3,7-dihydro-purine-2,6-dione,
1,3-Dipropyl-8-{3-[1-(3-trifluoromethyl-phenyl)-piperidin-4-yloxy]-isoxazol-5-yl}-3,7-dihydro-purine-2,6-dione,
1,3-Dipropyl-8-{6-[1-(4-trifluoromethyl-phenyl)-pyrrolidin-3-yloxy]-pyridin-3-yl}-3,7-dihydro-purine-2,6-dione,
8-{6-[1-(4-Fluoro-phenyl)-pyrrolidin-3-yloxy]-pyridin-3-yl}-1,3-dipropyl-3,7-dihydro-purine-2,6-dione,
8-{6-[5-Oxo-1-(4-trifluoromethyl-phenyl)-pyrrolidin-3-ylmethoxy]-pyridin-3-yl}-1,3-dipropyl-3,7-dihydro-purine-2,6-dione,
8-{3-[5-Oxo-1-(4-trifluoromethyl-phenyl)-pyrrolidin-3-ylmethoxy]-isoxazol-5-yl}-1,3-dipropyl-3,7-dihydro-purine-2,6-dione,
8-{4-[5-Oxo-1-(4-trifluoromethyl-phenyl)-pyrrolidin-3-ylmethoxy]-phenyl}-1,3-dipropyl-3,7-dihydro-purine-2,6-dione,
1,3-Dipropyl-8-{4-[1-(4-trifluoromethyl-phenyl)-pyrrolidin-3-yloxy]-phenyl}-3,7-dihydro-purine-2,6-dione,
1,3-Dipropyl-8-{3-[1-(4-trifluoromethyl-phenyl)-pyrrolidin-3-yloxy]-isoxazol-5-yl}-3,7-dihydro-purine-2,6-dione,
8-{3-[1-(3-Fluoro-phenyl)-pyrrolidin-3-yloxy]-isoxazol-5-yl}-1,3-dipropyl-3,7-dihydro-purine-2,6-dione,
8-{3-[1-(4-Fluoro-phenyl)-pyrrolidin-3-yloxy]-isoxazol-5-yl}-1,3-dipropyl-3,7-dihydro-purine-2,6-dione,
1,3-Dipropyl-8-{3-[1-(3-trifluoromethyl-phenyl)-pyrrolidin-3-yloxy]-isoxazol-5-yl}-3,7-dihydro-purine-2,6-dione,
8-{4-[1-(3-Fluoro-phenyl)-pyrrolidin-3-yloxy]-phenyl}-1,3-dipropyl-3,7-dihydro-purine-2,6-dione,
8-{3-[1-(2,4-Difluoro-phenyl)-5-oxo-pyrrolidin-3-ylmethoxy]-isoxazol-5-yl}-1,3-dipropyl-3,7-dihydro-purine-2,6-dione,
8-{5-[1-(3-Fluoro-phenyl)-5-oxo-pyrrolidin-3-ylmethoxy]-1-methyl-1H-pyrazol-3-yl}-1,3-dipropyl-3,7-dihydro-purine-2,6-dione,
8-{1-Methyl-5-[5-oxo-1-(4-trifluoromethyl-benzyl)-pyrrolidin-3-ylmethoxy]-1H-pyrazol-3-yl}-1,3-dipropyl-3,7-dihydro-purine-2,6-dione,
8-{5-[1-(4-Methoxy-phenyl)-5-oxo-pyrrolidin-3-ylmethoxy]-1-methyl-1H-pyrazol-3-yl}-1,3-dipropyl-3,7-dihydro-purine-2,6-dione,
8-{5-[1-(4-Fluoro-phenyl)-5-oxo-pyrrolidin-3-ylmethoxy]-1-methyl-1H-pyrazol-3-yl}-1,3-dipropyl-3,7-dihydro-purine-2,6-dione,
8-{1-Methyl-5-[5-oxo-1-(3-trifluoromethyl-phenyl)-pyrrolidin-3-ylmethoxy]-1H-pyrazol-3-yl}-1,3-dipropyl-3,7-dihydro-purine-2,6-dione,
8-{5-[1-(3-Methoxy-phenyl)-5-oxo-pyrrolidin-3-ylmethoxy]-1-methyl-1H-pyrazol-3-yl}-1,3-dipropyl-3,7-dihydro-purine-2,6-dione,
8-(1-{2-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-(1-{1-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-(1-{2-Oxo-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-(1-{2-Hydroxy-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-{1-[5-(4-Fluoro-benzyl)-4,5-dihydro-isoxazol-3-ylmethyl]-1H-pyrazol-4-yl}-1,3-dipropyl-3,7-dihydro-purine-2,6-dione,
8-(1-{2-Oxo-2-[4-(3-trifluoromethyl-phenyl)-piperazin-1-yl]-ethyl}-1H-pyrazol-4-yl)-1,3-dipropyl-3,7-dihydro-purine-2,6-dione,
8-(1-{2-[4-(4-Chloro-phenyl)-4-hydroxy-piperidin-1-yl]-2-oxo-ethyl}-1H-pyrazol-4-yl) 1,3-dipropyl-3,7-dihydro-purine-2,6-dione,
8-(1-{2-[4-(2,4-Difluoro-phenyl)-piperazin-1-yl]-2-oxo-ethyl}-1H-pyrazol-4-yl)-1,3-dipropyl-3,7-dihydro-purine-2,6-dione,
8-{1-[2-Oxo-2-(4-p-tolyl-piperazin-1-yl)-ethyl]-1H-pyrazol-4-yl}-1,3-dipropyl-3,7-dihydro-purine-2,6-dione, 8-(1-{2-Oxo-2-[4-(4-trifluoromethyl-phenyl)-piperazin-1-yl]-ethyl}-1H-pyrazol-4-yl)-1,3-dipropyl-3,7-dihydro-purine-2,6-dione, 8-(1-{2-[4-(3-Chloro-4-fluoro-phenyl)-piperazin-1-yl]-2-oxo-ethyl}-1H-pyrazol-4-yl)-1,3-dipropyl-3,7-dihydro-purine-2,6-dione, 3-Ethyl-8-(1-{2-oxo-2-[4-(3-trifluoromethyl-phenyl)-piperazin-1-yl]-ethyl}-1H-pyrazol-4-yl)-1-propyl-3,7-dihydro-purine-2,6-dione, 8-(1-{2-[4-(4-Fluoro-phenyl)-piperidin-1-yl]-2-oxo-ethyl}-1H-pyrazol-4-yl)-1,3-dipropyl-3,7-dihydro-purine-2,6-dione, 8-(1-{2-[4-(3-Fluoro-phenyl)-piperidin-1-yl]-2-oxo-ethyl}-1H-pyrazol-4-yl)-1,3-dipropyl-3,7-dihydro-purine-2,6-dione, 4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid, 3-(2-Amino-ethyl)-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione, 8-{1-[1-(4-Isopropyl-phenyl)-5-oxo-pyrrolidin-3-ylmethyl]-1H-pyrazol-4-yl}-7-methyl-1,3-dipropyl-3,7-dihydro-purine-2,6-dione, 7-Methyl-8-{1-[5-oxo-1-(4-trifluoromethyl-benzyl)-pyrrolidin-3-ylmethyl]-1H-pyrazol-4-yl}-1,3-dipropyl-3,7-dihydro-purine-2,6-dione, 8-{1-[1-(3-Fluoro-phenyl)-5-oxo-pyrrolidin-3-ylmethyl]-1H-pyrazol-4-yl}-7-methyl-1,3-dipropyl-3,7-dihydro-purine-2,6-dione, 7-Methyl-8-{1-[5-oxo-1-(2-trifluoromethyl-benzyl)-pyrrolidin-3-ylmethyl]-1H-pyrazol-4-yl}-1,3-dipropyl-3,7-dihydro-purine-2,6-dione, 8-{6-[1-(3-Fluoro-phenyl)-5-oxo-pyrrolidin-3-ylmethoxy]-pyridin-3-yl}-7-methyl-1,3-dipropyl-3,7-dihydro-purine-2,6-dione, 8-{6-[1-(4-Fluoro-phenyl)-5-oxo-pyrrolidin-3-ylmethoxy]-pyridin-3-yl}-7-methyl-1,3-dipropyl-3,7-dihydro-purine-2,6-dione, 8-{4-[1-(4-Fluoro-phenyl)-5-oxo-pyrrolidin-3-ylmethoxy]-phenyl}-7-methyl-1,3-dipropyl-3,7-dihydro-purine-2,6-dione, and 8-{4-[1-(3-Fluoro-phenyl)-5-oxo-pyrrolidin-3-ylmethoxy]-phenyl}-7-methyl-1,3-dipropyl-3,7-dihydro-purine-2,6-dione.

The present invention also relates to the process of preparation of compounds of formula (I), or pharmaceutically acceptable salts thereof.

The compounds of formula (I), may be prepared as outlined in the Scheme 1 and 3 below:

Scheme 1:

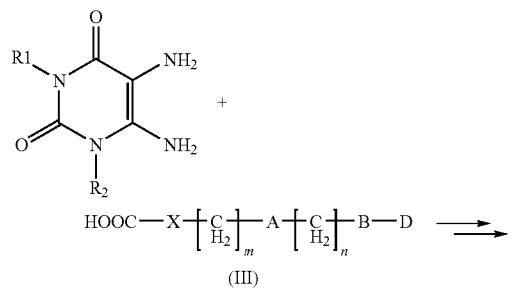

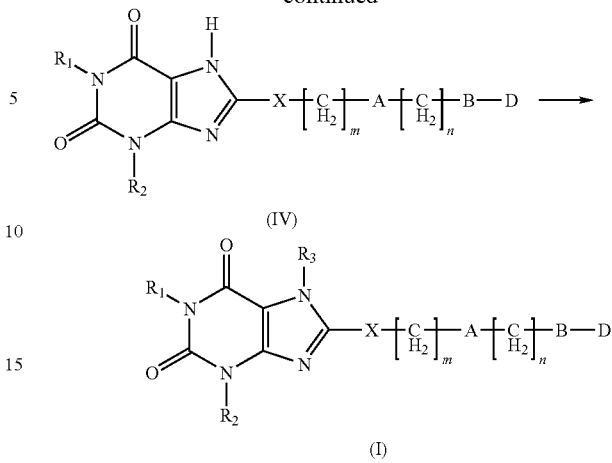

As exemplified in scheme 1 above, diamine of formula (II) wherein $R^1$ and $R^2$ are as defined herein above may be coupled with a carboxylic acid of formula (III) wherein all the symbols are as defined herein above and cyclised to provide compounds of formula (IV) which is reacted with $R^3$-Hal wherein $R^3$ is defined herein above to provide the desired compound of formula (I) wherein Y is N and all other symbols are as defined herein above.

Scheme 2:

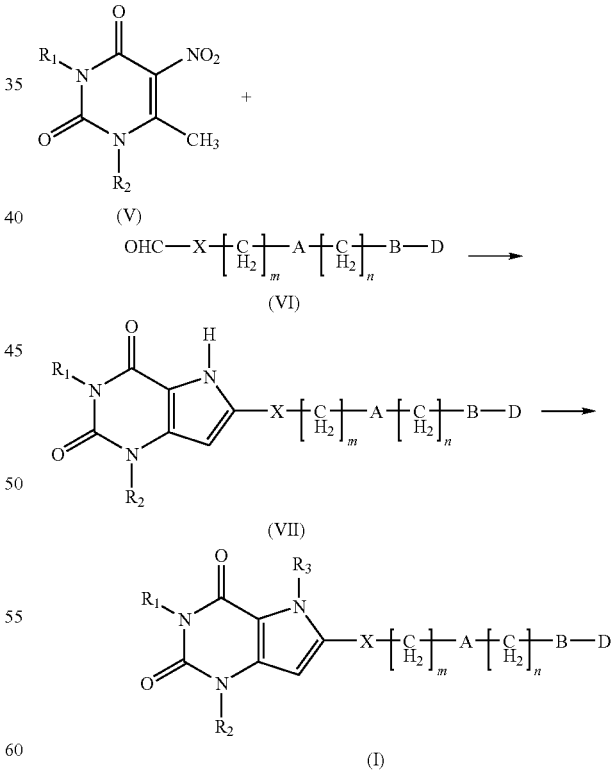

As exemplified in scheme 2 above, nitro pyrimidine dione of formula (V) wherein $R^1$ and $R^2$ are as defined herein above may be condensed with an aldehyde of formula (VI) wherein all the symbols are as defined herein above, followed by reductive cyclisation to provide compound of formula (VII)

which is reacted with $R^3$-Hal wherein $R^3$ is defined herein above to provide the desired compound of formula (I) wherein Y is CH and all other symbols are as defined herein above.

Scheme 3

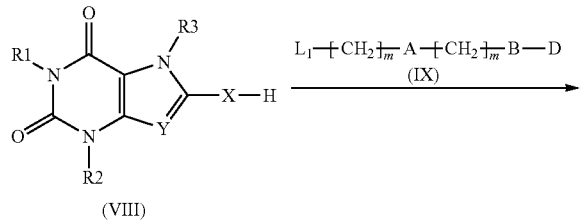

(VIII)

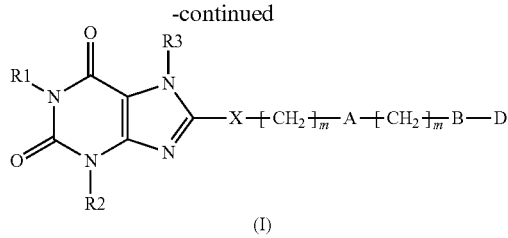

(I)

As exemplified in scheme 3 above, compound of formula (VIII) wherein all the symbols are as defined herein above may be condensed with compound of formula (IX) wherein $L_1$ is a leaving group such as hydroxyl, mesylate or halo such as bromine, chlorine or iodine and all other symbols are as defined herein above to provide the desired compound of formula (I) wherein all symbols are as defined herein above.

Schemes 4-9 further describes synthesis of compounds of formula (I)

Scheme 4:

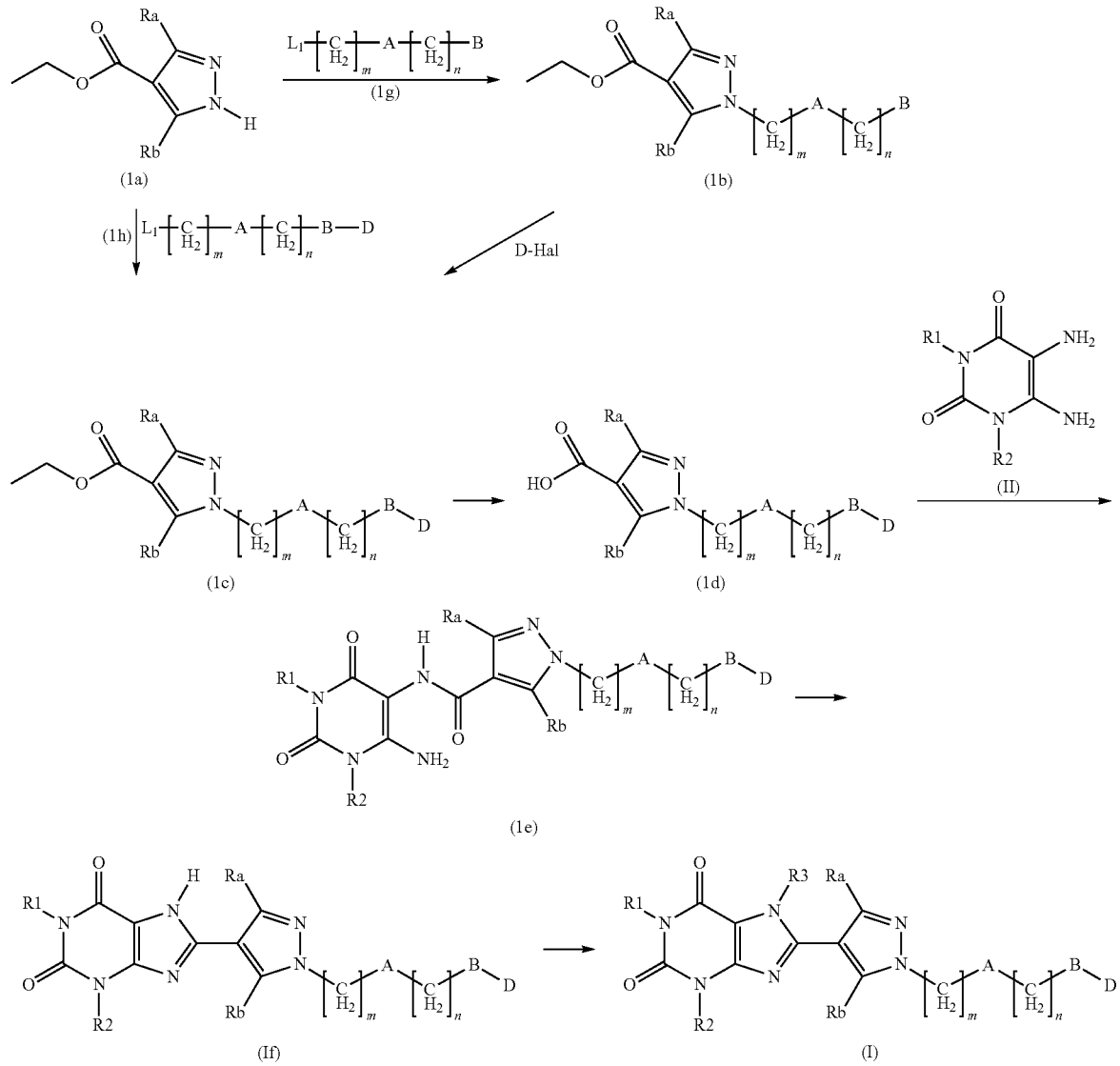

As exemplified in scheme 4, ethyl pyrazole-4-carboxylate of formula (1a) wherein all the symbols including $R^a$ and $R^b$ that are substituents on the pyrazole ring are defined herein above, may be reacted with compounds of formula (1g) wherein L1 is hydroxyl or halo such as bromine, chlorine or iodine, in the presence of a suitable coupling agents such as triaryl phosphine/dialkyl azo dicarboxylate, for example, $PPh_3$/DEAD, $PPh_3$/DIAD or $K_2CO_3$/acetone and the like. Inert atmosphere may be maintained using nitrogen or argon. Solvents such as tetrahydrofuran, toluene, dioxane and the like may be used. The reaction temperature may range from room temperature to reflux temperature of the solvent(s) used, preferably at room temperature to 60° C. The reaction time may range from 1 to 48 hours, preferably 1 to 16 hours. After completion of reaction, the compounds of formula (1b) wherein all symbols are defined herein above may be isolated by conventional methods. Compounds of formula (1b) may be further reacted with D-Hal wherein D is defined herein above to provide compounds of formula (1c) wherein all the symbols are defined herein above.

Alternatively, compounds of formula (1c) may be obtained by reacting, ethyl pyrazole-4-carboxylate of formula (1a) with compounds of formula (1h) wherein L1 is a group such as hydroxyl, tosylate, mesylate or halogen such as bromine, chlorine or iodine, in the presence of a base for example potassium carbonate in a polar solvent, for example N,N-dimethyl formamide, acetone and the like.

Compounds of formula (1c) may be hydrolysed by conventional methods for example in presence of a base, for example potassium hydroxide, sodium hydroxide, lithium hydroxide and the like in solvent such as methanol or ethanol, tetrahydrofuran or a mixture of ethanol, tetrahydrofuran and water, to obtain compound of formula (1d) wherein all symbols are defined herein above.

Compounds of formula (II) which are available commercially or may be prepared by procedures well known in the art may be reacted with carboxylic acids of formula (1d) wherein all symbols are defined herein above, to yield compounds of formula (1e). The reaction may be carried out with a suitable coupling agent for example EDCI, DCC, HBTU and the like in a protic solvent such as methanol, ethanol, propanol and the like or aprotic solvent such as DMF, $CH_2Cl_2$ and the like. The reaction temperature may range from 20-30° C. The reaction time may range from 4 to 16 hours. After completion of reaction, the product of formula (1e) wherein all symbols are defined herein above may be isolated by conventional methods. Alternatively, compounds of formula (1e) may also be prepared from reaction of (II) and acid chloride (1d) to yield (1e). The reaction of acid halides of (1d) may be preferably carried out in the absence of solvent, using excess of halogenating agent such as thionyl chloride. The reaction temperature may range from 0° C. to reflux temperature of the solvent or reagent used, preferably 60 to 70° C. The reaction time may range from 1 to 24 hours, preferably from 1 to 6 hours. After completion of the reaction the product may be isolated by removal of excess halogenating agent under reduced pressure. The isolated product may be treated with compounds of formula (II) in an inert solvent, for example acetonitrile, in the presence of tertiary base for example triethyl amine. The reaction temperature may range from 0° C. to reflux temperature of the solvent(s) used, preferably at 20-30° C. The reaction time may range from 4 to 48 hours, preferably from 4 to 16 hours. After completion of reaction, the compounds of formula (1 e) may be isolated by conventional methods.

Compounds of formula (1e) may be converted into compounds of formula (If) by a cyclisation reaction. The reaction may be carried out in a protic solvent, such as methanol, ethanol, propanol and the like, preferably methanol, in presence of a base, such as alkali metal hydroxide such as potassium hydroxide, sodium hydroxide and the like, or sodium methoxide, sodium ethoxide, potassium tert-butoxide, preferable aqueous sodium hydroxide. The reaction temperature may range from 50-100° C., preferably at 80° C. The reaction time may range from 1 to 12 hours, preferably about 6-10 hours. After completion of reaction, the compounds of formula (If) wherein all symbols are defined herein above may be isolated by conventional methods. Compounds of formula (If) may be reacted with $R^3$-Hal wherein $R^3$ is defined herein above. The reaction may be carried out in a solvent such as acetone or DMF, in the presence of a base such as $K_2CO_3$. The reaction temperature may range from room temperature to 80° C. The reaction time may range from 2 to 12 hours. After completion of reaction, the compounds of formula (I) wherein all symbols are defined herein above may be isolated by conventional methods.

Scheme 4 above can also be followed to obtain compounds wherein X of formula I is a aryl or heteroaryl rings such as phenyl, pyridyl, isoxazolyl, 3,5-pyrazolyl, oxazolyl and the like.

Scheme 5:

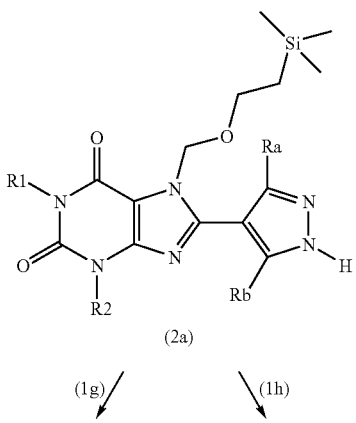

(2a)

(1g) (1h)

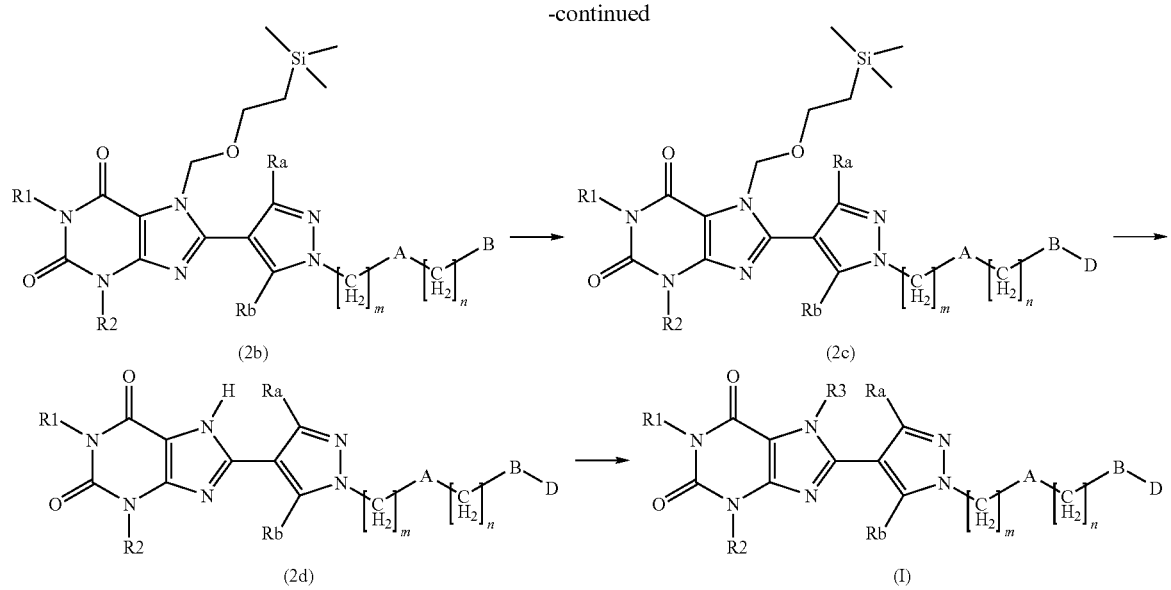

(2b) (2c) (2d) (I)

As exemplified in scheme 5, compounds of formula (2a) wherein all the symbols including $R^a$ and $R^b$ that are substituents on the pyrazole ring are defined herein above may be prepared by means well known in the art (U.S. Pat. No. 6,825,349). Compounds of formula (2a) may be converted to compounds of formula (2b) by reacting with compounds of formula (1g) wherein L1 is hydroxyl or halo such as bromine, chlorine or iodine, in the presence of suitable coupling agent such as triaryl phosphine/dialkyl azo dicarboxylate, for example, $PPh_3$/DEAD, $PPh_3$/DIAD or $K_2CO_3$/acetone and the like. Inert atmosphere may be maintained using nitrogen or argon. Solvents such as tetrahydrofuran, toluene, dioxane and the like may be used. The reaction temperature may range from 30° C. to reflux temperature of the solvent(s) used, preferably at 20-60° C. The reaction time may range from 1 to 48 hours, preferably 1 to 16 hours. After completion of reaction, the compounds of formula (2b) may be isolated by conventional methods.

The compounds of formula (2b) may be converted to compounds of formula (2c) wherein all the symbols are defined herein above, by reaction with D-Hal wherein D is defined herein above by methods well known in the art.

Alternatively, compounds of formula (2a) may be converted to compounds of formula (2c) directly by reacting with compounds of formula (1h) wherein D is defined herein above and L2 is hydroxyl, tosylate, mesylate or halogen such as bromine, chlorine or iodine in the presence of a base for example potassium carbonate in a polar solvent, for example N,N-dimethyl formamide, acetone and the like. The reaction temperature may range from 30° C. to reflux temperature of the solvent(s) used, preferably at 20-60° C. The reaction time may range from 1 to 48 hours, preferably 1 to 16 hours. After completion of reaction, the product of formula (2c) wherein all symbols are defined herein above may be isolated by conventional methods.

The SEM (2-(trimethylsilyl)-ethoxymethyl chloride) protecting group of the compounds of formula (2c) may be deprotected by suitable acidic reagent to get compounds of formula (2d). In general, the compound of formula (2c) may be dissolved in ethanol and treated with HCl. The reaction temperature may range from 30° C. to reflux temperature of the solvent(s) used, preferably at 80-100° C. The reaction time may range from 1 to 6 hours. After completion of reaction, the product of general formula (2d) wherein all symbols are defined herein above may be isolated by conventional methods.

Compounds of formula (2d) may be reacted with $R^3$-Hal wherein $R^3$ is defined herein above. The reaction may be carried out in a solvent such as acetone or DMF, in the presence of a base such as $K_2CO_3$. The reaction temperature may range from room temperature to 80° C. The reaction time may range from 2 to 12 hours. After completion of reaction, the compounds of formula (I) wherein all symbols are defined herein above may be isolated by conventional methods.

Scheme 5 above can also be followed to obtain compounds wherein X of formula I is a aryl or heteroaryl rings such as phenyl, pyridyl, isoxazolyl, 3,5-pyrazolyl, oxazolyl and the like.

Scheme 6:

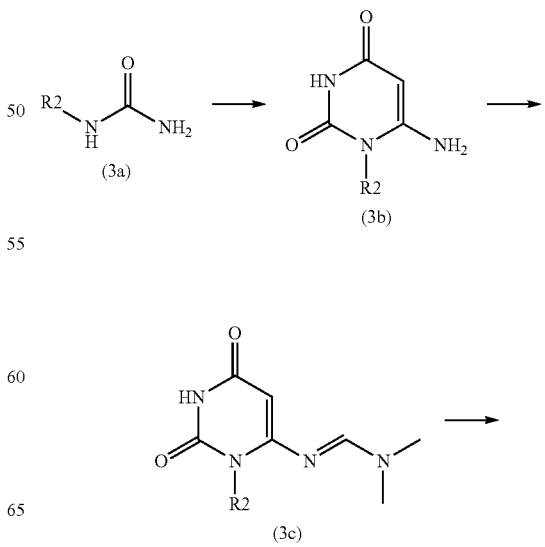

(3a) (3b) (3c)

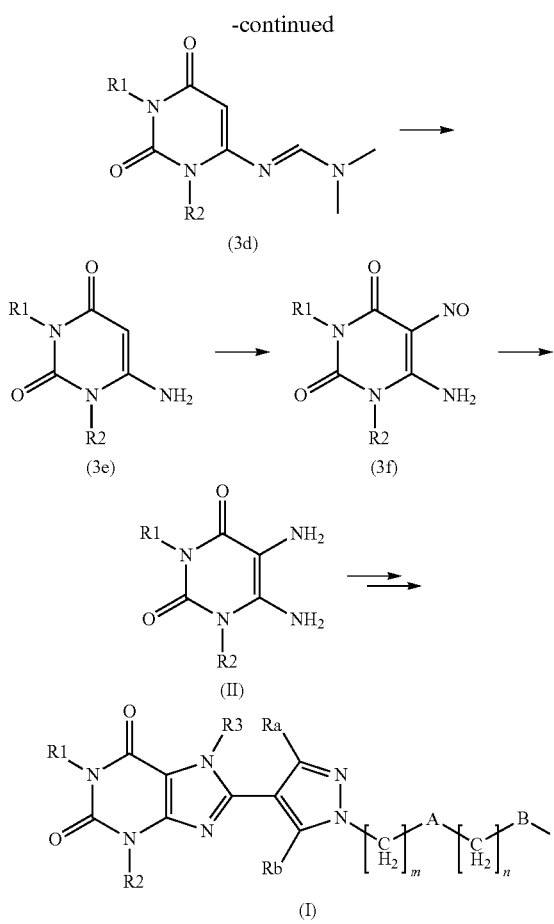

As exemplified in scheme 6, compounds of formula (3a) are either commercially available or may be prepared by means well known in the art. (3a) may be reacted with ethyl cyanoacetate in protic solvent, for example ethanol, in presence of strong base, for example sodium ethoxide. The reaction temperature may range from 30° C. to reflux temperature of the solvent(s) used, preferably at 60-70° C. The reaction time may range from 4 to 48 hours, preferably from 4 to 16 hours. After completion of reaction, the compounds of formula (3b) wherein $R^2$ is defined herein above may be isolated by conventional methods.

Compounds of formula (3b) may be reacted with N,N-dimethyl formamide, dimethyl acetal in a polar solvent, for example N,N-dimethyl formamide. The reaction temperature may range from 20 to 60° C., preferably at 40° C. The reaction time may range from 1 to 4 h hours, preferably 1 hour. After completion of reaction the compounds of formula (3c) may be reacted with $R^1$-Hal where Hal is chloro, bromo, or iodo in the presence of a base for example potassium carbonate in a polar solvent, for example N,N-dimethyl formamide, acetone and the like. The reaction temperature may range from 30° C. to reflux temperature of the solvent(s) used, preferably at 70-80° C. The reaction time may range from 1 to 48 hours, preferably from 4 to 30 hours. After completion of reaction, the compounds of formula (3d) wherein all symbols are defined herein above may be isolated by conventional methods.

Compounds of formula (3d) may be reacted with aqueous ammonia in a polar solvent, for example methanol. The reaction temperature may range from 20-30° C. to reflux temperature of the solvent(s) used, preferably at 20-30° C. The reaction time may range from 24 to 80 hours, preferably from 70 to 75 hours. After completion of reaction, the compounds of formula (3e) wherein all symbols are defined herein above may be isolated by conventional methods.

Compounds of formula (3e) may be reacted with sodium nitrite in aqueous acidic solvent, for 50% acetic acid in water. The reaction temperature may range from 50° C. to reflux temperature of the solvent(s) used, preferably at about 75° C. The reaction time may range from 1 to 8 hours, preferably from 1 to 3 hours. After completion of reaction, the compounds of formula (3f) wherein all symbols are defined herein above may be isolated by conventional methods.

Compounds of formula (3f) may be reduced to (II) by procedures well known in the art.

Compounds of formula (II) may be converted to compounds of formula I wherein all the symbols including $R^a$ and $R^b$ that are substituents on the pyrazole ring are defined herein above and $R^1$ is not equal to $R^2$, as described in scheme 3 herein above.

Scheme 6 above can also be followed to obtain compounds wherein X of formula I is a aryl or heteroaryl rings such as phenyl, pyridyl, isoxazolyl, 3,5-pyrazolyl, oxazolyl and the like.

Scheme 7:

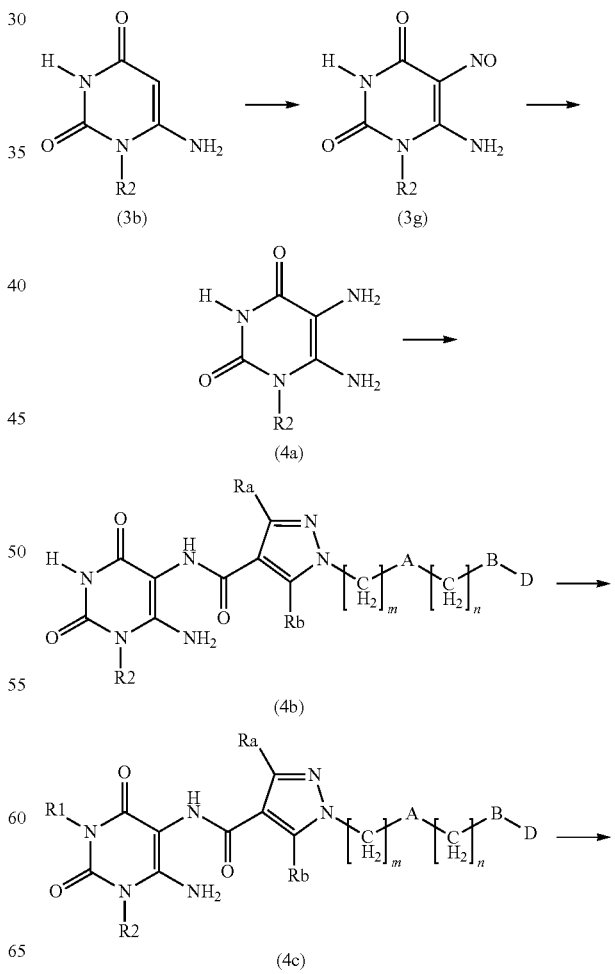

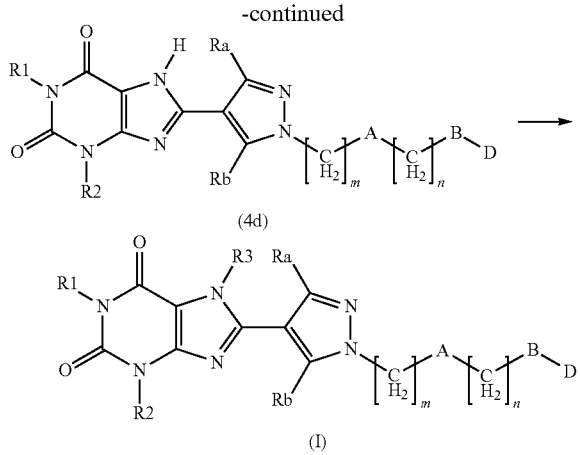

As exemplified in scheme 7, compounds of formula (3b) wherein $R^2$ is defined herein above, may be reacted with sodium nitrite in aqueous acidic solvent, for example 50% acetic acid in water. The reaction temperature may range from 50° C. to reflux temperature of the solvent(s) used, preferably at about 75° C. The reaction time may range from 1 to 8 hours, preferably from 1 to 3 hours. After completion of reaction, the compounds of formula (3g) wherein $R^1$ is hydrogen and $R^2$ is defined herein above may be isolated by conventional methods.

Compounds of formula (3g) may be converted to diamine derivative by a reduction step. The reaction may be carried out by conventional reducing techniques for example sodium dithionate in aqueous ammonia solution; preferably, reduction is carried out with hydrogen and a metal catalyst. The reaction may be carried out in an inert solvent, for example methanol or ethanol, in the presence of a catalyst, for example 10% palladium on carbon catalyst, under an atmosphere of hydrogen, preferably under pressure for example about 20 to 40 psi for 2 to 18 hours. After completion of reaction, the compounds of formula (4a) wherein $R^2$ is defined herein above may be isolated by conventional methods.

Compound of formula (4a) may be reacted with carboxylic acids of formula (1d) wherein all symbols are defined herein above, to yield compounds of formula (4b) wherein all other symbols including $R^a$ and $R^b$ that are substituents on the pyrazole ring are defined herein above. The reaction may be carried out with a suitable coupling agent for example EDCI, DCC, HOBt and the like, in protic solvent such as methanol, ethanol, propanol and the like or aprotic solvent such as DMF, $CH_2Cl_2$ and the like. The reaction temperature may range from 20-30° C. The reaction time may range from 4 to 16 hours. After completion of reaction, the compounds of formula (4b) wherein all other symbols are defined herein above may be isolated by conventional methods.

Compounds (4b) may also be prepared by reacting compounds of formula (4a) with the acid halide of the acid of formula (1d). The reaction of acid (1d) may be preferably carried out in the absence of solvent, using excess of halogenating agent (e.g. thionyl chloride). The reaction temperature may range from 0° C. to reflux temperature of the solvent or reagent used, preferably 60 to 70° C. The reaction time may range from 1 to 24 hours, preferably from 1 to 6 hours. After completion of reaction, the product may be isolated by removal of excess halogenating agent under reduced pressure. The isolated product may be treated with compounds of formula (4a) in an inert solvent, for example acetonitrile, in the presence of tertiary base for example triethyl amine. The reaction temperature may range from 0° C. to reflux temperature of the solvent(s) used, preferably at 20-30° C. The reaction time may range from 4 to 48 hours, preferably from 4 to 16 hours. After completion of reaction the compounds of formula (4b) wherein all symbols including $R^a$ and $R^b$ that are substituents on the pyrazole ring are defined herein above may be isolated by conventional methods.

The compounds of formula (4b) may be reacted with $R^1$-hal wherein $R^1$ is defined herein above and Hal is chloro, bromo, or iodo in the presence of a base for example potassium carbonate in a polar solvent, for example N,N-dimethyl formamide, acetone and the like. The reaction temperature may range from 30° C. to reflux temperature of the solvent(s) used, preferably at 70-80° C. The reaction time may range from 1 to 48 hours, preferably from 4 to 30 hours. After completion of reaction, the product of formula (4c) wherein $R^1$ is different from $R^2$ wherein all symbols are defined herein above may be isolated by conventional method.

Compounds of formula (4c) may be then converted into compounds of general formula (4d) wherein $R^1$ is different from $R^2$, by a cyclisation reaction. The reaction may be carried out in a protic solvent, such as methanol, ethanol, propanol and the like, preferably methanol, in presence of a base, such as alkali metal hydroxide such as potassium hydroxide, sodium hydroxide and the like, or sodium methoxide, sodium ethoxide, potassium tert-butoxide, preferable aqueous sodium hydroxide. The reaction temperature may range from 50-100° C., preferably at 80° C. The reaction time may range from 1 to 12 hours, preferably about 6-10 hours. After completion of reaction, the compounds of formula (4d) wherein all symbols are defined herein above may be isolated by conventional methods.

Compounds of formula (4d) may be reacted with $R^3$-Hal wherein $R^3$ is defined herein above. The reaction may be carried out in a solvent such as acetone or DMF, in the presence of a base such as $K_2CO_3$. The reaction temperature may range from room temperature to 80° C. The reaction time may range from 2 to 12 hours. After completion of reaction, the compounds of formula (I) wherein all symbols are defined herein above may be isolated by conventional methods.

Scheme 7 above can also be followed to obtain compounds wherein X of formula I is a aryl or heteroaryl rings such as phenyl, pyridyl, isoxazolyl, 3,5-pyrazolyl, oxazolyl and the like.

Scheme-8:

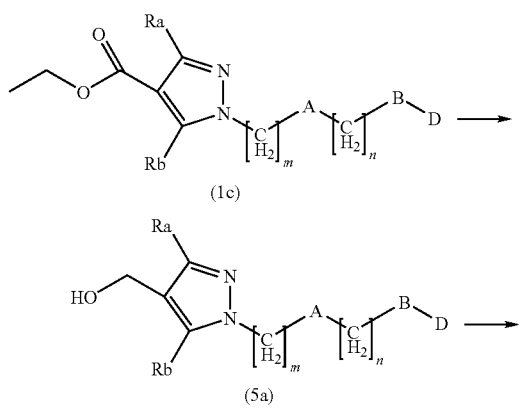

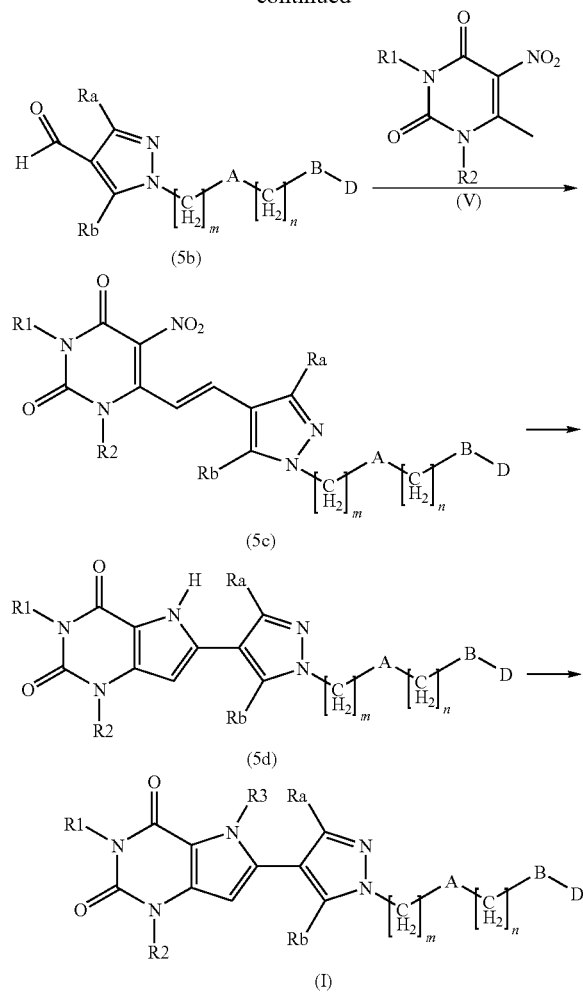

As exemplified in scheme 8, compounds of formula (1c) (obtained as mentioned in scheme 3) wherein all symbols are defined herein above may be converted into the analogous alcohol by a suitable reducing agent. In general, the compounds of formula (1c) may be dissolved in a suitable solvent, such as THF, and cooled to 0° C. under inert atmosphere and treated with lithium aluminium hydride. The reaction temperature may range from 0 to 25° C. The reaction time may range from 1 to 6 hours, preferably 1 to 3 hours. After completion of reaction, the compounds of formula (5a) wherein all the symbols including $R^a$ and $R^b$ that are substituents on the pyrazole ring are defined herein above may be isolated by conventional methods.

Compounds of formula (5a) may be converted into the analogous aldehyde by a suitable oxidizing agent such as Dess-Martin Periodinane, manganese dioxide. In general, the compound of formula (5a) is dissolved in a suitable solvent, such as chloroform under inert atmosphere and treated with manganese dioxide portion wise. The reaction temperature may range from 30° C. to reflux temperature of the solvent used, preferably at 50-60° C. The reaction time may range from 1 to 24 hours, preferably 1 to 12 hours. After completion of reaction, compounds of formula (5b) wherein all the symbols including $R^a$ and $R^b$ that are substituents on the pyrazole ring are defined herein above may be isolated by conventional methods.

The compound of formula (V) wherein all symbols are defined herein above may be prepared by means well known in the art. Compounds of formula (5b) wherein all symbols are defined herein above may be condensed with compounds of formula (V) in the presence of a suitable base such as piperidine. The reaction may be carried out in an inert solvent, for example ethanol, 1,4-dioxane and the like. The reaction temperature may range from 60-80° C. The reaction time may range from 4 to 24 hours. After completion of reaction, the compounds of formula (5c) wherein all the symbols including $R^a$ and $R^b$ that are substituents on the pyrazole ring are defined herein above may be isolated by conventional methods.

The compounds of formula (5c) may be converted into compounds of formula (5d) by a reduction and cyclization reaction. The reaction may be carried out in a suitable solvent such as N,N-dimethyl formamide (DMF) in presence of catalytic amount of $SnCl_2$. The reaction temperature may range from 100° C. to reflux temperature of the solvent used, preferably 140-150° C. The reaction time may range from 1 to 10 hours, preferably from 1 to 6 hours. After cooling, acid solution such as 2N HCl is added to get compound of formula (5d) wherein all the symbols including $R^a$ and $R^b$ that are substituents on the pyrazole ring are defined herein above may be isolated by conventional method.

Compounds of formula (5d) may be reacted with $R^3$-Hal. The reaction may be carried out in a solvent such as acetone or DMF, in the presence of a base such as $K_2CO_3$. The reaction temperature may range from room temperature to 80° C. The reaction time may range from 2 to 12 hours. After completion of reaction, the compounds of formula (I) wherein all symbols are defined herein above may be isolated by conventional methods.

Scheme 8 above can also be followed to obtain compounds wherein X of formula I is a aryl or heteroaryl rings such as phenyl, pyridyl, isoxazolyl, 3,5-pyrazolyl, oxazolyl and the like.

Scheme 9:

As exemplified in scheme 9, compounds of formula (6a) wherein all the symbols including $R^a$ and $R^b$ that are substituents on the pyrazole ring are defined herein above (may be prepared by means well known in the art J. Med. Chem. 2006, 49, 3682-3692), may be reacted with compound of formula (1g) wherein L1 is hydroxyl or halo such as bromine, chlorine or iodine, in the presence of suitable coupling agent such as triaryl phosphine/dialkyl azo dicarboxylate, for example, $PPh_3$/DEAD, $PPh_3$/DIAD, $K_2CO_3$ acetone and the like. Inert atmosphere may be maintained using nitrogen or argon. Solvents such as tetrahydrofuran, toluene, dioxane and the like may be used. The reaction temperature may range from 30° C. to reflux temperature of the solvent(s) used, preferably at 20-60° C. The reaction time may range from 1 to 48 hours, preferably 1 to 16 hours. After completion of reaction compounds of formula (6b) wherein all the symbols including $R^a$ and $R^b$ that are substituents on the pyrazole ring are defined herein above may be isolated by conventional methods.

Compounds of formula (6b) may be converted into compounds of formula (6c) by reaction with D-$CH_2$-Hal or D-Hal by well known methods in the art.

Alternatively, the compound of formula (6a) may be converted into a compound of formula (6c) directly by reacting with compounds of formula (1h) wherein L2 is a group such as hydroxyl, tosylate, mesylate or halogen such as bromine, chlorine or iodine, in the presence of a base for example potassium carbonate in a polar solvent, for example N,N-dimethyl formamide, acetone and the like. The reaction temperature may range from 30° C. to reflux temperature of the solvent(s) used, preferably at 20-60° C. The reaction time may range from 1 to 48 hours, preferably 1 to 16 hours. After completion of reaction, compounds of formula (6c) wherein all the symbols including $R^a$ and $R^b$ that are substituents on the pyrazole ring are defined herein above may be isolated by conventional methods.

The SEM (2-(trimethylsilyl)-ethoxymethyl chloride) protecting group of the compound of formula (6c) may be deprotected by suitable acidic reagent. In general, the compound of formula (6c) may be dissolved in ethanol and treated with 2N HCl. The reaction temperature may range from 30° C. to reflux temperature of the solvent(s) used, preferably at 80-100° C. The reaction time may range from 1 to 6 hours, preferably 1 to 6 hours. After completion of reaction, compounds of formula (6d) wherein all the symbols including $R^a$ and $R^b$ that are substituents on the pyrazole ring are defined herein above may be isolated by conventional method.

Compounds of formula (6d) may be reacted with $R^3$-Hal. The reaction may be carried out in a solvent such as acetone or DMF, in the presence of a base such as $K_2CO_3$. The reaction temperature may range from room temperature to 80° C. The reaction time may range from 2 to 12 hours. After completion of reaction, the compounds of formula (I) wherein all symbols are defined herein above may be isolated by conventional methods.

Scheme 9 above can also be followed to obtain compounds wherein X of formula I is a aryl or heteroaryl rings such as phenyl, pyridyl, isoxazolyl, 3,5-pyrazolyl, oxazolyl and the like.

Wherever desired or necessary, in any of the above mentioned processes, any of the compounds of formula (I) may be converted into a pharmaceutically acceptable salt or vice versa or converting one salt form into another pharmaceutically acceptable salt form.

According to an embodiment, the compounds of the present invention are adenosine $A_{2B}$ receptor antagonists. Thus, the present invention provides a method for the modulation of adenosine $A_{2B}$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

According to yet another embodiment, the compounds of the present invention are adenosine $A_1$ and $A_{2B}$ antagonist or adenosine $A_{2B}$ and $A_3$ antagonist or $A_1$, $A_{2B}$ and $A_3$ antagonist thereby providing dual or pan antagonistic activity through additive/synergistic effect. Thus, the present invention provides a method for the modulation of adenosine $A_1$ and $A_{2B}$ or $A_{2B}$ and $A_3$ or $A_{2B}$, $A_1$ and $A_3$ receptor activity in mammals which method comprises administering to a mammal in need thereof a therapeutically effective amount of compound of formula I or its tautomers, polymorphs, stereoisomers, prodrugs, solvate or a pharmaceutically acceptable salts thereof.

The present invention also provides a method of prophylactic or therapeutic treatment of disease or discoreder susceptible to improvement by antagonism of adenosine receptor comprising administering an effective amount of compound of formula I or its tautomers, polymorphs, stereoisomers, prodrugs, solvate or a pharmaceutically acceptable salts thereof, to a mammal in need of such treatment.

As used throughout the specification and in the claims, the term "treatment" embraces all the different forms or modes of treatment as known to those of the pertinent art and in particular includes preventive, curative, delay of progression and palliative treatment.

The term "therapeutically effective amount" as used herein refers to an amount of a drug or a therapeutic agent that will elicit the desired biological or medical response of a tissue, system or an animal (including man) that is being sought by a researcher or clinician.

The term "mammal" or "patient" are used interchangeably herein and include, but are not limited to, humans, dogs, cats, horses, pigs, cows, sheep, monkeys, rabbits, mice and laboratory animals. The preferred mammals are humans.

The present invention further provides pharmaceutical compositions comprising a therapeutically effective amount of a compound of the present invention, alone or in combination with one or more pharmaceutically acceptable carriers.

The pharmaceutical compositions according to the invention are those suitable for enteral, such as oral or rectal, transdermal and parenteral administration to mammals, including man, for the treatment of conditions mediated by the adenosine $A_{2B}$ receptor. Such conditions include, but are not limited to, asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases. Generally, the concentration of the compound(s) of the present invention in a liquid composition, such as a lotion, will be from about 0.01-about 25 wt %, preferably from about 0.1-about 10 wt %. The concentration in a semi-solid or a solid composition such as a gel or a powder will be about 0.1-about 5 wt %, preferably about 0.5-about 25 wt %.

The amount of a compound of the present invention required for use in treatment will vary not only with the particular salt selected but also with the route of administration, the nature of the condition being treated and the age and condition of the patient and will be ultimately at the discretion of the administering physician or clinician. In general, a suitable dose will be in the range of from about 0.001 mg/kg/day to about 20 mg/kg/day For example, a dosage may be from about 0.002 mg/kg to about 10 mg/kg of body weight per day, from about 0.01 mg/kg/day to about 1 mg/kg/day, and from about 0.1 mg/kg/day to about 5 mg/kg/day.

The compound is conveniently administered in unit dosage form, e.g, containing 5 to 1000 μg, about 10 to about 750 μg, about 50 to about 500 μg of active ingredient per unit dosage form.

The desired dose may conveniently be presented in a single dose or as divided doses administered at appropriate intervals, for example, as two, three, four or more sub-doses per day. The sub-dose itself may be further divided, e g, into a number of discrete loosely spaced administrations; such as multiple inhalations from an insufflator or by application of a plurality of drops into the eye Dosages above or below the range cited herein above are within the scope of the present invention and may be administered to the individual patient if desired and necessary.

Accordingly, in various embodiments, the present invention provides pharmaceutical compositions as described above for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

In various embodiments, the present invention provides pharmaceutical compositions comprising a therapeutically effective amount of a compound of the invention in combination with a therapeutically effective amount of another therapeutic agent, preferably selected from anti-inflammatory agents, anti-diabetic agents, anti-hypertensive agents and anti-dyslipidemic agents.

According to an embodiment, the pharmaceutical compositions may contain a therapeutically effective amount of a compound of the invention as defined above, either alone or in a combination with another therapeutic agent, e.g., each at an effective therapeutic dose as reported in the art. Such therapeutic agents include: a) anti-inflammatory agents, such as anticholinergic or antimuscarinic agents; steroids; LTB$_4$ (leukotriene B$_4$) antagonists; dopamine receptor agonists; PDE$_4$ (phosphodiesterase 4) inhibitors; and beta-2 adrenergic receptor agonists; b) anti-diabetic agents, such as insulin, insulin derivatives and mimetics; insulin secretagogues; insulinotropic sulfonylurea receptor ligands; thiazolidone derivatives; GSK3 (glycogen synthase kinase-3) inhibitors; sodium-dependent glucose co-transporter inhibitors; glycogen phosphorylase A inhibitors; biguanides; alpha-glucosidase inhibitors; GLP-1 (glucagon like peptide-1), GLP-1 analogs and GLP-1 mimetics; modulators of PPARs (peroxisome proliferator-activated receptors); DPPIV (dipeptidyl peptidase IV) inhibitors; SCD-1 (stearoyl-CoA desaturase-1) inhibitors; DGAT1 and DGAT2 (diacylglycerol acyltransferase 1 and 2) inhibitors; ACC2 (acetyl CoA carboxylase 2) inhibitors; and breakers of AGE (advanced glycation end products); c) anti-hypertensive agents, such as loop diuretics; angiotensin converting enzyme (ACE) inhibitors; inhibitors of the Na—K-ATPase membrane pump such as digoxin; neutralendopeptidase (NEP) inhibitors; ACE/NEP inhibitors; angiotensin II antagonists; renin inhibitors; β-adrenergic receptor blockers; inotropic agents; calcium channel blockers; aldosterone receptor antagonists; and aldosterone synthase inhibitors; and d) anti-dyslipidemic agents such as 3-hydroxy-3-methyl-glutaryl coenzyme A (HMG-CoA) reductase inhibitors; HDL increasing compounds such as cholesterol ester transfer protein (CETP) inhibitors; squalene synthase inhibitors; FXR (farnesoid X receptor) and LXR (liver X receptor) ligands; cholestyramine; fibrates; nicotinic acid; and aspirin.

As described above, a compound of the present invention may be administered either simultaneously, before or after another active ingredient, either separately by the same or different route of administration or together in the same pharmaceutical formulation.

In another embodiment of the present invention, the compound of formula (I) is use in treatment conditions mediated by adenosine receptor.

The present invention further relates to use of compound of formula (I) for the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

The present invention further relates to use of compound of formula (I) for use in preparation of medicament useful in the treatment of conditions mediated by adenosine receptor.

The present invention further relates to use of compound of formula (I) in preparation of medicament useful in the treatment of asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

The present invention further relates to pharmaceutical compositions as described above for use as a medicament.

The present invention further relates to use of pharmaceutical compositions or combinations as described above for the preparation of a medicament for the treatment of conditions mediated by adenosine receptor, such as asthma, chronic obstructive pulmonary disorder, angiogenesis, pulmonary fibrosis, emphysema, allergic diseases, inflammation, reperfusion injury, myocardial ischemia, atherosclerosis, hypertension, congestive heart failure, retinopathy, diabetes mellitus, obesity, inflammatory gastrointestinal tract disorders, and/or autoimmune diseases.

EXAMPLES

The invention is further illustrated by the following examples which in no way should be construed as being further limiting. One skilled in the art will readily appreciate that the specific methods and results described are merely illustrative. Structures of the intermediates as well as the final compounds were confirmed by nuclear magnetic resonance spectra for proton ($^1$H NMR) and LCMS.

Example A1

1,3-Dipropyl-8-[1-(3-p-tolyl-prop-2ynyl)-1H-pyrazol-4-yl]-3,7-dihydro-purine-2,6-dione

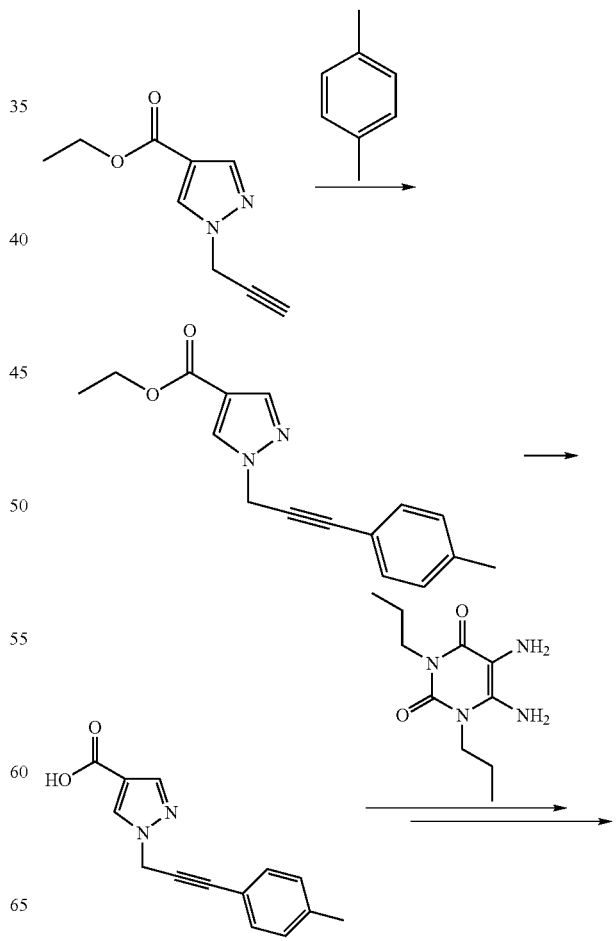

-continued

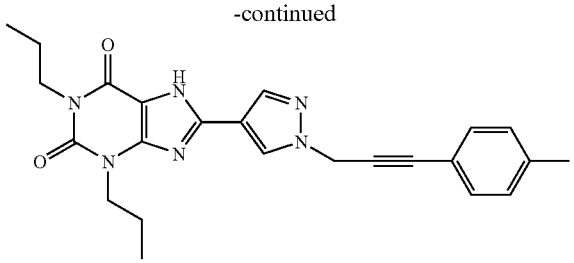

Step I 1-(3-p-Tolyl-prop-2-ynyl)-1H-pyrazole-4-carboxylic acid ethyl ester

A mixture of 1-prop-2-ynyl-1H-pyrazole-4-carboxylic acid ethyl ester obtained as given in example B1 (0.200 g, 1.1 mmol), 4-iodo toluene (0.254 g, 1.1 mol), copper iodide (0.021 g, 0.11 mmol), dichlorobis (triphenylphosphine)-palladium (II) (39 mg, 0.06 mmol), triethylamine (2 ml), DMF (2 ml) was degassed for 10 min. and stirred for 20 hrs at 25-25° C. Reaction mixture was diluted with water (10 ml) and extracted with ethyl acetate. Organic layer was washed with brine solution and dried over $Na_2SO_4$. The solvent was evaporated and crude product was purified by column chromatography (Ethyl acetate:hexane-12:78) to obtain pure 1-(3-p-tolyl-prop-2-ynyl)-1H-pyrazole-4-carboxylic acid ethyl ester compound (0.226 g, 75%).

$^1$HNMR (400 MHz, $CDCl_3$): δ 1.35 (t, J=6.8 Hz, 3H); 2.37 (s, 3H); 4.31 (q, J=6.8 Hz, 2H); 5.18 (s, 2H); 7.16 (d, J=7.6 Hz, 2H); 7.38 (d, J=8 Hz, 2H); 7.95 (s, 1H); 8.21 (s, 1H)

Step II 1-(3-p-Tolyl-prop-2-ynyl)-1H-pyrazole-4-carboxylic acid 1-(3-p-Tolyl-prop-2-ynyl)-1H-pyrazole-4-carboxylic acid ethyl ester (0.226 g, 0.84 mmol) was dissolved in a mixture of solvents THF: methanol:water (3:1:1, 10 ml) and LiOH (0.071 g, 1.7 mol) was added to the reaction mixture with stirring. The reaction mixture was then stirred at 20-25° C. for 2 hours. Solvents were evaporated and the residue was diluted with water (0.5 ml) and acidified with dil. HCl, filtered and dried to obtain off white precipitate, 1-(3-p-Tolyl-prop-2-ynyl)-1H-pyrazole-4-carboxylic acid (0.182 g, 90%).

$^1$HNMR (400 MHz, $CDCl_3$): δ 2.37 (s, 3H); 5.2 (s, 2H); 7.16 (d, J=7.6 Hz, 2H); 7.38 (d, J=8 Hz, 2H); 8.01 (s, 1H); 8.29 (s, 1H)

Step III 1,3-Dipropyl-8-[1-(3-p-tolyl-prop-2ynyl)-1H-pyrazol-4-yl]-3,7-dihydro-purine-2,6-dione A mixture of 5,6-diamino-1,3-dipropyl-1H-pyrimidine-2,4-dione (0.075 g, 0.33 mmol), 1-(3-p-tolyl-prop-2-ynyl)-1H-pyrazole-4-carboxylic acid (0.080 gm, 0.33 mmol), methanol (5 ml), EDCI (0.089 g, 0.46 mmol) were taken and stirred for 12 hours at 20-25° C. The reaction mixture was concentrated to obtain intermediate 1-(3-p-tolyl-prop-2-ynyl)-1H-pyrazole-4-carboxylic acid (6-amino-2,4-dioxo-1,3-dipropyl)-1,2,3,4-tetrahydro-pyrimidine-5-yl) amide (50 mg, 34%) which was dissolved in hexamethyldisilazane (HMDS). To this reaction mixture ammonium sulphate (0.010 g) was added. The reaction mixture was refluxed at 140° C. for 18 hrs. The organic volatiles were evaporated and the residue was treated with crushed ice, the precipitate formed was filtered off. The product was then purified by column chromatography (1% MeOH in $CHCl_3$) to obtain 1,3-dipropyl-8-[1-(3-p-tolyl-prop-2ynyl)-1H-pyrazol-4-yl]-3,7-dihydro-purine-2,6-dione (0.035 g, 92%).

$^1$HNMR (400 MHz, DMSO d6): δ 0.76-0.87 (m, 6H); 1.51-1.57 (m, 2H); 1.68-1.74 (m, 2H); 2.29 (s, 3H); 3.82 (t, J=7.2 Hz, 2H); 3.95 (t, J=7.2 Hz, 2H); 5.36 (s, 2H); 7.18 (d, J=8 Hz, 2H); 7.35 (d. J=8 Hz, 2H); 8.08 (s, 1H); 8.49 (s, 1H); 13.9 (bs, 1H)

Example B1

8-{1-[3-(3-Fluoro-phenyl)-prop-2-ynyl]-1H-pyrazol-4-yl}-1,3-dimethyl-3,7-dihydro-purine-2,6-dione

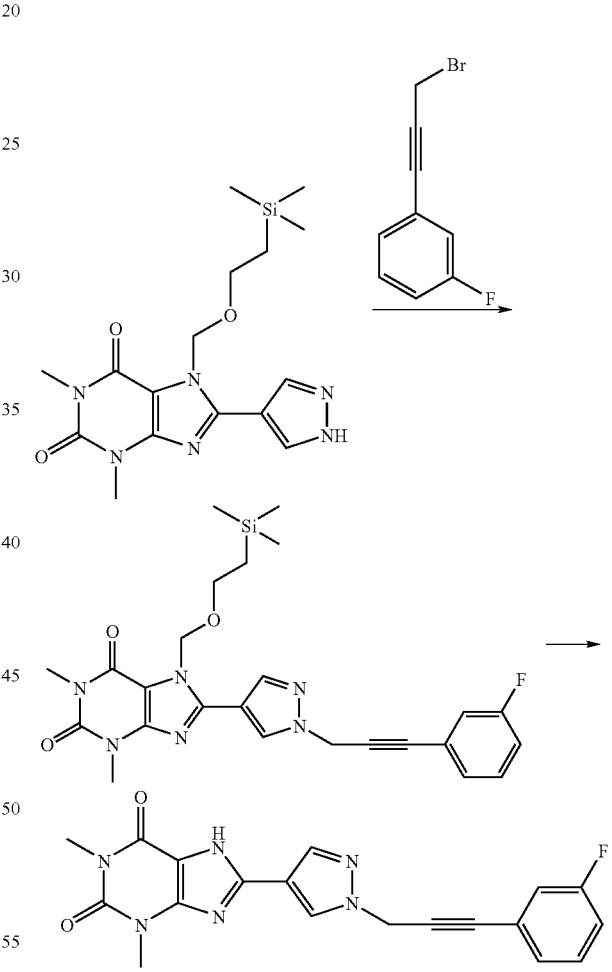

3-(3-Fluoro-phenyl)-prop-2-yn-1-ol

A mixture of propargyl alcohol (0.200 g, 5.4 mmol), 3-fluoro iodobenzene (0.63 ml, 5.4 mmol), copper iodide (0.103 g, 0.54 mol), dichlorobis (triphenylphosphine) palladium (II) (0.190 g, 0.3 mmol), diethylamine (10 ml) was degassed for 10 min. and stirred for 20 hrs at 25-25° C. Excess of diethyl amine was distilled off under vacuum. The residue was diluted with water (10 ml) and extracted with ethyl acetate. The organic layer was washed with brine solution and dried over Na$_2$SO$_4$. The solvent was evaporated and the crude product was purified by column chromatography (10% Ethyl acetate in hexane) to obtain pure 3-(3-fluoro-phenyl)-prop-2-yn-1-ol (0.750 g, 93%).

$^1$HNMR (400 MHz, CDCl$_3$): δ 1.68 (t, J=4.8 Hz, 1H); 4.50 (d, J=4.8 Hz, 2H); 7.04-7.05 (m, 1H); 7.13-7.15 (m, 1H); 7.21-7.23 (m, 1H); 7.27-7.30 (m, 1H)

1-(3-Bromo-prop-1-ynyl)-3-fluoro benzene 3-(3-Fluoro-phenyl)-prop-2-yn-1-ol (0.750 g, 0.005 mol) was taken in diethyl ether (10 ml) containing catalytic amount of pyridine (0.05 ml). The reaction mixture was then cooled to −5-0° C. Tribromo phosphine (0.26 ml, 0.003 mol) was added slowly at −5-0° C. and stirred at the same temperature for 3 hrs. The reaction mixture was quenched with saturated NaHCO$_3$ solution and extracted with ethyl acetate. The organic layer was washed with saturated brine solution, dried over Na$_2$SO$_4$, and evaporated under vacuum to get 1-(3-bromo-prop-1-ynyl)-3-fluoro benzene (0.805 gm, 76%).

$^1$HNMR (400 MHz, CDCl$_3$): δ 4.15 (s, 2H); 7.04-7.08 (m, 1H); 7.13-7.16 (m, 1H); 7.22-7.24 (m, 1H); 728-7.32 (m, 1H)

Step I

8-{1-[3-(3-Fluoro-phenyl)-prop-2-ynyl]-1H-pyrazol-4-yl}-1,3-dimethyl-7-(2-trimethylsilanyl-ethoxymethyl)-3,7-dihydro-purine-2,6-dione A mixture of 1,3-dimethyl-8-(1H-pyrazol-4-yl)-7-(2-trimethylsilanyl-ethoxymethyl)-3,7-dihydro-purine-2,6-dione (obtained following literature procedure U.S. Pat. No. 6,825,349) (0.100 g, 0.27 mmol), 1-(3-Bromo-prop-1-ynyl)-3-fluoro benzene (0.057 g, 0.27 mmol), K$_2$CO$_3$ (0.086 mg, 0.62 mmol) and acetone (5 ml) were refluxed at 80° C. for 5 hrs. The reaction mixture was cooled to room temperature and filtered off solid K$_2$CO$_3$ and evaporated excess of organic solvent under vacuum. The product was purified by column chromatography (2% methanol in dichloromethane) to get pure 8-{1-[3-(3-fluoro-phenyl)-prop-2-ynyl]-1H-pyrazol-4-yl}-1,3-dimethyl-7-(2-trimethylsilanyl-ethoxymethyl)-3,7-dihydro-purine-2,6-dione (0.111 g, 82%).

$^1$HNMR (400 MHz, CDCl$_3$): δ 0.12 (s, 9H); 0.96 (t, J=7.2 Hz, 2H); 3.45 (s, 3H); 3.66 (s, 3H); 3.82 (t, J=8.4 Hz, 2H); 5.26 (s, 2H); 5.82 (s, 2H); 7.09-7.1 (m, 1H); 7.20 (m, 1H); 7.28-7.33 (m, 2H); 8.20 (s, 1H); 8.43 (s, 1H)

Step II

8-{1-[3-(3-Fluoro-phenyl)-prop-2-ynyl]-1H-pyrazol-4-yl}-1,3-dimethyl-3,7-dihydro-purine-2,6-dione 8-{1-[3-(3-Fluoro-phenyl)-prop-2-ynyl]-1H-pyrazol-4-yl}-1,3-dimethyl-7-(2-trimethylsilanyl-ethoxymethyl)-3,7-dihydro-purine-2,6-dione (0.100 g, 0.19 mmol) in EtOH (5 mL) was treated with 2N HCl (1.1 mL) and heated at 80° C. for 2 hrs. The reaction mixture was concentrated in vacuo, and the residue was triturated with diethyl ether to afford 8-{1-[3-(3-Fluoro-phenyl)-prop-2-ynyl]-1H-pyrazol-4-yl}-1,3-dimethyl-3,7-dihydro-purine-2,6-dione in (0.040 mg, 54%) as a white solid.

$^1$HNMR (400 MHz, DMSO d6): δ 3.26 (s, 3H); 3.47 (s, 3H); 5.42 (s, 2H); 7.29-7.38 (m, 3H); 7.43-7.47 (m, 1H); 8.13 (s, 1H); 8.53 (s, 1H); 13.6 (bs, 1H)

Examples B2-B58 were prepared in an analogous manner of Example B1 from the appropriate intermediates.

| Example | IUPAC name |
|---|---|
| B2 | 8-{1-[3-(4-Fluoro-phenyl)-prop-2-ynyl]-1H-pyrazol-4-yl}-1,3-dimethyl-3,7-dihydro-purine-2,6-dione |
| B3 | 8-{1-[3-(4-Fluoro-phenyl)-prop-2-ynyl]-1H-pyrazol-4-yl}-1,3-dipropyl-3,7-dihydro-purine-2,6-dione |
| B4 | 8-{1-[3-(4-Methoxy-phenyl)-prop-2-ynyl]-1H-pyrazol-4-yl}-1,3-dimethyl-3,7-dihydro-purine-2,6-dione |
| B5 | 8-{1-[3-(4-Methoxy-phenyl)-prop-2-ynyl]-1H-pyrazol-4-yl}-1,3-dipropyl-3,7-dihydro-purine-2,6-dione |
| B6 | 8-{1-[3-(2,4-Difluoro-phenyl)-prop-2-ynyl]-1H-pyrazol-4-yl}-1,3-dipropyl-3,7-dihydro-purine-2,6-dione |
| B7 | 8-{1-[3-(3-trifluoromethoxy-phenyl)-prop-2-ynyl]-1H-pyrazol-4-yl}-1,3-dipropyl-3,7-dihydro-purine-2,6-dione |
| B8 | 8-{1-[3-(3-trifluoromethyl-phenyl)-prop-2-ynyl]-1H-pyrazol-4-yl}-1,3-dipropyl-3,7-dihydro-purine-2,6-dione |
| B9 | 8-{1-[3-(4-trifluoromethyl-phenyl)-prop-2-ynyl]-1H-pyrazol-4-yl}-1,3-dimethyl-3,7-dihydro-purine-2,6-dione |
| B10 | 4-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester |
| B11 | 3-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester |
| B12 | 3-{3-[4-(2,6-Dioxo-1,3-dipropyl-2,3,6,7-tetrahydro-1H-purin-8-yl)-pyrazol-1-yl]-prop-1-ynyl}-benzonitrile |
| B13 | 8-{1-[3-(3-Methoxy-phenyl)-prop-2-ynyl]-1H-pyrazol-4-yl}-1,3-dipropyl-3,7-dihydro-purine-2,6-dione |
| B14 | 2-{3-[4-(2,6-Dioxo-1,3-dipropyl-2,3,6,7-tetrahydro-1H-purin-8-yl)-pyrazol-1-yl]-prop-1-ynyl}-benzoic acid methyl ester |
| B15 | 8-{1-[4-(4-Fluoro-phenyl)-but-3-ynyl]-1H-pyrazol-4-yl}-1,3-dipropyl-3,7-dihydro-purine-2,6-dione. |
| B16 | 8-{1-[4-(3-Fluoro-phenyl)-but-3-ynyl]-1H-pyrazol-4-yl}-1,3-dipropyl-3,7-dihydro-purine-2,6-dione. |
| B17 | 1,3-Dipropyl-8-[1-(4-p-tolyl-but-3-ynyl)-1H-pyrazol-4-yl]-3,7-dihydro-purine-2,6-dione. |
| B18 | 1,3-Dipropyl-8-{1-[4-(3-trifluoromethyl-phenyl)-but-3-ynyl]-1H-pyrazol-4-yl}-3,7-dihydro-purine-2,6-dione. |
| B19 | 3-{3-[4-(2,6-Dioxo-1,3-dipropyl-2,3,6,7-tetrahydro-1H-purin-8-yl)-pyrazol-1-yl]-prop-1-ynyl}-benzoic acid. |
| B20 | 1,3-Dipropyl-8-{1-[3-(2-trifluoromethyl-phenyl)-prop-2-ynyl]-1H-pyrazol-4-yl}-3,7-dihydro-purine-2,6-dione. |
| B21 | 1,3-Dipropyl-8-[1-(3-m-tolyl-prop-2-ynyl)-1H-pyrazol-4-yl]-3,7-dihydro-purine-2,6-dione. |
| B22 | 3-Ethyl-1-propyl-8-{1-[3-(3-trifluoromethoxy-phenyl)-prop-2-ynyl]-1H-pyrazol-4-yl}-3,7-dihydro-purine-2,6-dione. |
| B23 | 3-Ethyl-1-propyl-8-{1-[3-(4-trifluoromethyl-phenyl)-prop-2-ynyl]-1H-pyrazol-4-yl}-3,7-dihydro-purine-2,6-dione. |
| B24 | 3-Ethyl-1-propyl-8-[1-(3-p-tolyl-prop-2-ynyl)-1H-pyrazol-4-yl]-3,7-dihydro-purine-2,6-dione. |
| B25 | 3-Ethyl-8-{1-[3-(3-fluoro-phenyl)-prop-2-ynyl]-1H-pyrazol-4-yl}-1-propyl-3,7-dihydro-purine-2,6-dione. |
| B26 | 1,3-Dipropyl-8-{1-[3-(4-trifluoromethyl-phenyl)-prop-2-ynyl]-1H-pyrazol-4-yl}-3,7-dihydro-purine-2,6-dione. |
| B27 | 1,3-Dipropyl-8-{1-[3-(4-trifluoromethoxy-phenyl)-prop-2-ynyl]-1H-pyrazol-4-yl}-3,7-dihydro-purine-2,6-dione. |
| B28 | 3-Ethyl-8-{1-[3-(4-fluoro-phenyl)-prop-2-ynyl]-1H-pyrazol-4-yl}-1-propyl-3,7-dihydro-purine-2,6-dione. |
| B29 | 3-{3-[4-(3-Ethyl-2,6-dioxo-1-propyl-2,3,6,7-tetrahydro-1H-purin-8-yl)-pyrazol-1-yl]-prop-1-ynyl}-benzoic acid. |
| B30 | 3-Ethyl-1-propyl-8-[1-(3-m-tolyl-prop-2-ynyl)-1H-pyrazol-4-yl]-3,7-dihydro-purine-2,6-dione. |
| B31 | 3-Ethyl-8-{1-[3-(4-methoxy-phenyl)-prop-2-ynyl]-1H-pyrazol-4-yl}-1-propyl-3,7-dihydro-purine-2,6-dione. |
| B32 | 3-Ethyl-1-propyl-8-{1-[3-(4-trifluoromethoxy-phenyl)-prop-2-ynyl]-1H-pyrazol-4-yl}-3,7-dihydro-purine-2,6-dione. |
| B33 | 3-Ethyl-8-{1-[3-(3-methoxy-phenyl)-prop-2-ynyl]-1H-pyrazol-4-yl}-1-propyl-3,7-dihydro-purine-2,6-dione. |
| B34 | 4-{3-[4-(3-Ethyl-2,6-dioxo-1-propyl-2,3,6,7-tetrahydro-1H-purin-8-yl)-pyrazol-1-yl]-prop-1-ynyl}-benzoic acid. |
| B35 | 4-{3-[4-(2,6-Dioxo-1,3-dipropyl-2,3,6,7-tetrahydro-1H-purin-8-yl)-pyrazol-1-yl]-prop-1-ynyl}-benzonitrile. |
| B36 | (3-{3-[4-(2,6-Dioxo-1,3-dipropyl-2,3,6,7-tetrahydro-1H-purin-8-yl)-pyrazol-1-yl]-prop-1-ynyl}-phenoxy)-acetic acid. |
| B37 | 8-{1-[3-(3-tert-Butyl-phenyl)-prop-2-ynyl]-1H-pyrazol-4-yl}-1,3-dipropyl-3,7-dihydro-purine-2,6-dione. |
| B38 | 4-{3-[4-(2,6-Dioxo-1,3-dipropyl-2,3,6,7-tetrahydro-1H-purin-8-yl)-pyrazol-1-yl]-prop-1-ynyl}-benzoic acid. |
| B39 | (3-{3-[4-(2,6-Dioxo-1,3-dipropyl-2,3,6,7-tetrahydro-1H-purin-8-yl)-pyrazol-1-yl]-prop-1-ynyl}-phenyl)-acetic acid. |

| Example | IUPAC name |
|---|---|
| B40 | (4-{3-[4-(2,6-Dioxo-1,3-dipropyl-2,3,6,7-tetrahydro-1H-purin-8-yl)-pyrazol-1-yl]-prop-1-ynyl}-phenyl)-acetic acid. |
| B41 | 8-{1-[3-(3-Fluoro-phenyl)-prop-2-ynyl]-1H-pyrazol-4-yl}-1,3-dipropyl-3,7-dihydro-purine-2,6-dione |
| B42 | 3-{3-[4-(2,6-Dioxo-1,3-dipropyl-2,3,6,7-tetrahydro-1H-purin-8-yl)-pyrazol-1-yl]-prop-1-ynyl}-N-isopropyl-benzamide |
| B43 | 1,3-Dipropyl-8-(1-{3-[3-(pyrrolidine-1-carbonyl)-phenyl]-prop-2-ynyl}-1H-pyrazol-4-yl)-3,7-dihydro-purine-2,6-dione |
| B44 | 3-{3-[4-(2,6-Dioxo-1,3-dipropyl-2,3,6,7-tetrahydro-1H-purin-8-yl)-pyrazol-1-yl]-prop-1-ynyl}-4-methyl-benzoic acid |
| B45 | 8-{1-[3-(3-Chloro-phenyl)-prop-2-ynyl]-1H-pyrazol-4-yl}-1,3-dipropyl-3,7-dihydro-purine-2,6-dione |
| B46 | 3-{3-[4-(2,6-Dioxo-1,3-dipropyl-2,3,6,7-tetrahydro-1H-purin-8-yl)-pyrazol-1-yl]-prop-1-ynyl}-4-methoxy-benzoic acid |
| B47 | 5-{3-[4-(2,6-Dioxo-1,3-dipropyl-2,3,6,7-tetrahydro-1H-purin-8-yl)-pyrazol-1-yl]-prop-1-ynyl}-pyridine-2-carboxylic acid methyl ester |
| B48 | 1,3-Dipropyl-8-{3-[3-(3-trifluoromethyl-phenyl)-prop-2-ynyloxy]-isoxazol-5-yl}-3,7-dihydro-purine-2,6-dione |
| B49 | 8-{3-[3-(2,4-Difluoro-phenyl)-prop-2-ynyloxy]-isoxazol-5-yl}-1,3-dipropyl-3,7-dihydro-purine-2,6-dione |
| B50 | 8-{3-[3-(4-Fluoro-phenyl)-prop-2-ynyloxy]-isoxazol-5-yl}-1,3-dipropyl-3,7-dihydro-purine-2,6-dione |
| B51 | 8-{3-[3-(3-Fluoro-phenyl)-prop-2-ynyloxy]-isoxazol-5-yl}-1,3-dipropyl-3,7-dihydro-purine-2,6-dione |
| B52 | 1,3-Dipropyl-8-{3-[3-(4-trifluoromethyl-phenyl)-prop-2-ynyloxy]-isoxazol-5-yl}-3,7-dihydro-purine-2,6-dione |
| B53 | 1,3-Dipropyl-8-{3-[3-(p-tolyl-prop-2-ynyloxy)-isoxazol-5-yl]-3,7-dihydro-purine-2,6-dione |
| B54 | 8-{3-[3-(3-tert-Butyl-phenyl)-prop-2-ynyloxy]-isoxazol-5-yl}-1,3-dipropyl-3,7-dihydro-purine-2,6-dione |
| B55 | 1,3-Dipropyl-8-{3-[3-(3-trifluoromethoxy-phenyl)-prop-2-ynyloxy]-isoxazol-5-yl}-3,7-dihydro-purine-2,6-dione |
| B56 | 8-{1-Methyl-5-[3-(3-trifluoromethyl-phenyl)-prop-2-ynyloxy]-1H-pyrazol-3-yl}-1,3-dipropyl-3,7-dihydro-purine-2,6-dione |
| B57 | 8-{1-Methyl-5-[3-(4-trifluoromethoxy-phenyl)-prop-2-ynyloxy]-1H-pyrazol-3-yl}-1,3-dipropyl-3,7-dihydro-purine-2,6-dione |
| B58 | 8-{5-[3-(3-Methoxy-phenyl)-prop-2-ynyloxy]-1-methyl-1H-pyrazol-3-yl}-1,3-dipropyl-3,7-dihydro-purine-2,6-dione |

Example C1

1,3-Dipropyl-8-{4-[3-(4-trifluoromethoxy-phenyl)-prop-2-ynyloxy]-phenyl}-3,7-dihydro-purine-2,6-dione

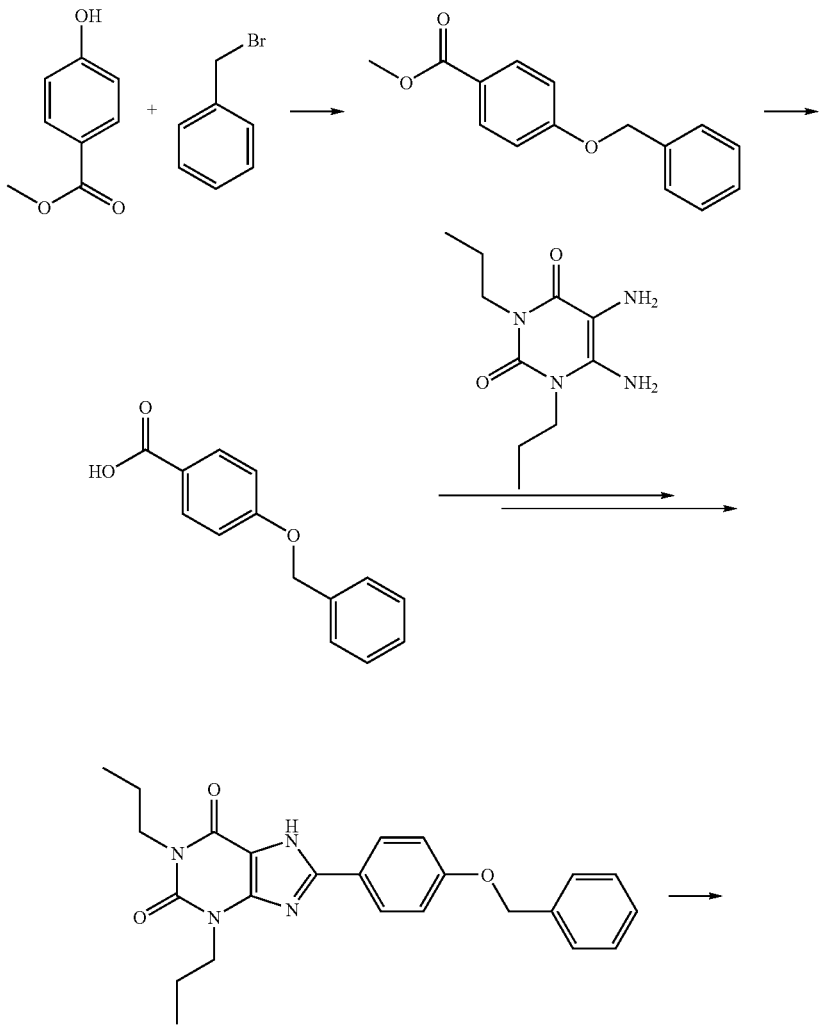

-continued
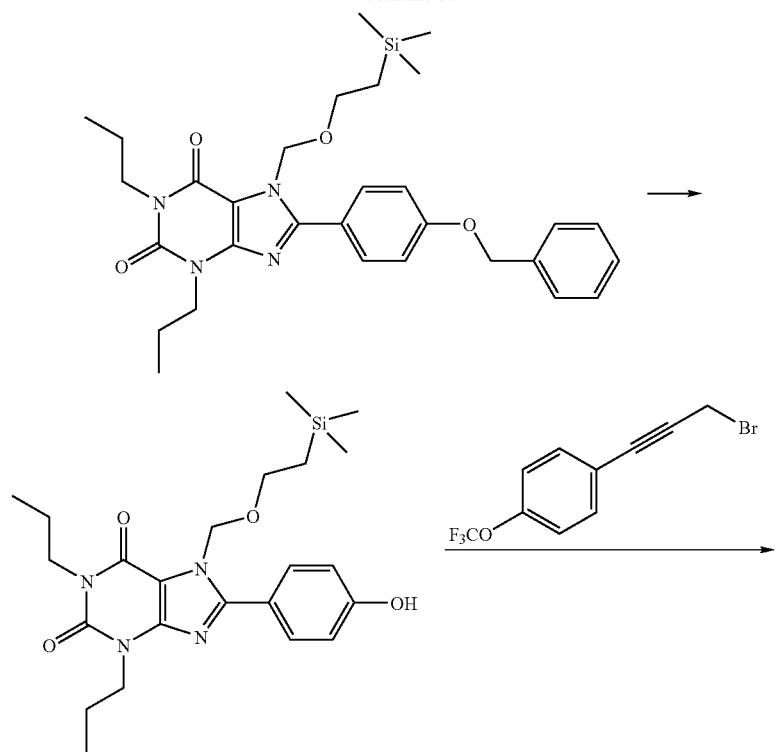
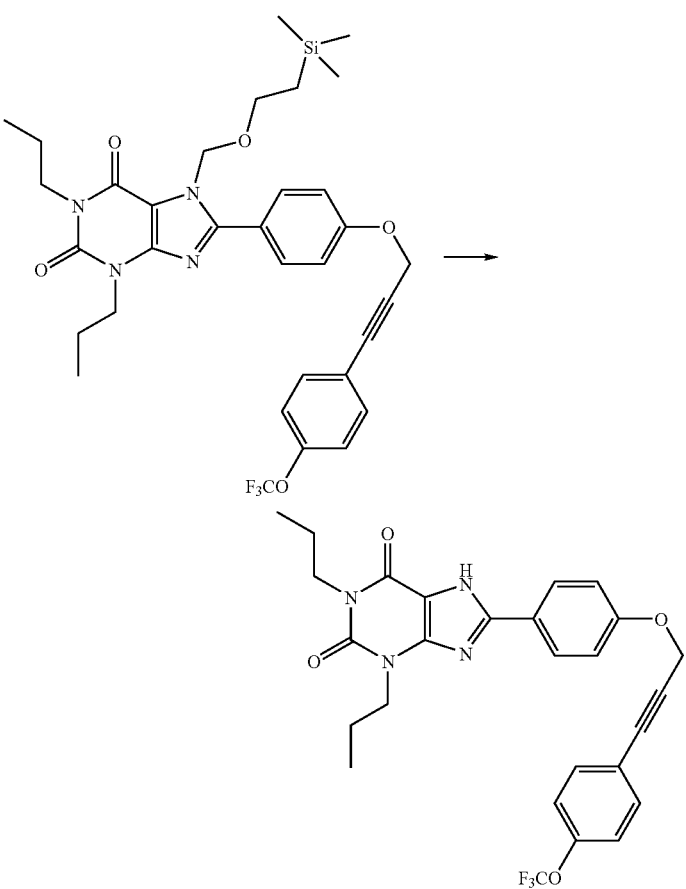

Step-I

4-Benzyloxy-benzoic acid methyl ester

A mixture of methyl 4-hydroxy-benzoate (10.0 g, 0.066 mol) and potassium carbonate (20.9 g, 0.098 mol), were taken in acetone (50 ml) and heated at 50° C. for 1 hour. To the reaction mixture, benzyl bromide (8.6 ml, 0.072 mol) was added and heated at 80° C. for 5 hours. The mixture was cooled to room temperature and filtered, washed with acetone. Solvent was removed to obtain pure 4-benzyloxy-benzoic acid methyl ester as white solid (16 g, 100%).

$^1$HNMR (400 MHz, CDCl$_3$): δ 3.85 (s, 3H); 5.17 (s, 2H); 6.99 (d, J=8.8 Hz, 2H); 7.38-7.42 (m, 5H); 8.00 (d, J=8.8 Hz, 2H)

Step II

4-Benzyloxy-benzoic acid

4-Benzyloxy-benzoic acid methyl ester (8.0 g, 0.033 mol) was dissolved in THF:methanol:water (3:2:1, 80 ml) and NaOH (1.98 g, 0.05 mol) was added to the reaction mixture and stirred at 50-55° C. for 3 hours. Solvents were removed and residue was diluted with water, washed with hexane and acidified with dil HCl to obtain 4-benzyloxy-benzoic acid (7.0 g, 92%) as a white solid.

$^1$HNMR (400 MHz, CDCl$_3$): δ 5.14 (s, 2H); 7.02 (d, J=8.8 Hz, 2H); 7.4-7.42 (m, 5H); 8.05 (d, J=8.8 Hz, 2H).

Step III

8-(4-Benzyloxy-phenyl)-1,3-dipropyl-3,7-dihydro-purine-2,6-dione

A mixture of 4-benzyloxy-benzoic acid (0.868 g, 3.8 mmol), 5,6-diamino-1,3-dipropyl-1H-pyrimidine-2,4-dione (1.0 g, 3.8 mmol), methanol (15 ml), EDCI (0.95 g, 4.9 mmol), was stirred for 20 hours at room temperature. The reaction mixture was concentrated and water was added to obtain the intermediate N-(6-amino-2,4-dioxo-1,3-dipropyl-1,2,3,4-tetrahydro-pyrimidin-5-yl)-4-benzyloxy-benzamide. It was dissolved in methanol (32 ml) and added 10% NaOH (24 ml). The mixture was heated at 80-90° C. for 3 hours. The mixture was cooled and solvent was removed. The residue was dissolved in water (20 ml) acidified with dil HCl to provide 8-(4-benzyloxy-phenyl)-1,3-dipropyl-3,7-dihydro-purine-2,6-dione (1.2 g, 75%) as a white solid.

$^1$HNMR (400 MHz, DMSO d6): δ 0.82-0.89 (m, 6H); 1.52-1.57 (m, 2H); 1.68-1.73 (m, 2H); 3.83 (t, J=7.2 Hz, 2H); 3.98 (t, J=6.8 Hz, 2H); 5.14 (s, 2H); 7.09 (d, J=8.8 Hz, 2H); 7.3-7.45 (m, 5H); 8.03 (d, J=8.8 Hz, 2H); 13.58 (bs, 1H)

Step IV

8-(4-Benzyloxy-phenyl)-1,3-dipropyl-7-(2-trimethyl-silanyl-ethoxymethyl)-3,7-dihydro-purine-2,6-dione A mixture of 8-(4-benzyloxy-phenyl)-1,3-dipropyl-3,7-dihydro-purine-2,6-dione (1.2 g, 2.9 mmol) and potassium carbonate (1.19 g, 8.6 mmol), were taken in DMF (15 ml) and 2-(trimethylsilyl)ethoxymethyl chloride (1.52 ml, 8.6 mmol) was added drop wise at 0° C. and mixture was stirred at room temperature for 20 hours. The mixture was cooled to 10° C. and diluted with water, extracted with ethyl acetate. The organic layer was washed with saturated brine solution and dried over Na$_2$SO$_4$. Solvent was removed and residue obtained was further purified by column chromatography to obtain pure 8-(4-benzyloxy-phenyl)-1,3-dipropyl-7-(2-trimethylsilanyl-ethoxymethyl)-3,7-dihydro-purine-2,6-dione (1.12 g, 71%).

$^1$HNMR (400 MHz, CDCl$_3$): δ 0.12 (s, 9H); 0.94-1.00 (m, 8H); 1.66-1.72 (m, 2H); 1.81-1.86 (m, 2H); 3.89 (t, J=8.4 Hz, 2H); 4.00 (t, J=7.6 Hz, 2H); 4.13 (t, J=7.2 Hz, 2H); 4.70 (s, 2H); 5.71 (s, 2H); 7.08 (d. J=8.8 Hz, 2H); 7.34-7.45 (m, 5H); 7.93 (d, J=8.8 Hz, 2H).

Step V

8-(4-Hydroxy-phenyl)-1,3-dipropyl-7-(2-trimethylsilanyl-ethoxymethyl)-3,7-dihydro-purine-2,6-dione To a solution of 8-(4-benzyloxy-phenyl)-1,3-dipropyl-7-(2-trimethylsilanyl-ethoxymethyl)-3,7-dihydro-purine-2,6-dione (0.500 g, 0.91 mmol) in methanol (10 ml), 10% Pd/C (0.150 g) was added and stirred at room temperature under hydrogen atmosphere for 2 hours. The mixture was filtered, solvent was removed and the residue was washed with hexane to obtain 8-(4-hydroxy-phenyl)-1,3-dipropyl-7-(2-trimethylsilanyl-ethoxymethyl)-3,7-dihydro-purine-2,6-dione as a white solid (0.398 g, 95%).

$^1$HNMR (400 MHz, CDCl$_3$): δ 0.12 (s, 9H); 0.94-1.00 (m, 8H); 1.66-1.72 (m, 2H); 1.81-1.86 (m, 2H); 3.89 (t, J=8.4 Hz, 2H); 4.00 (t, J=7.6 Hz, 2H); 4.13 (t, J=7.2 Hz, 2H); 5.71 (s, 2H); 7.08 (d. J=8.8 Hz, 2H); 7.93 (d, J=8.8 Hz, 2H).

Step VI

1,3-Dipropyl-8-{4-[3-(4-trifluoromethoxy-phenyl)-prop-2-ynyloxy]-phenyl}-7-(2-trimethylsilanyl-ethoxymethyl)-3,7-dihydro-purine-2,6-dione A mixture of 8-(4-hydroxy-phenyl)-1,3-dipropyl-7-(2-trimethylsilanyl-ethoxymethyl)-3,7-dihydro-purine-2,6-dione (0.100 g, 0.22 mmol) and potassium carbonate (0.076 g, 0.53 mmol), 1-(3-bromo-prop-1-ynyl)-4-trifluoromethoxy-benzene (prepared as given in example E1) (0.073 g, 0.26 mmol) in acetone (10 ml) was heated at 80° C. for 2 hours. The mixture was cooled to room temperature, filtered and washed with acetone. Solvent was evaporated to obtain a residue which was purified by preparative TLC to obtain 1,3-dipropyl-8-{4-[3-(4-trifluoromethoxy-phenyl)-prop-2-ynyloxy]-phenyl}-7-(2-trimethylsilanyl-ethoxymethyl)-3,7-dihydro-purine-2,6-dione as a pale yellow solid (0.053 g, 37%).

$^1$HNMR (400 MHz, CDCl$_3$): δ 0.10 (s, 9H); 0.97-10.5 (m, 8H); 1.71-1.74 (m, 2H); 1.86-1.88 (m, 2H); 3.90 (t, J=8 Hz, 2H); 4.03 (t, J=7.2 Hz, 2H); 4.22 (t, J=7.2 Hz, 2H); 5.01 (s, 2H); 5.75 (s, 2H); 7.18 (d, J=8.8 Hz, 2H); 7.26 (d, J=8.8 Hz, 2H); 7.49 (d, J=8.8 Hz, 2H); 8.04 (d, J=8.8 Hz, 2H)

Step VII

1,3-Dipropyl-8-{4-[3-(4-trifluoromethoxy-phenyl)-prop-2-ynyloxy]-phenyl}-3,7-dihydro-purine-2,6-dione A mixture of 1,3-dipropyl-8-{4-[3-(4-trifluoromethoxy-phenyl)-prop-2-ynyloxy]-phenyl}-7-(2-trimethylsilanyl-ethoxymethyl)-3,7-dihydro-purine-2,6-dione (0.053 g, 0.055 mmol), 2N HCl (2 ml), ethanol (2 ml) was heated at 85° C. for 2 hours. The mixture was cooled and the solvent was evaporated. The residue was washed with n-pentane to obtain 1,3-dipropyl-8-{4-[3-(4-trifluoromethoxy-phenyl)-prop-2-ynyloxy]-phenyl}-3,7-dihydro-purine-2,6-dione (0.038 g, 88%).

1HNMR (400 MHz, DMSO d6): δ 0.84-0.90 (m, 6H); 1.54-1.559 (m, 2H); 1.7-1.75 (m, 2H); 3.85 (t, J=7.6 Hz, 2H); 3.99 (t, J=7.2 Hz, 2H); 5.13 (s, 2H); 7.17 (d, J=8.8 Hz, 2H); 7.37 (d, J=8.4 Hz, 2H); 7.59 (d, J=8.4 Hz, 2H); 8.09 (d, J=8.8 Hz, 2H); 13.61 (s, 1H)

Examples C2-C15 were prepared in an analogous manner of Example C1 from the appropriate intermediates.

| Example | IUPAC name |
|---|---|
| C2 | 1,3-Dipropyl-8-[4-(3-p-tolyl-prop-2-ynyloxy)-phenyl]-3,7-dihydro-purine-2,6-dione |
| C3 | 8-{4-[3-(3-Fluoro-phenyl)-prop-2-ynyloxy]-phenyl}-1,3-dipropyl-3,7-dihydro-purine-2,6-dione |
| C4 | 3-{3-[4-(2,6-Dioxo-1,3-dipropyl-2,3,6,7-tetrahydro-1H-purin-8-yl)-phenoxy]-prop-1-ynyl}-benzoic acid ethyl ester |
| C5 | 3-{3-[4-(2,6-Dioxo-1,3-dipropyl-2,3,6,7-tetrahydro-1H-purin-8-yl)-phenoxy]-prop-1-ynyl}-benzoic acid |
| C6 | 1,3-Dipropyl-8-{4-[3-(4-trifluoromethyl-phenyl)-prop-2-ynyloxy]-phenyl}-3,7-dihydro-purine-2,6-dione |
| C7 | 8-{4-[3-(4-Fluoro-phenyl)-prop-2-ynyloxy]-phenyl}-1,3-dipropyl-3,7-dihydro-purine-2,6-dione |
| C8 | 1,3-Dipropyl-8-{4-[3-(3-trifluoromethoxy-phenyl)-prop-2-ynyloxy]-phenyl}-3,7-dihydro-purine-2,6-dione |
| C9 | 8-{4-[3-(3-Methoxy-phenyl)-prop-2-ynyloxy]-phenyl}-1,3-dipropyl-3,7-dihydro-purine-2,6-dione |
| C10 | 8-{6-[3-(4-Fluoro-phenyl)-prop-2-ynyloxy]-pyridin-3-yl}-1,3-dipropyl-3,7-dihydro-purine-2,6-dione |
| C11 | 1,3-Dipropyl-8-{3-[3-(3-trifluoromethyl-phenyl)-prop-2-ynyloxy]-phenyl}-3,7-dihydro-purine-2,6-dione |
| C12 | 1,3-Dipropyl-8-{3-[3-(3-trifluoromethoxy-phenyl)-prop-2-ynyloxy]-phenyl}-3,7-dihydro-purine-2,6-dione |
| C13 | 8-{3-[3-(3-Fluoro-phenyl)-prop-2-ynyloxy]-phenyl}-1,3-dipropyl-3,7-dihydro-purine-2,6-dione |
| C14 | 1,3-Dipropyl-8-{3-[3-(4-trifluoromethyl-phenyl)-prop-2-ynyloxy]-phenyl}-3,7-dihydro-purine-2,6-dione |
| C15 | 1,3-Dipropyl-8-[3-(3-p-tolyl-prop-2-ynyloxy)-phenyl]-3,7-dihydro-purine-2,6-dione |

Example D1

8-{1-[4-(4-Methyl-piperazin-1-yl)-but-2-ynyl]-1H-pyrazol-4-yl}-1,3-dipropyl-3,7-dihydro-purine-2,6-dione

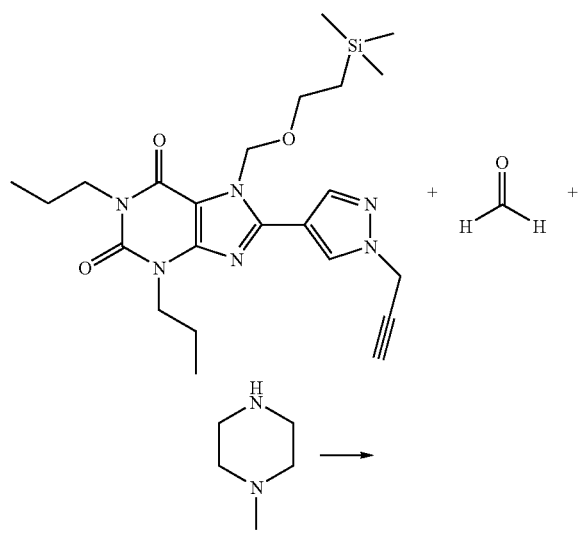

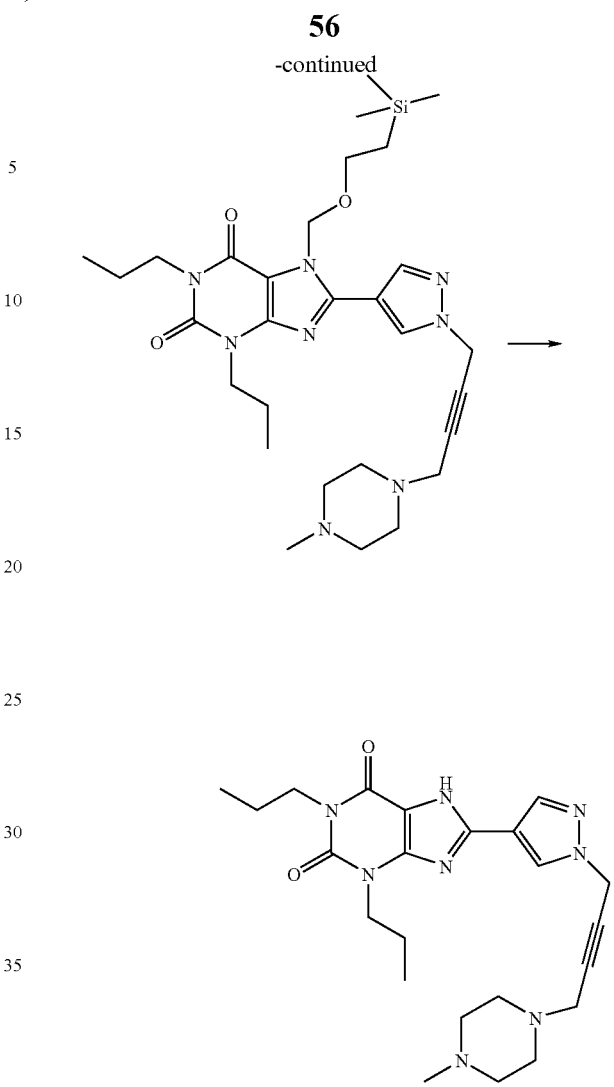

Step I

8-{1-[4-(4-Methyl-piperazin-1-yl)-but-2-ynyl]-1H-pyrazol-4-yl}-1,3-dipropyl-7-(2-trimethylsilanyl-ethoxymethyl)-3,7-dihydro-purine-2,6-dione A mixture of 1,3-dipropyl-8-(1-prop-2-ynyl-1H-pyrazol-4-yl)-7-(2-trimethylsilanyl-ethoxymethyl)-3,7-dihydro-purine-2,6-dione (0.1 g, 0.212 mmol), N-methyl piperazine (0.025 g, 0.254 mmol), formaldehyde (0.08 ml), CuI (0.008 g), and DMSO (2 ml) was stirred at 30° C. for 72 hours. The mixture was cooled to 25° C. and the residue was diluted with water (10 ml) and extracted with ethylacetate (2×10 ml). The organic layer was washed with saturated brine solution (50 ml) and dried over Na$_2$SO$_4$. The solvent was evaporated to obtain pure 8-{1-[4-(4-Methyl-piperazin-1-yl)-but-2-ynyl]-1H-pyrazol-4-yl}-1,3-dipropyl-7-(2-trimethylsilanyl-ethoxymethyl)-3,7-dihydro-purine-2,6-dione (0.105 g, 85%).

1HNMR (400 MHz, DMSO d6): δ 0.10 (s, 9H); 0.82-0.93 (m, 8H); 1.54-1.57 (m, 2H); 1.70-1.72 (m, 2H); 2.49-2.53 (m, 8H); 3.29 (s, 3H); 3.39-3.41 (m, 2H); 3.66 (t, J=8 Hz, 2H); 3.86 (t, J=6.4 Hz, 2H); 3.96-4.0 (m, 2H); 5.19 (s, 2H); 5.76 (s, 2H); 8.02 (s, 1H); 8.40 (s, 1H).

Step II

8-{1-[4-(4-Methyl-piperazin-1-yl)-but-2-ynyl]-1H-pyrazol-4-yl}-1,3-dipropyl-3,7-dihydro-purine-2,6-dione A mixture of 8-{1-[4-(4-Methyl-piperazin-1-yl)-but-2-ynyl]-1H-pyrazol-4-yl}-1,3-dipropyl-7-(2-trimethylsilanyl-ethoxymethyl)-3,7-dihydro-purine-2,6-dione (0.105 g, 0.180 mmol), 2N HCl (2 ml), ethanol (4 ml) was heated at 85° C. for 2 hours. The mixture was cooled and solvent was evaporated. The residue was triturated with diethyl ether and purified by preparative TLC to obtain pure 8-{1-[4-(4-Methyl-piperazin-1-yl)-but-2-ynyl]-1H-pyrazol-4-yl}-1,3-dipropyl-3,7-dihydro-purine-2,6-dione (0.042 g, 52%).

$^1$HNMR (400 MHz, DMSO d6): δ 0.82-0.89 (m, 6H); 1.51-1.53 (m, 2H); 1.68-1.70 (m, 2H); 2.12 (s, 2H); 2.44-2.50 (m, 8H); 3.31 (s, 3H); 3.81 (t, J=6.8 Hz, 2H); 3.92 (t, J=6.8 Hz, 2H); 5.07 (s, 2H); 7.82 (s, 1H); 8.09 (s, 1H).

Examples D2-D6 were prepared in an analogous manner of Example D1 from the appropriate intermediates.

| Example | IUPAC name |
|---|---|
| D2 | 1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid ethyl ester. |
| D3 | 1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid. |
| D4 | 8-(1-{4-[4-(4-Chloro-phenyl)-4-hydroxy-piperidin-1-yl]-but-2-ynyl}-1H-pyrazol-4-yl)-1,3-dipropyl-3,7-dihydro-purine-2,6-dione |
| D5 | 1,3-Dipropyl-8-(1-{4-[4-(3-trifluoromethyl-phenyl)-piperazin-1-yl]-but-2-ynyl}-1H-pyrazol-4-yl)-3,7-dihydro-purine-2,6-dione. |
| D6 | 1,3-Dimethyl-8-{1-[4-(4-methyl-piperazin-1-yl)-but-2-ynyl]-1H-pyrazol-4-yl}-3,7-dihydro-purine-2,6-dione |

Example E1

1-Propyl-8-[1-(3-p-tolyl-prop-2-ynyl)-1H-pyrazol-4-yl]-3,7-dihydro-purine-2,6-dione

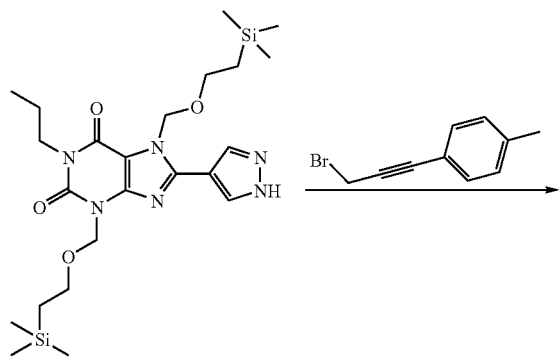

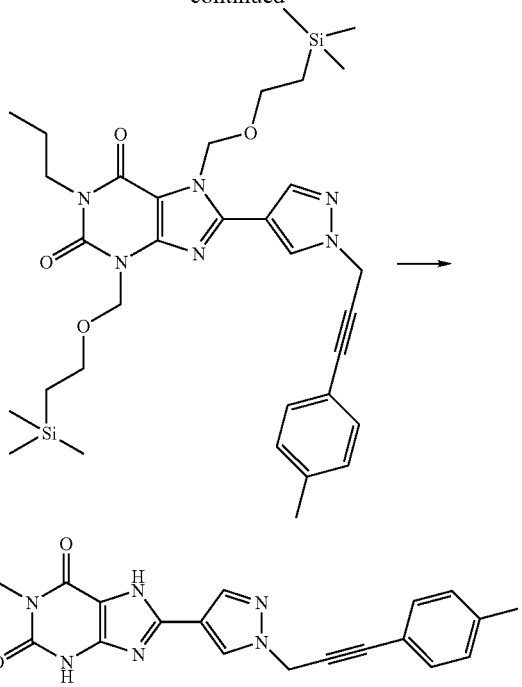

Step I

1-Propyl-8-[1-(3-p-tolyl-prop-2-ynyl)-1H-pyrazol-4-yl]-3,7-bis-(2-trimethylsilanyl-ethoxymethyl)-3,7-dihydro-purine-2,6-dione A mixture of 1-propyl-8-(1H-pyrazol-4-yl)-3,7-bis-(2-trimethylsilanyl-ethoxymethyl)-3,7-dihydro-purine-2,6-dione (prepared as per literature procedure US20080194593) (0.1 g, 0.18 mmol), 1-(3-bromo-prop-1-ynyl)-4-methyl-benzene (prepared according to example E1) (0.039 g, 0.18 mmol), potassium carbonate (0.051 g, 0.37 mmol), and acetone (10 ml) were heated at 50-55° C. for 16 hours. Reaction mixture was cooled to 20-25° C. and filtered off. The filtrate was evaporated and residue was purified by preparative TLC to afford 1-propyl-8-[1-(3-p-tolyl-prop-2-ynyl)-1H-pyrazol-4-yl]-3,7-bis-(2-trimethylsilanyl-ethoxymethyl)-3,7-dihydro-purine-2,6-dione (0.035 g, 28%) as a brown sticky mass.

$^1$HNMR (400 MHz, DMSO d6): δ 0.12 (s, 18H); 0.91-1.02 (m, 7H); 1.68-1.69 (m, 2H); 2.36 (s, 3H); 3.75-3.80 (m, 4H); 3.99 (t, J=7.6 Hz, 2H); 5.22 (s, 2H); 5.6 (s, 2H); 5.78 (s, 2H); 7.13 (d, J=7.6 Hz, 2H); 7.37 (d, J=7.6 Hz, 2H); 8.15 (s, 1H); 8.42 (s, 1H).

Step II

1-Propyl-8-[1-(3-p-tolyl-prop-2-ynyl)-1H-pyrazol-4-yl]-3,7-dihydro-purine-2,6-dione A mixture of 1-propyl-8-[1-(3-p-tolyl-prop-2-ynyl)-1H-pyrazol-4-yl]-3,7-bis-(2-trimethylsilanyl-ethoxymethyl)-3,7-dihydro-purine-2,6-dione obtained in step 1 (0.035 g, 0.053 mmol;), 2 N HCl (1.5 ml), ethanol (3 ml) were heated at 85° C. for 6 hours. The mixture was cooled to 10-15° C. The solid obtained was filtered and washed with water (1 ml), ethanol (1 ml) to afford 1-propyl-8-[1-(3-p-tolyl-prop-2-ynyl)-1H-pyrazol-4-yl]-3,7-dihydro-purine-2,6-dione (0.009 g, 47%) as a brown solid.

$^1$HNMR (400 MHz, DMSO d6): δ 0.84 (t, J=7.2 Hz, 3H); 1.50-1.55 (m, 2H); 2.24 (s, 3H); 3.76 (t, J=7.2 Hz, 2H); 5.34 (s, 2H); 7.17-7.19 (m, 2H); 7.34-7.36 (m, 2H); 8.04 (s, 1H); 8.44 (s, 1H); 11.81 (bs, 1H); 13.39 (bs, 1H)

Examples E2-E8 were prepared in an analogous manner of Example E1 from the appropriate intermediate.

| Example | IUPAC name |
|---------|------------|
| E2 | 1-Propyl-8-{1-[3-(3-trifluoromethyl-phenyl)-prop-2-ynyl]-1H-pyrazol-4-yl}-3,7-dihydro-purine-2,6-dione. |
| E3 | 1-Propyl-8-{1-[3-(3-trifluoromethoxy-phenyl)-prop-2-ynyl]-1H-pyrazol-4-yl}-3,7-dihydro-purine-2,6-dione. |
| E4 | 8-{1-[3-(4-Fluoro-phenyl)-prop-2-ynyl]-1H-pyrazol-4-yl}-1-propyl-3,7-dihydro-purine-2,6-dione. |
| E5 | 8-{1-[3-(3-Fluoro-phenyl)-prop-2-ynyl]-1H-pyrazol-4-yl}-1-propyl-3,7-dihydro-purine-2,6-dione. |
| E6 | 1-Propyl-8-{1-[3-(4-trifluoromethyl-phenyl)-prop-2-ynyl]-1H-pyrazol-4-yl}-3,7-dihydro-purine-2,6-dione. |
| E7 | 1-Propyl-8-{1-[3-(4-trifluoromethoxy-phenyl)-prop-2-ynyl]-1H-pyrazol-4-yl}-3,7-dihydro-purine-2,6-dione. |
| E8 | 3-{3-[4-(2,6-Dioxo-1-propyl-2,3,6,7-tetrahydro-1H-purin-8-yl)-pyrazol-1-yl]-prop-1-ynyl}-benzoic acid. |

Example F1

8-{1-[3-(4-Fluoro-phenyl)-prop-2-ynyl]-1H-pyrazol-4-yl}-7-methyl-1,3-dipropyl-3,7-dihydro-purine-2,6-dione

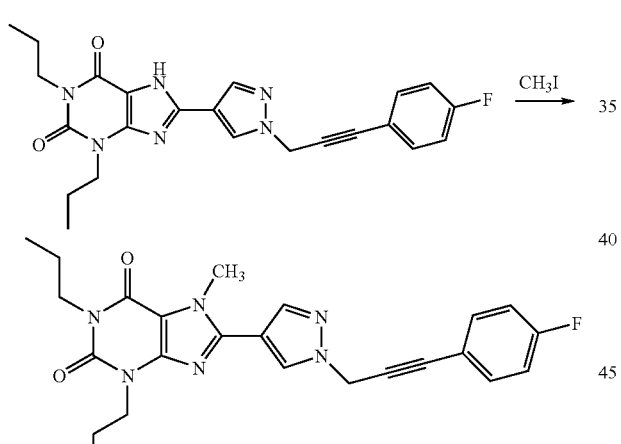

A mixture of 8-{1-[3-(4-fluoro-phenyl)-prop-2-ynyl]-1H-pyrazol-4-yl}-1,3-dipropyl-3,7-dihydro-purine-2,6-dione (0.035 g, 0.08 mmol), potassium carbonate (0.022 g, 0.16 mmol), methyl iodide (0.005 ml, 0.088 mmol) and DMF (2 ml) were heated at 50° C. for 20 hour. The mixture was cooled to room temperature and diluted with water (10 ml). The aqueous layer was extracted with ethyl acetate. The organic layer was washed with water and sat. brine solution, and dried over Na$_2$SO$_4$. Solvent was evaporated, the residue obtained was triturated with hexane to obtain the title compound (0.022 g, 61

$^1$HNMR (400 MHz, CDCl$_3$): δ 0.94-0.99 (m, 6H); 1.65-1.71 (m, 2H); 1.77-1.83 (m, 2H); 3.97 (t, J=7.6 Hz, 2H); 4.05 (t, J=7.6 Hz, 2H); 4.11 (s, 3H); 5.23 (s, 2H); 7.01-7.05 (m, 2H); 7.44-7.47 (m, 2H); 7.96 (s, 1H); 8.18 (s, 1H).

Examples F2-F8 were prepared in an analogous manner of Example F1 from the appropriate intermediate.

| Example | IUPAC name |
|---------|------------|
| F2 | 7-Methyl-1,3-dipropyl-8-{1-[3-(3-trifluoromethoxy-phenyl)-prop-2-ynyl]-1H-pyrazol-4-yl}-3,7-dihydro-purine-2,6-dione. |
| F3 | 7-Methyl-1,3-dipropyl-8-[1-(3-p-tolyl-prop-2-ynyl)-1H-pyrazol-4-yl]-3,7-dihydro-purine-2,6-dione. |
| F4 | 7-Methyl-8-{1-[4-(4-methyl-piperazin-1-yl)-but-2-ynyl]-1H-pyrazol-4-yl}-1,3-dipropyl-3,7-dihydro-purine-2,6-dione. |
| F5 | 8-{1-[3-(3-Fluoro-phenyl)-prop-2-ynyl]-1H-pyrazol-4-yl}--methyl-1,3-dipropyl-3,7-dihydro-purine-2,6-dione |
| F6 | 8-{1-[3-(3-Methoxy-phenyl)-prop-2-ynyl]-1H-pyrazol-4-yl}-7-methyl-1,3-dipropyl-3,7-dihydro-purine-2,6-dione |
| F7 | 8-{1-[3-(3-tert-Butyl-phenyl)-prop-2-ynyl]-1H-pyrazol-4-yl}-7-methyl-1,3-dipropyl-3,7-dihydro-purine-2,6-dione |
| F8 | (3-{3-[4-(7-Methyl-2,6-dioxo-1,3-dipropyl-2,3,6,7-tetrahydro-1H-purin-8-yl)-pyrazol-1-yl]-prop-1-ynyl}-phenoxy)-acetic acid |

Example G1

8-{1-[3-(3-Hydroxymethyl-phenyl)-prop-2-ynyl]-1H-pyrazol-4-yl}-1,3-dipropyl-3,7-dihydro-purine-2,6-dione -continued

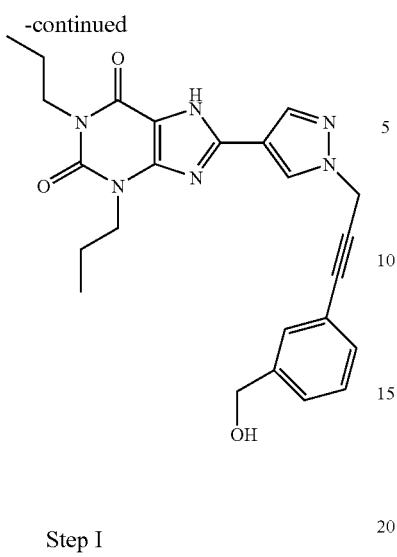

Step I

8-{1-[3-(3-Hydroxymethyl-phenyl)-prop-2-ynyl]-1H-pyrazol-4-yl}-1,3-dipropyl-7-(2-trimethylsilanyl-ethoxymethyl)-3,7-dihydro-purine-2,6-dione To a solution of 3-(3-{4-[2,6-dioxo-1,3-dipropyl-7-(2-trimethylsilanyl-ethoxymethyl)-2,3,6,7-tetrahydro-1H-purin-8-yl]-pyrazol-1-yl}-prop-1-ynyl)-benzoic acid ethyl ester (50 mg, 0.08 mmol) in THF (5 ml), $NaBH_4$ (5 mg, 0.16 mmol) was added slowly at 0° C. It was stirred for 3 h at room temperature. Water was added to reaction mixture and extracted with ethyl acetate. The organic layer was washed with brine, dried over $Na_2SO_4$ and then filtered and concentrated under vacuum. The residue obtained was purified by column chromatography to obtain 8-{1-[3-(3-hydroxymethyl-phenyl)-prop-2-ynyl]-1H-pyrazol-4-yl}-1,3-dipropyl-7-(2-trimethylsilanyl-ethoxymethyl)-3,7-dihydro-purine-2,6-dione (25 mg, 54%) as an yellow oil.

$^1$HNMR (400 MHz, $CDCl_3$): δ 0.86-1.01 (m, 8H); 1.66-1.72 (m, 2H); 1.80-1.86 (m, 2H); 3.79-3.83 (t, J=8.4 Hz, 2H); 3.98-4.01 (t, J=7.2 Hz, 2H); 4.09-4.13 (t, J=7.2 Hz); 4.69 (s, 2H); 5.24 (s, 2H); 5.79 (s, 2H); 7.26-7.42 (m, 3H); 7.50 (s, 1H); 8.16 (s, 1H); 8.39 (s, 1H)

Step II

8-{1-[3-(3-Hydroxymethyl-phenyl)-prop-2-ynyl]-1H-pyrazol-4-yl}-1,3-dipropyl-3,7-dihydro-purine-2,6-dione To a solution of 8-{1-[3-(3-hydroxymethyl-phenyl)-prop-2-ynyl]-1H-pyrazol-4-yl}-1,3-dipropyl-7-(2-trimethylsilanyl-ethoxymethyl)-3,7-dihydro-purine-2,6-dione (25 mg) in ethanol (3 ml), aq. HCl (2 N, 1 ml) was added and the reaction mixture was refluxed for 2 hrs. The volatiles were evaporated and the residue obtained was dissolved in ethyl acetate. The organic layer was washed with water, brine and dried over $Na_2SO_4$ and concentrated under vacuum. The residue obtained was purified by column to obtain 8-{1-[3-(3-hydroxymethyl-phenyl)-prop-2-ynyl]-1H-pyrazol-4-yl}-1,3-dipropyl-3,7-dihydro-purine-2,6-dione (10 mg, 52%) as white solid.

$^1$HNMR (400 MHz, $CDCl_3$): δ 0.96-1.00 (m, 6H); 1.69-1.75 (m, 2H); 1.80-1.86 (m, 2H); 4.05-4.14 (m, 4H); 4.68 (s, 2H); 5.24 (s, 2H); 7.25-7.40 (m, 3H); 7.51 (s, 1H); 8.3 (s, 1H); 8.42 (s, 1H).

Example H1

4-{3-[4-(2,6-Dioxo-1,3-dipropyl-2,3,6,7-tetrahydro-1H-purin-8-yl)-pyrazol-1-yl]-prop-1-ynyl}-benzenesulfonamide

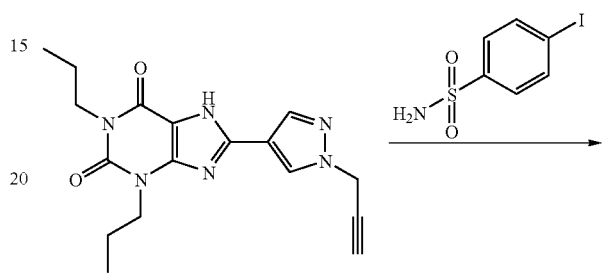

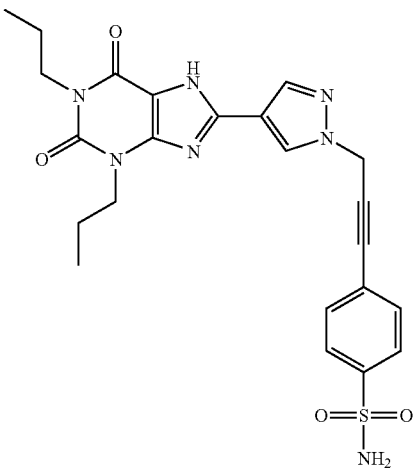

A mixture of 1,3-dipropyl-8-(1-prop-2-ynyl-1H-pyrazol-4-yl)-3,7-dihydro-purine-2,6-dione (200 mg, 0.59 mmol), 4-iodo-benzenesulfonamide (166 mg, 0.59 mmol), copper iodide (10 mg, 0.059 mmol), dichlorobis (triphenylphosphine)-palladium (II) (21 mg, 0.03 mmol), triethylamine (2 ml), DMF (2 ml) was degassed for 10 min. and stirred for 20 hrs at room temperature. The reaction mixture was diluted with water (10 ml) and extracted with DCM (3×10 ml). Organic layer was washed with brine (2×15 ml) and dried over $Na_2SO_4$. The organic volatile solvent was evaporated and the crude product was purified using HPLC to obtain pure 4-{3-[4-(2,6-dioxo-1,3-dipropyl-2,3,6,7-tetrahydro-1H-purin-8-yl)-pyrazol-1-yl]-prop-1-ynyl}-benzenesulfonamide (4.2 mg, 2%).

$^1$HNMR (400 MHz, DMSO d6): δ 0.87-0.90 (m, 6H); 3.86 (t, J=6.8 Hz, 2H); 3.99 (t, J=6.8 Hz, 2H); 5.45 (s, 2H) 7.5 (s, 2H); 7.70 (d, J=8.4 Hz, 2H); 7.85 (d, J=8.4 Hz, 2H); 8.12 (s, 1H); 8.41 (s, 1H); 8.51 (s, 1H).

Example I1

3-{3-[4-(2,6-Dioxo-1,3-dipropyl-2,3,6,7-tetrahydro-1H-purin-8-yl)-pyrazol-1-yl]-prop-1-ynyl}-benzamide

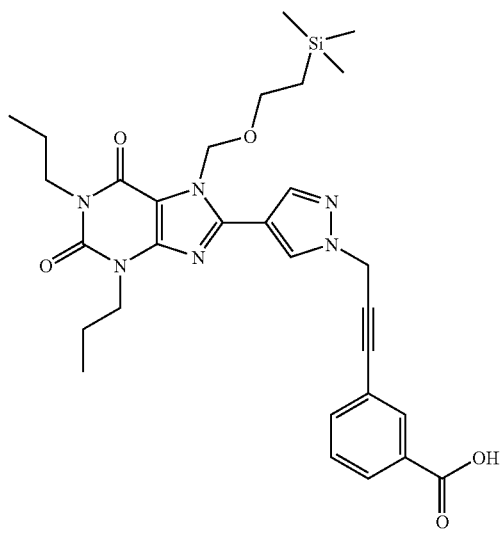

Step I 3-(3-{4-[2,6-Dioxo-1,3-dipropyl-7-(2-trimethylsilanyl-ethoxymethyl)-2,3,6,7-tetrahydro-1H-purin-8-yl]-pyrazol-1-yl}-prop-1-ynyl)-benzamide A mixture of 3-(3-{4-[2,6-dioxo-1,3-dipropyl-7-(2-trimethylsilanyl-ethoxymethyl)-2,3,6,7-tetrahydro-1H-purin-8-yl]-pyrazol-1-yl}-prop-1-ynyl)-benzoic acid (100 mg, 0.17 mmol), ammonium carbonate (33 mg, 0.34 mmol), HOBT (36 mg, 0.24 mmol), N-methyl morpholine (34 mg, 0.34 mmol) were taken in DMF (2 ml), EDCI (130 mg, 0.68 mmol) was added at cold condition and stirred for 18 hrs at room temperature. The reaction mixture was diluted with water (10 ml) and extracted with DCM (3×5 ml), the organic layer was washed with brine (2×10 ml), dried over $Na_2SO_4$. The organic solvent was evaporated and the crude product was purified using HPLC to obtain 3-(3-{4-[2,6-Dioxo-1,3-dipropyl-7-(2-trimethylsilanyl-ethoxymethyl)-2,3,6,7-tetrahydro-1H-purin-8-yl]-pyrazol-1-yl}-prop-1-ynyl)-benzamide (33 mg, 18%).
$^1$HNMR (400 MHz, DMSO d6): δ 0.12 (s, 9H); 0.84-0.91 (m, 8H); 1.58 (q, J=6.8 Hz, 2H); 1.73 (q, J=7.2 Hz, 2H); 3.69 (t, J=8.4 Hz, 2H); 3.87 (t, J=7.2 Hz, 2H); 4.01 (t, J=7.2 Hz, 2H); 5.47 (s, 2H); 5.80 (s, 2H); 7.49-7.53 (m, 2H); 7.65 (d, J=7.6 Hz, 1H); 7.92 (d, J=7.6 Hz, 1H); 7.99 (s, 1H); 8.10 (s, 1H); 8.14 (s, 1H); 8.56 (s, 1H).

Step II

3-{3-[4-(2,6-Dioxo-1,3-dipropyl-2,3,6,7-tetrahydro-1H-purin-8-yl)-pyrazol-1-yl]-prop-1-ynyl}-benzamide A solution of above product (33 mg, 0.056 mol) was taken in ethanol (1 ml) and 2N HCl (0.5 ml), refluxed for 3 hrs at 80° C. The reaction mixture was concentrated in vacuo and the residue was washed with ether to furnish 3-{3-[4-(2,6-dioxo-1,3-dipropyl-2,3,6,7-tetrahydro-1H-purin-8-yl)-pyrazol-1-yl]-prop-1-ynyl}-benzamide (15 mg, 60%).
$^1$HNMR (400 MHz, DMSO d6): δ 0.85-0.92 (m, 6H); 1.58 (q, J=6.8 Hz, 2H); 1.73 (q, J=7.2 Hz, 2H); 3.87 (t, J=7.6 Hz, 2H); 3.4 (t, J=7.2 Hz, 2H); 5.44 (s, 2H); 7.49-7.53 (m, 2H); 7.65 (d, J=7.6 Hz, 1H); 7.92 (d, J=7.6 Hz, 1H); 7.99 (s, 1H); 8.10 (s, 1H); 8.14 (s, 1H); 8.56 (s, 1H); 13.6 (bs, 1H).

Example J1

1,3-Dipropyl-8-{1-[2-(3-trifluoromethyl-phenyl)-cyclopropylmethyl]-1H-pyrazol-4-yl}-3,7-dihydro-purine-2,6-dione

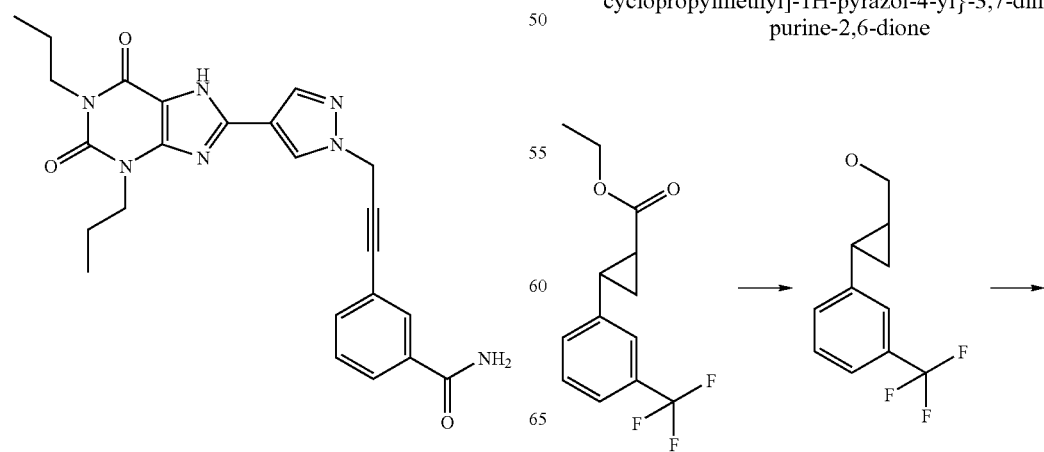

-continued

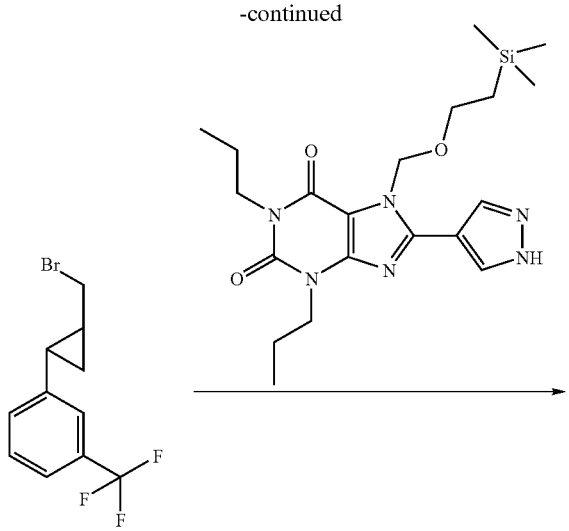

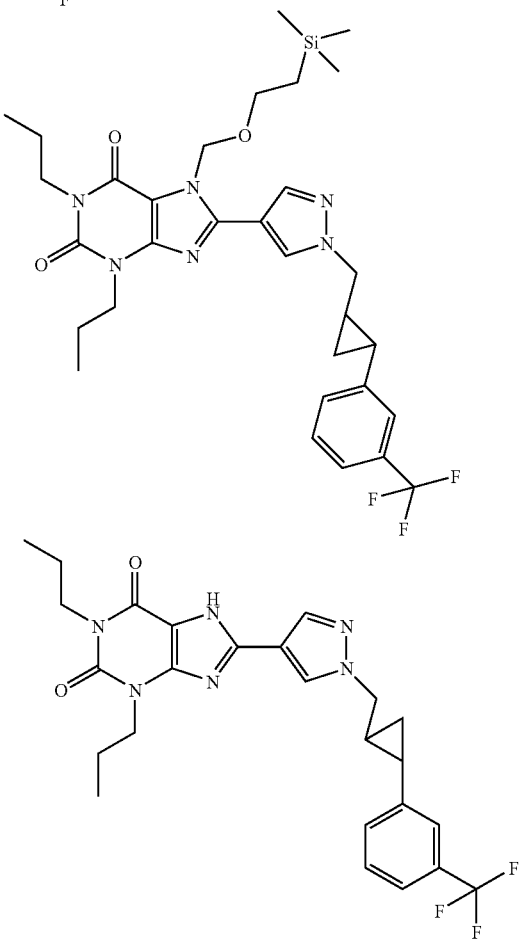

Step-1

[2-(3-Trifluoromethyl-phenyl)-cyclopropyl]-methanol 2-(3-Trifluoromethyl-phenyl)-cyclopropanecarboxylic acid ethyl ester (prepared as per literature procedure) (0.70 g, 2.7 mmol) in THF (5 ml) was added to a solution of lithium aluminium hydride (0.123 g, 3.25 mmol) in THF (5 ml) at 0° C. over a period of 10 min. and stirred further at 20-25° C. for 2 hours. The reaction mixture was diluted with THF (15 ml) and quenched with 10% NaOH solution (5 ml) and water (10 ml). The aqueous layer was extracted with ethyl acetate, washed with saturated brine solution and dried over $Na_2SO_4$. The organic layer was evaporated to afford [2-(3-trifluoromethyl-phenyl)-cyclopropyl]-methanol as a colorless oil (0.54 g, 92%).
$^1$HNMR (400 MHz, $CDCl_3$): δ 1.01 (t, J=7.2 Hz, 2H); 1.45-1.53 (m, 2H); 1.87-1.92 (m, 1H); 3.64-3.66 (m, 2H); 7.24 (m, 1H); 7.31 (s, 1H); 7.34-7.4 (m, 2H).

Step-2

1-(2-Bromomethyl-cyclopropyl)-3-trifluoromethyl-benzene

[2-(3-Trifluoromethyl-phenyl)-cyclopropyl]-methanol obtained in step 1 (0.250 g, 1.15 mmol) was taken in diethyl ether (4 ml) and cooled to 0° C. Tribromo phosphine (0.06 ml, 0.64 mmol) in diethyl ether (4 ml) was added slowly at 0° C. and stirred at 15-20° C. for 2 hrs. Reaction mixture was quenched with saturated $NaHCO_3$ solution (20 ml) and extracted with diethyl ether. Organic layer was washed with saturated brine solution, dried over $Na_2SO_4$, and evaporated under vacuum to get 1-(2-bromomethyl-cyclopropyl)-3-trifluoromethyl-benzene (0.26 g, 80%) as a sticky mass.
$^1$HNMR (400 MHz, $CDCl_3$): δ 1.08-1.13 (m, 1H); 1.19-1.28 (m, 1H); 1.58-1.67 (m, 1H); 1.97-2.02 (m, 1H); 3.46 (d, J=7.6 Hz, 2H); 7.26-7.28 (m, 1H); 7.33 (s, 1H); 7.37-7.39 (m, 1H); 7.42-7.44 (m, 1H).

Step-3

1,3-Dipropyl-8-{1-[2-(3-trifluoromethyl-phenyl)-cyclopropylmethyl]-1H-pyrazol-4-yl}-7-(2-trimethylsilanyl-ethoxymethyl)-3,7-dihydro-purine-2,6-dione A mixture of 1,3-dipropyl-8-(1H-pyrazol-4-yl)-7-(2-trimethylsilanyl-ethoxymethyl)-3,7-dihydro-purine-2,6-dione (0.100 g, 0.23 mmol), 1-(2-bromomethyl-cyclopropyl)-3-trifluoromethyl-benzene (0.64 g, 0.23 mmol), $K_2CO_3$ (0.063 g, 0.46 mmol) and acetone (10 ml) were heated at 50-55° C. for 16 hrs. Reaction mixture was cooled to 20-25° C. and filtered off. The filtrate was evaporated and residue was purified by column chromatography to afford 1,3-dipropyl-8-{1-[2-(3-trifluoromethyl-phenyl)-cyclopropylmethyl]-1H-pyrazol-4-yl}-7-(2-trimethylsilanyl-ethoxymethyl)-3,7-dihydro-purine-2,6-dione (0.55 g, 58%).
$^1$HNMR (400 MHz, $CDCl_3$): δ 0.12 (s, 9H); (s, 9H); 0.93-0.99 (m, 8H); 1.16 (t, J=6.8 Hz, 1H); 1.67-1.69 (m, 4H); 1.81-1.83 (m, 2H); 2.06-2.12 (m, 1H); 3.81 (t, J=8.4 Hz, 2H); 3.99 (t, J=7.2 Hz, 2H); 4.08-4.12 (m, 2H); 4.25 (d, J=6.8 Hz, 2H); 5.76 (s, 2H); 7.22-7.25 (m, 1H); 7.30 (s, 1H); 7.33-7.37 (m, 1H); 7.40-7.42 (m, 1H); 8.13 (s, 1H); 8.17 (s, 1H).

Step-4

1,3-Dipropyl-8-{1-[2-(3-trifluoromethyl-phenyl)-cyclopropylmethyl]-1H-pyrazol-4-yl}-3,7-dihydro-purine-2,6-dione A mixture of 1,3-dipropyl-8-{1-[2-(3-trifluoromethyl-phenyl)-cyclopropylmethyl]-1H-pyrazol-4-yl}-7-(2-trimethylsilanyl-ethoxymethyl)-3,7-dihydro-purine-2,6-dione (0.55 g, 0.087 mmol), 2 N HCl (2 ml), ethanol (3 ml) were heated at 85° C. for 3 hours. The mixture was cooled to 10-15° C. and solid material was separated. It was filtered off and washed with water (1 ml), diethyl ether (1 ml) to obtain the title compound (0.016 g, 37

¹HNMR (400 MHz, CDCl₃): δ 0.97-1.01 (m, 6H); 1.18 (t, J=7.2 Hz, 2H); 1.67-1.86 (m, 5H); 2.09-2.10 (m, 1H); 4.08-4.15 (m, 4H); 4.23-4.27 (m, 2H); 7.22-7.42 (m, 4H); 8.22 (s, 1H); 8.36 (s, 1H); 12.87 (bs, 1H).

Examples J2-J4 were prepared in an analogous manner of Example J1 from the appropriate intermediate.

| Example | IUPAC name |
|---------|------------|
| J2 | 8-{1-[2-(3-Fluoro-phenyl)-cyclopropylmethyl]-1H-pyrazol-4-yl}-1,3-dipropyl-3,7-dihydro-purine-2,6-dione. |
| J3 | 8-{1-[2-(4-Fluoro-phenyl)-cyclopropylmethyl]-1H-pyrazol-4-yl}-1,3-dipropyl-3,7-dihydro-purine-2,6-dione. |
| J4 | 1,3-Dipropyl-8-{1-[2-(4-trifluoromethyl-phenyl)-cyclopropylmethyl]-1H-pyrazol-4-yl}-3,7-dihydro-purine-2,6-dione. |

Example K1

8-{1-[1-(4-Isopropyl-phenyl)-5-oxo-pyrrolidin-3-ylmethyl]-1H-pyrazol-4-yl}-1,3-dipropyl-3,7-dihydro-purine-2,6-dione

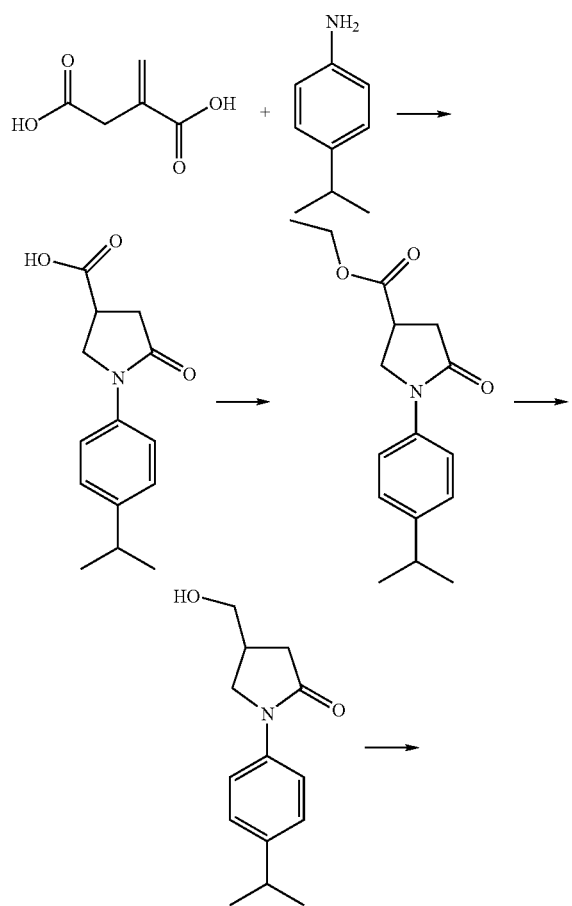

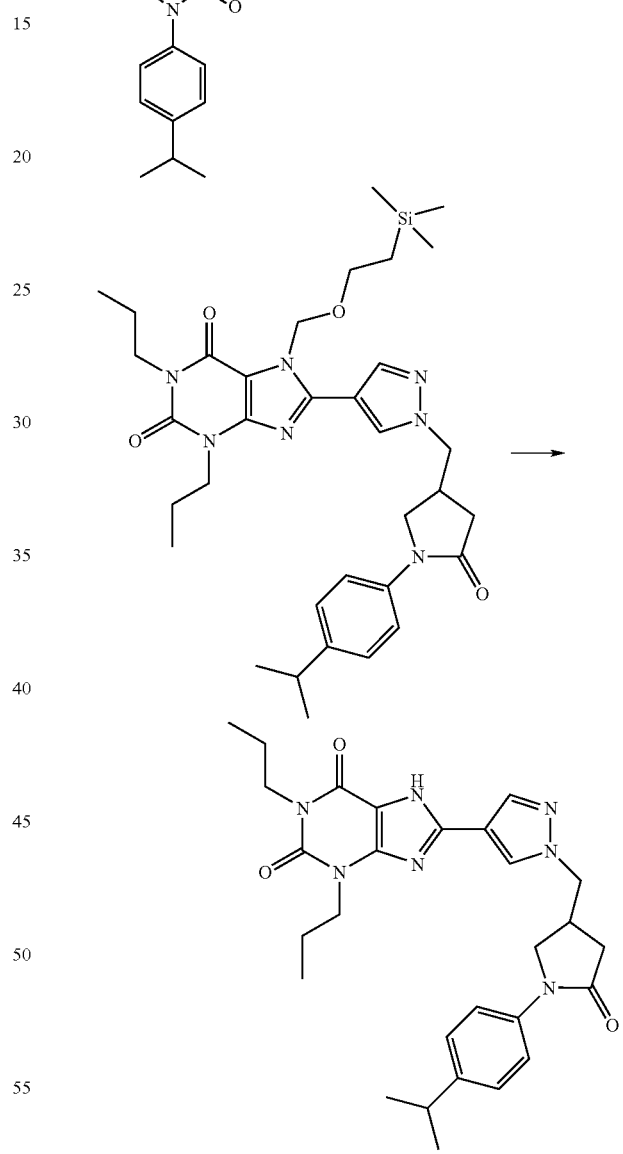

Step-1

1-(4-Isopropyl-phenyl)-5-oxo-pyrrolidine-3-carboxylic acid

A mixture of 4-isopropylaniline (0.76 g, 0.565 mmol) and itaconic acid (0.70 g, 0.538 mmol) was heated at 120-130° C. in a sealed tube for 2.5 hrs. The mixture was cooled and dissolved in 10% NaOH solution (15 ml) and stirred for 20 min. The aqueous layer was washed with ethyl acetate and acidified with dil. HCl. The precipitate was filtered to obtain 1-(4-isopropyl-phenyl)-5-oxo-pyrrolidine-3-carboxylic acid (1.0 g, 75%).

$^1$HNMR (400 MHz, CDCl$_3$): δ 1.25 (d, J=7.2 Hz, 6H); 2.90-2.98 (m, 3H); 3.41-3.45 (m, 1H); 4.06-4.08 (m, 1H); 4.14-4.18 (m, 1H); 7.26 (d, J=8.4 Hz, 2H); 7.49 (d, J=8.4 Hz, 2H)

Step-2

1-(4-Isopropyl-phenyl)-5-oxo-pyrrolidine-3-carboxylic acid ethyl ester

A mixture of 1-(4-isopropyl-phenyl)-5-oxo-pyrrolidine-3-carboxylic acid obtained in step 1 (0.6 g, 2.42 mmol), thionyl chloride (0.35 g, 2.90 mmol), and ethanol (10 ml) was heated at 55-60° C. for 2 hours. The mixture was cooled and solvent was removed. The residue was dissolved in ethyl acetate (20 ml). The organic layer was washed with saturated NaHCO$_3$ and saturated brine solution (20 ml). The organic layer was dried over Na$_2$SO$_4$ and evaporated to obtain 1-(4-isopropyl-phenyl)-5-oxo-pyrrolidine-3-carboxylic acid ethyl ester as yellow oil (0.7 g, 100%).

Step-3

4-Hydroxymethyl-1-(4-isopropyl-phenyl)-pyrrolidin-2-one

A mixture of 1-(4-isopropyl-phenyl)-5-oxo-pyrrolidine-3-carboxylic acid ethyl ester obtained in step 2 (0.7 g, 2.65 mmol) and ethanol were cooled to 10-15° C. Sodium borohydride (0.25 g, 6.6 mmol) was added portion wise over a period of 20 min and the reaction mixture was stirred for 3.5 hrs at 20-25° C. The organic volatiles were evaporated and the residue was taken into brine solution (15 ml). The aqueous layer was extracted with ethyl acetate, dried over Na$_2$SO$_4$ and evaporated to obtain 4-hydroxymethyl-1-(4-isopropyl-phenyl)-pyrrolidin-2-one as an off white solid (0.5 g, 81%).

$^1$HNMR (400 MHz, CDCl$_3$): δ 1.21 (d, J=6.8 Hz, 6H); 2.40-2.44 (m, 1H); 2.68-2.73 (m, 2H); 2.85-2.89 (m, 1H); 3.67-3.74 (m, 3H); 3.91-3.95 (m, 1H); 7.21 (d, J=8.4 Hz, 2H); 7.49 (d, J=8.4 Hz, 2H).

Step-4

Methanesulfonic acid 1-(4-isopropyl-phenyl)-5-oxo-pyrrolidin-3-ylmethyl ester

A mixture of 4-hydroxymethyl-1-(4-isopropyl-phenyl)-pyrrolidin-2-one obtained in step 3 (0.5 g, 2.14 mmol), dichloromethane (8 ml) and triethyl amine (0.30 g, 3.0 mol) was cooled to 0° C. and stirred for 15 min at that temperature. Methane sulfonyl chloride (0.3 g, 2.56 mmol) was added to the mixture over a period of 5 min and the reaction mixture was stirred for 1.5 hrs at 10-15° C. To this reaction mixture saturated NaHCO$_3$ solution (10 ml) was added and the organic layer was separated. The aqueous layer was extracted with dichloromethane (20 ml). The combined organic layer was washed with saturated brine solution, dried over Na$_2$SO$_4$ and evaporated to obtain methanesulfonic acid 1-(4-isopropyl-phenyl)-5-oxo-pyrrolidin-3-ylmethyl ester as a brown oil (0.6 g, 90%).

$^1$HNMR (400 MHz, CDCl$_3$): δ 1.21 (d, J=6.8 Hz, 6H); 2.4-2.46 (m, 1H); 2.46-2.91 (m, 3H); 3.04 (s, 3H); 3.7-3.74 (m, 1H); 3.97-4.02 (m, 1H); 4.24-4.3 (m, 2H); 7.22 (d, J=8.4 Hz, 2H); 7.46 (d, J=8.4 Hz, 2H).

Step-5

8-{1-[1-(4-Isopropyl-phenyl)-5-oxo-pyrrolidin-3-ylmethyl]-1H-pyrazol-4-yl}-1,3-dipropyl-7-(2-trimethylsilanyl-ethoxymethyl)-3,7-dihydro-purine-2,6-dione A mixture of 1,3-dipropyl-8-(1H-pyrazol-4-yl)-7-(2-trimethylsilanyl-ethoxymethyl)-3,7-dihydro-purine-2,6-dione (0.100 g, 0.23 mmol), methanesulfonic acid 1-(4-isopropyl-phenyl)-5-oxo-pyrrolidin-3-ylmethyl ester (0.107 g, 0.34 mmol), K$_2$CO$_3$ (0.048 g, 0.34 mmol) and DMF (1 ml) were heated at 75-80° C. for 16 hrs. Reaction mixture was cooled to 20-25° C. and water was added (10 ml). The aqueous layer was extracted with ethyl acetate, washed with saturated brine solution. The organic layer was dried over Na$_2$SO$_4$ and evaporated to obtain crude product (0.2 g). The crude product was purified by preparative TLC to obtain pure 8-{1-[1-(4-isopropyl-phenyl)-5-oxo-pyrrolidin-3-ylmethyl]-1H-pyrazol-4-yl}-1,3-dipropyl-7-(2-trimethylsilanyl-ethoxymethyl)-3,7-dihydro-purine-2,6-dione (0.12 g, 80%) as a light yellow oil.

$^1$HNMR (400 MHz, CDCl$_3$): δ 0.12 (s, 9H); (s, 9H); 0.83-0.87 (m, 8H); 1.16 (d, J=6.8 Hz, 6H); 1.53-1.58 (m, 2H); 1.67-1.72 (m, 2H); 2.34-2.38 (m, 1H); 2.66-2.89 (m, 2H); 3.17-3.21 (m, 1H); 3.72-3.78 (m, 2H); 3.8-3.88 (m, 2H); 3.91-4.12 (m, 2H); 4.17-4.21 (m, 2H); 4.26-4.38 (m, 2H); 5.79 (m, 2H); 7.21 (d, J=8.4 Hz, 2H); 7.46 (d, J=8.4 Hz, 2H); 8.18 (s, 1H); 8.40 (s, 1H).

Step-6

8-{1-[1-(4-Isopropyl-phenyl)-5-oxo-pyrrolidin-3-ylmethyl]-1H-pyrazol-4-yl}-1,3-dipropyl-3,7-dihydro-purine-2,6-dione A mixture of 8-{1-[1-(4-Isopropyl-phenyl)-5-oxo-pyrrolidin-3-ylmethyl]-1H-pyrazol-4-yl}-1,3-dipropyl-7-(2-trimethylsilanyl-ethoxymethyl)-3,7-dihydro-purine-2,6-dione obtained in step 5 (0.1 g, 0.23 mmol), 2 N HCl (3 ml), ethanol (2 ml) were heated at 85° C. for 3 hours. The mixture was cooled to 10-15° C. The solid obtained was filtered and washed with water (1 ml), diethyl ether (1 ml) to obtain 8-{1-[1-(4-isopropyl-phenyl)-5-oxo-pyrrolidin-3-ylmethyl]-1H-pyrazol-4-yl}-1,3-dipropyl-3,7-dihydro-purine-2,6-dione (0.071 g, 76%) as a white solid.

$^1$HNMR (400 MHz, CDCl$_3$): δ 0.83-0.87 (m, 6H); 1.15 (d, J=6.8 Hz, 6H); 1.53-1.58 (m, 2H); 1.69-1.72 (m, 2H); 2.34-2.38 (m, 1H); 2.59-2.65 (m, 1H); 2.82-2.85 (m, 1H); 2.89-3.01 (m, 1H); 3.61-3.65 (m, 1H); 3.83-3.91 (m, 3H); 3.96 (t, J=6.8 Hz, 2H); 4.31 (d, J=6.8 Hz, 2H); 7.19 (d, J=8.4 Hz, 2H); 7.47 (d, J=8.4 Hz, 2H); 8.08 (s, 1H); 8.43 (s, 1H); 13.46 (s, 1H).

Examples K2-K33 were prepared in an analogous manner of Example K1 from the appropriate intermediate.

| Example | IUPAC name |
| --- | --- |
| K2 | 8-{1-[1-(4-Fluoro-phenyl)-5-oxo-pyrrolidin-3-ylmethyl]-1H-pyrazol-4-yl}-1,3-dipropyl-3,7-dihydro-purine-2,6-dione. |
| K3 | 8-{1-[5-Oxo-1-(4-trifluoromethoxy-phenyl)-pyrrolidin-3-ylmethyl]-1H-pyrazol-4-yl}-1,3-dipropyl-3,7-dihydro- |

| Example | IUPAC name |
|---|---|
| | purine-2,6-dione. |
| K4 | 8-{1-[5-Oxo-1-(3-trifluoromethyl-phenyl)-pyrrolidin-3-ylmethyl]-1H-pyrazol-4-yl}-1,3-dipropyl-3,7-dihydro-purine-2,6-dione. |
| K5 | 8-[1-(5-Oxo-1-p-tolyl-pyrrolidin-3-ylmethyl)-1H-pyrazol-4-yl]-1,3-dipropyl-3,7-dihydro-purine-2,6-dione. |
| K6 | 8-[1-(5-Oxo-1-m-tolyl-pyrrolidin-3-ylmethyl)-1H-pyrazol-4-yl]-1,3-dipropyl-3,7-dihydro-purine-2,6-dione. |
| K7 | 8-{1-[5-Oxo-1-(3-trifluoromethyl-benzyl)-pyrrolidin-3-ylmethyl]-1H-pyrazol-4-yl}-1,3-dipropyl-3,7-dihydro-purine-2,6-dione. |
| K8 | 8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione. |
| K9 | 8-{1-[1-(3-Fluoro-phenyl)-5-oxo-pyrrolidin-3-ylmethyl]-1H-pyrazol-4-yl}-1,3-dipropyl-3,7-dihydro-purine-2,6-dione |
| K10 | 8-{1-[1-(3-Methoxy-phenyl)-5-oxo-pyrrolidin-3-ylmethyl]-1H-pyrazol-4-yl}-1,3-dipropyl-3,7-dihydro-purine-2,6-dione. |
| K11 | 3-Ethyl-8-{1-[1-(4-methoxy-phenyl)-5-oxo-pyrrolidin-3-ylmethyl]-1H-pyrazol-4-yl}-1-propyl-3,7-dihydro-purine-2,6-dione. |
| K12 | 3-Ethyl-8-{1-[5-oxo-1-(3-trifluoromethyl-benzyl)-pyrrolidin-3-ylmethyl]-1H-pyrazol-4-yl}-1-propyl-3,7-dihydro-purine-2,6-dione. |
| K13 | 8-{1-[1-(4-Methoxy-phenyl)-5-oxo-pyrrolidin-3-ylmethyl]-1H-pyrazol-4-yl}-1,3-dipropyl-3,7-dihydro-purine-2,6-dione. |
| K14 | 4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile. |
| K15 | 3-Ethyl-8-{1-[1-(4-fluoro-phenyl)-5-oxo-pyrrolidin-3-ylmethyl]-1H-pyrazol-4-yl}-1-propyl-3,7-dihydro-purine-2,6-dione. |
| K16 | 3-Ethyl-8-{1-[1-(3-fluoro-phenyl)-5-oxo-pyrrolidin-3-ylmethyl]-1H-pyrazol-4-yl}-1-propyl-3,7-dihydro-purine-2,6-dione. |
| K17 | 3-Ethyl-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione. |
| K18 | 8-{1-[5-Oxo-1-(3-trifluoromethoxy-phenyl)-pyrrolidin-3-ylmethyl]-1H-pyrazol-4-yl}-1,3-dipropyl-3,7-dihydro-purine-2,6-dione. |
| K19 | 3-Ethyl-8-{1-[5-oxo-1-(3-trifluoromethoxy-phenyl)-pyrrolidin-3-ylmethyl]-1H-pyrazol-4-yl}-1-propyl-3,7-dihydro-purine-2,6-dione. |
| K20 | 3-Ethyl-8-{1-[5-oxo-1-(4-trifluoromethyl-benzyl)-pyrrolidin-3-ylmethyl]-1H-pyrazol-4-yl}-1-propyl-3,7-dihydro-purine-2,6-dione. |
| K21 | 8-{1-[1-(3-Fluoro-benzyl)-5-oxo-pyrrolidin-3-ylmethyl]-1H-pyrazol-4-yl}-1,3-dipropyl-3,7-dihydro-purine-2,6-dione. |
| K22 | 8-{1-[5-Oxo-1-(2-trifluoromethyl-benzyl)-pyrrolidin-3-ylmethyl]-1H-pyrazol-4-yl}-1,3-dipropyl-3,7-dihydro-purine-2,6-dione. |
| K23 | 8-{1-[5-Oxo-1-(4-trifluoromethoxy-benzyl)-pyrrolidin-3-ylmethyl]-1H-pyrazol-4-yl}-1,3-dipropyl-3,7-dihydro-purine-2,6-dione. |
| K24 | 8-{1-[1-(4-Methyl-benzyl)-5-oxo-pyrrolidin-3-ylmethyl]-1H-pyrazol-4-yl}-1,3-dipropyl-3,7-dihydro-purine-2,6-dione. |
| K25 | 4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzoic acid. |
| K26 | 8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione |
| K27 | 3-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile |
| K28 | 8-{1-[5-Oxo-1-(4-trifluoromethyl-phenyl)-pyrrolidin-3-ylmethyl]-1H-pyrazol-4-yl}-1,3-dipropyl-3,7-dihydro-purine-2,6-dione |
| K29 | 8-{1-[1-(2,4-Difluoro-phenyl)-5-oxo-pyrrolidin-3-ylmethyl]-1H-pyrazol-4-yl}-1,3-dipropyl-3,7-dihydro-purine-2,6-dione |
| K30 | 8-{1-[1-(4-Fluoro-phenyl)-5-oxo-pyrrolidin-3-ylmethyl]-1H-pyrazol-4-yl}-1-propyl-3,7-dihydro-purine-2,6-dione |
| K31 | 8-{1-[1-(2-Chloro-4-fluoro-phenyl)-5-oxo-pyrrolidin-3-ylmethyl]-1H-pyrazol-4-yl}-1,3-dipropyl-3,7-dihydro-purine-2,6-dione |
| K32 | 8-{1-[1-(2-Chloro-4-trifluoromethyl-phenyl)-5-oxo-pyrrolidin-3-ylmethyl]-1H-pyrazol-4-yl}-1,3-dipropyl-3,7-dihydro-purine-2,6-dione |
| K33 | 3-Ethyl-8-{1-[5-oxo-1-(4-trifluoromethyl-phenyl)-pyrrolidin-3-ylmethyl]-1H-pyrazol-4-yl}-1-propyl-3,7-dihydro-purine-2,6-dione |

Example L1

8-{1-[2-Oxo-1-(3-trifluoromethyl-phenyl)-pyrrolidin-3-ylmethyl]-1H-pyrazol-4-yl}-1,3-dipropyl-3,7-dihydro-purine-2,6-dione

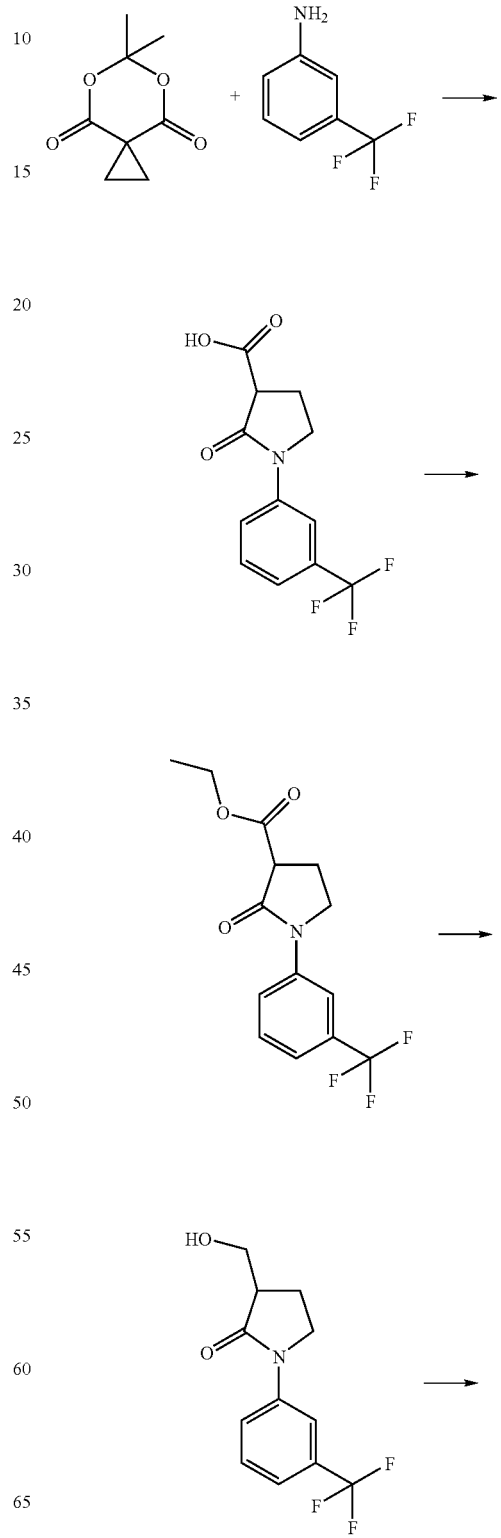

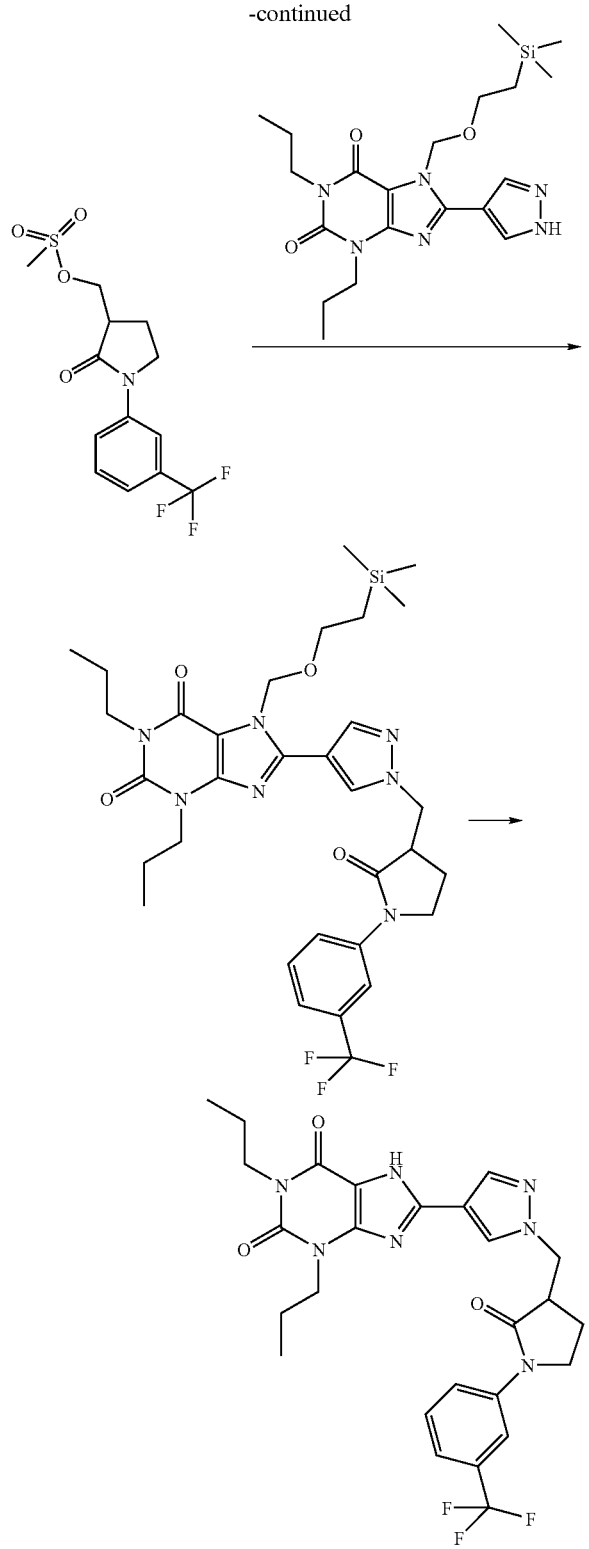

Step-1

2-Oxo-1-(3-trifluoromethyl-phenyl)-pyrrolidine-3-carboxylic acid

A mixture of 3-trifluoromethyl-phenylamine (2.8 g, 17.5 mmol) and 6,6-dimethyl-5,7-dioxa-spiro[2.5]octane-4,8-dione (1.0 g, 5.8 mmol) was stirred at 20-25° C. for 18 hrs. The reaction mixture was diluted with dichloromethane and washed with 10% NaOH solution (3×10 ml). The aqueous layer was cooled and acidified with dil HCl. The aqueous layer was extracted with dichloromethane, washed with saturated brine solution. The organic layer was dried over $Na_2SO_4$ and evaporated to obtain 2-oxo-1-(3-trifluoromethyl-phenyl)-pyrrolidine-3-carboxylic acid (1.1 g, 69%) as an off white solid.

$^1$HNMR (400 MHz, $CDCl_3$): δ 2.57-2.64 (m, 2H); 3.75 (t, J=9.6 Hz, 1H); 3.99-4.03 (m, 2H); 7.51-7.61 (m, 2H); 7.88-7.9 (m, 2H).

Step-2

2-Oxo-1-(3-trifluoromethyl-phenyl)-pyrrolidine-3-carboxylic acid ethyl ester

A mixture of 2-oxo-1-(3-trifluoromethyl-phenyl)-pyrrolidine-3-carboxylic acid obtained in step 1 (0.7 g, 2.56 mmol), thionyl chloride (0.36 g, 3.0 mmol), and ethanol (10 ml) were heated at 55-60° C. for 2 hours. The mixture was cooled and solvent was removed. The residue was dissolved in ethyl acetate (20 ml). The organic layer was washed with sat. $NaHCO_3$ and saturated brine solution, dried over $Na_2SO_4$ and evaporated to obtain 2-oxo-1-(3-trifluoromethyl-phenyl)-pyrrolidine-3-carboxylic acid ethyl ester as a yellow oil (0.5 g, 65%).

$^1$HNMR (400 MHz, $CDCl_3$): δ 1.31 (t, J=7.2 Hz, 3H); 2.46-2.49 (m, 1H); 2.60-2.65 (m, 1H); 3.71 (t, J=7.6 Hz, 1H); 3.89-3.95 (m, 1H); 4.04-4.09 (m, 1H); 4.31 (q, J=7.2 Hz, 2H); 7.45-7.47 (m, 1H); 7.51-7.55 (m, 1H); 7.92 (m, 1H).

Step-3

3-Hydroxymethyl-1-(3-trifluoromethyl-phenyl)-pyrrolidin-2-one

A mixture of 2-oxo-1-(3-trifluoromethyl-phenyl)-pyrrolidine-3-carboxylic acid ethyl ester obtained in step 2 (0.5 g, 1.6 mmol) and ethanol were cooled to 10-15° C. Sodium borohydride (0.126 g, 3.3 mmol) was added portion wise over a period of 20 min and the reaction mixture was stirred for 3.5 hrs at 20-25° C. The organic volatiles were evaporated and the residue was taken into brine solution (15 ml). The aqueous layer was extracted with ethyl acetate, dried over $Na_2SO_4$ and evaporated to obtain brown semi solid which was purified by preparative TLC to afford 3-Hydroxymethyl-1-(3-trifluoromethyl-phenyl)-pyrrolidin-2-one as a colorless oil (0.177 g, 43%).

Step-4

Methanesulfonic acid 2-oxo-1-(3-trifluoromethyl-phenyl)-pyrrolidin-3-ylmethyl ester A mixture of 3-hydroxymethyl-1-(3-trifluoromethyl-phenyl)-pyrrolidin-2-one obtained in step 3 (0.17 g, 0.6 mmol), dichloromethane (8 ml) and triethyl amine (0.085 g, 0.84 mol) was cooled to 0° C. and stirred for 15 min at that temperature. Methane sulfonyl chloride (0.090 g, 0.78 mmol) was added to the mixture over a period of 5 min and the reaction mixture was stirred for 1.5 hrs at 10-15° C. To this reaction mixture saturated $NaHCO_3$ solution (10 ml) was added and the organic layer was separated. The aqueous layer was extracted with dichloromethane. The combined organic layer was washed with saturated brine solution, dried over Na₂SO₄ and evaporated to obtain methanesulfonic acid 2-oxo-1-(3-trifluoromethyl-phenyl)-pyrrolidin-3-ylmethyl ester as a brown oil (0.23 g, 100%).

¹HNMR (400 MHz, CDCl₃): δ 2.29-2.34 (m, 1H); 2.45-2.51 (m, 1H); 3.05-3.13 (m, 3H); 3.91-3.95 (m, 3H); 4.54-4.57 (m, 1H); 4.63-4.67 (m, 1H); 7.46-7.48 (m, 1H); 7.52-7.56 (m, 1H); 7.89-7.93 (m, 2H).

Step-5

8-{1-[2-Oxo-1-(3-trifluoromethyl-phenyl)-pyrrolidin-3-ylmethyl]-1H-pyrazol-4-yl}-1,3-dipropyl-7-(2-trimethylsilanyl-ethoxymethyl)-3,7-dihydro-purine-2,6-dione A mixture of 1,3-dipropyl-8-(1H-pyrazol-4-yl)-7-(2-trimethylsilanyl-ethoxymethyl)-3,7-dihydro-purine-2,6-dione (0.100 g, 0.23 mmol), methanesulfonic acid 2-oxo-1-(3-trifluoromethyl-phenyl)-pyrrolidin-3-ylmethyl ester (0.10 g, 0.32 mmol), K₂CO₃ (0.045 g, 0.32 mmol) and DMF (1 ml) was heated at 75-80° C. for 16 hrs. Reaction mixture was cooled to 20-25° C. and diluted with water (10 ml). The aqueous layer was extracted with ethyl acetate, washed with saturated brine solution. The organic layer was dried over Na₂SO₄ and evaporated to obtain crude product (0.2 g). The crude product was purified by preparative TLC to obtain pure 8-{1-[2-oxo-1-(3-trifluoromethyl-phenyl)-pyrrolidin-3-ylmethyl]-1H-pyrazol-4-yl}-1,3-dipropyl-7-(2-trimethylsilanyl-ethoxymethyl)-3,7-dihydro-purine-2,6-dione (0.10 g, 65%).

¹HNMR (400 MHz, CDCl₃): δ 0.10 (s, 9H); 0.96-1.01 (m, 8H); 1.69-1.77 (m, 2H); 1.85-1.90 (m, 2H); 2.08-2.14 (m, 1H); 2.47-2.49 (m, 1H); 3.32-3.42 (m, 1H); 3.75-3.79 (m, 2H); 3.87 (t. J=8.4 Hz, 2H); 4.03 (t, J=7.6 Hz, 2H); 4.34 (t, J=7.6 Hz, 2H); 4.60-4.63 (m, 1H); 4.74-4.78 (m, 1H); 5.83-5.90 (m, 2H); 7.44-7.53 (m, 1H); 7.51-7.55 (m, 1H); 7.85-7.92 (m, 2H); 8.35 (s, 1H); 8.84 (s, 1H).

Step-6

8-{1-[2-Oxo-1-(3-trifluoromethyl-phenyl)-pyrrolidin-3-ylmethyl]-1H-pyrazol-4-yl}-1,3-dipropyl-3,7-dihydro-purine-2,6-dione A mixture of 8-{1-[2-oxo-1-(3-trifluoromethyl-phenyl)-pyrrolidin-3-ylmethyl]-1H-pyrazol-4-yl}-1,3-dipropyl-7-(2-trimethylsilanyl-ethoxymethyl)-3,7-dihydro-purine-2,6-dione obtained in step 5 (0.1 g, 0.148 mmol), 2 N HCl (3 ml), ethanol (2 ml) was heated at 85° C. for 3 hours. The mixture was cooled to 10-15° C. The solid obtained was filtered and washed with water, diethyl ether to obtain the title compound as a white solid (0.067 g, 83%).

¹HNMR (400 MHz, DMSO d6): δ 0.87-0.92 (m, 6H); 1.56-1.62 (m, 2H); 1.70-1.76 (m, 2H); 1.86-1.91 (m, 1H); 2.17-2.21 (m, 1H); 3.28-3.31 (m, 1H); 3.72-3.76 (m, 1H); 3.81-3.89 (m, 2H); 3.99 (t, J=7.2 Hz, 2H); 4.47-4.6 (m, 2H); 7.53 (d, J=8 Hz, 1H); 7.65 (dd, J=8 Hz, 1H); 7.84 (d, J=8 Hz, 1H); 8.11 (s, 1H); 8.21 (s, 1H); 8.42 (s, 1H); 13.59 (bs, 1H).

Examples L2 and L3 were prepared in an analogous manner of Example L1 from the appropriate intermediate.

| Example | IUPAC name |
|---|---|
| L2 | 8-{1-[1-(3-Fluoro-phenyl)-2-oxo-pyrrolidin-3-ylmethyl]-1H-pyrazol-4-yl}-1,3-dipropyl-3,7-dihydro-purine-2,6-dione |
| L3 | 8-{1-[2-Oxo-1-(4-trifluoromethoxy-phenyl)-pyrrolidin-3-ylmethyl]-1H-pyrazol-4-yl}-1,3-dipropyl-3,7-dihydro-purine-2,6-dione |

Example M1

1,3-Dipropyl-8-{1-[1-(3-trifluoromethyl-phenyl)-pyrrolidin-3-ylmethyl]-1H-pyrazol-4-yl}-3,7-dihydro-purine-2,6-dione

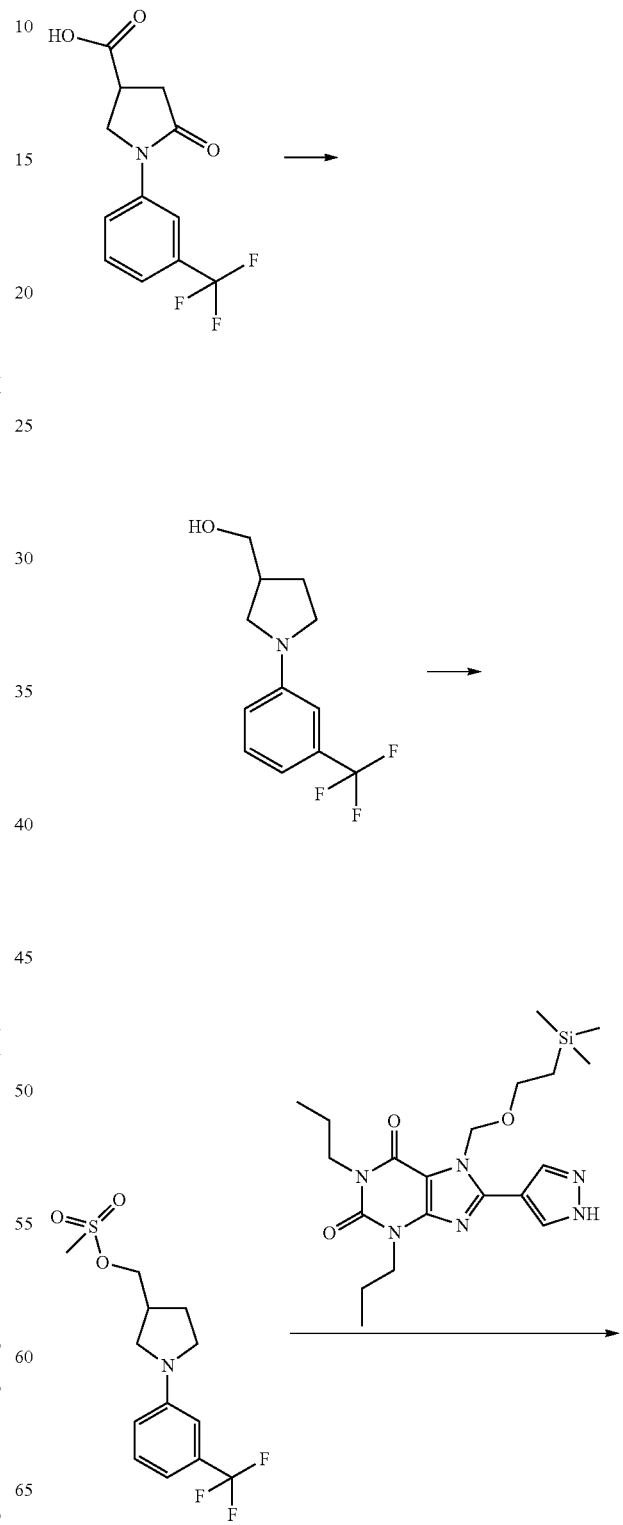

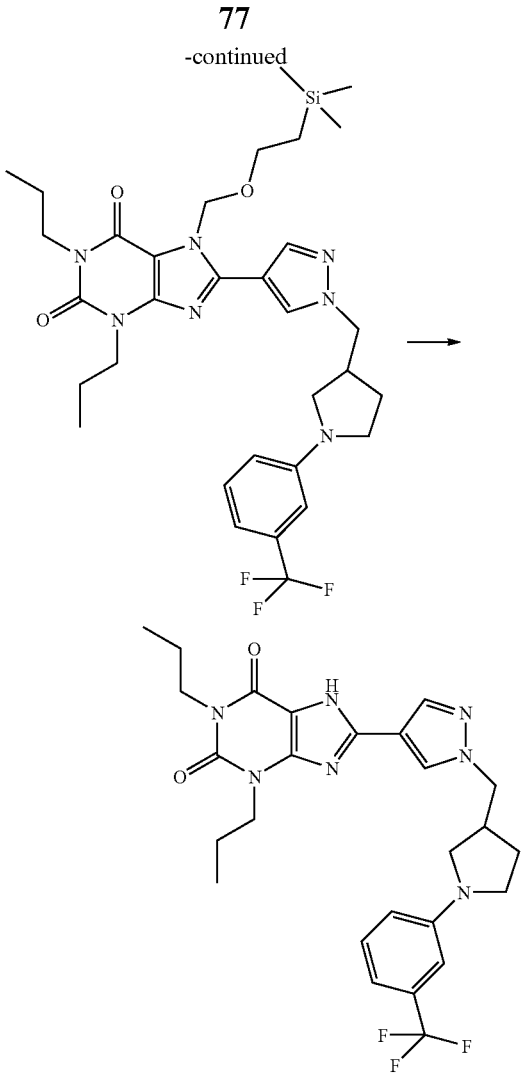

Step-1

[1-(3-Trifluoromethyl-phenyl)-pyrrolidin-3-yl]-methanol

5-Oxo-1-(3-trifluoromethyl-phenyl)-pyrrolidine-3-carboxylic acid (0.35 g, 1.28 mmol) in diethyl ether (5 ml) was added to a solution of lithium aluminium hydride (0.097 g, 2.56 mmol) in THF (5 ml) at temperature 0° C. over a period of 10 min. The mixture was refluxed for 2 hours and then stirred at room temperature for 20 hours. The reaction mixture was diluted with diethyl ether (15 ml) and quenched with water (10 ml). The organic layer was separated and aqueous layer was extracted with diethyl ether. The combined organic layer was washed with saturated brine solution, dried over $Na_2SO_4$ and evaporated to obtain a residue which was purified by preparative TLC to afford [1-(3-trifluoromethyl-phenyl)-pyrrolidin-3-yl]-methanol as a colorless mass (0.2 g, 64%).

$^1$HNMR (400 MHz, $CDCl_3$): δ 1.85-1.90 (m, 1H); 2.16-2.21 (m, 1H); 2.60-2.63 (m, 1H); 3.17-3.21 (m, 1H); 3.36-3.50 (m, 4H); 3.65-3.75 (m, 2H); 6.77-6.80 (m, 2H); 6.94 (d, J=7.6 Hz, 1H); 7.28-7.32 (m, 1H).

Step-2

Methanesulfonic acid 1-(3-trifluoromethyl-phenyl)-pyrrolidin-3-ylmethyl ester Prepared following the procedure similar to step 4 of Example K1.

$^1$HNMR (400 MHz, $CDCl_3$): δ 1.86-1.95 (m, 1H); 2.19-2.27 (m, 1H); 2.78-2.85 (m, 1H); 3.00 (s, 3H); 3.18-3.23 (m, 1H); 3.33-3.50 (m, 3H); 4.19-4.23 (m, 1H); 4.27-4.31 (m, 1H); 6.69-6.74 (m, 2H); 6.93 (d, J=7.6 Hz, 1H); 7.28-7.34 (m, 1H).

Step-3

1,3-Dipropyl-8-{1-[1-(3-trifluoromethyl-phenyl)-pyrrolidin-3-ylmethyl]-1H-pyrazol-4-yl}-7-(2-trimethylsilanyl-ethoxymethyl)-3,7-dihydro-purine-2,6-dione Prepared following the procedure similar to step 5 of Example K1.

$^1$HNMR (400 MHz, $CDCl_3$): δ 0.10 (s, 9H); 0.98-1.06 (m, 8H); 1.82-1.92 (m, 3H); 1.94-2.01 (m, 2H); 2.26-2.30 (m, 1H); 3.09-3.14 (m, 1H); 3.26-3.30 (m, 1H); 3.41-3.48 (m, 1H); 3.50-3.56 (m, 2H); 3.86 (t. J=8.0 Hz, 2H); 4.03 (t, J=7.2 Hz, 2H); 4.17 (t, J=7.6 Hz, 2H); 4.34 (d, J=7.6 Hz, 2H); 5.82-5.83 (m, 2H); 6.80-6.84 (m, 2H); 7.01-7.03 (m, 1H); 7.33-7.38 (m, 1H); 8.20 (s, 1H); 8.26 (s, 1H).

Step-4

1,3-Dipropyl-8-{1-[1-(3-trifluoromethyl-phenyl)-pyrrolidin-3-ylmethyl]-1H-pyrazol-4-yl}-3,7-dihydro-purine-2,6-dione Prepared following the procedure similar to step 6 of Example K1.

$^1$HNMR (400 MHz, DMSO d6): δ 0.83-0.88 (m, 6H); 1.52-1.58 (m, 2H); 1.67-1.78 (m, 3H); 2.01-2.04 (m, 1H); 2.85-2.88 (m, 1H); 3.08-3.12 (m, 1H); 3.23-3.25 (m, 1H); 3.34-3.38 (m, 2H); 3.83 (t, J=7.6 Hz, 2H); 3.95 (t, J=7.6 Hz, 2H); 4.27 (d, J=6.0 Hz, 2H); 6.66 (s, 1H); 6.75 (d, J=8.4 Hz, 1H); 6.85 (d, J=7.2 Hz, 1H); 7.31-7.35 (m, 1H); 8.09 (s, 1H); 8.41 (s, 1H); 13.46 (bs, 1H).

Examples M2-M6 were prepared in an analogous manner of Example M1 from the appropriate intermediate.

| Example | IUPAC name |
|---|---|
| M2 | 1,3-Dipropyl-8-{1-[1-(4-trifluoromethoxy-phenyl)-pyrrolidin-3-ylmethyl]-1H-pyrazol-4-yl}-3,7-dihydro-purine-2,6-dione |
| M3 | 1,3-Dipropyl-8-[1-(1-p-tolyl-pyrrolidin-3-ylmethyl)-1H-pyrazol-4-yl]-3,7-dihydro-purine-2,6-dione |
| M4 | 8-{1-[1-(4-Methoxy-phenyl)-pyrrolidin-3-ylmethyl]-1H-pyrazol-4-yl}-1,3-dipropyl-3,7-dihydro-purine-2,6-dione |
| M5 | 8-{1-[1-(3-Methoxy-phenyl)-pyrrolidin-3-ylmethyl]-1H-pyrazol-4-yl}-1,3-dipropyl-3,7-dihydro-purine-2,6-dione |
| M6 | 1,3-Dipropyl-8-{1-[1-(3-trifluoromethyl-benzyl)-pyrrolidin-3-ylmethyl]-1H-pyrazol-4-yl}-3,7-dihydro-purine-2,6-dione. |

Example N1

8-{4-[1-(4-Fluorophenyl)-5-oxo-pyrrolidin-3-yl-methoxy]phenyl}-1,3-dipropyl-3,7-dihydropurine-2,6-dione

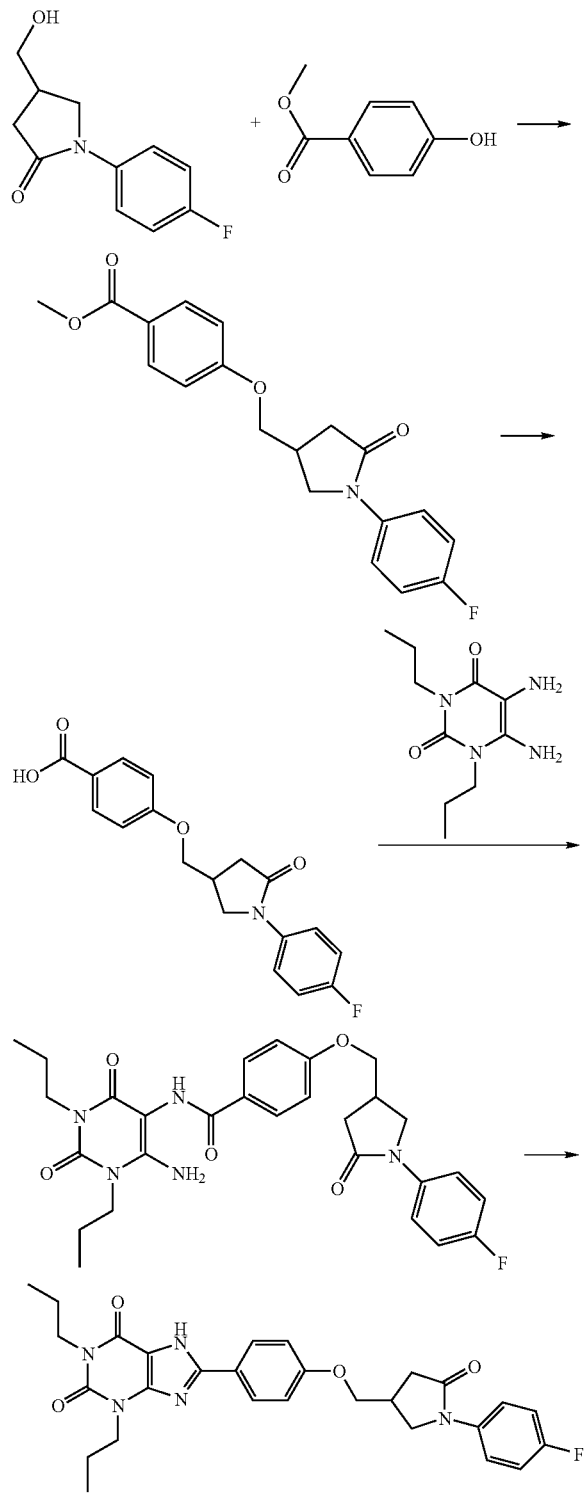

Step-1

4-[1-(4-Fluorophenyl)-5-oxo-pyrrolidin-3-yl-methoxy]-benzoic acid methyl ester

4-Hydroxybenzoic acid methyl ester (0.20 g, 1.314 mmol), 1-(4-fluoro-phenyl)-4-hydroxymethyl-pyrrolidin-2-one (0.33 g, 1.577 mmol), Ph$_3$P (0.345 g, 1.314 mmol) and triethyl amine (0.20 ml, 1.577 mmol) were mixed under argon atmosphere followed by the addition of the dry toluene (10 mL). The reaction mixture was cooled to 0° C. followed by addition of DIAD (0.3 mL, 0.788 mmol) drop wise. The reaction mixture was allowed to warm to room temperature and heated at 80° C. for 24 h. The reaction was quenched with 5% HCl (10 mL), extracted with DCM. The organic layer was dried over Na$_2$SO$_4$ and concentrated to afford the crude product which was purified by flash column chromatography to obtain 4-[1-(4-fluorophenyl)-5-oxo-pyrrolidin-3-yl-methoxy]-benzoic acid methyl ester (0.33 g, 73%) as a white solid.

$^1$HNMR (400 MHz, DMSO d6): δ 2.43 (dd, J=6.4, 6.4 Hz, 1H); 2.73 (dd, J=8.8, 9.2 Hz, 1H); 2.99-2.89 (m, 1H); 3.70 (dd, J=5.2, 5.6 Hz, 1H); 3.79 (s, 3H); 4.02 (t, J=9 Hz, 1H); 4.14-4.00 (m, 2H); 7.05 (d, J=8.8 Hz, 2H); 7.20 (t, J=8.8 Hz, 2H); 7.69-7.66 (m, 2H); 7.90 (d, J=8.8 Hz, 2H).

Step-2

4-[1-(4-Fluoro-phenyl)-5-oxo-pyrrolidin-3-yl-methoxy]-benzoic acid

To a stirred solution of 4-[1-(4-fluorophenyl)-5-oxo-pyrrolidin-3-ylmethoxy]-benzoic acid methyl ester obtained in step 1 (0.14 g, 0.408 mmol) in THF:MeOH:H$_2$O (6 mL, 2:1:3), LiOH.H$_2$O was added at 20-25° C. The reaction mixture was stirred for 16 hours at that temperature. The solvents were removed under reduced pressure and the residue was diluted with water (10 ml). The aqueous layer was washed with DCM, acidified with 2% HCl. The acidified mixture was extracted with ethyl acetate, washed with brine, dried over Na$_2$SO$_4$. The organic layer was evaporated under reduced pressure to obtain 4-[1-(4-fluoro-phenyl)-5-oxo-pyrrolidin-3-ylmethoxy]-benzoic acid (0.130 g, quantitative) as a white solid.

$^1$HNMR (400 MHz, DMSO d6): δ 2.42 (dd, J=4.0, 8.0 Hz, 1H); 2.73 (dd, J=8.0, 8.0 Hz, 1H); 2.96-2.89 (m, 1H); 3.70 (dd, J=8.0, 4.0 Hz, 1H); 4.02 (t, J=8.0 Hz, 1H); 4.14-4.11 (m, 2H); 7.03 (d, J=8.0 Hz, 2H); 7.20 (t, J=8.0 Hz, 2H); 7.69-7.66 (m, 2H); 7.87 (d, J=8.0 Hz, 2H); 12.6 (br s, 1H).

Step-3

N-(6-Amino-2,4-dioxo-1,3-dipropyl-1,2,3,4-tetrahydro-pyrimidin-5-yl)-4-[1-(4-fluorophenyl)-5-oxo-pyrrolidin-3-ylmethoxy]-benzamide To a stirred solution of 4-[1-(4-fluoro-phenyl)-5-oxo-pyrrolidin-3-ylmethoxy]-benzoic acid obtained in step 2 (0.140 g, 0.426 mmol) and HCl salt of 5,6-diamino-1,3-dipropyl-1H-pyrimidine-2,4-dione (0.112 g, 0.426 mmol) in MeOH (5 mL) was added EDCI (0.0136 g, 0.593 mmol). After stirring at 20-25° C. for 16 hours, the reaction mixture was quenched with water (5 mL). The solid obtained was filtered and washed with water to provide the crude product which was purified by column chromatography to afford N-(6-amino-2,4-dioxo-1,3-dipropyl-1,2,3,4-tetrahydro-pyrimidin-5-yl)-4-

[1-(4-fluorophenyl)-5-oxo-pyrrolidin-3-ylmethoxy]-benzamide (0.205 g, 90%) as a white solid.

$^1$HNMR (400 MHz, DMSO d6): δ 0.89-0.79 (m, 6H); 1.58-1.45 (m, 4H); 2.44 (dd, J=8, 8 Hz 1H); 2.74 (dd, J=9.2, 8 Hz, 1H); 2.95-2.86 (m, 1H); 3.73-3.68 (m, 3H); 3.82 (t, J=16 Hz, 2H); 4.03 (t, J=8 Hz, 1H); 4.11-4.13 (m, 2H); 6.68 (s, 2H); 7.02 (d, J=8.0 Hz, 2H); 7.21 (t, J=8.0 Hz, 2H); 7.70-7.67 (m, 2H); 7.94 (d, J=8.0 Hz, 2H); 8.76 (s, 1H).

Step-4

8-{4-[1-(4-Fluorophenyl)-5-oxo-pyrrolidin-3-ylmethoxy]phenyl}-1,3-dipropyl-3,7-dihydropurine-2,6-dione N-(6-Amino-2,4-dioxo-1,3-dipropyl-1,2,3,4-tetrahydropyrimidin-5-yl)-4-[1-(4-fluoro-phenyl)-5-oxo-pyrrolidin-3-ylmethoxy]-benzamide obtained in step 3 (0.90 g, 0.167 mmol) was dissolved in MeOH (4 mL) and 10% NaOH (0.020 g, 0.502 mmol) and stirred at 80° C. for 7 h. MeOH was distilled off and the residue was taken up in H$_2$O (2 mL), acidified with 2NHCl to pH 4-5. The precipitate was filtered, washed with water and methanol to provide the title compound as white solid (0.072 g, 83%).

$^1$HNMR (400 MHz, DMSO d6): δ 0.91-0.84 (m, 6H); 1.61-1.52 (m, 2H); 1.77-1.68 (m, 2H); 2.44 (dd, J=4 Hz, 1H); 2.74 (dd, J=8.0, 8.0 Hz, 1H); 2.97-2.89 (m, 1H); 3.71 (dd, J=8.0, 4.0 Hz, 1H); 3.85 (t, J=8.0 Hz, 2H); 4.05-3.98 (m, 3H); 4.14-4.11 (m, 2H); 7.08 (d, J=8.8 Hz, 2H); 7.20 (t, J=8.8 Hz, 2H); 7.68 (m, 2H); 8.06 (d, J=8.8 Hz, 2H); 13.6 (br s, 1H).

Examples N2-N43 were prepared in an analogous manner of Example N1 from the appropriate intermediate.

| Example | IUPAC name |
|---|---|
| N2 | 1,3-Dipropyl-8-{4-[1-(3-trifluoromethyl-phenyl)-pyrrolidin-3-yloxy]-phenyl}-3,7-dihydro-purine-2,6-dione. |
| N3 | 8-{3-[1-(4-Fluoro-phenyl)-5-oxo-pyrrolidin-3-ylmethoxy]-isoxazol-5-yl}-1,3-dipropyl-3,7-dihydro-purine-2,6-dione. |
| N4 | 8-{4-[5-Oxo-1-(3-trifluoromethyl-phenyl)-pyrrolidin-3-ylmethoxy]-phenyl}-1,3-dipropyl-3,7-dihydro-purine-2,6-dione. |
| N5 | 8-{4-[1-(4-Fluoro-phenyl)-pyrrolidin-3-yloxy]-phenyl}-1,3-dipropyl-3,7-dihydro-purine-2,6-dione. |
| N6 | 8-{6-[5-Oxo-1-(3-trifluoromethyl-phenyl)-pyrrolidin-3-ylmethoxy]-pyridin-3-yl}-1,3-dipropyl-3,7-dihydro-purine-2,6-dione. |
| N7 | 8-{3-[1-(3-Fluoro-phenyl)-5-oxo-pyrrolidin-3-ylmethoxy]-isoxazol-5-yl}-1,3-dipropyl-3,7-dihydro-purine-2,6-dione. |
| N8 | 8-{3-[5-Oxo-1-(3-trifluoromethyl-phenyl)-pyrrolidin-3-ylmethoxy]-isoxazol-5-yl}-1,3-dipropyl-3,7-dihydro-purine-2,6-dione. |
| N9 | 8-{6-[1-(3-Fluoro-phenyl)-5-oxo-pyrrolidin-3-ylmethoxy]-pyridin-3-yl}-1,3-dipropyl-3,7-dihydro-purine-2,6-dione. |
| N10 | 8-{6-[1-(4-Fluoro-phenyl)-5-oxo-pyrrolidin-3-ylmethoxy]-pyridin-3-yl}-1,3-dipropyl-3,7-dihydro-purine-2,6-dione. |
| N11 | 8-{4-[1-(3-Fluoro-phenyl)-5-oxo-pyrrolidin-3-ylmethoxy]-phenyl}-1,3-dipropyl-3,7-dihydro-purine-2,6-dione. |
| N12 | 8-{4-[1-(3-Fluoro-phenyl)-piperidin-4-yloxy]-phenyl}-1,3-dipropyl-3,7-dihydro-purine-2,6-dione. |
| N13 | 8-{6-[1-(3-Fluoro-phenyl)-piperidin-4-yloxy]-pyridin-3-yl}-1,3-dipropyl-3,7-dihydro-purine-2,6-dione. |
| N14 | 8-{3-[1-(3-Fluoro-phenyl)-piperidin-4-yloxy]-isoxazol-5-yl}-1,3-dipropyl-3,7-dihydro-purine-2,6-dione. |
| N15 | 8-{4-[1-(4-Fluoro-phenyl)-piperidin-4-yloxy]-phenyl}-1,3-dipropyl-3,7-dihydro-purine-2,6-dione. |
| N16 | 8-{3-[1-(4-Fluoro-phenyl)-piperidin-4-yloxy]-isoxazol-5-yl}-1,3-dipropyl-3,7-dihydro-purine-2,6-dione. |
| N17 | 1,3-Dipropyl-8-{4-[1-(4-trifluoromethyl-phenyl)-piperidin-4-yloxy]-phenyl}-3,7-dihydro-purine-2,6-dione. |
| N18 | 1,3-Dipropyl-8-{3-[1-(4-trifluoromethyl-phenyl)-piperidin-4-yloxy]-isoxazol-5-yl}-3,7-dihydro-purine-2,6-dione. |
| N19 | 8-{6-[1-(3-Fluoro-phenyl)-pyrrolidin-3-yloxy]-pyridin-3-yl}-1,3-dipropyl-3,7-dihydro-purine-2,6-dione. |
| N20 | 1,3-Dipropyl-8-{6-[1-(4-trifluoromethyl-phenyl)-piperidin-4-yloxy]-pyridin-3-yl}-3,7-dihydro-purine-2,6-dione. |
| N21 | 8-{6-[1-(4-Fluoro-phenyl)-piperidin-4-yloxy]-pyridin-3-yl}-1,3-dipropyl-3,7-dihydro-purine-2,6-dione. |
| N22 | 1,3-Dipropyl-8-{6-[1-(3-trifluoromethyl-phenyl)-piperidin-4-yloxy]-pyridin-3-yl}-3,7-dihydro-purine-2,6-dione. |
| N23 | 1,3-Dipropyl-8-{6-[1-(3-trifluoromethyl-phenyl)-pyrrolidin-3-yloxy]-pyridin-3-yl}-3,7-dihydro-purine-2,6-dione. |
| N24 | 1,3-Dipropyl-8-{4-[1-(3-trifluoromethyl-phenyl)-piperidin-4-yloxy]-phenyl}-3,7-dihydro-purine-2,6-dione. |
| N25 | 1,3-Dipropyl-8-{3-[1-(3-trifluoromethyl-phenyl)-piperidin-4-yloxy]-isoxazol-5-yl}-3,7-dihydro-purine-2,6-dione. |
| N26 | 1,3-Dipropyl-8-{6-[1-(4-trifluoromethyl-phenyl)-pyrrolidin-3-yloxy]-pyridin-3-yl}-3,7-dihydro-purine-2,6-dione. |
| N27 | 8-{6-[1-(4-Fluoro-phenyl)-pyrrolidin-3-yloxy]-pyridin-3-yl}-1,3-dipropyl-3,7-dihydro-purine-2,6-dione. |
| N28 | 8-{6-[5-Oxo-1-(4-trifluoromethyl-phenyl)-pyrrolidin-3-ylmethoxy]-pyridin-3-yl}-1,3-dipropyl-3,7-dihydro-purine-2,6-dione. |
| N29 | 8-{3-[5-Oxo-1-(4-trifluoromethyl-phenyl)-pyrrolidin-3-ylmethoxy]-isoxazol-5-yl}-1,3-dipropyl-3,7-dihydro-purine-2,6-dione. |
| N30 | 8-{4-[5-Oxo-1-(4-trifluoromethyl-phenyl)-pyrrolidin-3-ylmethoxy]-phenyl}-1,3-dipropyl-3,7-dihydro-purine-2,6-dione. |
| N31 | 1,3-Dipropyl-8-{4-[1-(4-trifluoromethyl-phenyl)-pyrrolidin-3-yloxy]-phenyl}-3,7-dihydro-purine-2,6-dione. |
| N32 | 1,3-Dipropyl-8-{3-[1-(4-trifluoromethyl-phenyl)-pyrrolidin-3-yloxy]-isoxazol-5-yl}-3,7-dihydro-purine-2,6-dione. |
| N33 | 8-{3-[1-(3-Fluoro-phenyl)-pyrrolidin-3-yloxy]-isoxazol-5-yl}1,3-dipropyl-3,7-dihydro-purine-2,6-dione. |
| N34 | 8-{3-[1-(4-Fluoro-phenyl)-pyrrolidin-3-yloxy]-isoxazol-5-yl}-1,3-dipropyl-3,7-dihydro-purine-2,6-dione. |
| N35 | 1,3-Dipropyl-8-{3-[1-(3-trifluoromethyl-phenyl)-pyrrolidin-3-yloxy]-isoxazol-5-yl}-3,7-dihydro-purine-2,6-dione. |
| N36 | 8-{4-[1-(3-Fluoro-phenyl)-pyrrolidin-3-yloxy]-phenyl}-1,3-dipropyl-3,7-dihydro-purine-2,6-dione. |
| N37 | 8-{3-[1-(2,4-Difluoro-phenyl)-5-oxo-pyrrolidin-3-ylmethoxy]-isoxazol-5-yl}-1,3-dipropyl-3,7-dihydro-purine-2,6-dione |
| N38 | 8-{5-[1-(3-Fluoro-phenyl)-5-oxo-pyrrolidin-3-ylmethoxy]-1-methyl-1H-pyrazol-3-yl}-1,3-dipropyl-3,7-dihydro-purine-2,6-dione |
| N39 | 8-{1-Methyl-5-[5-oxo-1-(4-trifluoromethyl-benzyl)-pyrrolidin-3-ylmethoxy]-1H-pyrazol-3-yl}-1,3-dipropyl-3,7-dihydro-purine-2,6-dione |
| N40 | 8-{5-[1-(4-Methoxy-phenyl)-5-oxo-pyrrolidin-3-ylmethoxy]-1-methyl-1H-pyrazol-3-yl}-1,3-dipropyl-3,7-dihydro-purine-2,6-dione |
| N41 | 8-{5-[1-(4-Fluoro-phenyl)-5-oxo-pyrrolidin-3-ylmethoxy]-1-methyl-1H-pyrazol-3-yl}-1,3-dipropyl-3,7-dihydro-purine-2,6-dione |
| N42 | 8-{1-Methyl-5-[5-oxo-1-(3-trifluoromethyl-phenyl)-pyrrolidin-3-ylmethoxy]-1H-pyrazol-3-yl}-1,3-dipropyl-3,7-dihydro-purine-2,6-dione |
| N43 | 8-{5-[1-(3-Methoxy-phenyl)-5-oxo-pyrrolidin-3-ylmethoxy]-1-methyl-1H-pyrazol-3-yl}-1,3-dipropyl-3,7-dihydro-purine-2,6-dione |

Example O1
8-(1-{2-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione
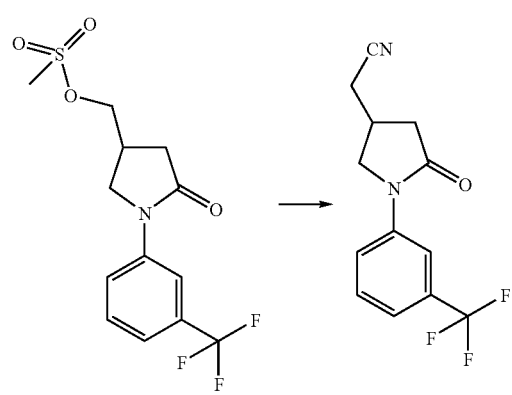
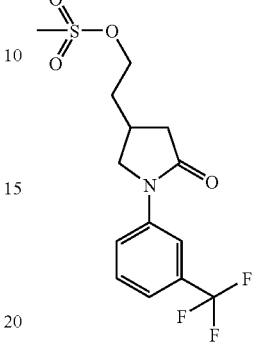
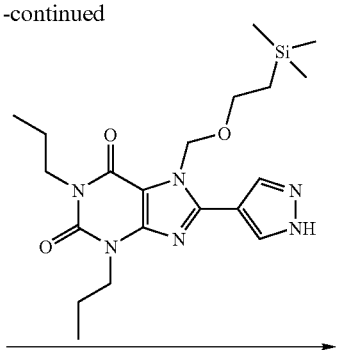
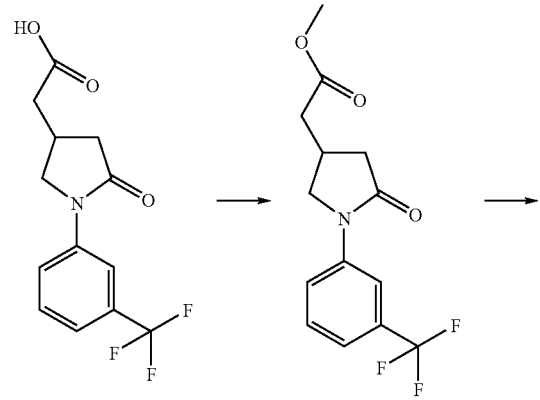
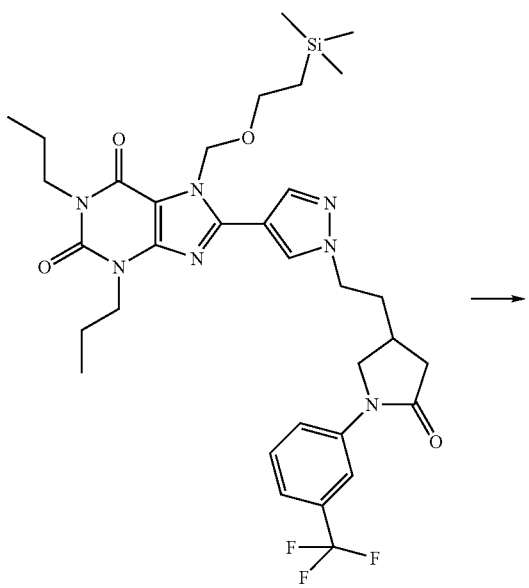
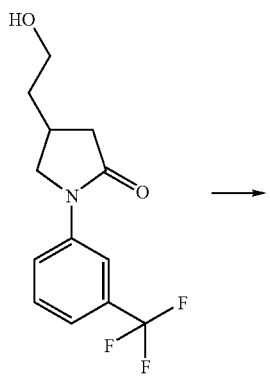
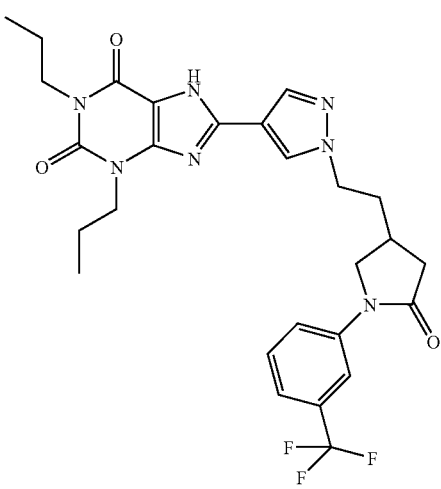

Step-1

[5-oxo-1-(3-trifluoromethyl-phenyl)-pyrrolidin-3-yl]-acetonitrile

A mixture of methanesulfonic acid 5-oxo-1-(3-trifluoromethyl-phenyl)-pyrrolidin-3-ylmethyl ester (prepared as given in Example B1)(0.9 g, 2.66 mmol), DMF (5 ml) and sodium cyanide (0.19 g, 4.0 mol) were heated to 50-55° C. and stirred for 20 hrs. To this reaction mixture water (50 ml) was added and extracted with ethyl acetate (3×20 ml), organic layer was washed with saturated brine solution (20 ml). The organic layer was dried over $Na_2SO_4$ and evaporated to obtain [5-oxo-1-(3-trifluoromethyl-phenyl)-pyrrolidin-3-yl]-acetonitrile (0.65 g, 91%) as brownish sticky mass.

$^1$HNMR (400 MHz, $CDCl_3$): δ 1.51 (m, 1H); 2.62-2.65 (m, 2H); 2.89-2.93 (m, 2H); 3.70-3.74 (m, 1H); 4.09-4.13 (m, 1H); 7.42-7.44 (m, 1H); 7.48-7.52 (m, 1H); 7.81-7.86 (m, 1H); 8.02 (s, 1H).

Step-2

[5-Oxo-1-(3-trifluoromethyl-phenyl)-pyrrolidin-3-yl]-acetic acid

To a stirred solution of [5-oxo-1-(3-trifluoromethyl-phenyl)-pyrrolidin-3-yl]-acetonitrile (0.25 g, 0.93 mmol) in ethanol (6 mL) was added sodium hydroxide solution (0.074 g, 1.86 mmol, in 3 ml water). The reaction mixture was refluxed for 3 hrs and the solvents were removed under reduced pressure, diluted with water (3 ml), washed with hexane (3×10 mL) and acidified with 2N HCl. The aqueous layer was extracted with DCM (3×15 mL) and the combined extract was washed with brine, dried with $Na_2SO_4$, evaporated under reduced pressure to obtain [5-oxo-1-(3-trifluoromethyl-phenyl)-pyrrolidin-3-yl]-acetic acid (0.2 g, 77%) as an off white semi solid.

$^1$HNMR (400 MHz, $CDCl_3$): δ 2.37-3.35 (m, 5H); 3.56-3.65 (m, 1H); 4.14-4.22 (m, 1H); 7.43-7.45 (m, 1H); 7.50-7.54 (m, 1H); 7.85-7.87 (m, 1H); 7.91-7.93 (m, 1H). Step-3 to Step-7 were carried out as described in Example K1

Step-3

[5-Oxo-1-(3-trifluoromethyl-phenyl)-pyrrolidin-3-yl]-acetic acid methylester $^1$HNMR (400 MHz, $CDCl_3$): δ 2.23-2.37 (m, 1H); 2.59-2.61 (m, 2H); 2.85-2.95 (m, 2H); 3.61-3.66 (m, 1H); 3.74 (s, 3H); 4.09-4.15 (m, 1H); 7.43-7.45 (m, 1H); 7.50-7.54 (m, 1H); 7.85-7.87 (m, 1H); 7.91-7.93 (m, 1H).

Step-4

4-(2-Hydroxy-ethyl)-1-(3-trifluoromethyl-phenyl)-pyrrolidin-2-one $^1$HNMR (400 MHz, $CDCl_3$): δ 1.81-1.89 (m, 2H); 2.38-2.45 (m, 1H); 2.69-2.73 (m, 1H); 2.80-2.86 (m, 1H); 3.62-3.72 (m, 1H); 3.78-3.85 (m, 2H); 4.02-4.06 (m, 1H); 7.41-7.43 (m, 1H); 7.49-7.53 (m, 1H); 7.84 (s, 1H); 7.91-7.94 (m, 1H).

Step-5

Methanesulfonic acid 2-[5-oxo-1-(3-trifluoromethyl-phenyl)-pyrrolidin-3-yl]-ethyl ester $^1$HNMR (400 MHz, $CDCl_3$): δ 2.02-2.09 (m, 2H); 2.39-2.45 (m, 1H); 2.72-2.76 (m, 1H); 2.84-2.91 (m, 1H); 3.08 (s, 3H); 3.61-3.64 (m, 1H); 4.04-4.09 (m, 1H); 4.35-4.39 (m, 2H); 7.42-7.44 (m, 1H); 7.50-7.54 (m, 1H); 7.85-7.89 (m, 2H).

Step-6

8-(1-{2-[5-Oxo-1-(3-trifluoromethyl-phenyl)-pyrrolidin-3-yl]-ethyl}-1H-pyrazol-4-yl)-1,3-dipropyl-7-(2-trimethylsilanyl-ethoxymethyl)-3,7-dihydro-purine 2,6-dione $^1$HNMR (400 MHz, $CDCl_3$): δ 0.10 (s, 9H); 0.97-1.04 (m, 8H); 1.68-1.74 (m, 2H); 1.83-1.88 (m, 2H); 2.21-2.26 (m, 2H); 2.36-2.42 (m, 1H); 2.49-2.57 (m, 1H); 2.77-2.83 (m, 1H); 3.58-3.62 (m, 1H); 3.85 (t, J=8.0 Hz, 2H); 3.99-4.04 (m, 3H); 4.13-4.18 (m, 2H); 4.35 (t, J=6.8 Hz, 2H); 5.82 (s, 2H); 7.42 (d, J=7.6 Hz, 1H); 7.49-7.53 (m, 1H); 7.79 (s, 1H); 7.90 (d, J=8.4 Hz, 1H); 8.19 (s, 1H); 8.29 (s, 1H).

Step-7

8-(1-{2-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione $^1$HNMR (400 MHz, DMSO d6): δ 0.84-0.91 (m, 6H); 1.55-1.60 (m, 2H); 1.69-1.75 (m, 2H); 2.03-2.05 (m, 2H); 2.32-2.38 (m, 2H); 2.63-2.68 (m, 1H); 3.62-3.66 (m, 1H); 3.86 (t, J=6.8 Hz, 2H); 3.96-4.01 (m, 3H); 4.30 (t, J=6.4 Hz, 2H); 7.48 (d, J=8.0 Hz, 1H); 7.60-7.64 (m, 1H); 7.85 (d, J=7.6 Hz, 1H); 8.11 (s, 2H); 8.45 (s, 1H); 13.55 (bs, 1H).

Example P1

8-(1-{1-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione

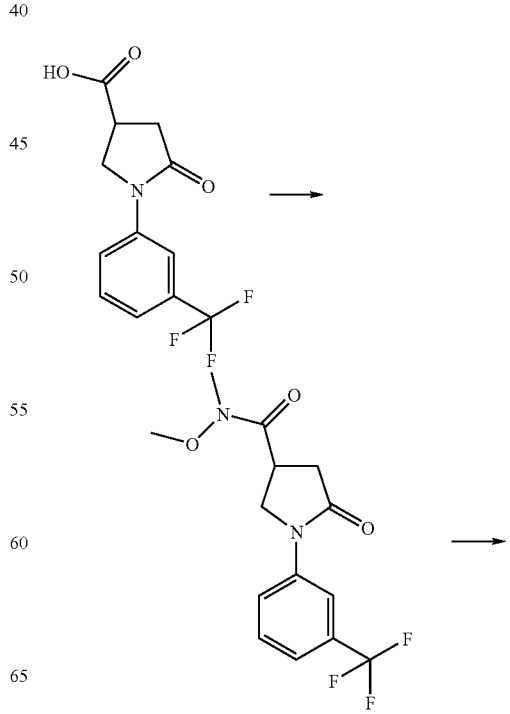

-continued

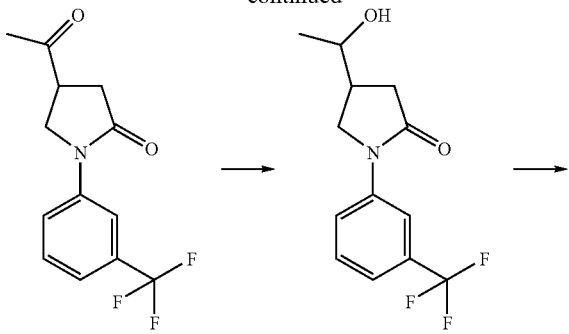

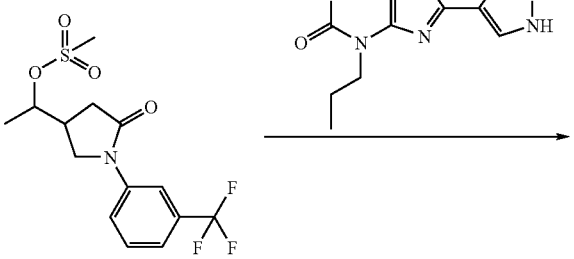

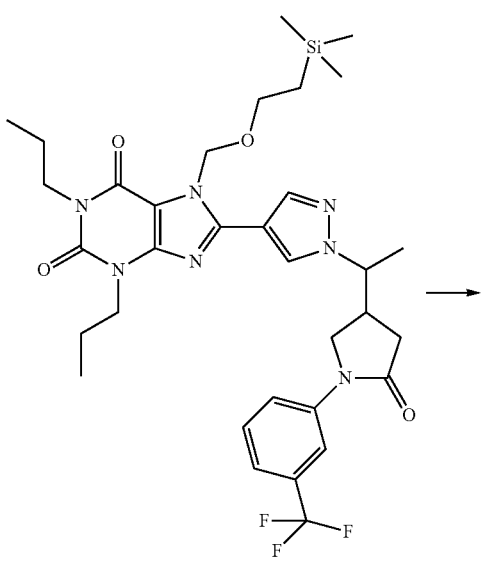

-continued

[structure shown]

Step-1

5-oxo-1-(3-trifluoromethyl-phenyl)-pyrrolidine-3-carboxylic acid methoxy-methyl-amide To a stirred solution of [5-oxo-1-(3-trifluoromethyl-phenyl)-pyrrolidine-3-carboxylic acid (1 g, 3.66 mmol) in DCM (15 mL) was added 1,1'-carbonyldiimidazole (0.65 g, 4.02 mmol) portion wise over a period of 10 min at 10-15° C. N,O-dimethylhydroxylamine hydrochloride (0.42 g, 4.39 mmol) was added portion wise and stirred for 5 min at that temperature. To the reaction mixture triethylamine (0.66 ml, 4.75 mmol) was added drop wise and it was stirred for 2 hr at 20-25° C. The reaction mixture was diluted with water (10 ml) and aqueous layer was separated. The aqueous layer was extracted with DCM (2×25 ml). The combined organic layer was washed with 5% HCl (25 ml) and saturated brine solution (25 ml). The organic layer was dried over $Na_2SO_4$, evaporated under reduced pressure to obtain 5-oxo-1-(3-trifluoromethyl-phenyl)-pyrrolidine-3-carboxylic acid methoxy-methyl-amide (0.95 g, 83%) as a colorless sticky mass.

$^1$HNMR (400 MHz, $CDCl_3$): δ 2.84-2.91 (m, 1H); 3.0-3.06 (m, 1H); 3.29 (s, 3H); 3.72-3.76 (m, 1H); 3.79 (s, 3H); 4.02-4.07 (m, 1H); 4.15-4.19 (m, 1H); 7.42-7.46 (m, 1H); 7.50-7.53 (m, 1H); 7.86 (s, 1H); 7.91-7.93 (m, 1H).

Step-2

4-Acetyl-1-(3-trifluoromethyl-phenyl)-pyrrolidin-2-one

To a stirred solution of 5-oxo-1-(3-trifluoromethyl-phenyl)-pyrrolidine-3-carboxylic acid methoxy-methyl-amide (0.6 g, 1.89 mmol) in THF (6 mL) was added methylmagnesium bromide (1.6 ml, 4.74 mmol, 3.0M in ether) drop wise over a period of 10 min at 0° C. The reaction mixture was stirred for 3 h at room temperature. The reaction mixture was quenched with saturated ammonium chloride solution (2 ml) and extracted with ethyl acetate (2×15 ml). The combined organic layer was washed with saturated brine solution (25 ml). The organic layer was dried over $Na_2SO_4$, evaporated to obtain 4-Acetyl-1-(3-trifluoromethyl-phenyl)-pyrrolidin-2-one as a brown oil (0.5 g, 97%).

$^1$HNMR (400 MHz, $CDCl_3$): δ 2.33 (s, 3H); 2.82-2.88 (m, 1H); 2.92-2.99 (m, 1H); 3.48-3.52 (m, 1H); 3.97-4.01 (m, 1H); 4.12-4.22 (m, 1H); 7.43-7.45 (m, 1H); 7.50-7.54 (m, 1H); 7.86-7.91 (m, 2H).

Step-3 to Step-6 were carried out similar to Example K1

Step-3

4-(1-Hydroxy-ethyl)-1-(3-trifluoromethyl-phenyl)-pyrrolidin-2-one $^1$HNMR (400 MHz, CDCl$_3$): δ 1.30-1.34 (m, 3H); 2.47-2.51 (m, 1H); 2.69-2.73 (m, 2H); 3.76-3.87 (m, 1H); 3.91-3.99 (m, 3H); 7.41-7.43 (m, 1H); 7.49-7.53 (m, 1H); 7.85-7.88 (m, 1H); 7.94-7.96 (m, 1H).

Step-4

Methanesulfonic acid 1-[5-oxo-1-(3-trifluoromethyl-phenyl)-pyrrolidin-3-yl]-ethyl ester $^1$HNMR (400 MHz, CDCl$_3$): δ 1.51-1.56 (m, 3H); 2.53-2.55 (m, 1H); 2.64-2.69 (m, 1H); 2.77-2.83 (m, 1H); 3.7 (s, 3H); 3.83-3.90 (m, 1H); 3.97-4.01 (m, 1H); 4.92-5.02 (m, 1H); 7.43-7.45 (m, 1H); 7.50-7.54 (m, 1H); 7.84-7.89 (m, 2H).

Step-5

8-(1-{1-[5-Oxo-1-(3-trifluoromethyl-phenyl)-pyrrolidin-3-yl]-ethyl}-1H-pyrazol-4-yl)-1,3-dipropyl-7-(2-trimethylsilanyl-ethoxymethyl)-3,7-dihydro-purine-2,6-dione Crude material was taken as such to the next step.

Step-6

8-(1-{1-[5-Oxo-1-(3-trifluoromethyl-phenyl)-pyrrolidin-3-yl]-ethyl}-1H-pyrazol-4-yl)-1,3-dipropyl-3,7-dihydro-purine-2,6-dione $^1$HNMR (400 MHz, DMSO d6): δ 0.86-0.91 (m, 6H); 1.51 (d, J=6.8 Hz, 3H); 1.55-1.61 (m, 2H); 1.69-1.74 (m, 2H); 2.53-2.59 (m, 1H); 2.98-3.04 (m, 2H); 3.66-3.69 (m, 2H); 3.86 (t, J=7.2 Hz, 2H); 3.98 (t, J=6.4 Hz, 2H); 4.58-4.62 (m, 1H); 7.45-7.47 (d, J=8.0 Hz, 1H); 7.54-7.58 (m, 1H); 7.66 (d, J=8.4 Hz, 1H); 8.11-8.13 (m, 2H); 8.46 (s, 1H); 13.51 (bs, 1H).

Example Q1

8-(1-{2-Oxo-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione

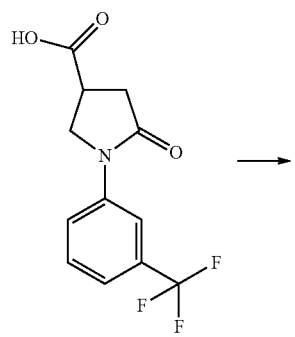

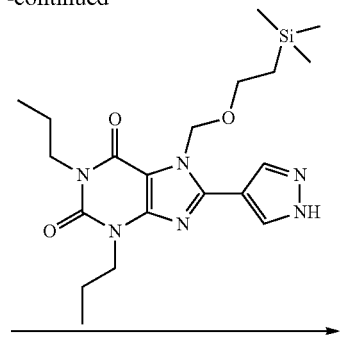

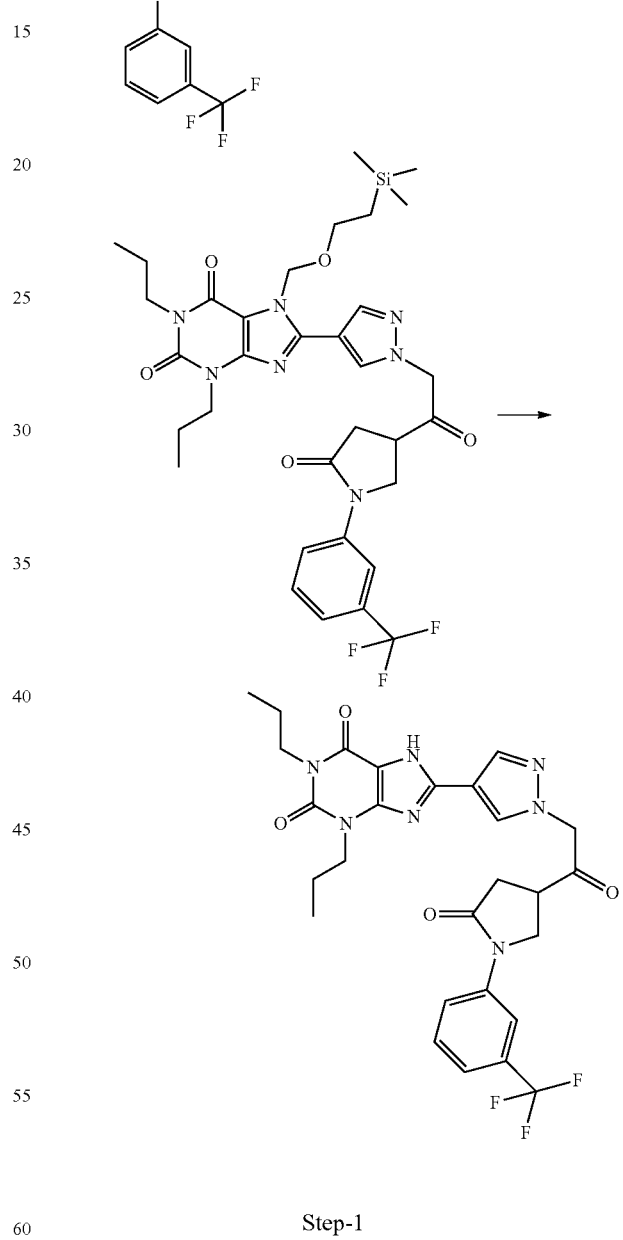

Step-1

4-(2-bromo-acetyl)-1-(3-trifluoromethyl-phenyl)-pyrrolidin-2-one

To a stirred solution of 5-oxo-1-(3-trifluoromethyl-phenyl)-pyrrolidine-3-carboxylic acid (1.0 g, 3.66 mmol) in DCM (10 ml) was added thionyl chloride (0.9 ml, 12.44 mmol) and DMF (2 drops). The reaction mixture was stirred for 1 hr at room temperature and the solvents were removed. The residue was taken in toluene (10 ml) and again concentrated to obtain brown oil. The resulting oil was taken in acetonitrile (10 ml) and trimethylsilyldiazomethane (9.15 ml, 18.3 mmol). It was stirred at room temperature for 1 hr. The reaction mixture was cooled to 0° C. and 33% HBr in acetic acid (4.17 ml, 23.79 mmol) was added drop wise and stirred for 1 hr at room temperature. To the reaction mixture sodium bicarbonate (20 ml) was added and extracted with ethyl acetate (3×15 ml). The combined organic layer was washed with saturated brine solution (35 ml). The organic layer was dried over $Na_2SO_4$, evaporated to obtain crude product. The crude product was purified by column chromatography using silicagel (100-200) and 12 to 16% ethyl acetate in hexane as an eluent to obtain 4-(2-bromo-acetyl)-1-(3-trifluoromethyl-phenyl)-pyrrolidin-2-one (0.9 g, 72%) as a brown mass.

$^1$HNMR (400 MHz, $CDCl_3$): δ 2.28-3.0 (m, 2H); 3.89-3.96 (m, 2H); 3.99-4.06 (m, 2H); 4.13-4.17 (m, 1H); 4.42-4.44 (m, 1H); 7.48-7.52 (m, 1H); 7.82 (s, 1H); 7.84-7.86 (m, 1H).

Step-2

8-(1-{2-Oxo-2-[5-oxo-1-(3-trifluoromethyl-phenyl)-pyrrolidin-3-yl]-ethyl}-1H-pyrazol-4-yl)-1,3-dipropyl-7-(2-trimethylsilanyl-ethoxymethyl)-3,7-dihydro-purine-2,6-dione A mixture of 1,3-dipropyl-8-(1H-pyrazol-4-yl)-7-(2-trimethylsilanyl-ethoxymethyl)-3,7-dihydro-purine-2,6-dione (0.200 g, 0.462 mmol), 4-(2-Bromo-acetyl)-1-(3-trifluoromethyl-phenyl)-pyrrolidin-2-one (0.240 g, 0.693 mmol), $Cs_2CO_3$ (0.30 g, 0.924 mmol) and acetonitrile (2 ml) were heated at 90-100° C. in a sealed tube for 6 hrs. Reaction mixture was cooled to 20-25° C. and filtered off. The organic volatiles were evaporated. The crude product was purified by preparative TLC to obtain pure 8-(1-{2-oxo-2-[5-oxo-1-(3-trifluoromethyl-phenyl)-pyrrolidin-3-yl]-ethyl}-1H-pyrazol-4-yl)-1,3-dipropyl-7-(2-trimethylsilanyl-ethoxymethyl)-3,7-dihydro-purine-2,6-dione (0.090 g, 28%) as a brown mass.

$^1$HNMR (400 MHz, $CDCl_3$): δ 0.10 (s, 9H); 0.93-1.03 (m, 8H); 1.70-1.85 (m, 4H); 2.82-2.86 (m, 2H); 3.55-3.59 (m, 1H); 3.80-3.84 (m, 2H); 3.93-4.01 (m, 3H); 4.10-4.14 (m, 2H); 4.19-4.23 (m, 1H); 5.15 (s, 2H); 5.81 (d, J=2.0 Hz, 2H); 7.42-7.44 (m, 1H); 7.48-7.52 (m, 1H); 7.80-7.85 (m, 2H); 8.23 (s, 1H); 8.28 (s, 1H).

Step-3

8-(1-{2-Oxo-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione The reaction was carried out as described before.

$^1$HNMR (400 MHz, DMSO d6): δ 0.82-0.87 (m, 6H); 1.51-1.57 (m, 2H); 1.65-1.71 (m, 2H); 2.80-2.83 (m, 2H); 3.64-3.68 (m, 1H); 3.82 (t, J=7.2 Hz, 2H); 3.94 (t, J=6.8 Hz, 2H); 4.09-4.11 (m, 2H); 5.43 (d, J=1.6 Hz, 2H); 7.48 (d, J=7.6 Hz, 1H); 7.59-7.63 (m, 1H); 7.83 (d, J=8.4 Hz, 1H); 8.08-8.11 (m, 2H); 8.34 (s, 1H); 13.56 (bs, 1H).

Example R1

8-(1-{2-Hydroxy-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione

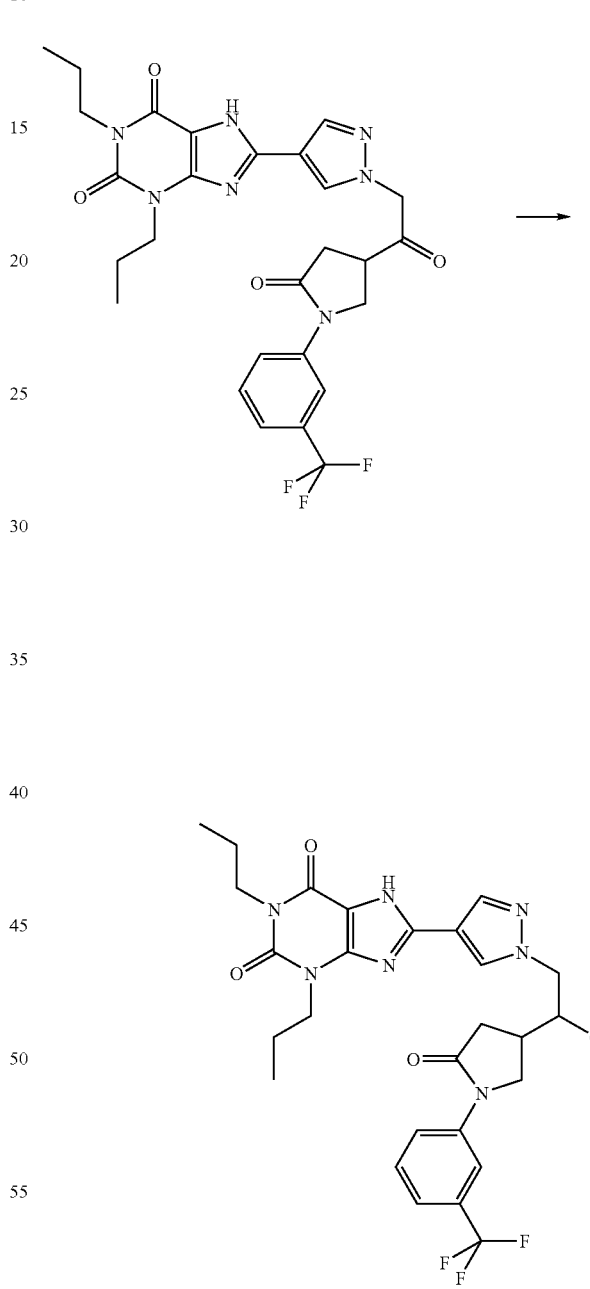

The reaction was carried out by following the reaction conditions and procedure as described before in step-3 of Example K1

$^1$HNMR (400 MHz, DMSO d6): δ 0.82-0.87 (m, 6H); 1.51-1.57 (m, 2H); 1.66-1.71 (m, 2H); 2.40-2.43 (m, 1H); 2.53-2.61 (m, 2H); 3.72-3.74 (m, 1H); 3.80-3.85 (m, 2H); 3.85-3.96 (m, 4H); 4.15-4.26 (m, 2H); 5.39-5.44 (m, 1H);

7.45 (d, J=7.6 Hz, 1H); 7.57-7.61 (m, 1H); 7.83 (d, J=8.0 Hz, 1H); 8.0 (s, 1H); 8.12 (s, 1H); 8.31 (s, 1H); 13.45 (bs, 1H).

Example S1

8-{1-[5-(4-Fluoro-benzyl)-4,5-dihydro-isoxazol-3-ylmethyl]1Hpyrazol4-yl}-1,3-dipropyl-3,7-dihydro-purine-2,6-dione

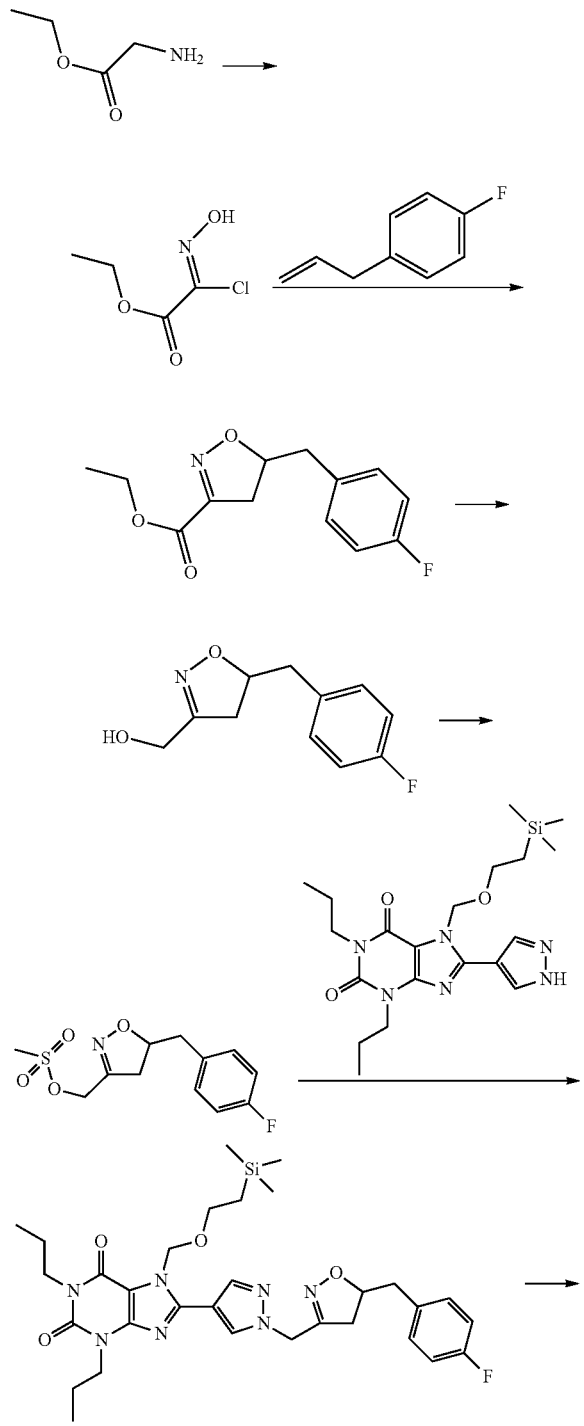

-continued

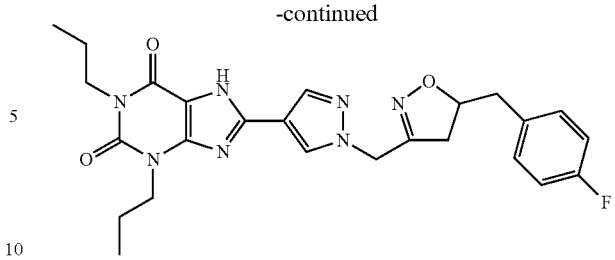

Step-1

Chloro oxime-acetic acid ethyl ester

A mixture of solution of amino-acetic acid ethyl ester (5 g, 48.53 mmol) in water (5 ml) and conc. HCl (8 ml), $NaNO_2$ (4.91 g, 145.6 mmol) with water (5 ml) was added slowly at 0° C. stirred for 1 hr at room temperature. After completion of reaction, the compound was extracted with ethyl acetate. The organic layer was dried over $Na_2SO_4$ and concentrated under vacuum to get 1.5 g (20%) of chloro oxime-acetic acid ethyl ester as white solid.
$^1$HNMR (400 MHz, $CDCl_3$): δ 1.37-1.41 (t, J=7.2 Hz, 3H); 4.38-4.43 (q, J=7.2 Hz, 2H); 9.59-9.61 (m, 1H).

Step-2

5-(4-Fluoro-benzyl)-4,5-dihydro-isoxazole-3-carboxylic acid ethyl ester

To a mixture of 1-Allyl-4-fluoro-benzene (0.27 g, 0.198 mmol) and $NaHCO_3$ (0.166 gm, 0.198 mmol) in [Bmim][BF4] (0.2 ml), chloro oxime-acetic acid ethyl ester (0.3 g, 0.198 mmol) was added at room temperature. After stirring the reaction mixture for 6 h, the sticky mass obtained was washed with diethyl ether. The ether layer was concentrated to obtain a yellow residue which was further purified by column chromatography to obtain 5-(4-Fluoro-benzyl)-4,5-dihydro-isoxazole-3-carboxylic acid ethyl ester (170 mg, 34%) as a white solid.
$^1$HNMR (400 MHz, $CDCl_3$): δ 1.34-1.41 (m, 3H); 2.87-2.94 (m, 2H); 3.02-3.07 (m, 1H); 3.17-3.24 (m, 1H); 4.30-4.41 (m, 2H); 5.00-5.05 (m, 1H); 6.98-7.03 (m, 2H); 7.18-7.26 (m, 2H).

Step-3

[5-(4-Fluoro-benzyl)-4,5-dihydro-isoxazol-3-yl]-methanol

To a solution of 5-(4-Fluoro-benzyl)-4,5-dihydro-isoxazole-3-carboxylic acid ethyl ester (0.17 g, 0.677 mmol) in THF (10 ml), $NaBH_4$ (0.051 g, 0.81 mmol) was added slowly at 0° C. The reaction mixture was stirred for 2 h at room temperature. Water was added to the reaction mixture and extracted with ethyl acetate. The ethyl acetate layer was washed with brine, dried over $Na_2SO_4$ and concentrated under vacuum. The residue obtained was purified by column chromatography to obtain [5-(4-Fluoro-benzyl)-4,5-dihydro-isoxazol-3-yl]-methanol (140 mg, 100%) as an yellow oil.
$^1$HNMR (400 MHz, $CDCl_3$): δ 2.78-2.91 (m, 2H); 3.09-3.17 (m, 2H); 4.41 (s, 2H); 4.92-4.99 (m, 1H); 7.01-7.09 (m, 2H); 7.21-7.25 (m, 2H).

Step-4

Methanesulfonic acid 5-(4-fluoro-benzyl)-4,5-dihydro-isoxazol-3-ylmethyl ester To a mixture of solution of [5-(4-Fluoro-benzyl)-4,5-dihydro-isoxazol-3-yl]-methanol (80 mg, 0.38 mmol), TEA (57 mg, 0.57 mmol) in DCM (10 ml), methanesulfonyl chloride (43 mg, 0.38 mmol) was added slowly at 0° C. and the mixture was stirred at room temperature for 3 hrs. Aqueous $NaHCO_3$ was added to the reaction mixture and extracted with methylene dichloride. The organic layer was washed with brine, dried over $Na_2SO_4$, filtered and concentrated under vacuum. The residue obtained was purified by column chromatography to obtain Methanesulfonic acid 5-(4-fluoro-benzyl)-4,5-dihydro-isoxazol-3-ylmethyl ester (82 mg, 75%) as brown oil.

Step-5

8-{1-[5-(4-Fluoro-benzyl)-4,5-dihydro-isoxazol-3-ylmethyl]-1H-pyrazol-4-yl}-1,3-dipropyl-7-(2-trimethylsilanyl-ethoxymethyl)-3,7-dihydro-purine-2,6-dione A mixture of solution of Methanesulfonic acid 5-(4-fluoro-benzyl)-4,5-dihydro-isoxazol-3-ylmethyl ester (73 mg, 0.25 mmol), 1,3-dipropyl-8-(1H-pyrazol-4-yl)-7-(2-trimethylsilanyl-ethoxymethyl)-3,7-dihydro-purine-2,6-dione (100 mg, 0.23 mmol) and $K_2CO_3$ (63 mg, 0.46 mmol) in acetonitrile (10 ml) was heated at 80° C. for 3 hrs. The reaction mixture was filtered through celite and washed with acetone. The organic layer was concentrated and the oil obtained was purified by column chromatography to obtain 8-{1-[5-(4-Fluoro-benzyl)-4,5-dihydro-isoxazol-3-ylmethyl]-1H-pyrazol-4-yl}-1,3-dipropyl-7-(2-trimethylsilanyl-ethoxymethyl)-3,7-dihydro-purine-2,6-dione (85 mg, 60%) as brown oil.

$^1$HNMR (400 MHz, $CDCl_3$): δ 0.01 (s, 9H); 0.98-1.08 (m 8H); 1.64-2.08 (m, 4H); 2.68-2.97 (m, 1H); 2.90-3.09 (m, 3H); 3.82-3.97 (m, 2H); 4.01-4.07 (m, 2H); 4.23-4.31 (m, 2H); 4.95-5.00 (m, 1H); 5.12 (s, 2H); 5.81-5.95 (m, 2H); 6.97-7.06 (m, 2H); 7.18-7.22 (m, 2H); 8.27 (s, 1H); 8.59 (s, 1H).

Step-6

8-{1-[5-(4-Fluoro-benzyl)-4,5-dihydro-isoxazol-3-ylmethyl]-1H-pyrazol-4-yl}-1,3-dipropyl-3,7-dihydro-purine-2,6-dione To a solution of 8-{1-[5-(4-Fluoro-benzyl)-4,5-dihydro-isoxazol-3-ylmethyl]-1H-pyrazol-4-yl}-1,3-dipropyl-7-(2-trimethylsilanyl-ethoxymethyl)-3,7-dihydro-purine-2,6-dione (80 mg) in ethanol (5 ml) aq. HCl (2 N, 5 ml) was added and the reaction mixture was refluxed for 2 hrs. The volatiles were evaporated and the residue obtained was dissolved in ethyl acetate and washed with water and brine. The organic layer was dried over $Na_2SO_4$ and concentrated under vacuum. The residue obtained was purified by column chromatography to obtain 8-{1-[5-(4-Fluoro-benzyl)-4,5-dihydro-isoxazol-3-ylmethyl]-1H-pyrazol-4-yl}-1,3-dipropyl-3,7-dihydro-purine-2,6-dione (100 mg, 98%) as white solid.

$^1$HNMR (400 MHz, $CDCl_3$): δ 0.82-0.98 (m, 6H); 1.56-1.64 (m, 2H); 1.71-1.8 (m, 2H); 2.58-2.62 (m, 2H); 2.78-2.98 (m, 3H); 3.82-3.97 (m, 2H); 4.01-4.07 (m, 2H); 4.79-4.84 (m, 1H); 5.19 (s, 1H); 7.07-7.16 (m, 2H); 7.24-7.28 (m, 2H); 8.17 (s, 1H); 8.41 (s, 1H).

Example T1

8-(1-{2-Oxo-2-[4-(3-trifluoromethyl-phenyl)-piperazin-1-yl]-ethyl}-1H-pyrazol-4-yl)-1,3-dipropyl-3,7-dihydro-purine-2,6-dione

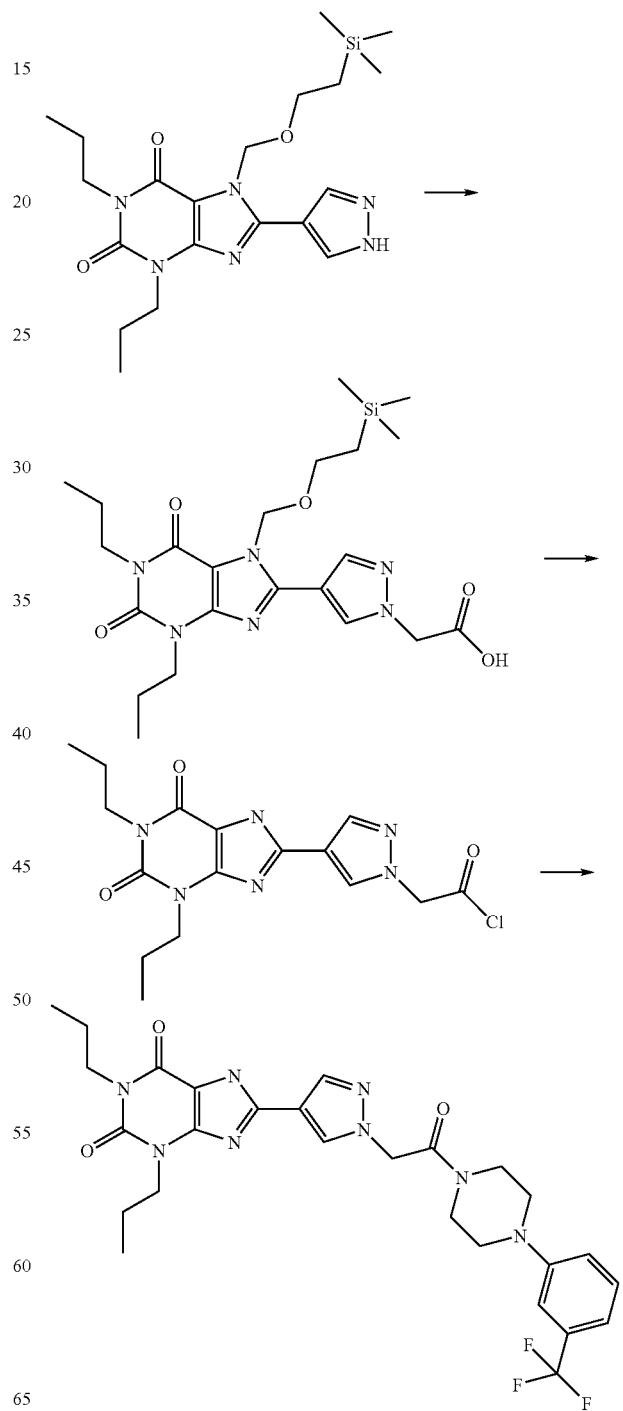

Step-1

{4-[2,6-Dioxo-1,3-dipropyl-7-(2-trimethylsilanyl-ethoxymethyl)-2,3,6,7-tetrahydro-1H-purin-8-yl]-pyrazol-1-yl}-acetic acid A mixture of solution of 1,3-dipropyl-8-(1H-pyrazol-4-yl)-7-(2-trimethylsilanyl-ethoxymethyl)-3,7-dihydro-purine-2,6-dione (600 mg, 1.38 mmol), bromo acetic acid (289 mg, 2.08 mmol) and $K_2CO_3$ (575 mg, 4.16 mmol) in acetone (10 ml) was heated at 80° C. for 3 hrs. The reaction mixture was filtered through celite and washed with acetone. The organic layer was concentrated and the residue obtained was purified by column chromatography to obtain {4-[2,6-dioxo-1,3-dipropyl-7-(2-trimethylsilanyl-ethoxymethyl)-2,3,6,7-tetrahydro-1H-purin-8-yl]-pyrazol-1-yl}-acetic acid (420 mg, 61%) as white solid.

Step-2

[4-(2,6-Dioxo-1,3-dipropyl-2,3,6,7-tetrahydro-1H-purin-8-yl)-pyrazol-1-yl]-acetyl chloride {4-[2,6-Dioxo-1,3-dipropyl-7-(2-trimethylsilanyl-ethoxymethyl)-2,3,6,7-tetrahydro-1H-purin-8-yl]-pyrazol-1-yl}-acetic acid (350 mg, 0.71 mmol) was taken with thionyl chloride (25 ml) and refluxed for 3 hrs. The volatiles were evaporated to obtain [4-(2,6-dioxo-1,3-dipropyl-2,3,6,7-tetrahydro-1H-purin-8-yl)-pyrazol-1-yl]-acetyl chloride (400 mg) as a yellow solid.

Step-3

8-(1-{2-Oxo-2-[4-(3-trifluoromethyl-phenyl)-piperazin-1-yl]-ethyl}-1H-pyrazol-4-yl)-1,3-dipropyl-3,7-dihydro-purine-2,6-dione To a solution of [4-(2,6-dioxo-1,3-dipropyl-2,3,6,7-tetrahydro-1H-purin-8-yl)-pyrazol-1-yl]-acetyl chloride (100 mg, 0.26 mmol) in THF (10 ml) was added TEA (53 mg, 0.53 mmol) and 1-(3-Trifluoromethyl-phenyl)-piperazine (66 mg, 0.29 mmol) at 0° C. and the mixture was stirred overnight. The reaction mixture was concentrated and purified by HPLC to obtain 8-(1-{2-Oxo-2-[4-(3-trifluoromethyl-phenyl)-piperazin-1-yl]-ethyl}-1H-pyrazol-4-yl)-1,3-dipropyl-3,7-dihydro-purine-2,6-dione (30 mg, 21%) as a white solid.

$^1$HNMR (400 MHz, DMSO d6)): δ 0.85-0.91 (m, 6H); 1.55-1.60 (m, 2H); 1.69-1.75 (m, 2H); 3.24-3.3 (m, 2H); 3.60-3.70 (m, 2H); 3.83-3.87 (t, J=7.6 Hz, 2H); 3.96-4.00 (t, J=6.8 Hz, 2H); 5.31 (s, 2H); 7.10-7.12 (d, J=7.2 Hz, 4H); 7.28 (s, 1H); 7.26-7.28 (d, J=8.4, 1H); 7.43-7.47 (t, J=8 Hz, 1H); 8.05 (s, 1H); 8.30 (s, 1H); 13.5 (bs, 1H).

Examples T2-T9 were prepared in an analogous manner of Example T1 from the appropriate intermediate.

| Example | IUPAC name |
|---|---|
| T2 | 8-(1-{2-[4-(4-Chloro-phenyl)-4-hydroxy-piperidin-1-yl]-2-oxo-ethyl}-1H-pyrazol-4-yl)1,3-dipropyl-3,7-dihydro-purine-2,6-dione |
| T3 | 8-(1-{2-[4-(2,4-Difluoro-phenyl)-piperazin-1-yl]-2-oxo-ethyl}-1H-pyrazol-4-yl)-1,3-dipropyl-3,7-dihydro-purine-2,6-dione |
| T4 | 8-{1-[2-Oxo-2-(4-p-tolyl-piperazin-1-yl)-ethyl]-1H-pyrazol-4-yl}-1,3-dipropyl-3,7-dihydro-purine-2,6-dione |
| T5 | 8-(1-{2-Oxo-2-[4-(4-trifluoromethyl-phenyl)-piperazin-1-yl]-ethyl}-1H-pyrazol-4-yl)-1,3-dipropyl-3,7-dihydro-purine-2,6-dione |
| T6 | 8-(1-{2-[4-(3-Chloro-4-fluoro-phenyl)-piperazin-1-yl]-2-oxo-ethyl}-1H-pyrazol-4-yl)-1,3-dipropyl-3,7-dihydro-purine-2,6-dione |
| T7 | 3-Ethyl-8-(1-{2-oxo-2-[4-(3-trifluoromethyl-phenyl)-piperazin-1-yl]-ethyl}-1H-pyrazol-4-yl)-1-propyl-3,7-dihydro-purine-2,6-dione |
| T8 | 8-(1-{2-[4-(4-Fluoro-phenyl)-piperidin-1-yl]-2-oxo-ethyl}-1H-pyrazol-4-yl)-1,3-dipropyl-3,7-dihydro-purine-2,6-dione |
| T9 | 8-(1-{2-[4-(3-Fluoro-phenyl)-piperidin-1-yl]-2-oxo-ethyl}-1H-pyrazol-4-yl)-1,3-dipropyl-3,7-dihydro-purine-2,6-dione |

Example U1

4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid

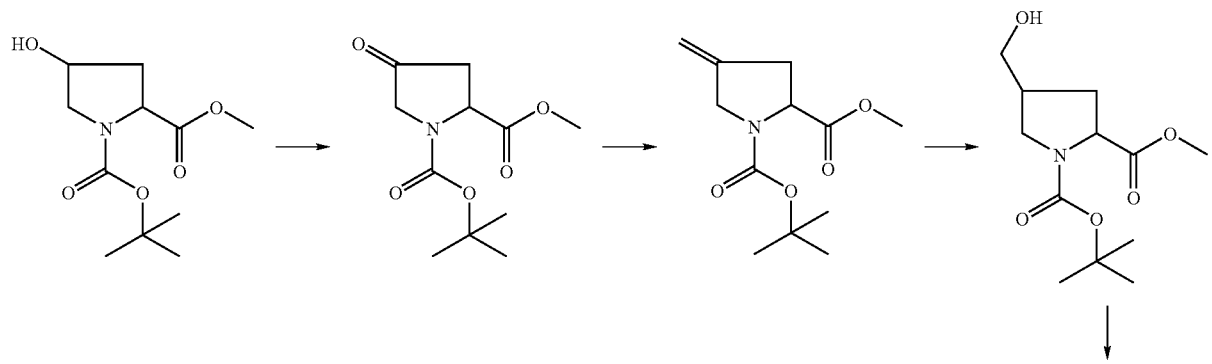

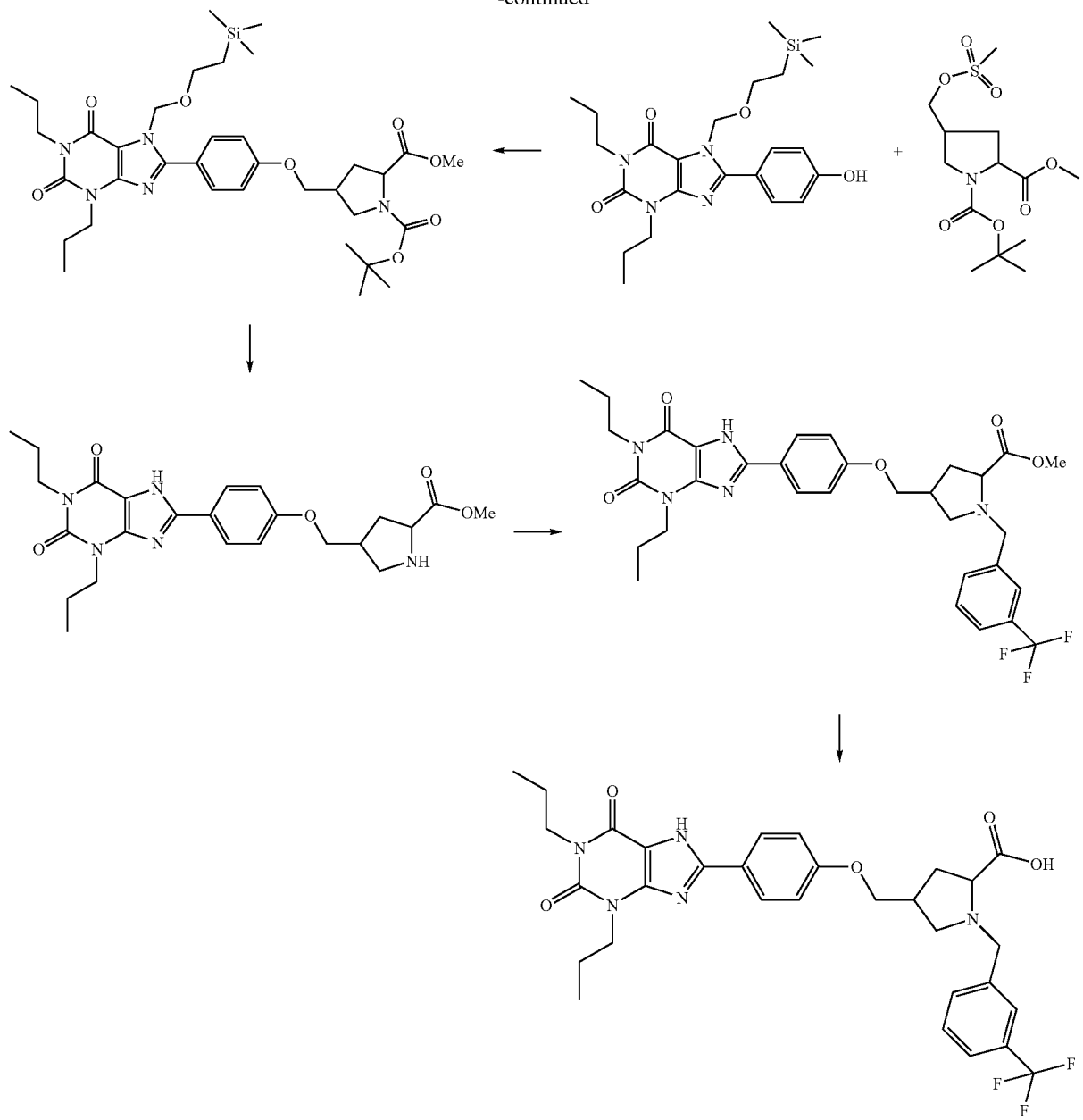

Step-1

4-Oxo-pyrrolidine-1,2-dicarboxylic acid 1-tert-butyl ester 2-methyl ester

To a solution of 4-hydroxy-pyrrolidine-1,2-dicarboxylic acid 1-tert-butyl ester 2-methyl ester (8 g, 32.65 mmol) in DCM (200 ml), pyridinium dichromate (24.55 g, 65.3 mmol) was added at 0° C. It was stirred at room temperature for overnight. Reaction mixture was filtered through celite pad and DCM layer was concentrated. Purification by column chromatography offered 4-oxo-pyrrolidine-1,2-dicarboxylic acid 1-tert-butyl ester 2-methyl ester as a white solid (6 g, 76%).

$^1$HNMR (400 MHz, CDCl$_3$): δ 1.45-1.47 (Two s, 9H); 2.55-2.60 (m, 1H); 2.88-3.0 (m, 1H); 3.75 (s, 3H); 3.87-3.90 (d, 2H, J=13.2 Hz); 4.69-4.82 (m, 1H).

Step-2

4-Methylene-pyrrolidine-1,2-dicarboxylic acid 1-tert-butyl ester 2-methyl ester

To a suspension of methyltriphenylphosphonium iodide (1.25 g, 3.08 mmol) in THF (20 ml) at 0° C., 4-oxo-pyrrolidine-1,2-dicarboxylic acid 1-tert-butyl ester 2-methyl ester (500 mg, 2.05 mmol) and potassium ter-butoxide (460 mg, 4.11 mmol) was added. It was stirred for overnight at room temperature. Water was added and the compound was extracted with ethyl acetate. The ethyl acetate layer was washed with brine, dried over sodium sulphate, filtered and concentrated under vacuum. Purification by column chromatography offered 4-methylene-pyrrolidine-1,2-dicarboxylic acid 1-tert-butyl ester 2-methyl ester as a colorless oil (0.23 g, 46%).

¹HNMR (400 MHz, CDCl₃): δ 1.45-1.50 (Two s, 9H); 2.62-2.68 (m, 1H); 2.93-3.06 (m, 1H); 3.76 (s, 3H); 4.08-4.12 (d, 2H, J=15.2 Hz); 4.41-4.55 (m, 1H); 5.03-5.06 (m, 2H).

Step-3

4-Hydroxymethyl-pyrrolidine-1,2-dicarboxylic acid 1-tert-butyl ester 2-methyl ester To a solution of 4-methylene-pyrrolidine-1,2-dicarboxylic acid 1-tert-butyl ester 2-methyl ester (1g, 4.149 mmol) in THF (25 ml), 0.5 M solution of 9-BBN in THF (9.8 ml, 4.979 mmol) was added at 0° C. and stirred for 2 hrs at room temperature. The reaction mixture was cooled to 0° C., and then 2N NaOH (2.43 ml, 4.979 mmol) and 30% H₂O₂ (1.6 ml, 14.93 mmol) were added. The reaction mixture was stirred at room temperature for 4 hr and later it was poured into water. The mixture was extracted with ethyl acetate. The ethyl acetate layer was washed with brine, filtered and concentrated under vacuum. Purification by column chromatography offered 4-hydroxymethyl-pyrrolidine-1,2-dicarboxylic acid 1-tert-butyl ester 2-methyl ester as a yellow oil (6 g, 56%).

¹HNMR (400 MHz, CDCl₃): δ 1.43-1.48 (Two s, 9H); 1.74-1.81 (m, 1H); 2.37-2.58 (m, 2H); 3.20-3.29 (m, 1H); 3.58-3.72 (m, 3H); 3.74 (s, 3H).

Step-4

4-Methanesulfonylmethyl-pyrrolidine-1,2-dicarboxylic acid 1-tert-butyl ester 2-methyl ester To a solution of 4-hydroxymethyl-pyrrolidine-1,2-dicarboxylic acid 1-tert-butyl ester 2-methyl ester (0.5 g, 1.93 mmol) and TEA (0.33 gm, 2.89 mmol) in DCM (20 ml), methane sulphonyl chloride (0.38 g, 3.86 mmol) was added at 0° C. The reaction mixture was stirred at room temperature for 4 h. Aqueous NaHCO₃ solution was added to it and extracted with DCM. The organic layer was washed with brine, dried over Na₂SO₄, filtered and concentrated under vacuum to offer 4-methanesulfonylmethyl-pyrrolidine-1,2-dicarboxylic acid 1-tert-butyl ester 2-methyl ester as a white solid (0.45 g, 69%). ¹HNMR (400 MHz, CDCl₃): δ 1.45-1.50 (Two s, 9H); 1.79-1.85 (m, 1H); 2.42-2.81 (m, 2H); 3.08 (s, 3H); 3.21-3.38 (m, 1H); 3.77 (s, 3H); 4.09-4.4 (m, 3H).

Step-5

4-{4-[2,6-Dioxo-1,3-dipropyl-7-(2-trimethylsilanyl-ethoxymethyl)-2,3,6,7-tetrahydro-1H-purin-8-yl]-phenoxymethyl}-pyrrolidine-1,2-dicarboxylic acid 1-tert-butyl ester 2-methyl ester A mixture of 8-(4-hydroxy-phenyl)-1,3-dipropyl-7-(2-trimethylsilanyl-ethoxymethyl)-3,7-dihydro-purine-2,6 dione (100 mg, 0.231 mmol), 4-methanesulfonyl methyl-pyrrolidine-1,2-dicarboxylic acid 1-tert-butyl ester 2-methyl ester (82 mg, 0.254 mmol) and K₂CO₃ (63 mg, 0.462 mmol) in DMF (8 ml) was heated at 80° C. for 3 hrs. The reaction mixture was filtered through celite and washed with ethyl acetate. The filtrate was washed with water, brine, dried over sodium sulphate, filtered and concentrated under vacuum. The residue obtained was purified by column chromatography to offer 4-{4-[2,6-dioxo-1,3-dipropyl-7-(2-trimethylsilanyl-ethoxymethyl)-2,3,6,7-tetrahydro-1H-purin-8-yl]-phenoxymethyl}-pyrrolidine-1,2-dicarboxylic acid 1-tert-butyl ester 2-methyl ester as a yellow oil (110 mg, 36%).

¹HNMR (400 MHz, CDCl₃): δ 0.1 (s, 9H); 0.98-1.04 (m, 8H); 1.45-1.47 (Two s, 9H); 1.62-1.78 (m, 3H); 1.82-1.96 (m, 2H); 2.52-2.95 (m, 3H); 3.38-3.42 (m, 1H); 3.77 (s, 3H); 3.81-3.95 (m, 3H); 3.98-4.09 (m, 4H); 4.17-4.22 (m, 2H); 5.72 (s, 2H); 6.98-7.03 (m, 2H); 7.94-7.98 (m, 2H).

Step-6

4-[4-(2,6-Dioxo-1,3-dipropyl-2,3,6,7-tetrahydro-1H-purin-8-yl)-phenoxymethyl]-pyrrolidine-2-carboxylic acid methyl ester To a solution of 4-{4-[2,6-Dioxo-1,3-dipropyl-7-(2-trimethylsilanyl-ethoxymethyl)-2,3,6,7-tetrahydro-1H-purin-8-yl]-phenoxymethyl}-pyrrolidine-1,2-dicarboxylic acid 1-tert-butyl ester 2-methyl ester (100 mg) in methanol (3 ml), methanolic HCl (3 N, 0.5 ml) was added at 0° C., reaction mixture was stirred at room temperature for 2 hrs. The reaction mixture was evaporated and the residue obtained was purified by column chromatography to offer 4-[4-(2,6-Dioxo-1,3-dipropyl-2,3,6,7-tetrahydro-1H-purin-8-yl)-phenoxymethyl]-pyrrolidine-2-carboxylic acid methyl ester as a yellow solid (50 mg, 74%).

¹HNMR (400 MHz, CDCl₃): δ 0.65-0.79 (m, 6H); 1.37-1.59 (m, 4H); 1.98-2.86 (m, 3H); 3.15-3.18 (m, 2H); 3.37-3.42 (m, 1H); 3.61-3.68 (m, 2H); 3.69-3.79 (m, 5H); 3.91-3.98 (m, 2H); 6.78-6.83 (m, 2H); 7.48-7.58 (m, 2H).

Step-7

4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid methyl ester To a solution of 4-[4-(2,6-Dioxo-1,3-dipropyl-2,3,6,7-tetrahydro-1H-purin-8-yl)-phenoxymethyl]-pyrrolidine-2-carboxylic acid methyl ester (50 mg, 0.106 mmol) and TEA (32 mg, 0.319 mmol) in DCM (5 ml), 3-trifluoro methyl benzyl bromide (30 mg, 0.127 mmol) was added at 0° C. Reaction mixture was stirred at room temperature for 4 hr. Water was added into it and extracted with DCM. The organic layer was washed with brine, dried over Na₂SO₄, filtered and concentrated under vacuum to offer 4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid methyl ester as an off white solid (25 mg, 37%).

¹HNMR (400 MHz, CDCl₃): δ 0.98-1.14 (m, 6H); 1.62-1.78 (m, 3H); 1.82-1.96 (m, 2H); 2.84-3.15 (m, 2H); 3.38-3.78 (m, 2H); 3.81-3.98 (m, 5H); 3.98-4.21 (m, 5H); 4.51-4.77 (m, 2H); 6.98-7.03 (m, 2H); 7.62-7.78 (m, 3H); 8.07-8.12 (m, 1H); 8.31-8.42 (bs, 2H); 13.91 (bs, 1H).

Step-8

4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid A mixture of solution of 4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid methyl ester (25 mg, 0.039 mmol) in THF (3 ml) and MeOH (1 ml) was added aq. solution of LiOH (3 mg, 0.079 mmol) in H₂O (1 ml) at 0° C. and it was stirred for 2 hrs. Reaction mixture was concentrated, residue was diluted with water and acidified with aq. HCl. The aqueous layer was extracted with ethyl acetate and washed with brine. The ethyl acetate layer was concentrated and purified by column chromatography to offer 4-[4-(2,6-Dioxo-1,3-dipropyl-2,3,6,7-tetrahydro-1H-purin-8-yl)-phenoxymethyl]-1-(3-trifluoromethyl-benzyl)-pyrrolidine-2-carboxylic acid as viscous oil (18 mg, 75%).

$^1$HNMR (400 MHz, CDCl$_3$): δ 0.82-0.99 (m, 6H); 1.58-1.62 (m, 2H); 1.62-1.78 (m, 2H); 2.64-3.87 (m, 1H); 2.98-3.08 (m, 1H); 3.23-3.38 (m, 1H); 3.61-3.68 (m, 1H); 3.81-3.98 (m, 2H); 3.98-4.18 (m, 5H); 4.27-4.34 (m, 1H); 4.75-4.87 (m, 2H); 6.98-7.03 (m, 2H); 7.52-7.78 (m, 2H); 7.81-8.92 (m, 2H); 8.11-8.14 (m, 2H); 13.62 (bs, 1H).

Example V1

3-(2-Amino-ethyl)-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione

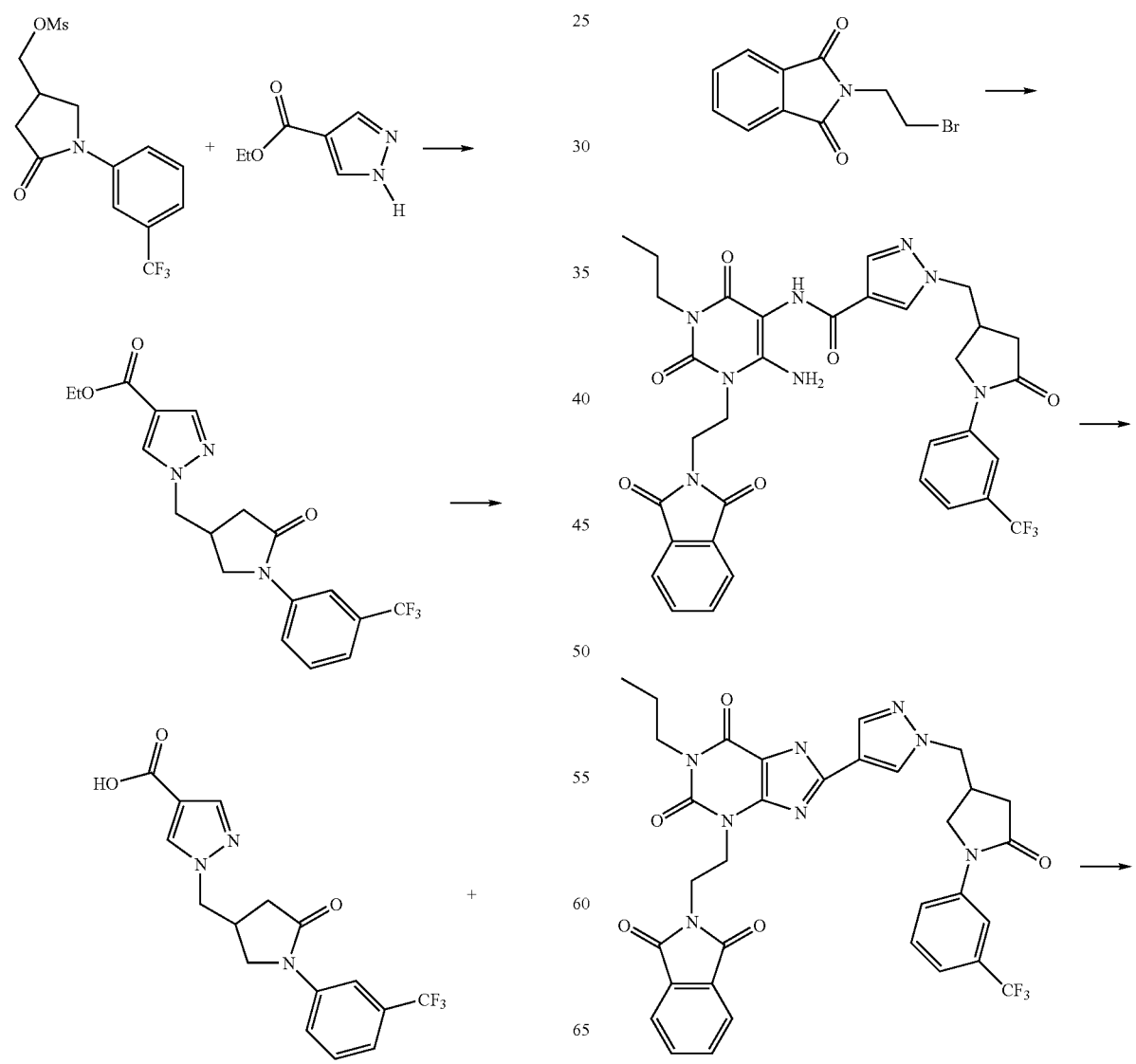

-continued

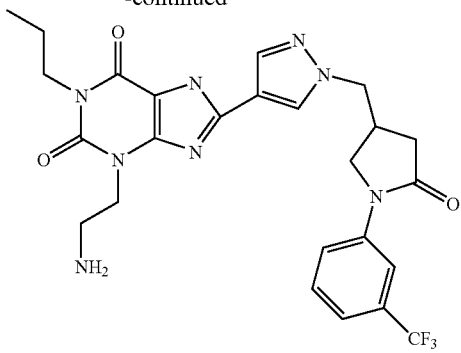

Step-1

1-[5-Oxo-1-(3-trifluoromethyl-phenyl)-pyrrolidin-3-ylmethyl]-1H-pyrazole-4-carboxylic acid ethyl ester In an oven dried two-necked round-bottomed flask, the methanesulfonic acid 5-oxo-1-(3-trifluoromethyl-phenyl)-pyrrolidin-3-yl ester (3.2 g, 9.4 mmol), 1H-pyrazole-4-carboxylic acid ethyl ester (1.46 g, 10.0 mmol), and potassium carbonate (3.93 g, 28.0 mmol) were mixed under an argon atmosphere followed by the addition of the dry acetone (60 mL) at room temperature. The reaction mixture was refluxed at 80° C. for 24 h. The reaction mixture was filtered, evaporated and extracted with DCM (100×3 mL), dried over $Na_2SO_4$ and concentrated on a rotary evaporator to afford the crude product mixture. The product was isolated by flash column chromatography (eluting with hexane:EtOAc, 2:3) as a viscous oil (2.7 g, 75%).

$^1$HNMR (400 MHz, $CDCl_3$): δ 1.35 (t, J=7.0 Hz, 3H), 2.46 (dd, J=17.0, 7.0 Hz, 1H), 2.83 (dd, J=17.6, 8.0 Hz, 1H), 3.14 (m, 1H), 3.74 (dd, J=9.6, 6.0 Hz, 1H), 3.97 (t, J=8.0 Hz, 1H), 4.26-4.33 (m, 4H), 7.41 (d, J=8.0 Hz, 1H), 7.47 (t, J=8.0 Hz, 1H), 7.81 (br s, 2H), 7.94 (d, J=6.8 Hz, 2H).

Step-2

1-[5-Oxo-1-(3-trifluoromethyl-phenyl)-pyrrolidin-3-ylmethyl]-1H-pyrazole-4-carboxylic acid To a stirred solution of 1-[5-Oxo-1-(3-trifluoromethyl-phenyl)-pyrrolidin-3-ylmethyl]-1H-pyrazole-4-carboxylic acid ethyl ester (2.6 g, 6.81 mmol) in 14 mL $MeOH:H_2O$ (3:11), NaOH (0.4 g, 10.5 mmol) was added at room temperature. The mixture was heated at 100° C. for 2 h. The reaction mixture was cooled; MeOH was removed under reduced pressure, diluted with water, washed with DCM and acidified with 1% HCl. The acidified mixture was extracted with EtOAc (3×50 mL) and the combined extract was washed with brine, dried with $Na_2SO_4$, evaporated under reduced pressure to give the title compound in 88% yield (2.1 g).

$^1$HNMR (400 MHz, DMSO $d_6$): δ 2.43 (dd, J=17.0, 6.0 Hz, 1H), 2.69 (dd, J=17.2, 8.8 Hz, 1H), 3.01 (m, 1H), 3.72 (dd, J=10.0, 5.0 Hz, 1H), 3.98 (t, J=8.0 Hz, 1H), 4.31 (d, J=6.8 Hz, 2H), 7.49 (d, J=7.6 Hz, 1H), 7.612 (t, J=8.0 Hz, 1H), 7.75 (d, J=8.0 Hz, 1H), 7.82 (s, 1H), 8.13 (s, 1H), 8.36 (s, 1H), 12.4 (br s, 1H).

Step-3

1-[5-Oxo-1-(3-trifluoromethyl-phenyl)-pyrrolidin-3-ylmethyl]-1H-pyrazole-4-carboxylic acid (6-amino-2,4-dioxo-3-propyl-1,2,3,4-tetrahydro-pyrimidin-5-yl)-amide To a stirred solution of 1-[5-Oxo-1-(3-trifluoromethyl-phenyl)-pyrrolidin-3-ylmethyl]-1H-pyrazole-4-carboxylic acid (1 g, 2.83 mmol) and 5,6-Diamino-3-propyl-1H-pyrimidine-2,4-dione (521 mg, 2.83 mmol) in MeOH (40 mL) was added EDCI (813 mg, 4.24 mmol) under argon atmosphere. After stirring at overnight at room temperature the reaction mixture was quenched with water (10 mL) and white solid was precipitated out. The solid was filtered and washed with water to give the crude product which on purification by column chromatography (eluting with 5% MeOH:DCM) furnished the title compound as a white solid (1.3 g, 88%).

$^1$HNMR (400 MHz, DMSO $d_6$): δ 0.80 (t, J=7.0 Hz, 3H), 1.47 (m, 2H), 2.40 (dd, J=17.0, 6.4 Hz, 1H), 2.66 (dd, J=16.8, 8.8 Hz, 1H), 2.98 (m, 1H), 3.62 (t, J=7.8 Hz, 2H), 3.69 (dd, J=9.0, 5.0 Hz, 1H), 3.96 (t, J=8.0 Hz, 1H), 4.29 (d, J=6.4 Hz, 2H), 6.00 (br s, 2H), 7.47 (d, J=7.2 Hz, 1H), 7.60 (t, J=8.0 Hz, 1H), 7.74 (d, J=8.0 Hz, 1H), 7.97 (s, 1H), 8.15 (s, 1H), 8.29 (s, 1H), 8.53 (s, 1H), 10.4 (br s, 1H).

Step-4

1-[5-Oxo-1-(3-trifluoromethyl-phenyl)-pyrrolidin-3-ylmethyl]-1H-pyrazole-4-carboxylic acid {6-amino-1-[2-(1,3-dioxo-1,3-dihydro-isoindol-2-yl)-ethyl]-2,4-dioxo-3-propyl-1,2,3,4-tetrahydro-pyrimidin-5-yl}-amide A mixture of compound I-[5-Oxo-1-(3-trifluoromethyl-phenyl)-pyrrolidin-3-ylmethyl]-1H-pyrazole-4-carboxylic acid (6-amino-2,4-dioxo-3-propyl-1,2,3,4-tetrahydro-pyrimidin-5-yl)-amide (250 mg, 0.48 mmol), $K_2CO_3$ (133 mg, 0.96 mmol), dry DMF (4 ml) and 2-(2-bromo-ethyl)-isoindole-1,3-dione (183 mg, 0.72 mmol) was stirred at room temperature for over night. After that brine was added to the reaction mixture and extracted with EtOAc (5×10 ml). The combined extract was dried over $Na_2SO_4$, filtered and concentrated under vacuum. The residue was purified by column chromatography using 3% MeOH and DCM as eluent to furnish the title compound (120 mg, 36%).

$^1$HNMR (400 MHz, DMSO $d_6$): δ 0.55 (t, J=7.6 Hz, 3H), 1.05 (m, 2H), 2.45 (m, 1H), 2.7 (m, 1H), 3.0 (m, 1H), 3.3-3.5 (m, 2H), 3.76 (m, 1H), 3.83 (br t, 2H), 4.03 (m, 1H), 4.25 (br t, 2H), 4.35 (m, 2H), 6.78 (s, 2H), 7.50 (m, 1H), 7.64 (m, 1H), 7.78 (m, 1H), 7.84 (s, 4H), 8.06 (s, 1H), 8.2 (s, 1H), 8.36 (s, 1H), 8.64 (s, 1H).

Step-5

3-[2-(1,3-Dioxo-1,3-dihydro-isoindol-2-yl)-ethyl]-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione 1-[5-Oxo-1-(3-trifluoromethyl-phenyl)-pyrrolidin-3-ylmethyl]-1H-pyrazole-4-carboxylic acid {6-amino-1-[2-(1,3-dioxo-1,3-dihydro-isoindol-2-yl)-ethyl]-2,4-dioxo-3-propyl-1,2,3,4-tetrahydro-pyrimidin-5-yl}-amide (100 mg, 0.14 mmol) was taken in dry DMF (3 ml) under argon atmosphere, added $P_2O_5$ (61.4 mg, 0.43 mmol) and dipped the reaction flask in a oil bath at 100° C. and stirred the reaction mixture for 5 min. Then the reaction mixture was cooled to room temperature and diluted with water and filtered the solid (56 mg, 57%) as pure product.

¹HNMR (400 MHz, DMSO d₆): δ 0.79 (t, J=7.6 Hz, 3H), 1.42 (m, 2H), 2.42 (dd, J=11.2 Hz, 6.0 Hz 1H), 2.7 (m, 1H), 3.0 (m, 1H), 3.75 (m 3H), 3.9-4.04 (m, 3H), 4.3 (m, 4H), 7.50 (d, J=7.6 Hz 1H), 7.62-7.67 (m, 3H), 7.73-7.83 (m, 4H), 8.06 (s, 1H), 8.18 (s, 1H), 13.4 (s, 1H).

Step-6

3-(2-Amino-ethyl)-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione 3-[2-(1,3-Dioxo-1,3-dihydro-isoindol-2-yl)-ethyl]-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione (56 mg, 0.083 mmol) was taken in EtOH (10 ml) to this monohydrated N₂H₄ (8.3 mg, 0.16 mmol) was added and stirred the reaction mixture for 1 h at room temperature. After completion of the reaction, solvent was evaporated under vacuum, solid was filtered, washed with DCM and the fitrate was concentrated to give the pure product (20 mg, 44%) as white solid.

¹HNMR (400 MHz, DMSO d₆): δ 0.89 (t, J=8.4 Hz, 3H), 1.59 (m, 2H), 2.45 (m, 1H), 2.71 (dd, J=17.2, 8.8 Hz 1H), 3.03 (m, 3H), 3.74 (m 1H), 3.85 (t J=7.6 Hz, 2H), 4.02 (t, J=8.4 Hz. 1H), 4.15 (br t 2H), 4.36 (d, J=6.8 Hz 2H), 7.49 (d, J=7.6 Hz 1H), 7.62 (t, J=8.0 Hz 1H), 7.76 (d, J=8.0 Hz 1H), 8.08 (s, 1H), 8.14 (s, 1H), 8.41 (s, 1H).

Example W1

8-{1-[1-(4-Isopropyl-phenyl)-5-oxo-pyrrolidin-3-ylmethyl]-1H-pyrazol-4-yl}-7-methyl-1,3-dipropyl-3,7-dihydro-purine-2,6-dione

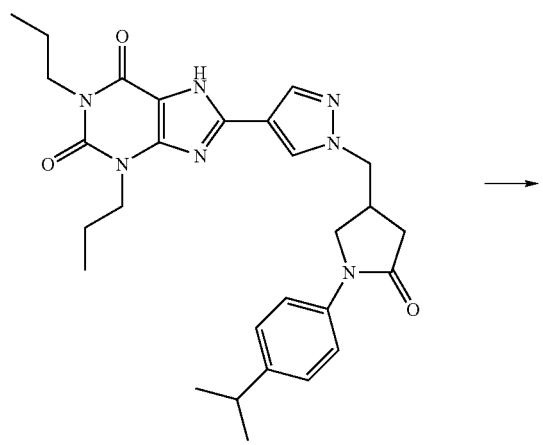

A mixture of 8-{1-[1-(4-Isopropyl-phenyl)-5-oxo-pyrrolidin-3-ylmethyl]-1H-pyrazol-4-yl}-1,3-dipropyl-3,7-dihydro-purine-2,6-dione (0.030 g, 0.057 mmol), potassium carbonate (0.016 g, 0.115 mmol), methyl iodide (0.0039 ml, 0.0639 mmol) and DMF (1 ml) was heated at 50° C. for 20 hour. The mixture was cooled to room temperature and diluted with water (10 ml). The aqueous layer was extracted with ethyl acetate. The organic layer was washed with water and saturated brine solution, and dried over Na₂SO₄. The solvent was evaporated and the residue obtained was triturated with hexane to obtain the title compound (0.026 g, 84%).

¹HNMR (400 MHz, DMSO d6): δ 0.85-0.90 (m, 6H); 1.24 (d, J=6.8 Hz, 6H); 1.53-1.58 (m, 2H); 1.69-1.72 (m, 2H); 2.40-2.44 (m, 1H); 2.63-2.74 (m, 1H); 2.82-2.85 (m, 1H); 2.89-3.01 (m, 1H); 3.61-3.65 (m, 1H); 3.83-3.91 (m, 3H); 3.96 (t, J=6.8 Hz, 2H); 4.00 (s, 3H); 4.38 (d, J=6.8 Hz, 2H); 7.22 (d, J=8.4 Hz, 2H); 7.50 (d, J=8.4 Hz, 2H); 8.05 (s, 1H); 8.54 (s, 1H); 13.46 (s, 1H).

Examples W2-W8 were prepared in an analogous manner of Example W1 from the appropriate intermediate.

| Example | IUPAC name |
|---|---|
| W2 | 7-Methyl-8-{1-[5-oxo-1-(4-trifluoromethyl-benzyl)-pyrrolidin-3-ylmethyl]-1H-pyrazol-4-yl}-1,3-dipropyl-3,7-dihydro-purine-2,6-dione |
| W3 | 8-{1-[1-(3-Fluoro-phenyl)-5-oxo-pyrrolidin-3-ylmethyl]-1H-pyrazol-4-yl}-7-methyl-1,3-dipropyl-3,7-dihydro-purine-2,6-dione |
| W4 | 7-Methyl-8-{1-[5-oxo-1-(2-trifluoromethyl-benzyl)-pyrrolidin-3-ylmethyl]-1H-pyrazol-4-yl}-1,3-dipropyl-3,7-dihydro-purine-2,6-dione |
| W5 | 8-{6-[1-(3-Fluoro-phenyl)-5-oxo-pyrrolidin-3-ylmethoxy]-pyridin-3-yl}-7-methyl-1,3-dipropyl-3,7-dihydro-purine-2,6-dione |
| W6 | 8-{6-[1-(4-Fluoro-phenyl)-5-oxo-pyrrolidin-3-ylmethoxy]-pyridin-3-yl}-7-methyl-1,3-dipropyl-3,7-dihydro-purine-2,6-dione |
| W7 | 8-{4-[1-(4-Fluoro-phenyl)-5-oxo-pyrrolidin-3-ylmethoxy]-phenyl}-7-methyl-1,3-dipropyl-3,7-dihydro-purine-2,6-dione |
| W8 | 8-{4-[1-(3-Fluoro-phenyl)-5-oxo-pyrrolidin-3-ylmethoxy]-phenyl}-7-methyl-1,3-dipropyl-3,7-dihydro-purine-2,6-dione |

Biological Activity

Radioligand Binding for A₂ᵦ Adenosine Receptor

Human A₂ᵦ adenosine receptor cDNA was stably transfected into HEK-293 cells. HEK-A₂ᵦ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 1.6 nM [3H]-MRS-1754 with various concentrations of test compounds and 10 µg membrane protein in Reaction buffer (50 mM Tris pH 6.5, 5 mM $MgCl_2$, 1 mM EDTA) supplemented with 1 U/ml Adenosine deaminase. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 µM NECA. Radioligand binding was read at Liquid scintillation counter (Perkin Elmer) and the affinities of compounds (i.e. $K_i$ values) were calculated using GraphPad software. Compounds tested had micromolar to nanomolar activity.

Radioligand Binding for $A_1$ Adenosine Receptor

Human $A_1$ adenosine receptor cDNA was stably transfected into HEK-293 cells. HEK-$A_{2B}$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM Tris (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4), 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, (pH-7.4) supplemented with 1 Unit/ml ADA and 10% sucrose. Frozen aliquots were stored at −80° C.

Competition assays were started by mixing 1 nM [3H]-DPCPX with various concentrations of test compounds and 5 µg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 µM NECA. Radioligand binding was read at Liquid scintillation counter (Perkin Elmer) and the affinities of compounds (i.e. $K_i$ values) were calculated using GraphPad software. Compounds tested had micromolar to nanomolar activity.

Radioligand Binding for A2A Adenosine Receptor

Human $A_{2A}$ adenosine receptor cDNA was stably transfected into HEK-293 cells. HEK-$A_{2B}$ cells were harvested by trypsinization with 0.25% Trypsin-EDTA (Sigma), and washed in 1×PBS at 1500 rpm for 5 minutes at room temperature. The cells were washed twice in wash buffer containing 150 mM NaCl, 1 mM EDTA, 50 mM Tris (pH-7.4) at 1500 rpm for 10 minutes at room temperature and incubated for 10 min at 4° C. in sonication buffer containing 1 mM EDTA, 5 mM (Tris pH 7.4). The cells were sonicated on ice for 6 min with six intermittent pulses of 9 second each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 5 mM Tris (pH-7.4) supplemented with 1 Unit/ml adenosine deaminase (ADA) and incubated for 30 minutes at room temperature. The lysate was washed twice with buffer containing 1 mM EDTA, 5 mM Tris (pH-7.4) at 49,000×g for 45 minutes at 4° C. and the protein pellet was resuspended in 50 mM Tris, pH-7.4 supplemented with 1 Unit/ml ADA and 10% sucrose. Frozen aliquots were stored at −80° C.

Competition assays were started by mixing 2 n-M [3H]-ZM-241385 with various concentrations of test compounds and 5 µg membrane protein in Reaction buffer (50 mM Tris pH 7.4, 1 mM EDTA) supplemented with 1 Unit/ml ADA. The assay reactions were incubated for 90 minutes at room temperature and stopped by filtration using 96 well-plate harvester (Molecular Devices) and washed four times with ice cold 50 mM Tris (pH 7.4). Non specific binding was determined in presence of 200 µM NECA. Radioligand binding was read at Liquid scintillation counter (Perkin Elmer) and the affinities of compounds (i.e. $K_i$ values) were calculated using GraphPad software. Compounds tested had micromolar to nanomolar activity.

Radioligand Binding for $A_3$ Adenosine Receptor

Human $A_3$ adenosine receptor cDNA was stably transfected into HEK-293 cells. HEK-$A_{2B}$ cells were harvested by trypsinization with 0.25% Trypsin-EDTA (Sigma), and washed in 1×PBS at 1500 rpm for 5 minutes at room temperature. The cells were washed twice in wash buffer containing 10 mM EDTA, 10 mM HEPES (pH-7.4) at 1500 rpm for 10 minutes at room temperature and incubated for 10 min at 4° C. in sonication buffer containing 1 mM EDTA, 10 mM HEPES (pH 7.4). The cells were sonicated on ice for 6 min with six intermittent pulses of 9 seconds each and centrifuged at 1000×g for 10 minutes at 4° C. The pellet was discarded and the supernatant was centrifuged at 49,000×g for 45 minutes at 4° C. The protein pellet was resuspended in buffer containing 1 mM EDTA, 10 mM HEPES (pH 7.4) supplemented with 1 Unit/ml adenosine deaminase (ADA) and incubated for 30 minutes at room temperature. The lysate was washed twice with buffer containing 1 mM EDTA, 10 mM HEPES (pH-7.4) at 49,000×g for 45 minutes at 4° C. and the protein pellet was resuspended in buffer containing 1 mM EDTA, 5 mM Tris (pH-7.4) supplemented with 1 Unit/ml ADA and 10% sucrose. Frozen aliquots were stored at −80° C.

Competition assays were started by mixing 2 nM [3H]-HEM-ADO with various concentrations of test compounds and 5 µg membrane protein in Reaction buffer (50 mM Tris pH 7.4, 1 mM EDTA, 10 mM $MgCl_2$) supplemented with 1 Unit/ml ADA. The assay reactions were incubated for 90 minutes at room temperature and stopped by filtration using 96 well-plate harvester (Molecular Devices) and washed four times with ice cold 50 mM Tris pH 7.4. Non specific binding was determined in presence of 200 µM NECA. Radioligand binding was read at Liquid scintillation counter (Perkin Elmer) and the affinities of compounds (i.e. $K_i$ values) were calculated using GraphPad software.

Compounds tested had micromolar to nanomolar activity.

Although the subject matter has been described in considerable detail with reference to certain preferred embodiments thereof, other embodiments are possible. As such, the spirit and scope of the appended claims should not be limited to the description of the preferred embodiment contained therein.

We claim:
1. A compound of formula (I):

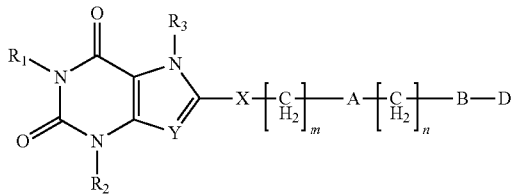

I or its tautomers, polymorphs, stereoisomers, prodrugs, or a pharmaceutically acceptable salts thereof, wherein, Y is N;

$R^1$ and $R^2$ are independently selected from a group consisting of hydrogen, alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl;

wherein alkyl, alkenyl, alkynyl, alkoxyalkyl, carboxyalkyl, cycloalkyl, cycloalkylalkyl, arylalkyl, aryl, heteroaryl, heteroarylalkyl, heterocyclyl and heterocyclylalkyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, carboxy, alkylcarboxy, carboxyalkyl, —SO₃H, aryl, aryloxy, cycloalkyloxy, heteroaryl, aminocarbonylamino, heteroaryloxy, heterocyclyl, heterocyclyloxy, hydroxyamino, alkoxyamino, nitro, —S(O)₂NR$^a$R$^a$, —NR$^a$S(O)₂R$^a$ and —S(O)$_p$R$^b$;

wherein each substituent is unsubstituted or substituted with 1, 2, or 3 substituents independently selected from alkyl, carboxy, carboxyalkyl, aminocarbonyl, hydroxy, alkoxy, halogen, CF₃, amino, substituted amino, cyano and —S(O)$_p$R$^c$;

wherein each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; R$^b$ is hydrogen, alkyl, aryl, heteroaryl or heterocyclyl; R$^c$ is alkyl, aryl, or heteroaryl; and p is 0, 1 or 2;

$R^3$ is selected from a group consisting of hydrogen and alkyl;

wherein alkyl is unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, carboxy, alkylcarboxy, carboxyalkyl, carboxyalkyloxy, alkylcarboxyalkyloxy, —SO₃H, aryl, aryloxy, cycloalkyloxy, heteroaryl, aminocarbonylamino, heteroaryloxy, heterocyclyl, heterocyclyloxy, hydroxyamino, alkoxyamino, CF₃, nitro, S(O)₂NR$^a$R$^a$, —NR$^a$S(O)₂R$^a$ and —S(O)$_p$R$^b$;

wherein each substituent is unsubstituted or substituted with 1, 2, or 3 substituents independently selected from alkyl, carboxy, carboxyalkyl, aminocarbonyl, hydroxy, alkoxy, halogen, CF₃, amino, substituted amino, cyano and —S(O)$_p$R$^c$;

wherein each R$^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; R$^b$ is hydrogen, alkyl, aryl, heteroaryl or heterocyclyl; R$^c$ is alkyl, aryl, or heteroaryl; and p is 0, 1 or 2;

X is either an unsubstituted or substituted arylene or an unsubstituted or substituted heteroarylene;

A is selected from a group consisting of —O— and —(CR$^5$R$^6$)$_q$—;

wherein q is 1 or 2, $R^5$ and $R^6$ are independently selected from a group consisting of hydrogen, halogen, alkyl, hydroxyl, alkoxy and —C(O)R$^7$;

wherein alkyl and alkoxy are unsubstituted, or substituted with halogen, hydroxy, hydroxyalkyl, CF₃;

or $R^5$ and $R^6$ together represent O, S or cycloalkyl;

$R^7$ is selected from hydroxyl, and unsubstituted or substituted amino;

m and n are independently selected from 0, 1, 2, 3, 4, 5, and 6;

B is selected from a group consisting of unsubstituted or substituted alkynyl, unsubstituted or substituted alkenyl, unsubstituted or substituted cycloalkyl and unsubstituted or substituted heterocyclyl; and D is selected from the group consisting of substituted aryl, substituted heteroaryl, substituted arylalkyl, substituted heteroarylalkyl, substituted cycloalkylalkyl and substituted heterocyclylalkyl, wherein aryl, heteroaryl, arylalkyl, heteroarylalkyl, cycloalkylalkyl and heterocyclylalkyl are substituted with 1, 2, or 3 substituents independently selected from alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, alkoxycarbonylamino, azido, cyano, halogen, hydroxy, hydroxyalkyl, CF3, OCF3, carboxy, alkylcarboxy, carboxyalkyl, —SO₃H, aryl, aryloxy, cycloalkyloxy, heteroaryl, aminocarbonylamino, heteroaryloxy, heterocyclyl, heterocyclyloxy, hydroxyamino, alkoxyamino, nitro, —C(O)R, —S(O)₂NR$^a$R$^a$, —NR$^a$S(O)₂R$^a$ and —S(O)$_p$R$^b$;

wherein each substituent is unsubstituted or substituted with 1, 2, or 3 substituents independently selected from alkyl, carboxy, carboxyalkyl, aminocarbonyl, hydroxy, alkoxy, halogen, CF₃, —OCF₃, amino, substituted amino, cyano and —S(O)$_p$R$^c$;

wherein R is selected from a group consisting of hydrogen, hydroxyl, alkyl, alkoxy, amino, monoalkylamino, dialkylamino and heterocyclyl; each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl;

$R^b$ is hydrogen, alkyl, aryl, heteroaryl or heterocyclyl; $R^c$ is alkyl, aryl, or heteroaryl; and p is 0, 1 or 2;
wherein X is monocyclic when A is $—(CR^5R^6)_q—$ and q is 1, m is 0 and n is 0.

2. A compound of formula (I) as claimed in claim 1 or its tautomers, polymorphs, stereoisomers, prodrugs, or a pharmaceutically acceptable salts thereof, wherein
Y is N;
$R^1$ and $R^2$ are independently selected from a group consisting of hydrogen, alkyl, alkenyl and alkynyl;
wherein alkyl, alkenyl and alkynyl are unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, carboxy, alkylcarboxy, carboxyalkyl, $—SO_3H$, aryl, aryloxy, cycloalkyloxy, heteroaryl, aminocarbonylamino, heteroaryloxy, heterocyclyl, heterocyclyloxy, hydroxyamino, alkoxyamino, nitro, $—S(O)_2NR^aR^a$, $—NR^aS(O)_2R^a$ and $—S(O)_pR^b$;
wherein each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; and p is 0, 1 or 2;
$R^3$ is selected from a group consisting of hydrogen and alkyl;
wherein alkyl is unsubstituted or substituted with alkyl, alkenyl, alkynyl, alkoxy, cycloalkyl, cycloalkenyl, acyl, acylamino, acyloxy, amino, monoalkylamino, dialkylamino, arylamino, cycloalkylamino, heteroarylamino, heterocyclylamino, aminocarbonyl, alkoxycarbonylamino, azido, cyano, halogen, hydroxy, hydroxyalkyl, carboxy, alkylcarboxy, carboxyalkyl, carboxyalkyloxy, alkylcarboxyalkyloxy $—SO_3H$, aryl, aryloxy, cycloalkyloxy, heteroaryl, aminocarbonylamino, heteroaryloxy, heterocyclyl, heterocyclyloxy, hydroxyamino, alkoxyamino, $CF_3$, nitro, $S(O)_2NR^aR^a$, $—NR^aS(O)_2R^a$ and $—S(O)_pR^b$;
wherein each $R^a$ is independently selected from the group consisting of hydrogen, alkyl, cycloalkyl, cycloalkylalkyl, aryl, arylalkyl, heteroaryl, heteroarylalkyl, heterocyclyl and heterocyclylalkyl; $R^b$ is hydrogen, alkyl, aryl, heteroaryl or heterocyclyl; and p is 0, 1 or 2;
X is either an unsubstituted or substituted arylene or an unsubstituted or substituted heteroarylene;
A is selected from a group consisting of —O— and $—(CR^5R^6)_q—$;
wherein q is 1, or 2;
$R^5$ and $R^6$ are independently selected from a group consisting of hydrogen, halogen, alkyl and hydroxyl;
or
$R^5$ and $R^6$ together represent O or cycloalkyl;
m and n are independently selected from 0, 1 and 2;
B is selected from a group consisting of unsubstituted or substituted alkynyl, unsubstituted or substituted cycloalkyl and unsubstituted or substituted heterocyclyl; and
D is selected from the group consisting of substituted aryl, substituted heteroaryl, substituted arylalkyl, substituted heteroarylalkyl, substituted cycloalkylalkyl and substituted heterocyclylalkyl,
wherein aryl, heteroaryl, arylalkyl, heteroarylalkyl, cycloalkylalkyl and heterocyclylalkyl are substituted with 1, 2, or 3 substituents independently selected from alkyl, alkoxy, acyl, acylamino, acyloxy, amino, monoalkylamino, dialkylamino, arylamino, cycloalkylamino, cyano, halogen, hydroxy, hydroxyalkyl, $CF_3$, $OCF_3$, carboxy, alkylcarboxy, carboxyalkyl, $—SO_3H$, aryl, heteroaryl, heterocyclyl, $—C(O)R$, $—S(O)_2NR^aR^a$, $—NR^aS(O)_2R^a$ and $—S(O)_pR^b$;
wherein each substituent is unsubstituted or substituted with 1, 2, or 3 substituents independently selected from alkyl, carboxy, carboxyalkyl, aminocarbonyl, hydroxy, alkoxy, halogen, $CF_3$, $—OCF_3$, amino, substituted amino, cyano and $—S(O)_pR^c$;
wherein R is selected from a group consisting of amino, monoalkylamino, dialkylamino and heterocyclyl; each $R^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; $R^b$ is hydrogen, alkyl, aryl, heteroaryl or heterocyclyl; $R^c$ is alkyl, aryl, or heteroaryl; and p is 0, 1 or 2;
wherein X is monocyclic when A is $—(CR^5R^6)_q—$, q is 1, m is 0, and n is 0.

3. A compound of formula (I) as claimed in claim 1 or its tautomers, polymorphs, stereoisomers, prodrugs, or a pharmaceutically acceptable salts thereof,
wherein Y is N;
$R^1$ and $R^2$ are independently selected from a group consisting of hydrogen and alkyl;
wherein alkyl is unsubstituted or substituted with alkenyl, alkoxy, acylamino, amino, monoalkylamino, dialkylamino, halogen, hydroxy, hydroxyalkyl, carboxy, alkylcarboxy, carboxyalkyl, $—SO_3H$ and aryl;
$R^3$ is selected from a group consisting of hydrogen and alkyl;
X is either an unsubstituted or substituted arylene or an unsubstituted or substituted heteroarylene;
A is selected from a group consisting of —O— and $—(CR^5R^6)_q—$;
wherein q is 1;
$R^5$ and $R^6$ are independently selected from a group consisting of hydrogen, halogen, alkyl and hydroxyl;
or
$R^5$ and $R^6$ together represent O or cycloalkyl;
m and n are independently selected from 0, 1 and 2;
B is selected from a group consisting of unsubstituted or substituted alkynyl, unsubstituted or substituted cycloalkyl and unsubstituted or substituted heterocyclyl; and
D is selected from the group consisting of substituted aryl, substituted heteroaryl, substituted arylalkyl, substituted heteroarylalkyl, substituted cycloalkylalkyl and substituted heterocyclylalkyl,
wherein aryl, heteroaryl, arylalkyl, heteroarylalkyl, cycloalkylalkyl and heterocyclylalkyl are substituted with 1, 2, or 3 substituents independently selected from alkyl, alkoxy, acyl, acylamino, acyloxy, amino, monoalkylamino, dialkylamino, arylamino, cycloalkylamino, cyano, halogen, hydroxy, hydroxyalkyl, $CF_3$, $OCF_3$, carboxy, alkylcarboxy, carboxyalkyl, $—SO_3H$, aryl, heteroaryl, heterocyclyl, $—C(O)R$, $—S(O)_2NR^aR^a$, $—NR^aS(O)_2R^a$ and $—S(O)_pR^b$;
wherein each substituent is unsubstituted or substituted with 1, 2, or 3 substituents independently selected from alkyl, carboxy, carboxyalkyl, aminocarbonyl, hydroxy, alkoxy, halogen, CF₃, —OCF₃, amino, substituted amino, cyano and —S(O)$_p$R$^c$;

wherein R is selected from a group consisting of amino, monoalkylamino, dialkylamino and heterocyclyl; each R$^a$ is independently selected from the group consisting of hydrogen, alkyl, cycloalkyl, cycloalkylalkyl, aryl, arylalkyl, heteroaryl heteroarylalkyl, heterocyclyl and heterocyclylalkyl; R$^b$ is hydrogen, alkyl, aryl, heteroaryl or heterocyclyl; R$^c$ is alkyl, aryl, or heteroaryl; and p is 0, 1 or 2;

wherein X is monocyclic when A is —(CR⁵R⁶)$_q$—, m is 0, and n is 0.

4. A compound of formula (I) as claimed in claim 1 or its tautomers, polymorphs, stereoisomers, prodrugs, or a pharmaceutically acceptable salts thereof, wherein X is pyrazolyl, isoxazolyl, phenyl, pyridyl, oxazolyl or pyrimidyl.

5. A compound of formula (I) as claimed in claim 1 or its tautomers, polymorphs, stereoisomers, prodrugs, or a pharmaceutically acceptable salts thereof, wherein B is an alkynylene.

6. A compound of formula (I) as claimed in claim 1 or its tautomers, polymorphs, stereoisomers, prodrugs, or a pharmaceutically acceptable salts thereof, wherein B is heterocyclyl or cycloalkyl.

7. A compound of formula (I) as claimed in claim 1 or its tautomers, polymorphs, stereoisomers, prodrugs, or a pharmaceutically acceptable salts thereof, which is 1,3-Dipropyl-8-[1-(3-p-tolyl-prop-2ynyl)-1H-pyrazol-4-yl]-3,7-dihydro-purine-2,6-dione,
8-{1-[3-(3-Fluoro-phenyl)-prop-2-ynyl]-1H-pyrazol-4-yl}-1,3-dimethyl-3,7-dihydro-purine-2,6-dione,
8-{1-[3-(4-Fluoro-phenyl)-prop-2-ynyl]-1H-pyrazol-4-yl}-1,3-dimethyl-3,7-dihydro-purine-2,6-dione,
8-{1-[3-(4-Fluoro-phenyl)-prop-2-ynyl]-1H-pyrazol-4-yl}-1,3-dipropyl-3,7-dihydro-purine-2,6-dione,
8-{1-[3-(4-Methoxy-phenyl)-prop-2-ynyl]-1H-pyrazol-4-yl}-1,3-dimethyl-3,7-dihydro-purine-2,6-dione,
8-{1-[3-(4-Methoxy-phenyl)-prop-2-ynyl]-1H-pyrazol-4-yl}-1,3-dipropyl-3,7-dihydro-purine-2,6-dione,
8-{1-[3-(2,4-Difluoro-phenyl)-prop-2-ynyl]-1H-pyrazol-4-yl}-1,3-dipropyl-3,7-dihydro-purine-2,6-dione,
8-{1-[3-(3-trifluoromethoxy-phenyl)-prop-2-ynyl]-1H-pyrazol-4-yl}-1,3-dipropyl-3,7-dihydro-purine-2,6-dione,
8-{1-[3-(3-trifluoromethyl-phenyl)-prop-2-ynyl]-1H-pyrazol-4-yl}-1,3-dipropyl-3,7-dihydro-purine-2,6-dione,
8-{1-[3-(4-trifluoromethyl-phenyl)-prop-2-ynyl]-1H-pyrazol-4-yl}-1,3-dimethyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester,
3-{3-[4-(2,6-Dioxo-1,3-dipropyl-2,3,6,7-tetrahydro-1H-purin-8-yl)-pyrazol-1-yl]-prop-1-ynyl}-benzoic acid ethyl ester,
3-{3-[4-(2,6-Dioxo-1,3-dipropyl-2,3,6,7-tetrahydro-1H-purin-8-yl)-pyrazol-1-yl]-prop-1-ynyl}-benzonitrile,
8-{1-[3-(3-Methoxy-phenyl)-prop-2-ynyl]-1H-pyrazol-4-yl}-1,3-dipropyl-3,7-dihydro-purine-2,6-dione,
2-{3-[4-(2,6-Dioxo-1,3-dipropyl-2,3,6,7-tetrahydro-1H-purin-8-yl)-pyrazol-1-yl]-prop-1-ynyl-benzoic acid methyl ester,
8-{1-[4-(4-Fluoro-phenyl)-but-3-ynyl]-1H-pyrazol-4-yl}-1,3-dipropyl-3,7-dihydro-purine-2,6-dione,
8-{1-[4-(3-Fluoro-phenyl)-but-3-ynyl]-1H-pyrazol-4-yl}-1,3-dipropyl-3,7-dihydro-purine-2,6-dione,
1,3-Dipropyl-8-[1-(4-p-tolyl-but-3-ynyl)-1H-pyrazol-4-yl]-3,7-dihydro-purine-2,6-dione,
1,3-Dipropyl-8-{1-[4-(3-trifluoromethyl-phenyl)-but-3-ynyl]-1H-pyrazol-4-yl}-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-benzoic acid,
1,3-Dipropyl-8-{1-[3-(2-trifluoromethyl-phenyl)-prop-2-ynyl]-1H-pyrazol-4-yl}-3,7-dihydro-purine-2,6-dione,
1,3-Dipropyl-8-[1-(3-m-tolyl-prop-2-ynyl)-1H-pyrazol-4-yl]-3,7-dihydro-purine-2,6-dione,
3-Ethyl-1-propyl-8-{1-[3-(3-trifluoromethoxy-phenyl)-prop-2-ynyl]-1H-pyrazol-4-yl}-3,7-dihydro-purine-2,6-dione,
3-Ethyl-1-propyl-8-{1-[3-(4-trifluoromethyl-phenyl)-prop-2-ynyl]-1H-pyrazol-4-yl}-3,7-dihydro-purine-2,6-dione,
3-Ethyl-1-propyl-8-[1-(3-p-tolyl-prop-2-ynyl)-1H-pyrazol-4-yl]-3,7-dihydro-purine-2,6-dione,
3-Ethyl-8-{1-[3-(3-fluoro-phenyl)-prop-2-ynyl]-1H-pyrazol-4-yl}-1-propyl-3,7-dihydro-purine-2,6-dione,
1,3-Dipropyl-8-{1-[3-(4-trifluoromethyl-phenyl)-prop-2-ynyl]-1H-pyrazol-4-yl}-3,7-dihydro-purine-2,6-dione,
1,3-Dipropyl-8-{1-[3-(4-trifluoromethoxy-phenyl)-prop-2-ynyl]-1H-pyrazol-4-yl}-3,7-dihydro-purine-2,6-dione,
3-Ethyl-8-{1-[3-(4-fluoro-phenyl)-prop-2-ynyl]-1H-pyrazol-4-yl}-1-propyl-3,7-dihydro-purine-2,6-dione,
3-{3-[4-(3-Ethyl-2,6-dioxo-1-propyl-2,3,6,7-tetrahydro-1H-purin-8-yl)-pyrazol-1-yl]-prop-1-ynyl}-benzoic acid,
3-Ethyl-1-propyl-8-[1-(3-m-tolyl-prop-2-ynyl)-1H-pyrazol-4-yl]-3,7-dihydro-purine-2,6-dione,
3-Ethyl-8-{1-[3-(4-methoxy-phenyl)-prop-2-ynyl]-1H-pyrazol-4-yl}-1-propyl-3,7-dihydro-purine-2,6-dione,
3-Ethyl-1-propyl-8-{1-[3-(4-trifluoromethoxy-phenyl)-prop-2-ynyl]-1H-pyrazol-4-yl}-3,7-dihydro-purine-2,6-dione,
3-Ethyl-8-{1-[3-(3-methoxy-phenyl)-prop-2-ynyl]-1H-pyrazol-4-yl}-1-propyl-3,7-dihydro-purine-2,6-dione,
4-{3-[4-(3-Ethyl-2,6-dioxo-1-propyl-2,3,6,7-tetrahydro-1H-purin-8-yl)-pyrazol-1-yl]-prop-1-ynyl}-benzoic acid,
4-{3-[4-(2,6-Dioxo-1,3-dipropyl-2,3,6,7-tetrahydro-1H-purin-8-yl)-pyrazol-1-yl]-prop-1-ynyl-benzonitrile,
(3-{3-[4-(2,6-Dioxo-1,3-dipropyl-2,3,6,7-tetrahydro-1H-purin-8-yl)-pyrazol-1-yl]-prop-1-ynyl}-phenoxy)-acetic acid,
8-{1-[3-(3-tert-Butyl-phenyl)-prop-2-ynyl]-1H-pyrazol-4-yl}-1,3-dipropyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzoic acid,
(3-{3-[4-(2,6-Dioxo-1,3-dipropyl-2,3,6,7-tetrahydro-1H-purin-8-yl)-pyrazol-1-yl]-prop-1-ynyl}-phenyl)-acetic acid,
(4-{3-[4-(2,6-Dioxo-1,3-dipropyl-2,3,6,7-tetrahydro-1H-purin-8-yl)-pyrazol-1-yl]-prop-1-ynyl}-phenyl)-acetic acid,
8-{1-[3-(3-Fluoro-phenyl)-prop-2-ynyl]-1H-pyrazol-4-yl}-1,3-dipropyl-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl}-N-isopropyl-benzamide,
1,3-Dipropyl-8-(1-{3-[3-(pyrrolidine-1-carbonyl)-phenyl]-prop-2-ynyl}-1H-pyrazol-4-yl)-3,7-dihydro-purine-2,6-dione, 3-{3-[4-(2,6-Dioxo-1,3-dipropyl-2,3,6,7-tetrahydro-1H-purin-8-yl)-pyrazol-1-yl]-prop-1-ynyl}-4-methyl-benzoic acid,
8-{1-[3-(3-Chloro-phenyl)-prop-2-ynyl]-1H-pyrazol-4-yl}-1,3-dipropyl-3,7-dihydro-purine-2,6-dione,
3-{3-[4-(2,6-Dioxo-1,3-dipropyl-2,3,6,7-tetrahydro-1H-purin-8-yl)-pyrazol-1-yl]-prop-1-ynyl-4-methoxy-benzoic acid,
5-{3-[4-(2,6-Dioxo-1,3-dipropyl-2,3,6,7-tetrahydro-1H-purin-8-yl)-pyrazol-1-yl]-prop-1-ynyl}-pyridine-2-carboxylic acid methyl ester,
1,3-Dipropyl-8-{3-[3-(3-trifluoromethyl-phenyl)-prop-2-ynyloxy]-isoxazol-5-yl}-3,7-dihydro-purine-2,6-dione,
8-{3-[3-(2,4-Difluoro-phenyl)-prop-2-ynyloxy]-isoxazol-5-yl}-1,3-dipropyl-3,7-dihydro-purine-2,6-dione,
8-{3-[3-(4-Fluoro-phenyl)-prop-2-ynyloxy]-isoxazol-5-yl}-1,3-dipropyl-3,7-dihydro-purine-2,6-dione,
8-{3-[3-(3-Fluoro-phenyl)-prop-2-ynyloxy]-isoxazol-5-yl}-1,3-dipropyl-3,7-dihydro-purine-2,6-dione,
1,3-Dipropyl-8-{3-[3-(4-trifluoromethyl-phenyl)-prop-2-ynyloxy]-isoxazol-5-yl}-3,7-dihydro-purine-2,6-dione,
1,3-Dipropyl-8-[3-(3-p-tolyl-prop-2-ynyloxy)-isoxazol-5-yl]-3,7-dihydro-purine-2,6-dione,
8-{3-[3-(3-tert-Butyl-phenyl)-prop-2-ynyloxy]-isoxazol-5-yl}-1,3-dipropyl-3,7-dihydro-purine-2,6-dione,
1,3-Dipropyl-8-{3-[3-(3-trifluoromethoxy-phenyl)-prop-2-ynyloxy]-isoxazol-5-yl}-3,7-dihydro-purine-2,6-dione,
8-{1-Methyl-5-[3-(3-trifluoromethyl-phenyl)-prop-2-ynyloxy]-1H-pyrazol-3-yl}-1,3-dipropyl-3,7-dihydro-purine-2,6-dione,
8-{1-Methyl-5-[3-(4-trifluoromethoxy-phenyl)-prop-2-ynyloxy]-1H-pyrazol-3-yl}-1,3-dipropyl-3,7-dihydro-purine-2,6-dione,
8-{5-[3-(3-Methoxy-phenyl)-prop-2-ynyloxy]-1-methyl-1H-pyrazol-3-yl}-1,3-dipropyl-3,7-dihydro-purine-2,6-dione,
1,3-Dipropyl-8-{4-[3-(4-trifluoromethoxy-phenyl)-prop-2-ynyloxy]-phenyl}-3,7-dihydro-purine-2,6-dione,
1,3-Dipropyl-8-[4-(3-p-tolyl-prop-2-ynyloxy)-phenyl]-3,7-dihydro-purine-2,6-dione,
8-{4-[3-(3-Fluoro-phenyl)-prop-2-ynyloxy]-phenyl}-1,3-dipropyl-3,7-dihydro-purine-2,6-dione,
3-{3-[4-(2,6-Dioxo-1,3-dipropyl-2,3,6,7-tetrahydro-1H-purin-8-yl)-phenoxy]-prop-1-ynyl}-benzoic acid ethyl ester,
3-{3-[4-(2,6-Dioxo-1,3-dipropyl-2,3,6,7-tetrahydro-1H-purin-8-yl)-phenoxy]-prop-1-ynyl}-benzoic acid,
1,3-Dipropyl-8-{4-[3-(4-trifluoromethyl-phenyl)-prop-2-ynyloxy]-phenyl}-3,7-dihydro-purine-2,6-dione,
8-{4-[3-(4-Fluoro-phenyl)-prop-2-ynyloxy]-phenyl}-1,3-dipropyl-3,7-dihydro-purine-2,6-dione,
1,3-Dipropyl-8-{4-[3-(3-trifluoromethoxy-phenyl)-prop-2-ynyloxy]-phenyl}-3,7-dihydro-purine-2,6-dione,
8-{4-[3-(3-Methoxy-phenyl)-prop-2-ynyloxy]-phenyl}-1,3-dipropyl-3,7-dihydro-purine-2,6-dione,
8-{6-[3-(4-Fluoro-phenyl)-prop-2-ynyloxy]-pyridin-3-yl}-1,3-dipropyl-3,7-dihydro-purine-2,6-dione,
1,3-Dipropyl-8-{3-[3-(3-trifluoromethyl-phenyl)-prop-2-ynyloxy]-phenyl}-3,7-dihydro-purine-2,6-dione,
1,3-Dipropyl-8-{3-[3-(3-trifluoromethoxy-phenyl)-prop-2-ynyloxy]-phenyl}-3,7-dihydro-purine-2,6-dione,
8-{3-[3-(3-Fluoro-phenyl)-prop-2-ynyloxy]-phenyl}-1,3-dipropyl-3,7-dihydro-purine-2,6-dione,
1,3-Dipropyl-8-{3-[3-(4-trifluoromethyl-phenyl)-prop-2-ynyloxy]-phenyl}-3,7-dihydro-purine-2,6-dione, 1,3-Dipropyl-8-[3-(3-p-tolyl-prop-2-ynyloxy)-phenyl]-3,7-dihydro-purine-2,6-dione,
8-{1-[4-(4-Methyl-piperazin-1-yl)-but-2-ynyl]-1H-pyrazol-4-yl}-1,3-dipropyl-3,7-dihydro-purine-2,6-dione,
1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid ethyl ester,
1-{4-[4-(2,6-Dioxo-1,3-dipropyl-2,3,6,7-tetrahydro-1H-purin-8-yl)-pyrazol-1-yl]-but-2-ynyl}-piperidine-3-carboxylic acid,
8-(1-{4-[4-(4-Chloro-phenyl)-4-hydroxy-piperidin-1-yl]-but-2-ynyl}-1H-pyrazol-4-yl)-1,3-dipropyl-3,7-dihydro-purine-2,6-dione,
1,3-Dipropyl-8-(1-{4-[4-(3-trifluoromethyl-phenyl)-piperazin-1-yl]-but-2-ynyl}-1H-pyrazol-4-yl)-3,7-dihydro-purine-2,6-dione,
1,3-Dimethyl-8-{1-[4-(4-methyl-piperazin-1-yl)-but-2-ynyl]-1H-pyrazol-4-yl}-3,7-dihydro-purine-2,6-dione,
1-Propyl-8-[1-(3-p-tolyl-prop-2-ynyl)-1H-pyrazol-4-yl]-3,7-dihydro-purine-2,6-dione,
1-Propyl-8-{1-[3-(3-trifluoromethyl-phenyl)-prop-2-ynyl]-1H-pyrazol-4-yl}-3,7-dihydro-purine-2,6-dione,
1-Propyl-8-{1-[3-(3-trifluoromethoxy-phenyl)-prop-2-ynyl]-1H-pyrazol-4-yl}-3,7-dihydro-purine-2,6-dione,
8-{1-[3-(4-Fluoro-phenyl)-prop-2-ynyl]-1H-pyrazol-4-yl}-1-propyl-3,7-dihydro-purine-2,6-dione,
8-{1-[3-(3-Fluoro-phenyl)-prop-2-ynyl]-1H-pyrazol-4-yl}-1-propyl-3,7-dihydro-purine-2,6-dione,
1-Propyl-8-{1-[3-(4-trifluoromethyl-phenyl)-prop-2-ynyl]-1H-pyrazol-4-yl}-3,7-dihydro-purine-2,6-dione,
1-Propyl-8-{1-[3-(4-trifluoromethoxy-phenyl)-prop-2-ynyl]-1H-pyrazol-4-yl}-3,7-dihydro-purine-2,6-dione,
3-{3-[4-(2,6-Dioxo-1-propyl-2,3,6,7-tetrahydro-1H-purin-8-yl)-pyrazol-1-yl]-prop-1-ynyl}-benzoic acid,
8-{1-[3-(4-Fluoro-phenyl)-prop-2-ynyl]-1H-pyrazol-4-yl}-7-methyl-1,3-dipropyl-3,7-dihydro-purine-2,6-dione,
7-Methyl-1,3-dipropyl-8-{1-[3-(3-trifluoromethoxy-phenyl)-prop-2-ynyl]-1H-pyrazol-4-yl}-3,7-dihydro-purine-2,6-dione,
7-Methyl-1,3-dipropyl-8-[1-(3-p-tolyl-prop-2-ynyl)-1H-pyrazol-4-yl]-3,7-dihydro-purine-2,6-dione,
7-Methyl-8-{1-[4-(4-methyl-piperazin-1-yl)-but-2-ynyl]-1H-pyrazol-4-yl}-1,3-dipropyl-3,7-dihydro-purine-2,6-dione,
8-{1-[3-(3-Fluoro-phenyl)-prop-2-ynyl]-1H-pyrazol-4-yl}-methyl-1,3-dipropyl-3,7-dihydro-purine-2,6-dione,
8-{1-[3-(3-Methoxy-phenyl)-prop-2-ynyl]-1H-pyrazol-4-yl}-7-methyl-1,3-dipropyl-3,7-dihydro-purine-2,6-dione,
8-{1-[3-(3-tert-Butyl-phenyl)-prop-2-ynyl]-1H-pyrazol-4-yl}-7-methyl-1,3-dipropyl-3,7-dihydro-purine-2,6-dione,
(3-{3-[4-(7-Methyl-2,6-dioxo-1,3-dipropyl-2,3,6,7-tetrahydro-1H-purin-8-yl)-pyrazol-1-yl]-prop-1-ynyl}-phenoxy)-acetic acid,
8-{1-[3-(3-Hydroxymethyl-phenyl)-prop-2-ynyl]-1H-pyrazol-4-yl}-1,3-dipropyl-3,7-dihydro-purine-2,6-dione,
4-{3-[4-(2,6-Dioxo-1,3-dipropyl-2,3,6,7-tetrahydro-1H-purin-8-yl)-pyrazol-1-yl]-prop-1-ynyl}-benzenesulfonamide,
3-{3-[4-(2,6-Dioxo-1,3-dipropyl-2,3,6,7-tetrahydro-1H-purin-8-yl)-pyrazol-1-yl]-prop-1-ynyl}-benzamide,
4-(3-Trifluoromethyl-phenyl)-but-3-ynoic acid [5-(2,6-dioxo-1,3-dipropyl-2,3,6,7-tetrahydro-1H-purin-8-yl)-2-methyl-2H-pyrazol-3-yl]-amide, 4-(3-Fluoro-phenyl)-but-3-ynoic acid [5-(2,6-dioxo-1,3-dipropyl-2,3,6,7-tetrahydro-1H-purin-8-yl)-2-methyl-2H-pyrazol-3-yl]-amide, 4-(2,6-Dioxo-1,3-dipropyl-2,3,6,7-tetrahydro-1H-purin-8-yl)-N-[3-(3-trifluoromethyl-phenyl)-prop-2-ynyl]-benzamide, 8-{1-[4-(3-Fluoro-phenyl)-2-hydroxy-but-3-ynyl]-1H-pyrazol-4-yl}-1,3-dipropyl-3,7-dihydro-purine-2,6-dione, 2-[4-(2,6-Dioxo-1,3-dipropyl-2,3,6,7-tetrahydro-1H-purin-8-yl)-pyrazol-1-yl]-4-(3-fluoro-phenyl)-but-3-ynoic acid, 2-[4-(2,6-Dioxo-1,3-dipropyl-2,3,6,7-tetrahydro-1H-purin-8-yl)-pyrazol-1-yl]-4-(3-fluoro-phenyl)-but-3-ynoic acid amide, 8-{1-[4-(4-Fluoro-phenyl)-4-hydroxy-but-2-ynyl]-1H-pyrazol-4-yl}-1,3-dipropyl-3,7-dihydro-purine-2,6-dione, 8-{1-[4-(4-Fluoro-phenyl)-but-2-ynyl]-1H-pyrazol-4-yl}-1,3-dipropyl-3,7-dihydro-purine-2,6-dione, 8-{1-[3-(4-Fluoro-phenyl)-1,1-dimethyl-prop-2-ynyl]-1H-pyrazol-4-yl}-1,3-dipropyl-3,7-dihydro-purine-2,6-dione, 1,3-Dipropyl-8-{1-[(E)-3-(3-trifluoromethyl-phenyl)-allyl]-1H-pyrazol-4-yl}-3,7-dihydro-purine-2,6-dione, 1,3-Dipropyl-8-{1-[(Z)-3-(3-trifluoromethyl-phenyl)-allyl]-1H-pyrazol-4-yl}-3,7-dihydro-purine-2,6-dione, 1,3-dimethyl-6-{1-[3-(3-fluorophenyl)prop-2-ynyl]pyrazol-4-yl}-5H-pyrrolo[3,2-d]pyrimidine-2,4-dione, 8-[1-[3-(3-fluorophenyl)prop-2-ynyl]pyrazol-4-yl]-1,3-dipropyl-7H-purine-2,6-dione, 8-[1-[4-(3-fluorophenyl)-2-hydroxy-but-3-ynyl]pyrazol-4-yl]-1,3-dipropyl-7H-purine-2,6-dione, 8-[1-[3-(4-fluorophenyl)-1,1-dimethyl-prop-2-ynyl]pyrazol-4-yl]-1,3-dipropyl-7H-purine-2,6-dione, 1,3-Dipropyl-8-{1-[2-(3-trifluoromethyl-phenyl)-cyclopropylmethyl]-1H-pyrazol-4-yl}-3,7-dihydro-purine-2,6-dione, 8-{1-[2-(3-Fluoro-phenyl)-cyclopropylmethyl]-1H-pyrazol-4-yl}-1,3-dipropyl-3,7-dihydro-purine-2,6-dione, 8-{1-[2-(4-Fluoro-phenyl)-cyclopropylmethyl]-1H-pyrazol-4-yl}-1,3-dipropyl-3,7-dihydro-purine-2,6-dione, 1,3-Dipropyl-8-{1-[2-(4-trifluoromethyl-phenyl)-cyclopropylmethyl]-1H-pyrazol-4-yl}-3,7-dihydro-purine-2,6-dione, 8-{1-[1-(4-Isopropyl-phenyl)-5-oxo-pyrrolidin-3-ylmethyl]-1H-pyrazol-4-yl}-1,3-dipropyl-3,7-dihydro-purine-2,6-dione, 8-{1-[1-(4-Fluoro-phenyl)-5-oxo-pyrrolidin-3-ylmethyl]-1H-pyrazol-4-yl}-1,3-dipropyl-3,7-dihydro-purine-2,6-dione, 8-{1-[5-Oxo-1-(4-trifluoromethoxy-phenyl)-pyrrolidin-3-ylmethoxy]-ylmethyl-1H-pyrazol-4-yl}-1,3-dipropyl-3,7-dihydro-purine-2,6-dione, 8-{1-[5-Oxo-1-(3-trifluoromethyl-phenyl)-pyrrolidin-3-ylmethyl]-1H-pyrazol-4-yl}-1,3-dipropyl-3,7-dihydro-purine-2,6-dione, 8-[1-(5-oxo-1-p-tolyl-pyrrolidin-3-ylmethyl)-1H-pyrazol-4-yl]-1,3-dipropyl-3,7-dihydro-purine-2,6-dione, 8-[1-(5-Oxo-1-ylmethyl)-1H-pyrazol-4-yl]-1,3-dipropyl-3,7-dihydro-purine-2,6-dione, 8-{1-[5-Oxo-1-(3-trifluoromethyl-benzyl)-pyrrolidin-3-ylmethyl]-1H-pyrazol-4-yl}-1,3-dipropyl-3,7-dihydro-purine-2,6-dione, 8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione, 8-{1-[1-(3-Fluoro-phenyl)-5-oxo-pyrrolidin-3-ylmethyl]-1H-pyrazol-4-yl}-1,3-dipropyl-3,7-dihydro-purine-2,6-dione, 8-{1-[1-(3-Methoxy-phenyl)-5-oxo-pyrrolidin-3-ylmethyl]-1H-pyrazol-4-yl}-1,3-dipropyl-3,7-dihydro-purine-2,6-dione, 3-Ethyl-8-{1-[1-(4-methoxy-phenyl)-5-oxo-pyrrolidin-3-ylmethyl]-1H-pyrazol-4-yl}-1-propyl-3,7-dihydro-purine-2,6-dione, 3-Ethyl-8-{1-[5-oxo-1-(3-trifluoromethyl-benzyl)-pyrrolidin-3-ylmethyl]-1H-pyrazol-4-yl}-1-propyl-3,7-dihydro-purine-2,6-dione, 8-{1-[1-(4-Methoxy-phenyl)-5-oxo-pyrrolidin-3-ylmethyl]-1H-pyrazol-4-yl}-1,3-dipropyl-3,7-dihydro-purine-2,6-dione, 4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile, 3-Ethyl-8-{1-[1-(4-fluoro-phenyl)-5-oxo-pyrrolidin-3-ylmethyl]-1H-pyrazol-4-yl}-1-propyl-3,7-dihydro-purine-2,6-dione, 3-Ethyl-8-{1-[1-(3-fluoro-phenyl)-5-oxo-pyrrolidin-3-ylmethyl]-1H-pyrazol-4-yl}-1-propyl-3,7-dihydro-purine-2,6-dione, 3-Ethyl-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione, 8-{1-[5-oxo-1-(3-trifluoromethoxy-phenyl)-pyrrolidin-3-ylmethyl]-1H-pyrazol-4-yl}-1,3-dipropyl-3,7-dihydro-purine-2,6-dione, 3-Ethyl-8-{1-[5-oxo-1-(3-trifluoromethoxy-phenyl)-pyrrolidin-3-ylmethyl]-1H-pyrazol-4-yl}-1-propyl-3,7-dihydro-purine-2,6-dione, 3-Ethyl-8-{1-[5-oxo-1-(4-trifluoromethyl-benzyl)-pyrrolidin-3-ylmethyl]-1H-pyrazol-4-yl}-1-propyl-3,7-dihydro-purine-2,6-dione, 8-{1-[1-(3-Fluoro-benzyl)-5-oxo-pyrrolidin-3-ylmethyl]-1H-pyrazol-4-yl}-1,3-dipropyl-3,7-dihydro-purine-2,6-dione, 8-{1-[5-oxo-1-(2-trifluoromethyl-benzyl)-pyrrolidin-3-ylmethyl]-1H-pyrazol-4-yl}-1,3-dipropyl-3,7-dihydro-purine-2,6-dione, 8-{1-[5-Oxo-1-(4-trifluoromethoxy-benzyl)-pyrrolidin-3-ylmethyl]-1H-pyrazol-4-yl}-1,3-dipropyl-3,7-dihydro-purine-2,6-dione, 8-{1-[1-(4-Methyl-benzyl)-5-oxo-pyrrolidin-3-ylmethyl]-1H-pyrazol-4-yl}-1,3-dipropyl-3,7-dihydro-purine-2,6-dione, 4-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzoic acid, 8-{1-[1-(4-Fluoro-benzyl)-5-oxo-pyrrolidin-3-ylmethyl]-1H-pyrazol-4-yl}-1,3-dipropyl-3,7-dihydro-purine-2,6-dione, 3-{4-[4-(2,6-Dioxo-1,3-dipropyl-2,3,6,7-tetrahydro-1H-purin-8-yl)-pyrazol-1-ylmethyl]-2-oxo-pyrrolidin-1-yl}-benzonitrile, 8-{1-[5-Oxo-1-(4-trifluoromethyl-phenyl)-pyrrolidin-3-ylmethyl]-1H-pyrazol-4-yl}-1,3-dipropyl-3,7-dihydro-purine-2,6-dione, 8-{1-[1-(2,4-Difluoro-phenyl)-5-oxo-pyrrolidin-3-ylmethyl]-1H-pyrazol-4-yl}-1,3-dipropyl-3,7-dihydro-purine-2,6-dione, 8-{1-[1-(4-Fluoro-phenyl)-5-oxo-pyrrolidin-3-ylmethyl]-1H-pyrazol-4-yl}-1-propyl-3,7-dihydro-purine-2,6-dione, 8-{1-[1-(2-Chloro-4-fluoro-phenyl)-5-oxo-pyrrolidin-3-ylmethyl]-1H-pyrazol-4-yl}-1,3-dipropyl-3,7-dihydro-purine-2,6-dione,
8-{1-[1-(2-Chloro-4-trifluoromethyl-phenyl)-5-oxo-pyrrolidin-3-ylmethyl]-1H-pyrazol-4-yl}-1,3-dipropyl-3,7-dihydro-purine-2,6-dione,
3-Ethyl-8-{1-[5-oxo-1-(4-trifluoromethyl-phenyl)-pyrrolidin-3-ylmethyl]-1H-pyrazol-4-yl}-1-propyl-3,7-dihydro-purine-2,6-dione,
8-{1-[2-oxo-1-(3-trifluoromethyl-phenyl)-pyrrolidin-3-ylmethyl]-1H-pyrazol-4-yl}-1,3-dipropyl-3,7-dihydro-purine-2,6-dione,
8-{1-[1-(3-Fluoro-phenyl)-2-oxo-pyrrolidin-3-ylmethyl]-1H-pyrazol-4-yl}-1,3-dipropyl-3,7-dihydro-purine-2,6-dione,
8-{1-[2-oxo-1-(4-trifluoromethoxy-phenyl)-pyrrolidin-3-ylmethyl]-1H-pyrazol-4-yl}-1,3-dipropyl-3,7-dihydro-purine-2,6-dione,
1,3-Dipropyl-8-{1-[1-(3-trifluoromethyl-phenyl)-pyrrolidin-3-ylmethyl]-1H-pyrazol-4-yl}-3,7-dihydro-purine-2,6-dione,
1,3-Dipropyl-8-{1-{1-(4-trifluoromethoxy-phenyl)-pyrrolidin-1H-pyrazol-4-yl}-3,7-dihydro-purine-2,6-dione,
1,3-Dipropyl-8-[1-(1-p-tolyl-pyrrolidin-3-ylmethyl)-1H-pyrazol-4-yl]-3,7-dihydro-purine-2,6-dione,
8-{1-[1-(4-Methoxy-phenyl)-pyrrolidin-3-ylmethyl]-1H-pyrazol-4-yl}-1,3-dipropyl-3,7-dihydro-purine-2,6-dione,
8-{1-[1-(3-Methoxy-phenyl)-pyrrolidin-3-ylmethyl]-1H-pyrazol-4-yl}-1,3-dipropyl-3,7-dihydro-purine-2,6-dione,
1,3-Dipropyl-8-{1-[1-(3-trifluoromethyl-benzyl)-pyrrolidin-3-ylmethyl]-1H-pyrazol-4-yl}-3,7-dihydro-purine-2,6-dione,
8-{4-[1-(4-Fluorophenyl)-5-oxo-pyrrolidin-3-ylmethoxy]phenyl}-1,3-dipropyl-3,7-dihydropurine-2,6-dione,
1,3-Dipropyl-8-{4-[1-(3-trifluoromethyl-phenyl)-pyrrolidin-3-yloxy]-phenyl}-3,7-dihydro-purine-2,6-dione,
8-{3-[1-(4-Fluoro-phenyl)-5-oxo-pyrrolidin-3-ylmethoxy]-isoxazol-5-yl}-1,3-dipropyl-3,7-dihydro-purine-2,6-dione,
8-{4-[5-Oxo-1-(3-trifluoromethyl-phenyl)-pyrrolidin-3-ylmethoxy]-phenyl}-1,3-dipropyl-3,7-dihydro-purine-2,6-dione,
8-{4-[1-(4-Fluoro-phenyl)-pyrrolidin-3-yloxy]-phenyl}-1,3-dipropyl-3,7-dihydro-purine-2,6-dione,
8-{6-[5-Oxo-1-(3-trifluoromethyl-phenyl)-pyrrolidin-3-ylmethoxy]-pyridin-3-yl}-1,3-dipropyl-3,7-dihydro-purine-2,6-dione,
8-{3-[1-(3-Fluoro-phenyl)-5-oxo-pyrrolidin-3-ylmethoxy]-isoxazol-5-yl}-1,3-dipropyl-3,7-dihydro-purine-2,6-dione,
8-{3-[5-oxo-1-(3-trifluoromethyl-phenyl)-pyrrolidin-3-ylmethoxy]-isoxazol-5-yl}-1,3-dipropyl-3,7-dihydro-purine-2,6-dione,
8-{6-[1-(3-Fluoro-phenyl)-5-oxo-pyrrolidin-3-ylmethoxy]-pyridin-3-yl}-1,3-dipropyl-3,7-dihydro-purine-2,6-dione,
8-{6-[1-(4-Fluoro-phenyl)-5-oxo-pyrrolidin-3-ylmethoxy]-pyridin-3-yl}-1,3-dipropyl-3,7-dihydro-purine-2,6-dione,
8-{4-[1-(3-Fluoro-phenyl)-5-oxo-pyrrolidin-3-ylmethoxy]-phenyl}-1,3-dipropyl-3,7-dihydro-purine-2,6-dione,
8-{4-[1-(3-Fluoro-phenyl)-piperidin-4-yloxy]-phenyl}-1,3-dipropyl-3,7-dihydro-purine-2,6-dione,
8-{6-[1-(3-Fluoro-phenyl)-piperidin-4-yloxy]-pyridin-3-yl}-1,3-dipropyl-3,7-dihydro-purine-2,6-dione,
8-{3-[1-(3-Fluoro-phenyl)-piperidin-4-yloxy]-isoxazol-5-yl}-1,3-dipropyl-3,7-dihydro-purine-2,6-dione,
8-{4-[1-(4-Fluoro-phenyl)-piperidin-4-yloxy]-phenyl}-1,3-dipropyl-3,7-dihydro-purine-2,6-dione,
8-{3-[1-(4-Fluoro-phenyl)-piperidin-4-yloxy]-isoxazol-5-yl}-1,3-dipropyl-3,7-dihydro-purine-2,6-dione,
1,3-Dipropyl-8-{4-[1-(4-trifluoromethyl-phenyl)-piperidin-4-yloxy]-phenyl}-3,7-dihydro-purine-2,6-dione,
1,3-Dipropyl-8-{3-[1-(4-trifluoromethyl-phenyl)-piperidin-4-yloxy]-isoxazol-5-yl}-3,7-dihydro-purine-2,6-dione,
8-{6-[1-(3-Fluoro-phenyl)-pyrrolidin-3-yloxy]-pyridin-3-yl}-1,3-dipropyl-3,7-dihydro-purine-2,6-dione,
1,3-Dipropyl-8-{6-[1-(4-trifluoromethyl-phenyl)-piperidin-4-yloxy]-pyridin-3-yl}-3,7-dihydro-purine-2,6-dione,
8-{6-[1-(4-Fluoro-phenyl)-piperidin-4-yloxy]-pyridin-3-yl}-1,3-dipropyl-3,7-dihydro-purine-2,6-dione,
1,3-Dipropyl-8-{6-[1-(3-trifluoromethyl-phenyl)-piperidin-4-yloxy]-pyridin-3-yl}-3,7-dihydro-purine-2,6-dione,
1,3-Dipropyl-8-{6-[1-(3-trifluoromethyl-phenyl)-pyrrolidin-3-yloxy]-pyridin-3-yl}-3,7-dihydro-purine-2,6-dione,
1,3-Dipropyl-8-{4-[1-(3-trifluoromethyl-phenyl)-piperidin-4-yloxy]-phenyl}-3,7-dihydro-purine-2,6-dione,
1,3-Dipropyl-8-{3-[1-(3-trifluoromethyl-phenyl)-piperidin-4-yloxy]-isoxazol-5-yl}-3,7-dihydro-purine-2,6-dione,
1,3-Dipropyl-8-{6-[1-(4-trifluoromethyl-phenyl)-pyrrolidin-3-yloxy]-pyridin-3-yl}-3,7-dihydro-purine-2,6-dione,
8-{6-[1-(4-Fluoro-phenyl)-pyrrolidin-3-yloxy]-pyridin-3-yl}-1,3-dipropyl-3,7-dihydro-purine-2,6-dione,
8-{6-[5-Oxo-1-(4-trifluoromethyl-phenyl)-pyrrolidin-3-ylmethoxy]-pyridin-3-yl}-1,3-dipropyl-3,7-dihydro-purine-2,6-dione,
8-{3-[5-oxo-1-(4-trifluoromethyl-phenyl)-pyrrolidin-3-ylmethoxy]-isoxazol-5-yl}-1,3-dipropyl-3,7-dihydro-purine-2,6-dione,
8-{4-[5-Oxo-1-(4-trifluoromethyl-phenyl)-pyrrolidin-3-ylmethoxy]-phenyl}-1,3-dipropyl-3,7-dihydro-purine-2,6-dione,
1,3-Dipropyl-8-{4-[1-(4-trifluoromethyl-phenyl)-pyrrolidin-3-yloxy]-phenyl}-3,7-dihydro-purine-2,6-dione,
1,3-Dipropyl-8-{3-[1-(4-trifluoromethyl-phenyl)-pyrrolidin-3-yloxy]-isoxazol-5-yl}-3,7-dihydro-purine-2,6-dione,
8-{3-[1-(3-Fluoro-phenyl)-pyrrolidin-3-yloxy]-isoxazol-5-yl}-1,3-dipropyl-3,7-dihydro-purine-2,6-dione,
8-{3-[1-(4-Fluoro-phenyl)-pyrrolidin-3-yloxy]-isoxazol-5-yl}-1,3-dipropyl-3,7-dihydro-purine-2,6-dione,
1,3-Dipropyl-8-{3-[1-(3-trifluoromethyl-phenyl)-pyrrolidin-3-yloxy]-isoxazol-5-yl}-3,7-dihydro-purine-2,6-dione,
8-{4-[1-(3-Fluoro-phenyl)-pyrrolidin-3-yloxy]-phenyl}-1,3-dipropyl-3,7-dihydro-purine-2,6-dione,
8-{3-[1-(2,4-Difluoro-phenyl)-5-oxo-pyrrolidin-3-ylmethoxy]-isoxazol-5-yl}-1,3-dipropyl-3,7-dihydro-purine-2,6-dione,
8-{5-[1-(3-Fluoro-phenyl)-5-oxo-pyrrolidin-3-ylmethoxy]-1-methyl-1H-pyrazol-3-yl}-1,3-dipropyl-3,7-dihydro-purine-2,6-dione,
8-{1-Methyl-5-[5-oxo-1-(4-trifluoromethyl-benzyl)-pyrrolidin-3-ylmethoxy]-1H-pyrazol-3-yl}-1,3-dipropyl-3,7-dihydro-purine-2,6-dione,
8-{5-[1-(4-Methoxy-phenyl)-5-oxo-pyrrolidin-3-ylmethoxy]-1-methyl-1H-pyrazol-3-yl}-1,3-dipropyl-3,7-dihydro-purine-2,6-dione,
8-{5-[1-(4-Fluoro-phenyl)-5-oxo-pyrrolidin-3-ylmethoxy]-1-methyl-1H-pyrazol-3-yl}-1,3-dipropyl-3,7-dihydro-purine-2,6-dione, 8-{1-Methyl-5-[5-oxo-1-(3-trifluoromethyl-phenyl)-pyr-rolidin-3-ylmethoxy]-1H-pyrazol-3-yl}-1,3-dipropyl-3,7-dihydro-purine-2,6-dione,
8-{5-[1-(3-Methoxy-phenyl)-5-oxo-pyrrolidin-3-yl-methoxy]-1-methyl-1H-pyrazol-3-yl}-1,3-dipropyl-3,7-dihydro-purine-2,6-dione,
8-(1-{2-[5-oxo-1-(3-trifluoromethyl-phenyl)-pyrrolidin-3-yl]ethyl}-1H-pyrazol-4-yl)-1,3-dipropyl-3,7-dihydro-purine-2,6-dione,
8-(1-{1-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-(1-{2-Oxo-2-[5-oxo-1-(3-trifluoromethyl-phenyl)-pyr-rolidin-3-yl]-ethyl}-1H-pyrazol-4-yl)-1,3-dipropyl-3,7-dihydro-purine-2,6-dione,
8-(1-{2-Hydroxy-2-[5-oxo-1-(3-trifluoromethyl-phenyl)-pyrrolidin-3-yl]-ethyl}-1H-pyrazol-4-yl)-1,3-dipropyl-3,7-dihydro-purine-2,6-dione,
8-{1-[5-(4-Fluoro-benzyl)-4,5-dihydro-isoxazol-3-ylm-ethyl]-1H-pyrazol-4-yl}-1,3-dipropyl-3,7-dihydro-purine-2,6-dione,
8-(1-{2-oxo-2-[4-(3-trifluoromethyl-phenyl)-piperazin-1-yl]-ethyl}-1H-pyrazol-4-yl)-1,3-dipropyl-3,7-dihydro-purine-2,6-dione,
8-(1-{2-[4-(4-Chloro-phenyl)-4-hydroxy-piperidin-1-yl]-2-oxo-ethyl}-1H-pyrazol-4-yl)1,3-dipropyl-3,7-dihydro-purine-2,6-dione,
8-(1-{2-[4-(2,4-Difluoro-phenyl)-piperazin-1-yl]-2-oxo-ethyl}-1H-pyrazol-4-yl)-1,3-dipropyl-3,7-dihydro-purine-2,6-dione,
8-{1-[2-oxo-2-(4-p-tolyl-piperazin-1-yl)-ethyl]-1H-pyra-zol-4-yl}-1,3-dipropyl-3,7-dihydro-purine-2,6-dione,
8-(1-{2-Oxo-2-[4-(4-trifluoromethyl-phenyl)-piperazin-1-yl]-ethyl}-1H-pyrazol-4-yl)-1,3-dipropyl-3,7-dihydro-purine-2,6-dione,
8-(1-{2-[4-(3-Chloro-4-fluoro-phenyl)-piperazin-1-yl]-2-oxo-ethyl}-1H-pyrazol-4-yl)-1,3-dipropyl-3,7-dihydro-purine-2,6-dione,
3-Ethyl-8-(1-{2-oxo-2-[4-(3-trifluoromethyl-phenyl)-piperazin-1-yl]-ethyl}-1H-pyrazol-4-yl)-1-propyl-3,7-dihydro-purine-2,6-dione,
8-(1-{2-[4-(4-Fluoro-phenyl)-piperidin-1-yl]-2-oxo-ethyl}-1H-pyrazol-4-yl)-1,3-dipropyl-3,7-dihydro-purine-2,6-dione,
8-(1-{2-[4-(3-Fluoro-phenyl)-piperidin-1-yl]-2-oxo-ethyl}-1H-pyrazol-4-yl)-1,3-dipropyl-3,7-dihydro-purine-2,6-dione,
4-[4-(2,6-Dioxo-1,3-dipropyl-2,3,6,7-tetrahydro-1H-pu-rin-8-yl)-phenoxymethyl]-1-(3-trifluoromethyl-ben-zyl)-pyrrolidine-2-carboxylic acid,
3-(2-Amino-ethyl)-8-{1-[5-oxo-1-(3-trifluoromethyl-phenyl)-pyrrolidin-3-ylmethyl]-1H-pyrazol-4-yl}-1-propyl-3,7-dihydro-purine-2,6-dione,
8-{1-[1-(4-Isopropyl-phenyl)-5-oxo-pyrrolidin-3-ylm-ethyl]-1H-pyrazol-4-yl}-7-methyl-1,3-dipropyl-3,7-di-hydro-purine-2,6-dione,
7-Methyl-8-{1-[5-oxo-1-(4-trifluoromethyl-benzyl)-pyr-rolidin-3-ylmethyl]-1H-pyrazol-4-yl}-1,3-dipropyl-3,7-dihydro-purine-2,6-dione,
8-{1-[1-(3-Fluoro-phenyl)-5-oxo-pyrrolidin-3-ylmethyl]-1H-pyrazol-4-yl}-7-methyl-1,3-dipropyl-3,7-dihydro-purine-2,6-dione,
7-Methyl-8-{1-[5-oxo-1-(2-trifluoromethyl-benzyl)-pyr-rolidin-3-ylmethyl]-1H-pyrazol-4-yl}-1,3-dipropyl-3,7-dihydro-purine-2,6-dione,
8-{6-[1-(3-Fluoro-phenyl)-5-oxo-pyrrolidin-3-yl-methoxy]-pyridin-3-yl}-7-methyl-1,3-dipropyl-3,7-di-hydro-purine-2,6-dione,
8-{6-[1-(4-Fluoro-phenyl)-5-oxo-pyrrolidin-3-yl-methoxy]-pyridin-3-yl}-7-methyl-1,3-dipropyl-3,7-di-hydro-purine-2,6-dione,
8-{4-[1-(4-Fluoro-phenyl)-5-oxo-pyrrolidin-3-yl-methoxy]-phenyl}-7-methyl-1,3-dipropyl-3,7-dihydro-purine-2,6-dione, and
8-{4-[1-(3-Fluoro-phenyl)-5-oxo-pyrrolidin-3-yl-methoxy]-phenyl}-7-methyl-1,3-dipropyl-3,7-dihydro-purine-2,6-dione.

8. A compound of formula (I), as claimed in claim 1, or its tautomers, polymorphs, stereoisomers, prodrugs, or a pharmaceutically acceptable salts thereof, which are adenosine $A_{2B}$ antagonist, adenosine $A_1$ and $A_{2B}$ antagonist, adenosine $A_{2B}$ and $A_3$ antagonist, or $A_1$, $A_{2B}$ and $A_3$ antagonist thereby providing mono, dual or pan antagonistic activity through additive or/and synergistic effect.

9. A pharmaceutical composition comprising a compound of formula (I), as claimed in any of claims 1 to 7, or its tautomers, polymorphs, stereoisomers, prodrugs, or a pharmaceutically acceptable salts thereof, in combination with one or more therapeutic agents.

10. The pharmaceutical composition as claimed in claim 9 wherein, the one or more therapeutic agents is selected from anti-inflammatory agent, anti-diabetic agent, anti-hypertensive agent or anti-dyslipidemic agent.

11. The pharmaceutical composition as claimed in claim 9, wherein the one or more therapeutic agents is selected from anticholinergic agent, antimuscarinic agent, steroid, LTB4 (leukotriene B4) antagonist, dopamine receptor agonists, phosphodiesterase 4 inhibitor, beta-2 adrenergic receptor agonist, insulin, insulin mimetics, insulin secretagogues, insulinotropic sulfonylurea receptor ligands, thiazolidone, glycogen synthase kinase-3 inhibitor, sodium-dependent glucose co-transporter inhibitor, glycogen phosphorylase A inhibitor, biguanide, alpha-glucosidase inhibitor, glucagon like peptide-1 (GLP-1), GLP-1 analogs and GLP-1 mimetics, modulators of peroxisome proliferator-activated receptors, dipeptidyl peptidase IV inhibitor, stearoyl-CoA desaturase-1 inhibitor, diacylglycerol acyltransferase 1 and 2 inhibitor, acetyl CoA carboxylase 2 inhibitor, and breakers of advanced glycation end products, loop diuretics, angiotensin converting enzyme inhibitor, inhibitor of the Na-K-ATPase membrane pump such as digoxin, neutralendopeptidase (NEP) inhibitor, ACE/NEP inhibitors, angiotensin II antagonists, renin inhibitors, β-adrenergic receptor blockers, inotropic agents, calcium channel blockers, aldosterone receptor antagonists, and aldosterone synthase inhibitors, 3-hydroxy-3-methyl-glutaryl coenzyme A reductase inhibitor, HDL increasing compounds such as cholesterol ester transfer protein inhibitor, squalene synthase inhibitor, farnesoid X receptor and liver X receptor ligand, cholestyramine, fibrates, nicotinic acid, and aspirin.

12. A process for the preparation of a compound of formula (I), as claimed in any of the claims 1 to 7, or its tautomers, polymorphs, stereoisomers, prodrugs, or a pharmaceutically acceptable salts thereof, said process comprising:

reacting a diamine of formula (II)

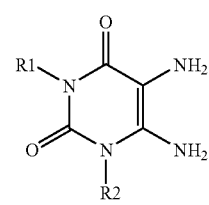

(II)

with a carboxylic acid of formula (III)
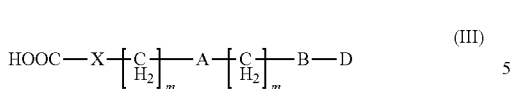
(III)
to provide a compound of formula (IV)
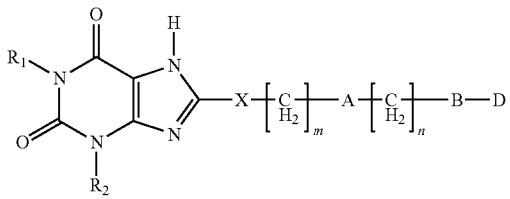
(IV)
which is reacted with $R^3$-Hal to obtain the compound of formula (I)
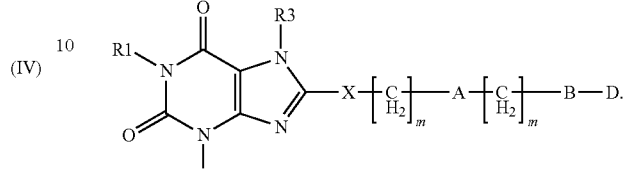
(I)
* * * * *